(12) United States Patent
Thompson et al.

(10) Patent No.: US 11,096,686 B2
(45) Date of Patent: *Aug. 24, 2021

(54) END EFFECTORS, SURGICAL STAPLING DEVICES, AND METHODS OF USING SAME

(71) Applicant: Standard Bariatrics, Inc., Cincinnati, OH (US)

(72) Inventors: Jonathan Thompson, Cincinnati, OH (US); Bennie Thompson, Blue Ash, OH (US); Richard P. Nuchols, Williamsburg, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/256,932

(22) Filed: Jan. 24, 2019

(65) Prior Publication Data
US 2019/0150924 A1    May 23, 2019

Related U.S. Application Data

(63) Continuation of application No. 15/920,196, filed on Mar. 13, 2018, now Pat. No. 10,278,699, which is a
(Continued)

(51) Int. Cl.
*A61B 17/072* (2006.01)
*A61B 17/34* (2006.01)
(Continued)

(52) U.S. Cl.
CPC .... *A61B 17/07207* (2013.01); *A61B 17/3468* (2013.01); *A61F 5/0089* (2013.01);
(Continued)

(58) Field of Classification Search
CPC .......... A61B 17/07207; A61B 17/0725; A61B 2017/07257; A61B 2017/07271; A61B 2017/07278; A61B 2017/07285
(Continued)

(56) References Cited

U.S. PATENT DOCUMENTS

| 848,126 A | 3/1907 | Roosevelt |
| 1,413,896 A | 4/1922 | Brix |

(Continued)

FOREIGN PATENT DOCUMENTS

| CA | 2663002 A1 | 10/2009 |
| EP | 0140552 A2 | 5/1985 |

(Continued)

OTHER PUBLICATIONS

Australian Examination Report in Application No. 2015241267; dated Feb. 25, 2019; 6 pages.
(Continued)

*Primary Examiner* — Michelle Lopez
(74) *Attorney, Agent, or Firm* — Ulmer & Berne LLP

(57) ABSTRACT

An end effector for use by a surgeon to staple an anatomical structure of a patient during a minimally invasive procedure, the anatomical structure having a first side and a second side, the end effector including an anvil that includes a first end, a second end, and a face, and a cartridge that is configured to house a plurality of staples and that includes a first end, a second end, and a face, and an engagement element that movably couples the first end of the anvil to the first end of the cartridge, and a knife, the knife having a first flange, a second flange, and a web including a cutting edge, and where the second end of the anvil is movably coupled to the second end of the cartridge, each of the anvil and the cartridge is insertable through a trocar, and the end effector is remotely operable from outside the patient.

16 Claims, 67 Drawing Sheets

Related U.S. Application Data continuation of application No. 15/129,385, filed on Sep. 26, 2016, now Pat. No. 9,936,953.

(60) Provisional application No. 61/972,274, filed on Mar. 29, 2014, provisional application No. 62/046,726, filed on Sep. 5, 2014.

(51) Int. Cl.
*A61F 5/00* (2006.01)
*A61B 17/00* (2006.01)
*A61B 17/29* (2006.01)

(52) U.S. Cl.
CPC .............. *A61B 2017/00367* (2013.01); *A61B 2017/00477* (2013.01); *A61B 2017/00818* (2013.01); *A61B 2017/00876* (2013.01); *A61B 2017/0725* (2013.01); *A61B 2017/07214* (2013.01); *A61B 2017/07221* (2013.01); *A61B 2017/07257* (2013.01); *A61B 2017/07271* (2013.01); *A61B 2017/07278* (2013.01); *A61B 2017/07285* (2013.01); *A61B 2017/2919* (2013.01); *A61B 2017/2927* (2013.01); *A61B 2017/2937* (2013.01); *A61B 2017/2939* (2013.01); *A61B 2017/2944* (2013.01)

(58) Field of Classification Search
USPC ..................................................... 227/175.1
See application file for complete search history.

(56) References Cited

U.S. PATENT DOCUMENTS

| | | | |
|---|---|---|---|
| 2,659,371 | A | 11/1953 | Schnee |
| 2,686,520 | A | 8/1954 | Jarvis et al. |
| 3,017,637 | A | 1/1962 | Sampson |
| 3,490,675 | A | 1/1970 | Green et al. |
| 3,551,987 | A | 1/1971 | Wilkinson |
| 3,877,434 | A | 4/1975 | Ferguson et al. |
| 4,269,190 | A | 5/1981 | Behney |
| 4,319,576 | A | 3/1982 | Rothfuss |
| 4,354,628 | A | 10/1982 | Green |
| 4,442,964 | A | 4/1984 | Becht |
| 4,458,681 | A | 7/1984 | Hopkins |
| 4,520,817 | A | 6/1985 | Green |
| 4,527,724 | A | 7/1985 | Chow et al. |
| 4,558,699 | A | 12/1985 | Bashour |
| 4,605,001 | A | 8/1986 | Rothfuss et al. |
| 4,605,004 | A | 8/1986 | Giovanni et al. |
| 4,608,981 | A | 9/1986 | Rothfuss et al. |
| 4,610,383 | A | 9/1986 | Rothfuss et al. |
| 4,632,290 | A | 12/1986 | Green et al. |
| 4,633,861 | A | 1/1987 | Chow et al. |
| 4,784,137 | A | 11/1988 | Kulik et al. |
| 4,803,985 | A | 2/1989 | Hill |
| 4,819,853 | A | 4/1989 | Green |
| 4,848,637 | A | 7/1989 | Pruitt |
| 4,930,503 | A | 6/1990 | Pruitt |
| 4,941,623 | A | 7/1990 | Pruitt |
| 4,951,861 | A | 8/1990 | Schulze et al. |
| 4,976,721 | A | 12/1990 | Blasnik et al. |
| 4,978,049 | A | 12/1990 | Green |
| 5,040,715 | A | 8/1991 | Green et al. |
| 5,176,651 | A | 1/1993 | Allgood et al. |
| 5,205,459 | A | 4/1993 | Brinkerhoff et al. |
| 5,219,111 | A | 6/1993 | Bilotti et al. |
| 5,222,961 | A | 6/1993 | Nakao et al. |
| 5,307,976 | A | 5/1994 | Olson |
| 5,308,576 | A | 5/1994 | Green et al. |
| 5,312,410 | A | 5/1994 | Miller et al. |
| 5,327,914 | A | 7/1994 | Shlain |
| 5,333,772 | A | 8/1994 | Rothfuss et al. |
| 5,345,949 | A | 9/1994 | Shlain |
| 5,389,098 | A | 2/1995 | Tsuruta et al. |
| 5,395,030 | A | 3/1995 | Kuramoto et al. |
| 5,395,034 | A | 3/1995 | Allen et al. |
| 5,415,334 | A | 5/1995 | Williamson, IV et al. |
| 5,431,323 | A | 7/1995 | Smith et al. |
| 5,443,475 | A | 8/1995 | Auerbach et al. |
| 5,452,836 | A | 9/1995 | Huitema et al. |
| 5,452,837 | A | 9/1995 | Williamson, IV et al. |
| 5,456,401 | A | 10/1995 | Green et al. |
| 5,465,895 | A | 11/1995 | Knodel et al. |
| 5,465,896 | A | 11/1995 | Allen et al. |
| 5,470,009 | A | 11/1995 | Rodak |
| 5,485,952 | A | 1/1996 | Fontayne |
| 5,487,500 | A | 1/1996 | Knodel et al. |
| 5,496,333 | A | 3/1996 | Sackier et al. |
| 5,503,638 | A | 4/1996 | Cooper et al. |
| 5,507,426 | A | 4/1996 | Young et al. |
| 5,507,773 | A | 4/1996 | Huitema et al. |
| 5,514,098 | A | 5/1996 | Pfoslgraf et al. |
| 5,531,744 | A | 7/1996 | Nardella et al. |
| 5,549,621 | A | 8/1996 | Bessler et al. |
| 5,551,622 | A | 9/1996 | Yoon |
| 5,554,169 | A | 9/1996 | Green et al. |
| 5,560,530 | A | 10/1996 | Bolanos et al. |
| 5,562,702 | A | 10/1996 | Huitema et al. |
| 5,571,116 | A | 11/1996 | Bolanos et al. |
| 5,571,131 | A | 11/1996 | Ek et al. |
| 5,586,711 | A | 12/1996 | Plyley et al. |
| 5,597,107 | A | 1/1997 | Knodel et al. |
| 5,630,540 | A | 5/1997 | Blewelt |
| 5,632,432 | A | 5/1997 | Schulze et al. |
| 5,636,780 | A | 6/1997 | Green et al. |
| 5,662,667 | A | 9/1997 | Knodel |
| 5,697,542 | A | 12/1997 | Knodel et al. |
| 5,702,409 | A | 12/1997 | Rayburn et al. |
| 5,704,534 | A | 1/1998 | Huitema et al. |
| 5,732,871 | A | 3/1998 | Clark et al. |
| 5,762,256 | A | 6/1998 | Mastri et al. |
| 5,779,130 | A | 7/1998 | Alesi et al. |
| 5,779,132 | A | 7/1998 | Knodel et al. |
| 5,782,396 | A | 7/1998 | Mastri et al. |
| 5,797,538 | A | 8/1998 | Heaton et al. |
| 5,810,240 | A | 9/1998 | Robertson |
| 5,814,055 | A | 9/1998 | Knodel et al. |
| 5,819,240 | A | 10/1998 | Kara |
| 5,820,009 | A | 10/1998 | Melling et al. |
| 5,865,361 | A | 2/1999 | Milliman et al. |
| 5,868,760 | A | 2/1999 | McGuckin, Jr. |
| 5,871,135 | A | 2/1999 | Williamson, IV et al. |
| 5,901,895 | A | 5/1999 | Heaton et al. |
| 5,902,312 | A | 5/1999 | Frater et al. |
| 5,954,259 | A | 9/1999 | Viola et al. |
| 5,964,394 | A | 10/1999 | Robertson |
| 5,988,479 | A | 11/1999 | Palmer |
| 6,032,849 | A | 3/2000 | Mastri et al. |
| 6,099,551 | A | 8/2000 | Gabbay |
| 6,264,087 | B1 | 7/2001 | Whitman |
| 6,270,507 | B1 | 8/2001 | Callicrate |
| 6,315,184 | B1 | 11/2001 | Whitman |
| 6,325,810 | B1 | 12/2001 | Hamilton et al. |
| 6,488,196 | B1 | 12/2002 | Fenton |
| 6,505,768 | B2 | 1/2003 | Whitman |
| 6,511,490 | B2 | 1/2003 | Robert |
| 6,716,233 | B1 | 4/2004 | Whitman |
| 6,835,199 | B2 | 12/2004 | McGuckin et al. |
| RE38,708 | E | 3/2005 | Bolanos et al. |
| 6,978,921 | B2 | 12/2005 | Shelton, IV et al. |
| 6,986,451 | B1 | 1/2006 | Mastri et al. |
| 6,988,649 | B2 | 1/2006 | Shelton, IV et al. |
| 7,025,791 | B2 | 4/2006 | Levine et al. |
| 7,032,799 | B2 | 4/2006 | Viola et al. |
| 7,037,344 | B2 | 5/2006 | Kagan et al. |
| 7,044,353 | B2 | 5/2006 | Mastri et al. |
| 7,070,083 | B2 | 7/2006 | Jankowski |
| 7,128,253 | B2 | 10/2006 | Mastri et al. |
| 7,134,587 | B2 | 11/2006 | Schwemberger et al. |
| 7,175,648 | B2 | 2/2007 | Nakao |
| 7,207,472 | B2 | 4/2007 | Wukusick et al. |
| 7,225,964 | B2 | 6/2007 | Mastri et al. |
| 7,229,428 | B2 | 6/2007 | Gannoe et al. |

(56) References Cited

U.S. PATENT DOCUMENTS

| | | |
|---|---|---|
| 7,235,089 B1 | 6/2007 | McGuckin, Jr. |
| 7,258,262 B2 | 8/2007 | Mastri et al. |
| 7,288,100 B2 | 8/2007 | Trigueros |
| 7,278,562 B2 | 10/2007 | Mastri et al. |
| 7,278,563 B1 | 10/2007 | Green |
| 7,308,998 B2 | 12/2007 | Mastri et al. |
| RE40,237 E | 4/2008 | Bilotti et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,076 B2 | 8/2008 | Racenet et al. |
| 7,422,138 B2 | 9/2008 | Bilotti et al. |
| 7,434,716 B2 | 10/2008 | Viola |
| 7,434,717 B2 | 10/2008 | Shelton, IV et al. |
| 7,438,209 B1 | 10/2008 | Hess et al. |
| 7,455,676 B2 | 11/2008 | Holsten et al. |
| 7,467,740 B2 | 12/2008 | Shelton, IV et al. |
| 7,472,815 B2 | 1/2009 | Shelton, IV et al. |
| 7,481,349 B2 | 1/2009 | Holsten et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,549,654 B2 | 6/2009 | Anderson et al. |
| 7,565,993 B2 | 7/2009 | Milliman et al. |
| 7,588,175 B2 | 9/2009 | Timm et al. |
| 7,588,176 B2 | 9/2009 | Timm et al. |
| 7,588,177 B2 | 9/2009 | Racenet |
| 7,604,151 B2 | 10/2009 | Hess et al. |
| 7,617,961 B2 | 11/2009 | Viola |
| 7,635,074 B2 | 12/2009 | Olson et al. |
| 7,641,091 B2 | 1/2010 | Olson et al. |
| 7,645,285 B2 | 1/2010 | Cosgrove et al. |
| 7,658,312 B2 | 2/2010 | Vidal et al. |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,673,781 B2 | 3/2010 | Swayze et al. |
| 7,673,782 B2 | 3/2010 | Hess et al. |
| 7,690,547 B2 | 4/2010 | Racenet et al. |
| 7,694,864 B2 | 4/2010 | Okada et al. |
| 7,704,264 B2 | 4/2010 | Ewers et al. |
| 7,708,684 B2 | 5/2010 | Demarais et al. |
| 7,717,312 B2 | 5/2010 | Beetel |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,744,613 B2 | 6/2010 | Ewers et al. |
| 7,758,493 B2 | 7/2010 | Gingras |
| 7,770,774 B2 | 8/2010 | Mastri et al. |
| 7,775,967 B2 | 8/2010 | Gertner |
| D624,182 S | 9/2010 | Thouement |
| 7,793,812 B2 | 9/2010 | Moore et al. |
| 7,794,475 B2 | 9/2010 | Hess et al. |
| 7,815,092 B2 | 10/2010 | Whitman et al. |
| 7,819,896 B2 | 10/2010 | Racenet |
| 7,828,188 B2 | 11/2010 | Jankowski |
| 7,837,079 B2 | 11/2010 | Holsten et al. |
| 7,846,149 B2 | 12/2010 | Jankowski |
| 7,857,184 B2 | 12/2010 | Viola |
| 7,866,525 B2 | 1/2011 | Scirica |
| 7,871,416 B2 | 1/2011 | Phillips |
| 7,891,531 B1 | 2/2011 | Ward |
| 7,891,533 B2 | 2/2011 | Green et al. |
| 7,913,893 B2 | 3/2011 | Mastri et al. |
| 7,918,869 B2 | 4/2011 | Saadat et al. |
| 7,934,630 B2 | 5/2011 | Shelton, IV et al. |
| 7,955,340 B2 | 6/2011 | Michlitsch et al. |
| 7,959,050 B2 | 6/2011 | Smith et al. |
| 7,963,907 B2 | 6/2011 | Gertner |
| 7,966,799 B2 | 6/2011 | Morgan et al. |
| 7,992,757 B2 | 8/2011 | Wheeler et al. |
| 8,016,176 B2 | 9/2011 | Kasvikis et al. |
| 8,020,741 B2 | 9/2011 | Cole et al. |
| 8,028,884 B2 | 10/2011 | Sniffin et al. |
| 8,033,442 B2 | 10/2011 | Racenet et al. |
| 8,034,077 B2 | 10/2011 | Smith et al. |
| 8,052,697 B2 | 11/2011 | Phillips |
| 8,056,788 B2 | 11/2011 | Mastri et al. |
| 8,061,577 B2 | 11/2011 | Racenet et al. |
| 8,062,236 B2 | 11/2011 | Soltz |
| 8,066,168 B2 | 11/2011 | Vidal et al. |
| 8,070,034 B1 | 12/2011 | Knodel |
| 8,070,036 B1 | 12/2011 | Knodel |
| 8,087,563 B2 | 1/2012 | Milliman et al. |
| 8,091,756 B2 | 1/2012 | Viola |
| 8,096,459 B2 | 1/2012 | Ortiz et al. |
| 8,132,704 B2 | 3/2012 | Whitman et al. |
| 8,141,762 B2 | 3/2012 | Bedi et al. |
| 8,147,506 B2 | 4/2012 | Ortiz et al. |
| 8,167,186 B2 | 5/2012 | Racenet et al. |
| 8,172,122 B2 | 5/2012 | Kasvikis et al. |
| 8,186,560 B2 | 5/2012 | Hess et al. |
| 8,196,795 B2 | 6/2012 | Moore et al. |
| 8,205,780 B2 | 6/2012 | Sorrentino et al. |
| 8,216,159 B1 | 7/2012 | Leiboff |
| 8,220,690 B2 | 7/2012 | Hess et al. |
| 8,226,602 B2 | 7/2012 | Quijana et al. |
| 8,245,898 B2 | 8/2012 | Smith et al. |
| 8,252,009 B2 | 8/2012 | Weller et al. |
| 8,256,655 B2 | 9/2012 | Sniffin et al. |
| 8,276,801 B2 | 10/2012 | Zemlok et al. |
| 8,292,153 B2 | 10/2012 | Jankowski |
| 8,308,725 B2 | 11/2012 | Bell et al. |
| 8,317,070 B2 | 11/2012 | Hueil et al. |
| 8,322,455 B2 | 12/2012 | Shelton, IV et al. |
| 8,328,061 B2 | 12/2012 | Kasvikis |
| 8,328,064 B2 | 12/2012 | Racenet et al. |
| 8,343,175 B2 | 1/2013 | Ewers et al. |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,436 B2 | 1/2013 | Kasvikis |
| 8,360,297 B2 | 1/2013 | Shelton, IV et al. |
| 8,365,973 B1 | 2/2013 | White et al. |
| 8,365,976 B2 | 2/2013 | Hess et al. |
| 8,382,775 B1 | 2/2013 | Bender et al. |
| 8,393,513 B2 | 3/2013 | Jankowski |
| 8,393,514 B2 | 3/2013 | Shelton, IV et al. |
| 8,403,956 B1 | 3/2013 | Thompson et al. |
| 8,408,442 B2 | 4/2013 | Racenet et al. |
| 8,424,739 B2 | 4/2013 | Racenet et al. |
| 8,439,244 B2 | 5/2013 | Holcolmb et al. |
| 8,439,246 B1 | 5/2013 | Knodel |
| 8,449,560 B2 | 5/2013 | Roth et al. |
| 8,453,912 B2 | 6/2013 | Mastri et al. |
| 8,453,914 B2 | 6/2013 | Laurent et al. |
| 8,464,923 B2 | 6/2013 | Shelton, IV |
| 8,465,507 B2 | 6/2013 | Cosgrove et al. |
| 8,469,252 B2 | 6/2013 | Holcomb et al. |
| 8,485,412 B2 | 7/2013 | Shelton, IV et al. |
| 8,496,155 B2 | 7/2013 | Knodel |
| 8,496,156 B2 | 7/2013 | Sniffin et al. |
| 8,499,993 B2 | 8/2013 | Shelton, IV et al. |
| 8,523,041 B2 | 9/2013 | Ishitsuki et al. |
| 8,529,585 B2 | 9/2013 | Jacobs et al. |
| 8,540,128 B2 | 9/2013 | Shelton, IV et al. |
| 8,540,130 B2 | 9/2013 | Moore et al. |
| 8,544,712 B2 | 10/2013 | Jankowski |
| 8,561,872 B2 | 10/2013 | Wheeler et al. |
| 8,574,243 B2 | 11/2013 | Saadat et al. |
| 8,579,176 B2 | 11/2013 | Smith et al. |
| 8,579,178 B2 | 11/2013 | Holsten et al. |
| 8,590,762 B2 | 11/2013 | Hess et al. |
| 8,596,513 B2 | 12/2013 | Olson et al. |
| 8,608,043 B2 | 12/2013 | Scirica |
| 8,613,384 B2 | 12/2013 | Pastorelli et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |

(56) References Cited

U.S. PATENT DOCUMENTS

| | | |
|---|---|---|
| 8,663,245 B2 | 3/2014 | Francischelli et al. |
| 8,668,130 B2 | 3/2014 | Hess et al. |
| 8,672,208 B2 | 3/2014 | Hess et al. |
| 8,672,830 B2 | 3/2014 | Dlugos, Jr. et al. |
| 8,701,958 B2 | 4/2014 | Shelton, IV et al. |
| 8,714,429 B2 | 5/2014 | Demmy |
| 8,720,766 B2 | 5/2014 | Hess et al. |
| 8,727,197 B2 | 5/2014 | Hess et al. |
| 8,733,613 B2 | 5/2014 | Huitema et al. |
| 8,740,035 B2 | 6/2014 | Mastri et al. |
| 8,758,392 B2 | 6/2014 | Crainich |
| 8,763,875 B2 | 7/2014 | Morgan et al. |
| 8,800,838 B2 | 8/2014 | Shelton, IV |
| 8,800,840 B2 | 8/2014 | Jankowski |
| 8,801,732 B2 | 8/2014 | Harris et al. |
| 8,808,325 B2 | 8/2014 | Hess et al. |
| 8,840,004 B2 | 9/2014 | Holsten et al. |
| 8,852,218 B2 | 10/2014 | Hughett, Sr. et al. |
| 8,864,009 B2 | 10/2014 | Shelton, IV et al. |
| 8,899,465 B2 | 12/2014 | Shelton, IV et al. |
| 8,925,788 B2 | 1/2015 | Hess et al. |
| 8,945,163 B2 | 2/2015 | Voegele et al. |
| 8,956,390 B2 | 2/2015 | Shah et al. |
| 8,973,804 B2 | 3/2015 | Hess et al. |
| 8,991,676 B2 | 3/2015 | Hess et al. |
| 8,991,677 B2 | 3/2015 | Moore et al. |
| 8,998,058 B2 | 4/2015 | Moore et al. |
| 9,016,541 B2 | 4/2015 | Viola et al. |
| 9,033,203 B2 | 5/2015 | Woodard, Jr. et al. |
| 9,066,721 B2 | 6/2015 | Ichihara et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,119,627 B2 | 9/2015 | Cosgrove et al. |
| 9,138,226 B2 | 9/2015 | Racenet et al. |
| 9,155,528 B2 | 10/2015 | Bender et al. |
| 9,168,039 B1 | 10/2015 | Knodel |
| 9,179,911 B2 | 11/2015 | Morgan et al. |
| 9,180,035 B2 | 11/2015 | Stack et al. |
| 9,216,019 B2 | 12/2015 | Schmid et al. |
| 9,289,206 B2 | 3/2016 | Hess et al. |
| 9,307,981 B2 | 4/2016 | Mikkaichi et al. |
| 9,314,362 B2 | 4/2016 | Bender et al. |
| 9,326,768 B2 | 5/2016 | Shelton, IV |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,408,604 B2 | 8/2016 | Shelton, IV et al. |
| 9,433,411 B2 | 9/2016 | Racenet et al. |
| 9,439,633 B2 | 9/2016 | O'Dea |
| 9,498,219 B2 | 11/2016 | Moore et al. |
| 9,549,733 B2 | 1/2017 | Knodel |
| 9,561,032 B2 | 2/2017 | Shelton, IV et al. |
| 9,603,595 B2 | 3/2017 | Shelton, IV et al. |
| 9,603,598 B2 | 3/2017 | Shelton, IV et al. |
| 9,615,952 B2 | 4/2017 | Scott et al. |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,801,627 B2 | 10/2017 | Harris et al. |
| 9,801,628 B2 | 10/2017 | Harris et al. |
| 9,808,246 B2 | 11/2017 | Shelton, IV et al. |
| 9,808,257 B2 | 11/2017 | Armenteros et al. |
| 9,820,742 B2 | 11/2017 | Covach et al. |
| 9,827,002 B2 | 11/2017 | Hausen et al. |
| 9,844,370 B2 | 12/2017 | Viola et al. |
| 9,848,873 B2 | 12/2017 | Shelton, IV |
| 9,848,878 B2 | 12/2017 | Racenet et al. |
| 9,855,040 B2 | 1/2018 | Kostrzewski |
| 9,861,366 B2 | 1/2018 | Aranyi |
| 9,872,682 B2 | 1/2018 | Hess et al. |
| 9,901,344 B2 | 2/2018 | Moore et al. |
| 9,901,346 B2 | 2/2018 | Moore et al. |
| 9,913,646 B2 | 3/2018 | Shelton, IV |
| 9,924,947 B2 | 3/2018 | Shelton, IV et al. |
| 9,936,953 B2 * | 4/2018 | Thompson ....... A61B 17/07207 |
| 9,980,729 B2 | 5/2018 | Moore et al. |
| 9,999,426 B2 | 6/2018 | Moore et al. |
| 9,999,431 B2 | 6/2018 | Shelton, IV et al. |
| 10,004,505 B2 | 6/2018 | Moore et al. |
| 10,045,780 B2 | 8/2018 | Adams et al. |
| 10,085,754 B2 | 10/2018 | Sniffin et al. |
| 10,130,360 B2 | 11/2018 | Olson et al. |
| 10,130,363 B2 | 11/2018 | Huitema et al. |
| 10,172,616 B2 | 1/2019 | Murray et al. |
| 10,226,250 B2 | 3/2019 | Beckman et al. |
| 10,231,734 B2 | 3/2019 | Thompson et al. |
| 10,238,517 B2 | 3/2019 | Gingras |
| 10,245,032 B2 | 4/2019 | Shelton, IV |
| 10,258,334 B2 | 4/2019 | Adams et al. |
| 10,278,695 B2 | 5/2019 | Milo |
| 10,278,699 B2 * | 5/2019 | Thompson ............ A61F 5/0089 |
| 10,278,707 B2 | 5/2019 | Thompson et al. |
| 10,285,712 B2 | 5/2019 | Cosgrove, III et al. |
| 10,285,837 B1 | 5/2019 | Thompson et al. |
| 10,292,706 B2 | 5/2019 | Jankowski |
| 10,307,161 B2 | 6/2019 | Jankowski |
| 10,307,163 B2 | 6/2019 | Moore et al. |
| 10,314,589 B2 | 6/2019 | Shelton, IV et al. |
| 10,342,538 B2 | 7/2019 | Racenet et al. |
| 10,390,826 B2 | 8/2019 | Badawi |
| 10,405,856 B2 | 9/2019 | Knodel |
| 10,405,860 B2 | 9/2019 | Thompson et al. |
| 10,420,559 B2 | 9/2019 | Marczyk et al. |
| 10,420,560 B2 | 9/2019 | Shelton, IV et al. |
| 10,441,283 B1 | 10/2019 | Thompson et al. |
| 10,456,571 B2 | 10/2019 | Cairns |
| 10,470,911 B2 | 11/2019 | Thompson et al. |
| 10,542,986 B2 | 1/2020 | Thompson et al. |
| 10,548,597 B2 | 2/2020 | Dunki-Jacobs et al. |
| 10,624,638 B2 | 4/2020 | Thompson et al. |
| 10,687,814 B2 | 6/2020 | Dunki-Jacobs et al. |
| 10,849,623 B2 | 12/2020 | Dunki-Jacobs et al. |
| 2001/0044656 A1 | 11/2001 | Williamson, IV et al. |
| 2003/0125734 A1 | 7/2003 | Mollenauer |
| 2003/0135091 A1 | 7/2003 | Nakazawa et al. |
| 2004/0006351 A1 | 1/2004 | Gannoe et al. |
| 2004/0068267 A1 | 4/2004 | Harvie et al. |
| 2004/0181239 A1 | 9/2004 | Dorn et al. |
| 2005/0006432 A1 | 1/2005 | Racenet et al. |
| 2005/0080444 A1 | 4/2005 | Kraemer |
| 2005/0139633 A1 | 6/2005 | Wukusick et al. |
| 2005/0203547 A1 | 9/2005 | Weller et al. |
| 2006/0011698 A1 | 1/2006 | Okada et al. |
| 2006/0016853 A1 | 1/2006 | Racenet |
| 2006/0020277 A1 | 1/2006 | Gostout et al. |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | McGuckin, Jr. et al. |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0034667 A1 | 2/2007 | Holsten et al. |
| 2007/0039997 A1 | 2/2007 | Mather et al. |
| 2007/0075114 A1 | 4/2007 | Shelton, IV et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0213743 A1 | 9/2007 | McGuckin, Jr. |

(56) References Cited

U.S. PATENT DOCUMENTS

| | | |
|---|---|---|
| 2007/0246505 A1 | 10/2007 | Pace-Floridia et al. |
| 2007/0262116 A1 | 11/2007 | Hueil et al. |
| 2008/0015631 A1 | 1/2008 | Lee et al. |
| 2008/0023522 A1 | 1/2008 | Olson et al. |
| 2008/0033457 A1 | 2/2008 | Francischelli et al. |
| 2008/0035702 A1 | 2/2008 | Holsten et al. |
| 2008/0078800 A1 | 4/2008 | Hess et al. |
| 2008/0082124 A1 | 4/2008 | Hess et al. |
| 2008/0087707 A1 | 4/2008 | Jankowski |
| 2008/0097332 A1 | 4/2008 | Greenhalgh et al. |
| 2008/0149684 A1 | 6/2008 | Viola |
| 2008/0164297 A1 | 7/2008 | Holsten et al. |
| 2008/0169329 A1 | 7/2008 | Shelton et al. |
| 2008/0169332 A1 | 7/2008 | Shelton et al. |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2008/0294179 A1 | 11/2008 | Balbierz et al. |
| 2008/0308602 A1 | 12/2008 | Timm et al. |
| 2009/0001122 A1 | 1/2009 | Prommersberger et al. |
| 2009/0001130 A1 | 1/2009 | Hess et al. |
| 2009/0012556 A1 | 1/2009 | Boudreaux et al. |
| 2009/0134200 A1 | 5/2009 | Tarinelli et al. |
| 2009/0173766 A1 | 7/2009 | Wenchell |
| 2009/0209946 A1 | 8/2009 | Swayze et al. |
| 2009/0209986 A1 | 8/2009 | Stewart et al. |
| 2009/0212088 A1 | 8/2009 | Okada et al. |
| 2009/0261144 A1 | 10/2009 | Sniffin et al. |
| 2009/0308907 A1 | 12/2009 | Nalagatla et al. |
| 2010/0010512 A1 | 1/2010 | Taylor et al. |
| 2010/0072258 A1 | 3/2010 | Farascioni et al. |
| 2010/0108739 A1 | 5/2010 | Holsten et al. |
| 2010/0114124 A1 | 5/2010 | Kelleher et al. |
| 2010/0121356 A1 | 5/2010 | Hartmann et al. |
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0004062 A1 | 1/2011 | Asai et al. |
| 2011/0017800 A1 | 1/2011 | Viola |
| 2011/0046653 A1 | 2/2011 | Addington et al. |
| 2011/0071555 A1 | 3/2011 | McBrayer et al. |
| 2011/0084113 A1 | 4/2011 | Bedi et al. |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 6/2011 | Gagner et al. |
| 2011/0186614 A1 | 8/2011 | Kasvikis |
| 2011/0190791 A1 | 8/2011 | Jacobs et al. |
| 2011/0208211 A1 | 8/2011 | Whitfield et al. |
| 2011/0278343 A1 | 11/2011 | Knodel et al. |
| 2011/0290851 A1 | 12/2011 | Shelton, IV |
| 2011/0315739 A1 | 12/2011 | Sniffin et al. |
| 2012/0059400 A1 | 3/2012 | Williamson, IV et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0234899 A1 | 9/2012 | Scheib et al. |
| 2012/0234900 A1 | 9/2012 | Swayze |
| 2012/0277525 A1 | 11/2012 | O'Dea |
| 2012/0286022 A1 | 11/2012 | Olson et al. |
| 2013/0062394 A1 | 3/2013 | Smith et al. |
| 2013/0075447 A1 | 3/2013 | Weisenburgh, II et al. |
| 2013/0075450 A1 | 3/2013 | Schmid et al. |
| 2013/0092718 A1 | 4/2013 | Soltz et al. |
| 2013/0105549 A1 | 5/2013 | Holsten et al. |
| 2013/0146638 A1 | 6/2013 | Vasudevan et al. |
| 2013/0146641 A1 | 6/2013 | Shelton, IV et al. |
| 2013/0146642 A1 | 6/2013 | Shelton, IV et al. |
| 2013/0153625 A1 | 6/2013 | Felder et al. |
| 2013/0153634 A1 | 6/2013 | Carter et al. |
| 2013/0153642 A1 | 6/2013 | Felder et al. |
| 2013/0161374 A1 | 6/2013 | Swayze et al. |
| 2013/0165774 A1 | 6/2013 | Nocca |
| 2013/0172929 A1 | 7/2013 | Hess et al. |
| 2013/0193190 A1 | 8/2013 | Carter et al. |
| 2013/0214025 A1 | 8/2013 | Zemlok et al. |
| 2013/0245652 A1 | 9/2013 | Cosgrove et al. |
| 2013/0256375 A1 | 10/2013 | Shelton, IV et al. |
| 2013/0256377 A1 | 10/2013 | Schmid et al. |
| 2013/0284791 A1 | 10/2013 | Olson et al. |
| 2013/0306704 A1 | 11/2013 | Balbierz et al. |
| 2013/0327809 A1 | 12/2013 | Shelton, IV et al. |
| 2013/0334288 A1 | 12/2013 | Shelton, IV |
| 2013/0341374 A1 | 12/2013 | Shelton, IV et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0082497 A1 | 3/2014 | Chalouhi et al. |
| 2014/0107698 A1 | 4/2014 | Inge |
| 2014/0110457 A1 | 4/2014 | Zhang et al. |
| 2014/0114121 A1 | 4/2014 | Trivedi |
| 2014/0131418 A1 | 5/2014 | Kostrzewski |
| 2014/0131419 A1 | 5/2014 | Bettuchi |
| 2014/0144968 A1 | 5/2014 | Shelton, IV |
| 2014/0171744 A1 | 6/2014 | Racenet et al. |
| 2014/0184519 A1 | 7/2014 | Benchenaa et al. |
| 2014/0191015 A1 | 7/2014 | Shelton, IV |
| 2014/0214025 A1 | 7/2014 | Worrell et al. |
| 2014/0231489 A1 | 8/2014 | Balbierz et al. |
| 2014/0257353 A1 | 9/2014 | Whitman et al. |
| 2014/0263570 A1 | 9/2014 | Hopkins et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0133740 A1 | 5/2015 | Dierking et al. |
| 2015/0157318 A1 | 6/2015 | Beardsley et al. |
| 2015/0173755 A1 | 6/2015 | Baxter, III et al. |
| 2015/0173762 A1 | 6/2015 | Shelton, IV et al. |
| 2015/0209034 A1 | 7/2015 | Viola et al. |
| 2015/0265276 A1 | 9/2015 | Huitema et al. |
| 2015/0297224 A1 | 10/2015 | Hall et al. |
| 2015/0297227 A1 | 10/2015 | Huitema et al. |
| 2015/0320423 A1 | 11/2015 | Aranyi |
| 2015/0351764 A1 | 12/2015 | Shelton, IV |
| 2016/0058447 A1 | 3/2016 | Posada et al. |
| 2016/0058594 A1 | 3/2016 | Armenteros et al. |
| 2016/0066916 A1 | 3/2016 | Overmyer et al. |
| 2016/0067074 A1 | 3/2016 | Thompson et al. |
| 2016/0089148 A1 | 3/2016 | Harris et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0262744 A1 | 9/2016 | Milo et al. |
| 2016/0262750 A1 | 9/2016 | Hausen et al. |
| 2016/0262921 A1 | 9/2016 | Balbierz et al. |
| 2016/0270792 A1 | 9/2016 | Sniffin et al. |
| 2016/0324527 A1 | 11/2016 | Thompson et al. |
| 2016/0354085 A1 | 12/2016 | Shelton, IV et al. |
| 2016/0367250 A1 | 12/2016 | Racenet et al. |
| 2017/0007248 A1 | 1/2017 | Shelton, IV et al. |
| 2017/0014125 A1 | 1/2017 | Shelton, IV et al. |
| 2017/0055991 A1 | 3/2017 | Kang |
| 2017/0086847 A1 | 3/2017 | DiNardo et al. |
| 2017/0095251 A1 | 4/2017 | Thompson et al. |
| 2017/0105728 A1 | 4/2017 | Scheib et al. |
| 2017/0172571 A1 | 6/2017 | Thompson et al. |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2017/0360447 A1 | 12/2017 | Armenteros et al. |
| 2017/0367697 A1 | 12/2017 | Shelton, IV et al. |
| 2018/0014826 A1 | 1/2018 | Scheib et al. |

(56) References Cited

U.S. PATENT DOCUMENTS

| | | |
|---|---|---|
| 2018/0036005 A1 | 2/2018 | Covach et al. |
| 2018/0092641 A1 | 4/2018 | Aranyi |
| 2018/0168620 A1 | 6/2018 | Huang et al. |
| 2018/0168633 A1 | 6/2018 | Shelton, IV et al. |
| 2018/0199939 A1 | 7/2018 | Thompson et al. |
| 2018/0199941 A1 | 7/2018 | Thompson et al. |
| 2018/0235625 A1 | 8/2018 | Shelton, IV et al. |
| 2018/0235626 A1 | 8/2018 | Shelton, IV et al. |
| 2018/0280020 A1 | 10/2018 | Hess et al. |
| 2018/0317905 A1 | 11/2018 | Olson et al. |
| 2019/0000455 A1 | 1/2019 | Adams et al. |
| 2019/0046186 A1 | 2/2019 | Dunki-Jacobs et al. |
| 2019/0046189 A1 | 2/2019 | Dunki-Jacobs et al. |
| 2019/0046190 A1 | 2/2019 | Dunki-Jacobs et al. |
| 2019/0046191 A1 | 2/2019 | Dunki-Jacobs et al. |
| 2019/0046192 A1 | 2/2019 | Dunki-Jacobs et al. |
| 2019/0046193 A1 | 2/2019 | Dunki-Jacobs et al. |
| 2019/0105042 A1 | 4/2019 | Huitema et al. |
| 2019/0209173 A1 | 7/2019 | Thompson et al. |
| 2019/0209175 A1 | 7/2019 | Thompson et al. |
| 2019/0224029 A1 | 7/2019 | Thompson et al. |
| 2019/0261985 A1 | 8/2019 | Adams et al. |
| 2019/0261991 A1 | 8/2019 | Beckman et al. |
| 2019/0269408 A1 | 9/2019 | Jankowski |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0307450 A1 | 10/2019 | Thompson et al. |
| 2019/0343519 A1 | 11/2019 | Thompson et al. |
| 2019/0380742 A1 | 12/2019 | Hall et al. |
| 2019/0388092 A1 | 12/2019 | Thompson et al. |
| 2020/0008964 A1 | 1/2020 | Thompson et al. |
| 2020/0015822 A1 | 1/2020 | Marczyk et al. |
| 2020/0100790 A1 | 4/2020 | DiNardo et al. |
| 2020/0214703 A1 | 7/2020 | Thompson et al. |
| 2020/0229818 A1 | 7/2020 | Thompson et al. |
| 2020/0268385 A1 | 8/2020 | Dunki-Jacobs et al. |
| 2020/0297344 A1 | 9/2020 | Dunki-Jacobs et al. |
| 2020/0305873 A1 | 10/2020 | Dunki-Jacobs et al. |
| 2020/0390443 A1 | 12/2020 | Thompson et al. |

FOREIGN PATENT DOCUMENTS

| | | |
|---|---|---|
| EP | 399699 A1 | 11/1990 |
| EP | 503662 A1 | 9/1992 |
| EP | 0666057 A2 | 8/1995 |
| EP | 669104 A1 | 8/1995 |
| EP | 0399699 B1 | 11/1995 |
| EP | 0503662 B1 | 6/1997 |
| EP | 1090592 A1 | 4/2001 |
| EP | 1616526 A1 | 1/2006 |
| EP | 1769766 A1 | 4/2007 |
| EP | 1774916 A1 | 4/2007 |
| EP | 1806101 A1 | 7/2007 |
| EP | 1875868 A1 | 1/2008 |
| EP | 1875870 A1 | 1/2008 |
| EP | 1938759 A2 | 7/2008 |
| EP | 2005896 A2 | 12/2008 |
| EP | 2005897 A2 | 12/2008 |
| EP | 2005898 A2 | 12/2008 |
| EP | 2005899 A2 | 12/2008 |
| EP | 2005900 A2 | 12/2008 |
| EP | 2005901 A1 | 12/2008 |
| EP | 1774916 B1 | 2/2009 |
| EP | 2019633 A1 | 2/2009 |
| EP | 2090247 A1 | 8/2009 |
| EP | 2111803 A2 | 10/2009 |
| EP | 2245993 A2 | 11/2010 |
| EP | 2319424 A1 | 5/2011 |
| EP | 2382928 A1 | 11/2011 |
| EP | 2019633 B1 | 8/2012 |
| FR | 2731895 A1 | 9/1996 |
| GB | 2298905 A | 9/1996 |
| WO | 01/54594 A1 | 8/2001 |
| WO | 03/094747 A1 | 11/2003 |
| WO | 2007/009099 A2 | 1/2007 |
| WO | 2007019268 A2 | 2/2007 |
| WO | 2007102152 A2 | 9/2007 |
| WO | 2008/042022 A1 | 4/2008 |
| WO | 2008039238 A1 | 4/2008 |
| WO | 2008039249 A1 | 4/2008 |
| WO | 2008039250 A1 | 4/2008 |
| WO | 2008039270 A1 | 4/2008 |
| WO | 2008042021 A1 | 4/2008 |
| WO | 2008042043 A1 | 4/2008 |
| WO | 2008042044 A2 | 4/2008 |
| WO | 2008042045 A2 | 4/2008 |
| WO | 2008094210 A1 | 8/2008 |
| WO | 2008141288 A1 | 11/2008 |
| WO | 2009038550 A1 | 3/2009 |
| WO | 2010/011661 A1 | 1/2010 |
| WO | 2011/044032 A3 | 4/2011 |
| WO | 2011044032 A2 | 4/2011 |
| WO | 2011094700 A1 | 8/2011 |
| WO | 2012/141679 A1 | 10/2012 |
| WO | 2013/151888 A1 | 10/2013 |
| WO | 2014026170 A2 | 2/2014 |
| WO | 2014/085099 A1 | 6/2014 |
| WO | 2015063609 A2 | 5/2015 |
| WO | 2015153324 A1 | 10/2015 |
| WO | 2015153340 A2 | 10/2015 |
| WO | 2016033221 A1 | 3/2016 |

OTHER PUBLICATIONS

Felicien M. Steichen and Mark M. Ravitch, Stapling in Surgery, Figure 1-11C, Year Book Medical Publishers, Inc. 1984; 3 pages.
Geoffrey Parker, A New Stomach Clamp, 26 Postgrad Med. J. 550; 1 page.
Parikh, M.D. et al., Surgical Strategies That May Decrease Leak After Laparoscopic Sleeve Gastrectomy, 257 Annals of Surgery 231, Feb. 2013; 7 pages.
Aladar de Petz, M.D., Aseptic Technic of Stomach Resections, 86 Annals of Surgery 388, Sep. 1927; 5 pages.
John D. Harrah, M.D., A Lung Clamp for Use with Mechanical Staplers, 28 The Annals of Thoracic Surgery 489, Nov. 1979; 2 pages.
Bram D. Zuckerman, M.D., Food and Drug Administration, Letter to AtriCure, Inc. Addressing Indication For Use of AtriClip LAA Exclusion System w/Pre-loaded Gillnov-Cosgrove Clip, Jun. 10, 2010; 3 pages.
510(k) Summary for AtriClip LAA Exclusion System with preloaded Gillinov-Cosgrove Clip, published Jun. 10, 2010; 6 pages.
CMS Description of Open Left Atrial Appendage Occlusion with "U" Fastener Implant, 1 page.
510(k) Summary for TigerPaw(R) System, published Oct. 29, 2010; 6 pages.
Pfiedler Enterprises, Science of Stapling: Urban Legend and Fact, Published Jun. 4, 2012; 38 pages.
Written Opinion of the Int'l Searching Authority and International Search Report for PCT/US2015/048740 dated Feb. 17, 2016; 12 pages.
Written Opinion of the Int'l Searching Authority and International Search Report for PCT/US2015/022990 dated Sep. 30, 2015; 10 pages.
Written Opinion of the Int'l Searching Authority and International Search Report for PCT/US2015/022904 dated Jun. 25, 2015; 6 pages.
Search Report and Written Opinion of the International Searching Authority for International Patent App. No. PCT/US2014/070869 dated Apr. 21, 2015; 17 pages.
Supplementary Partial European Search Report of the European Patent Office, Issued in European Application No. 14872137; dated Dec. 12, 2016; 5 pages.
Supplementary European Search Report of the European Patent Office, Issued in European Application No. 15772561.5-1664; dated Mar. 15, 2017; 8 pages.

(56) References Cited

OTHER PUBLICATIONS

International Preliminary Report on Patentability and Written Opinion of the International Searching Authority in Application No. PCT/US2015/048740 dated Mar. 7, 2017; 8 pages.
Supplementary European Search Report of the European Patent Office, Issued in European Application No. 14872137.6-1664/3082620; dated Mar. 28, 2017; 15 pages.
European Search Report of the European Patent Office, Issued in European Application No. 15774247.9-1654; dated Dec. 23, 2016; 11 pages.
Australian Examination Report in Application No. 2016208416; dated May 18, 2017; 4 pages.
M Jacobs et al., Laparoscopic sleeve gastrectomy: a retrospective review of 1- and 2-year results, Surg Endosc. Apr. 2010;24(4):781-5. doi: 10.1007/S00464-009-0619-8. Epub Aug. 1, 20099; abstract only; 2 pages.
JP Regan et al., Early experience with two-stage laparoscopic Roux-en-Y gastric bypass as an alternative in the super-super obese patient, Obes Surg. Dec. 2003;13(6):861-4; abstract only; 2 pages.
Australian Examination Report in Application No. 2018203527; dated Oct. 22, 2018; 5 pages.
International Search Report and Written Opinion of the International Searching Authority for International Patent App. No. PCT/US2018/046743 dated Dec. 4, 2018; 20 pages.
Australian Examination Report in Application No. 2015241193; dated Dec. 11, 2018; 5 pages.
Examination Report of the European Patent Office, Issued in European Application No. 15772561.5-1122; dated Oct. 29, 2018; 7 pages.
Search Report of the State Intellectual Property Office of the People's Republic of China, Issued in Chinese Application No. 201480075706.2; dated Nov. 28, 2018; 3 pages.
International Preliminary Report on Patentability and Written Opinion of the International Searching Authority received in Application No. PCT/US2018/046743; dated Feb. 18, 2020; 17 pages.

* cited by examiner

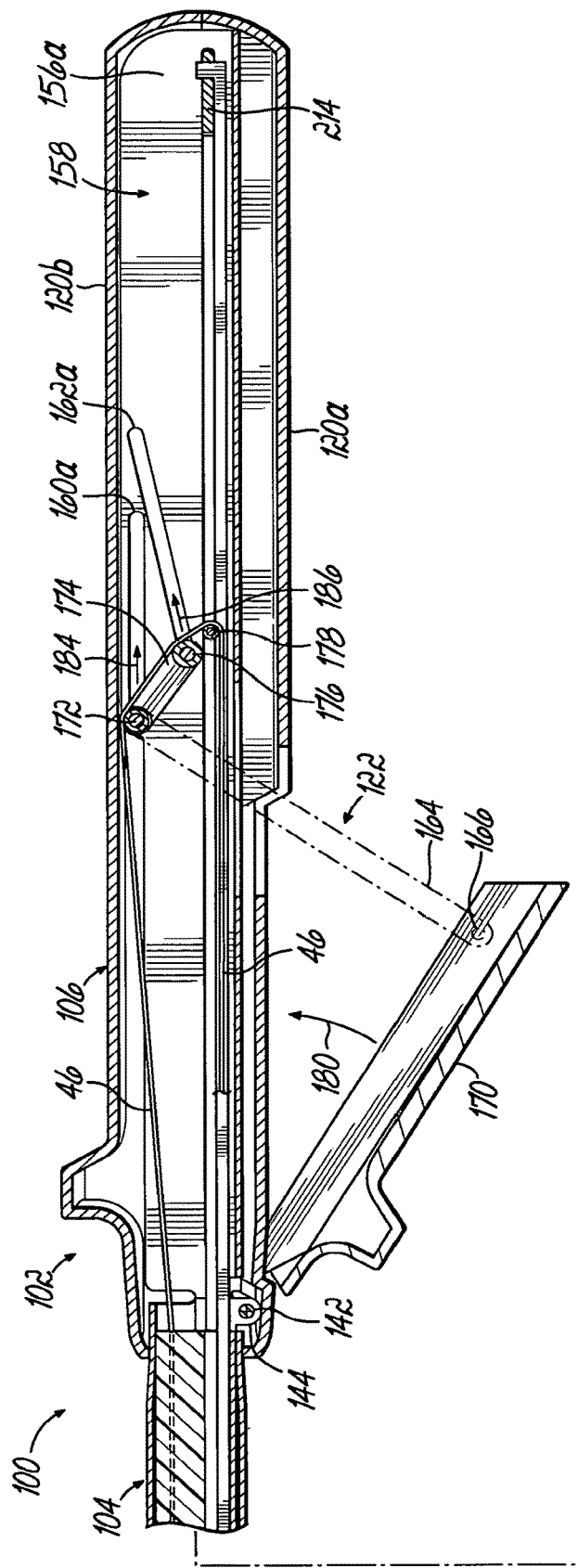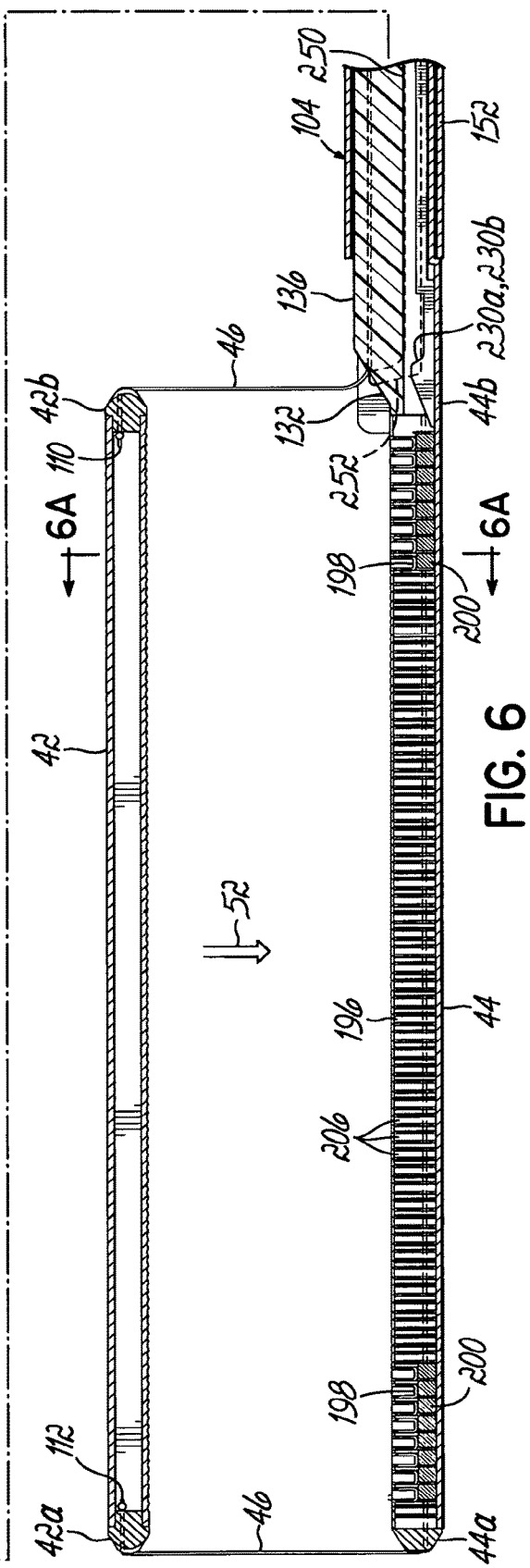
FIG. 6

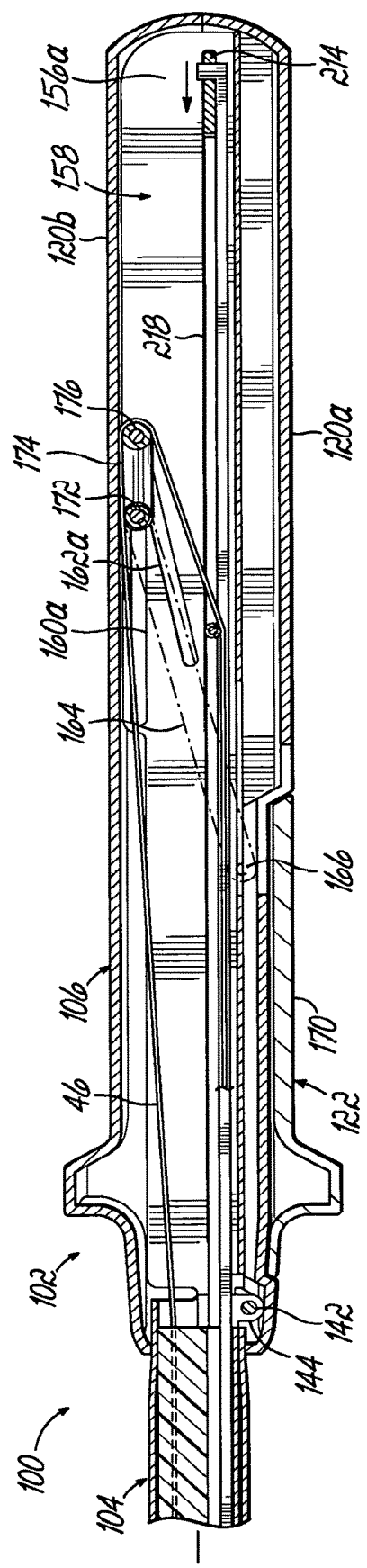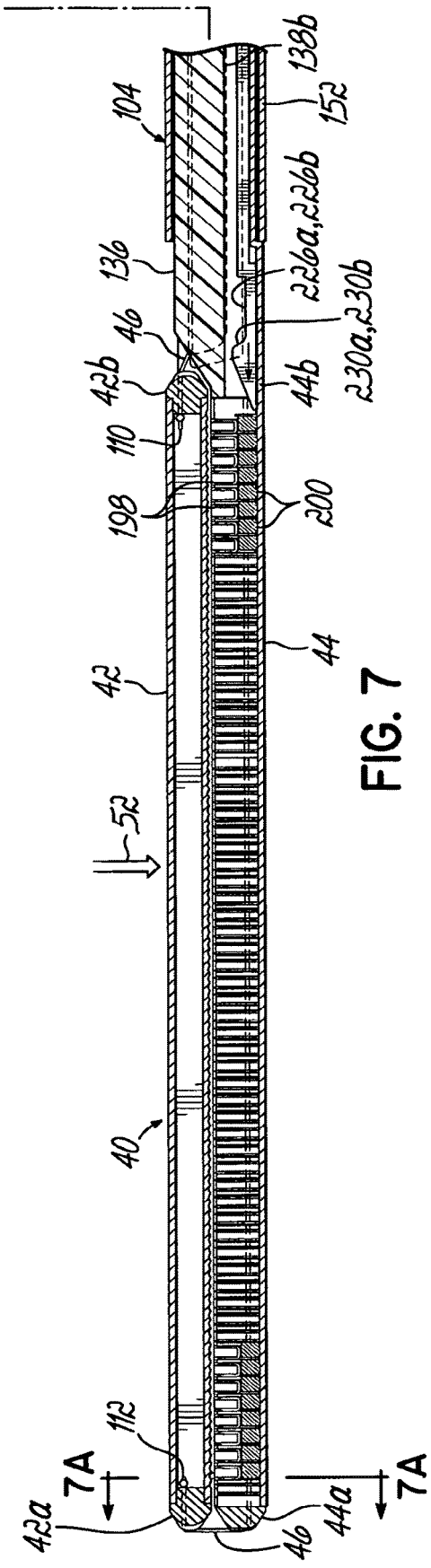
FIG. 7

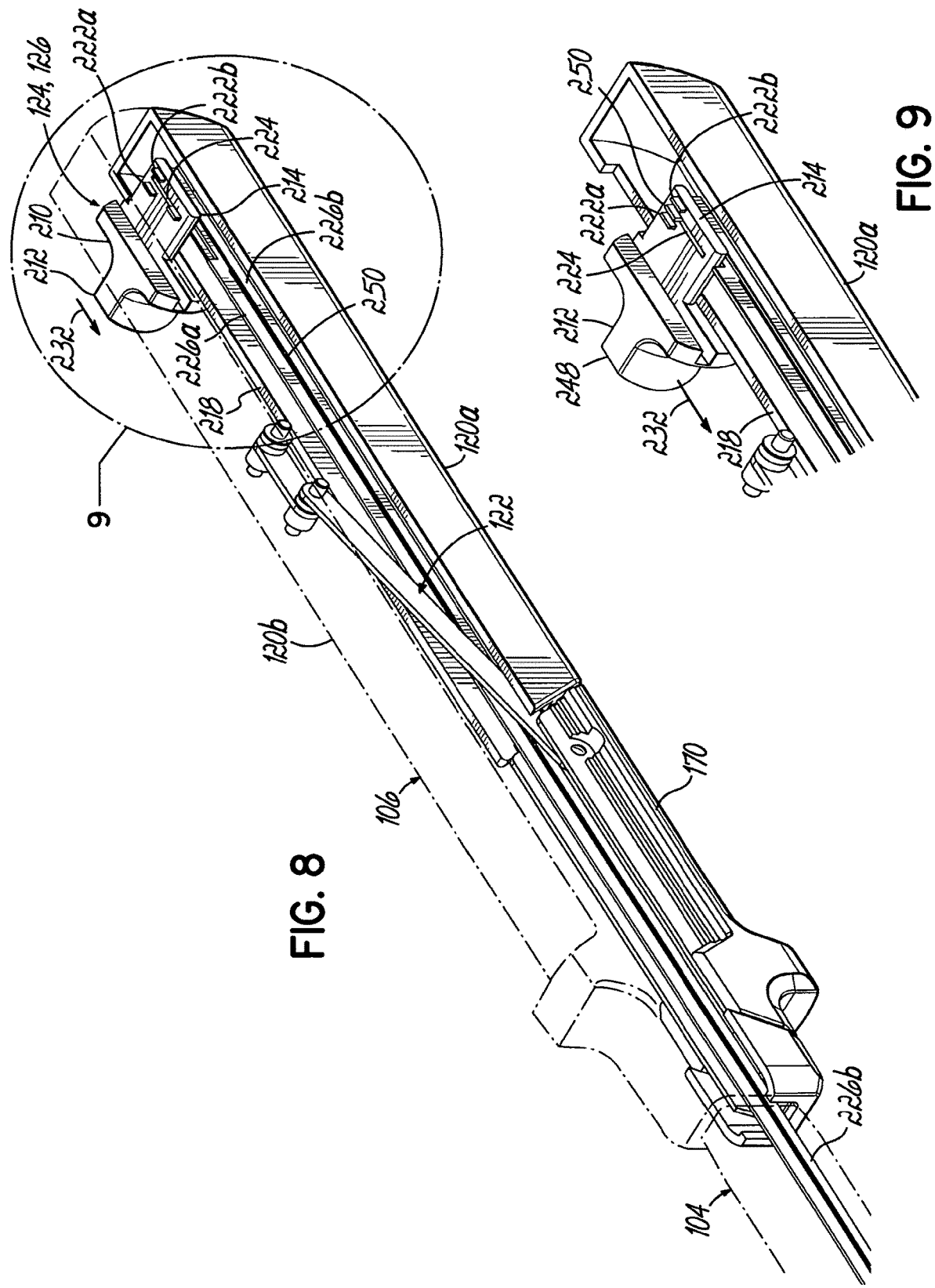

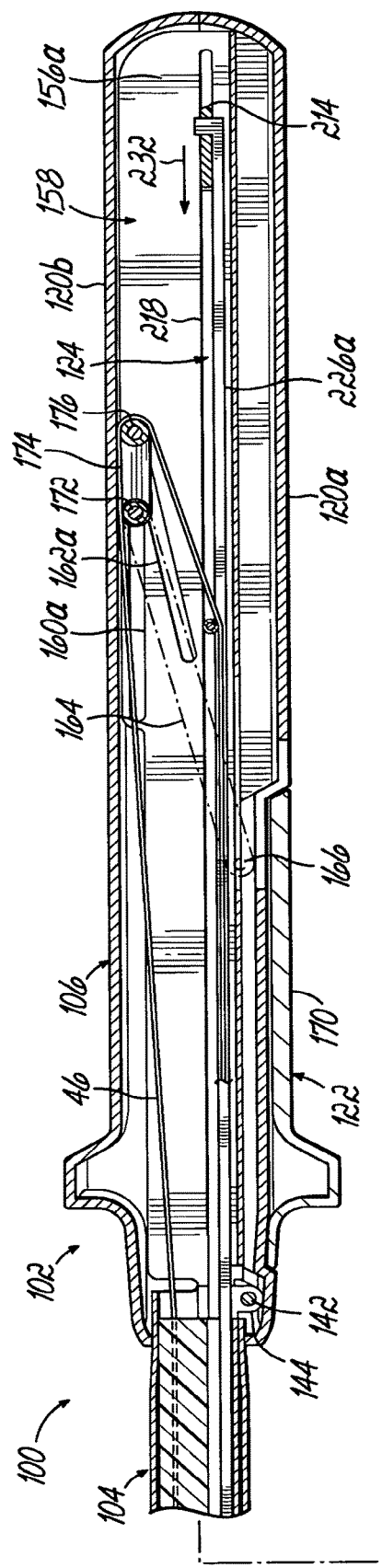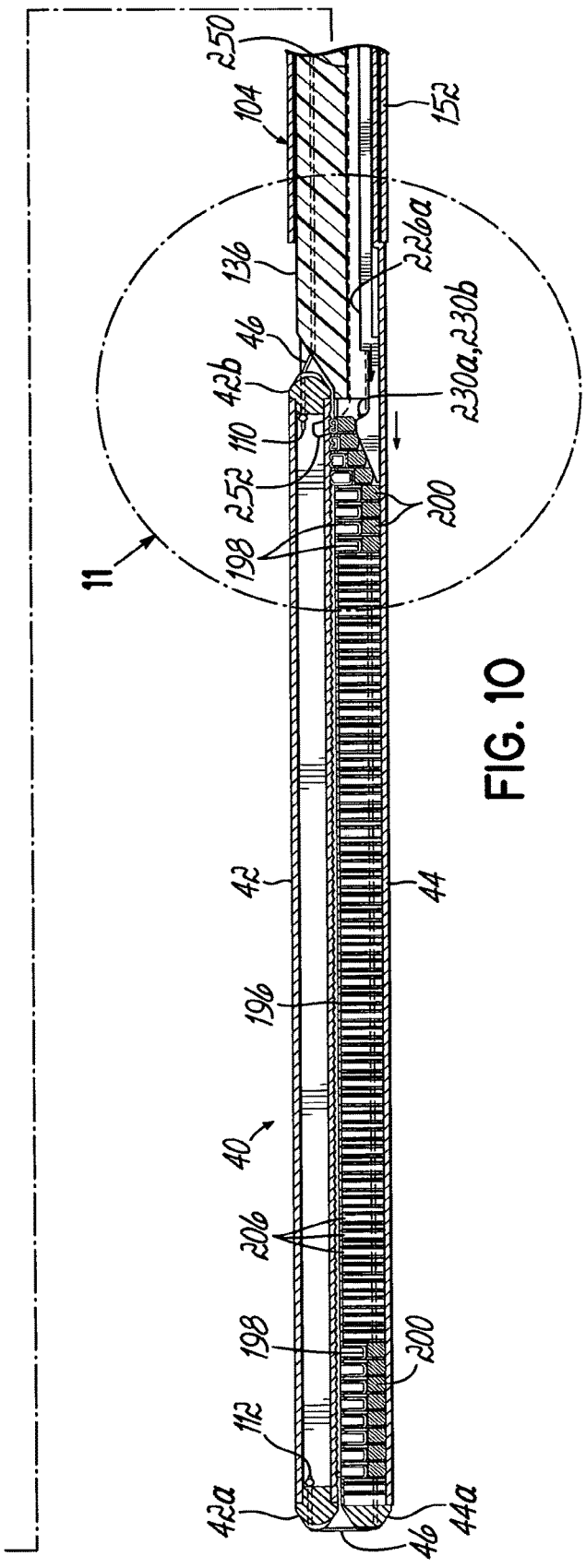
FIG. 10

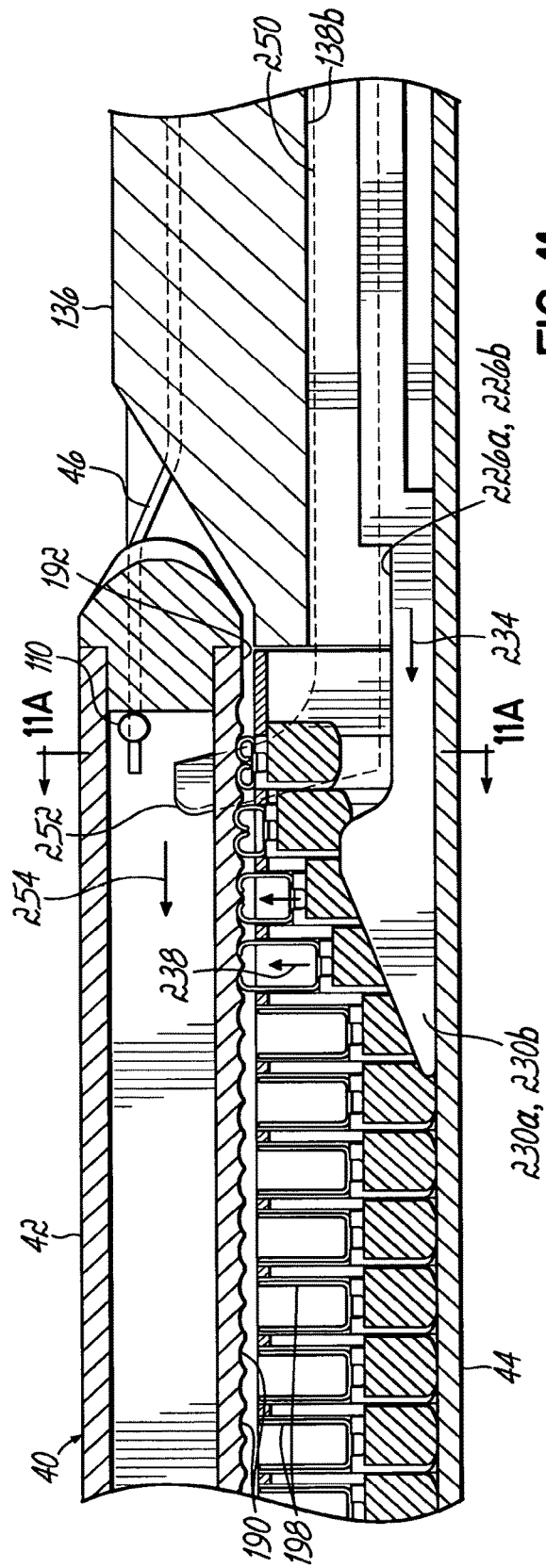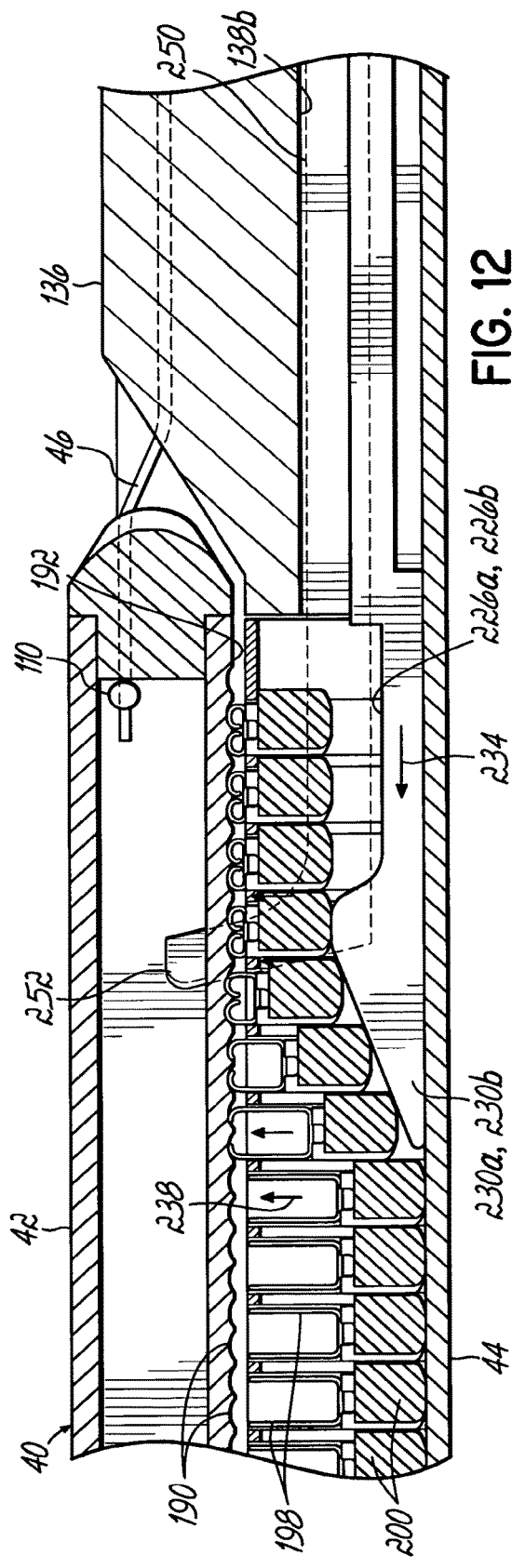

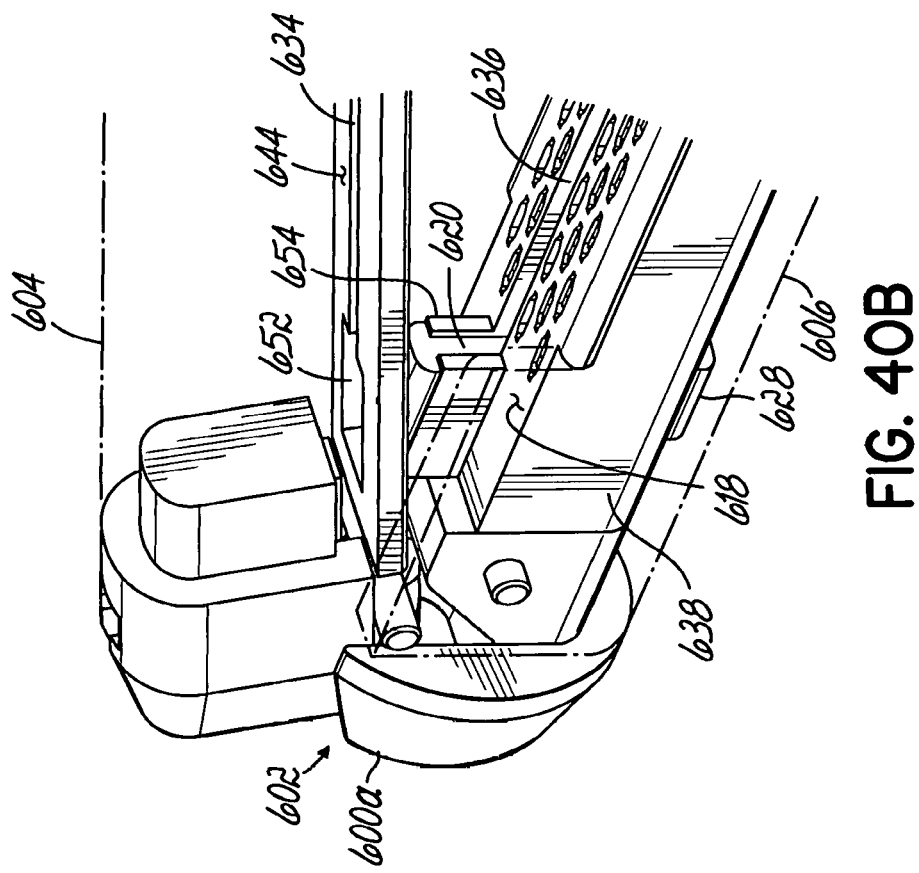
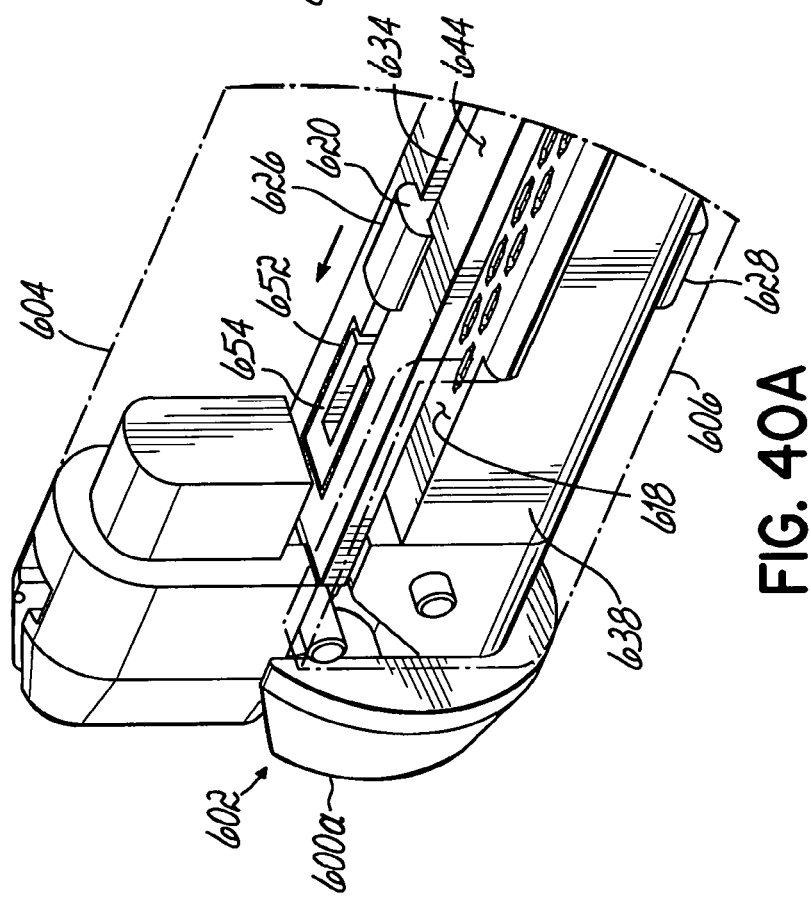

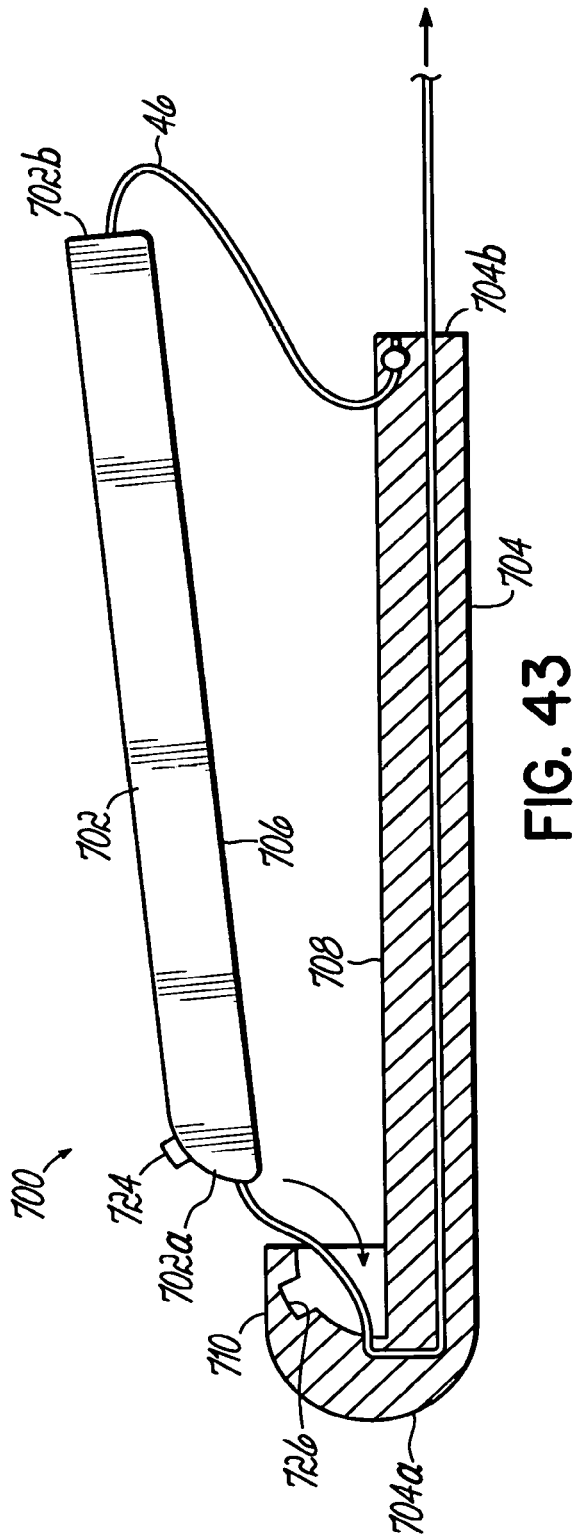
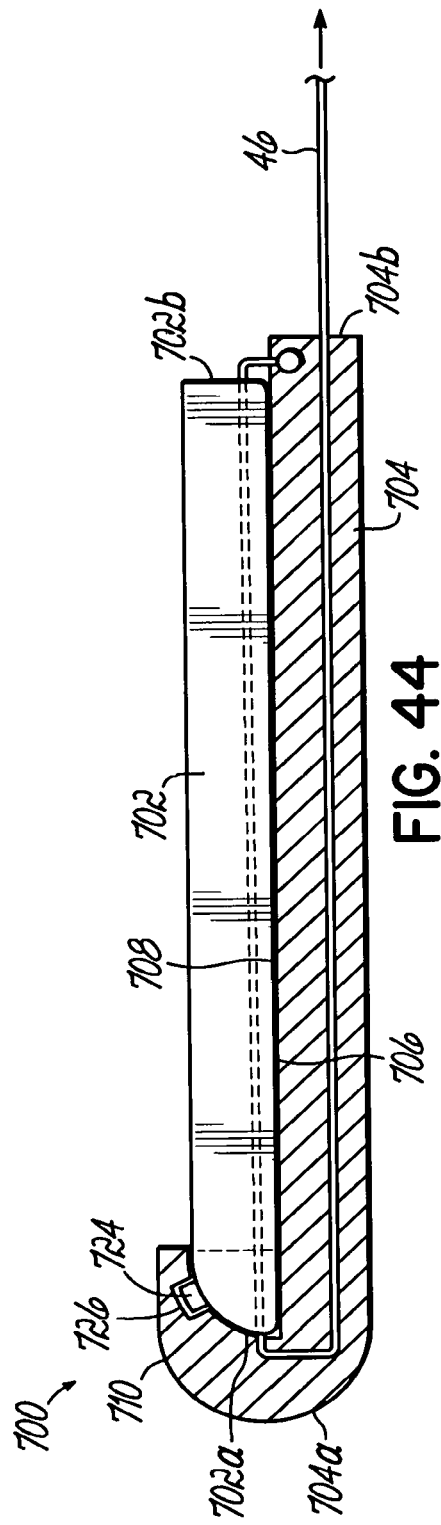
FIG. 43
FIG. 44

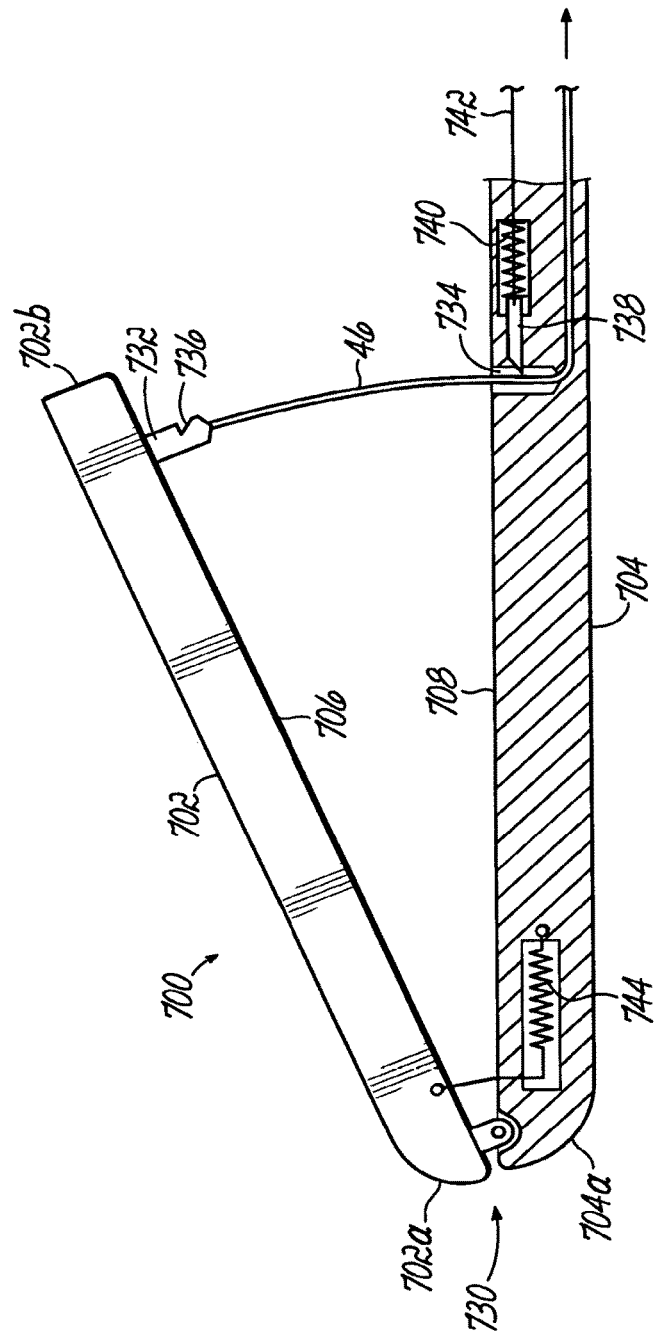
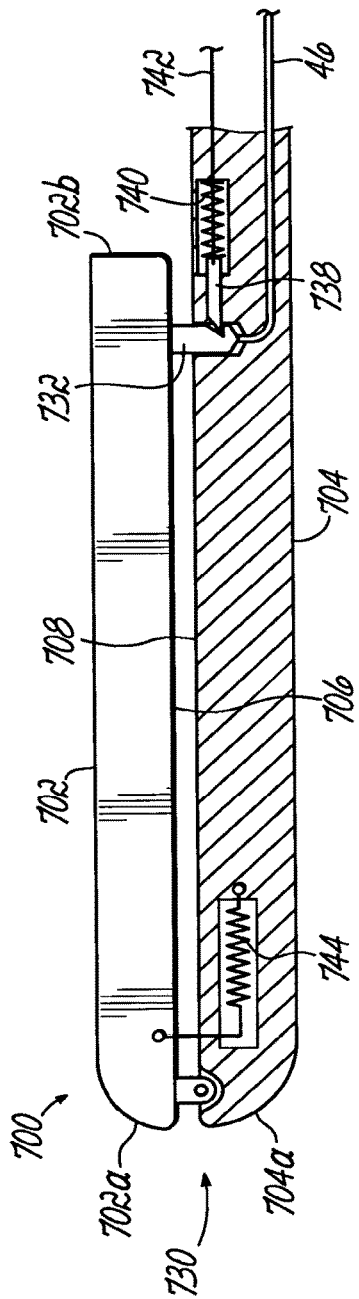
FIG. 45A
FIG. 45B

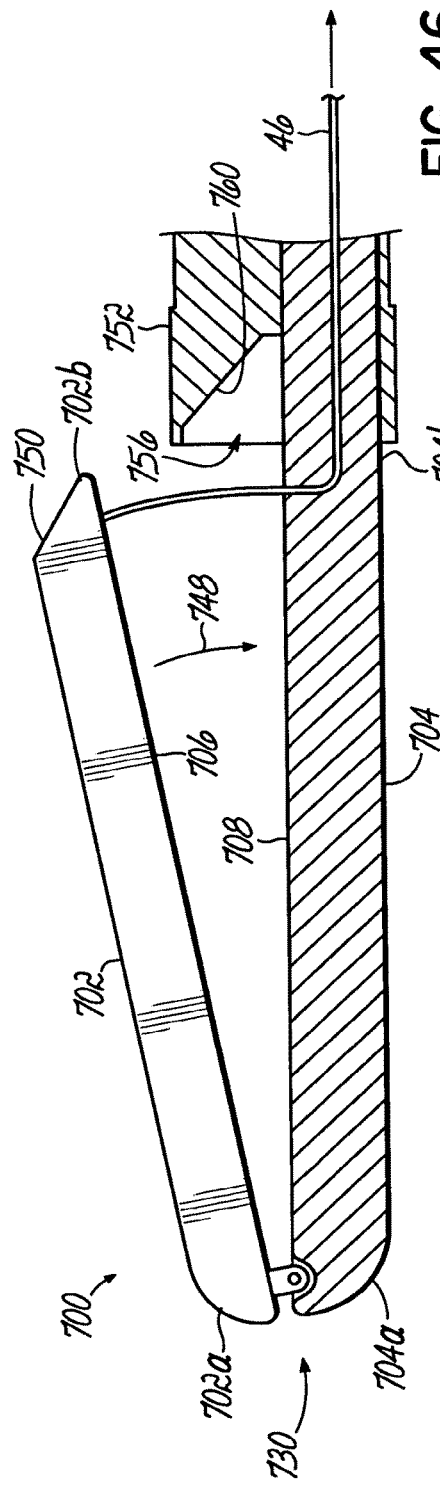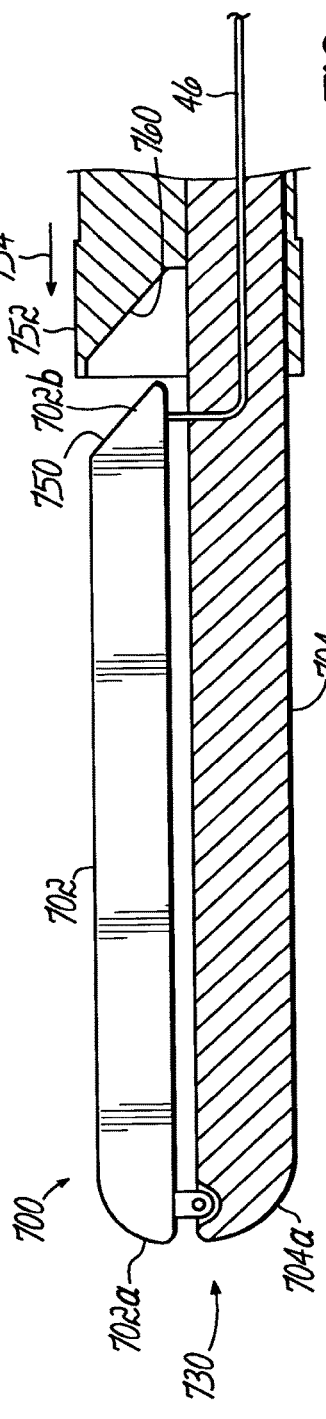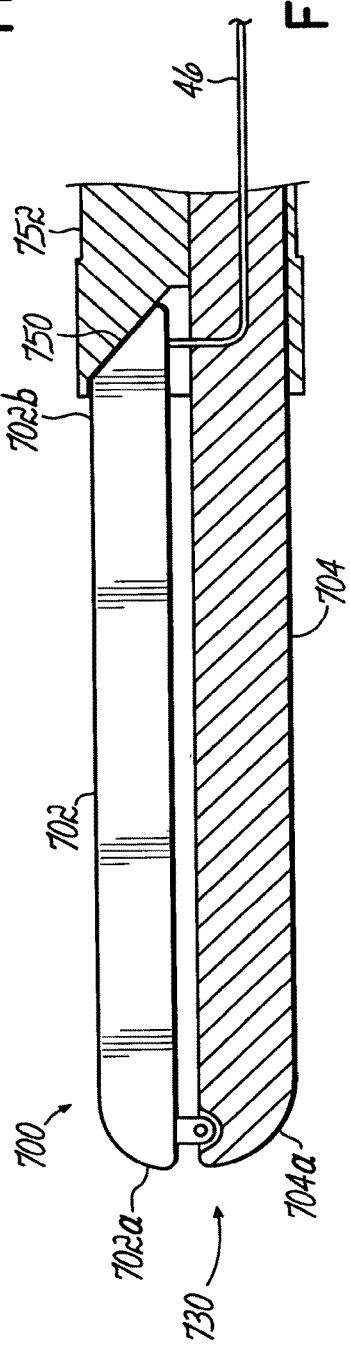

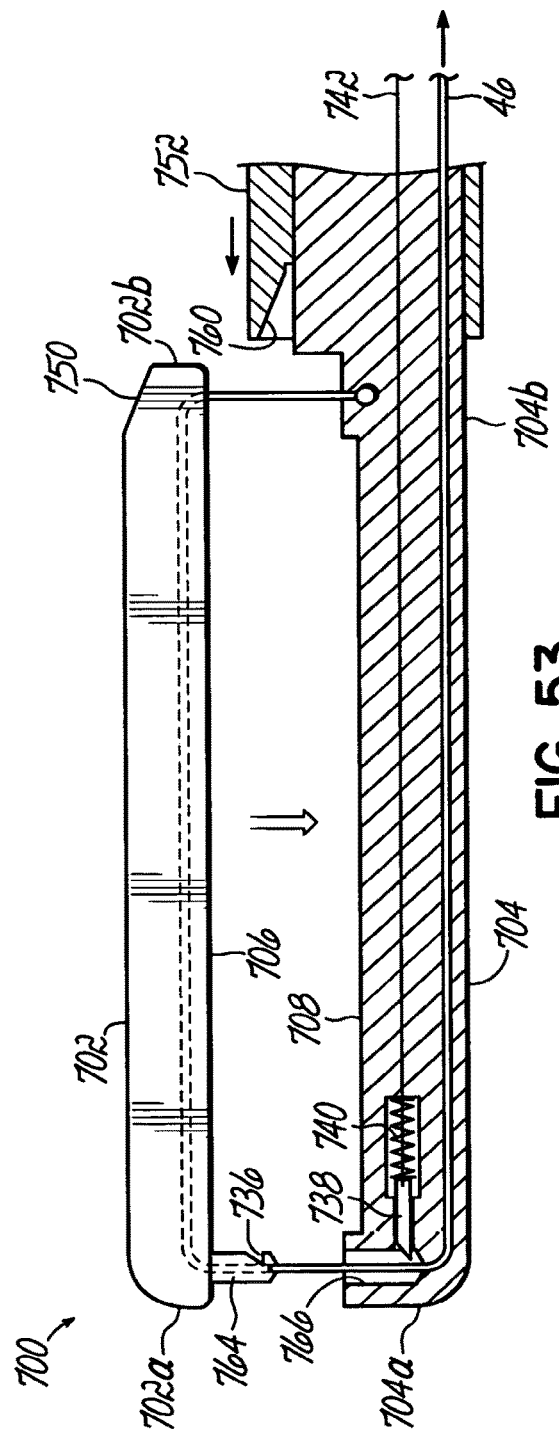
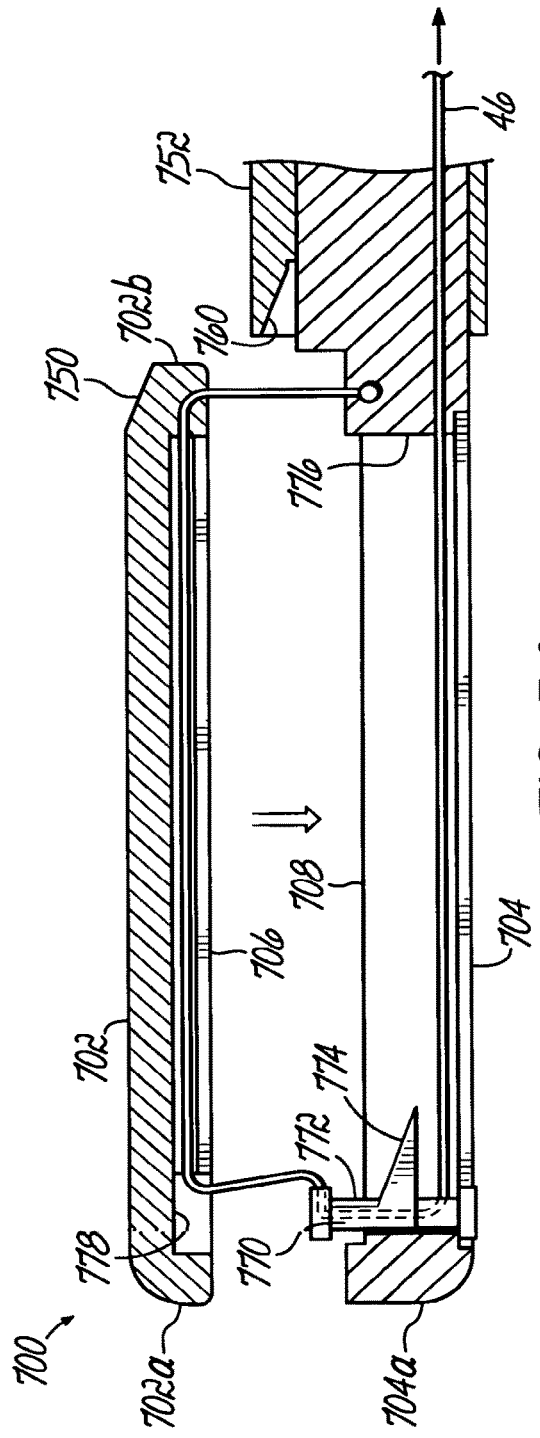

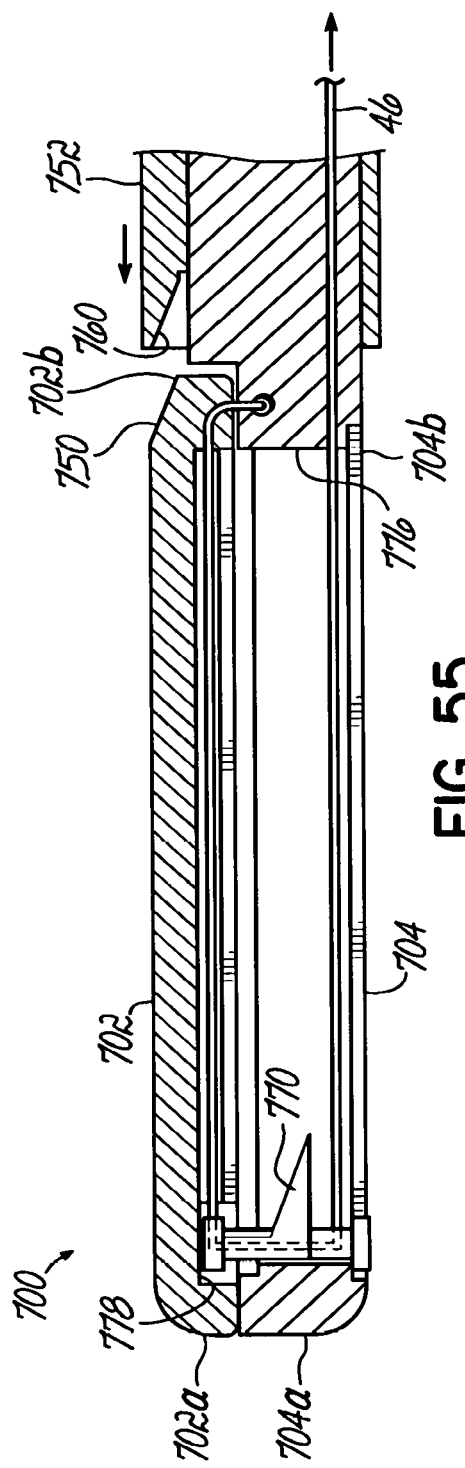
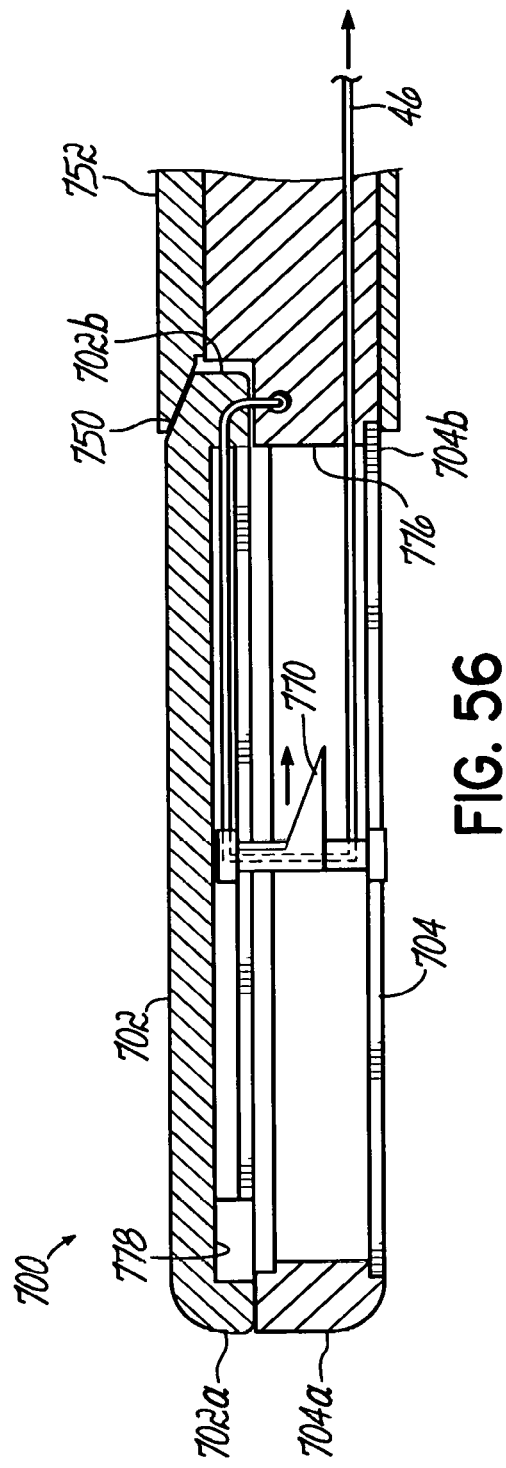
FIG. 55
FIG. 56

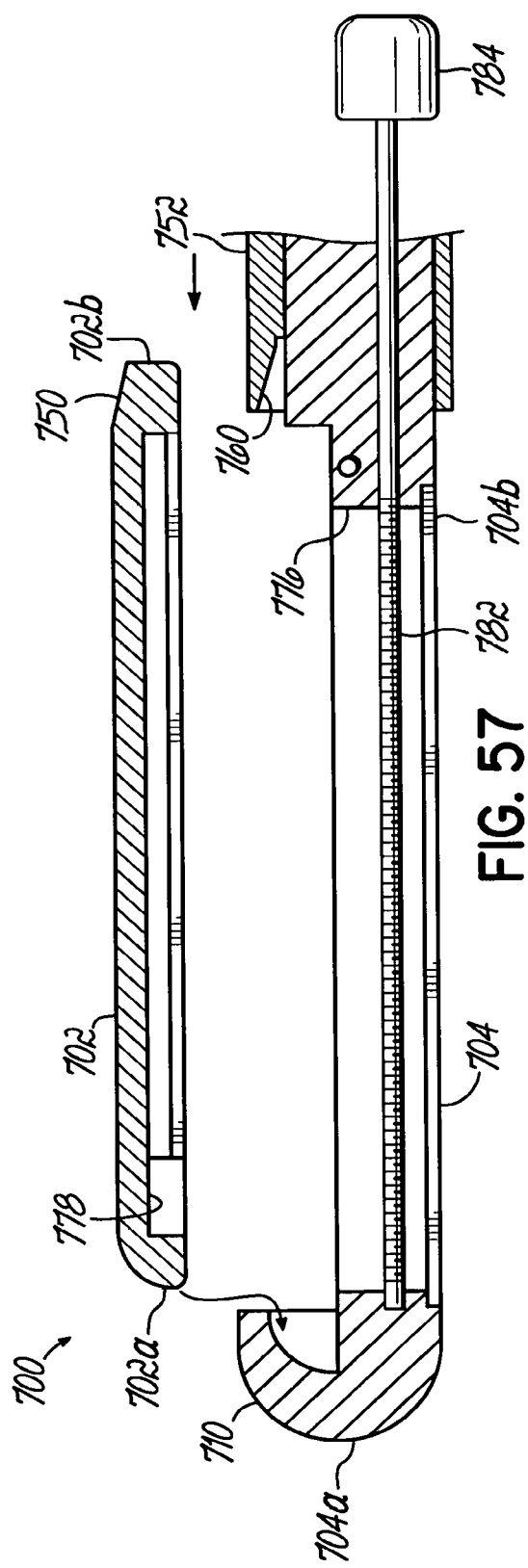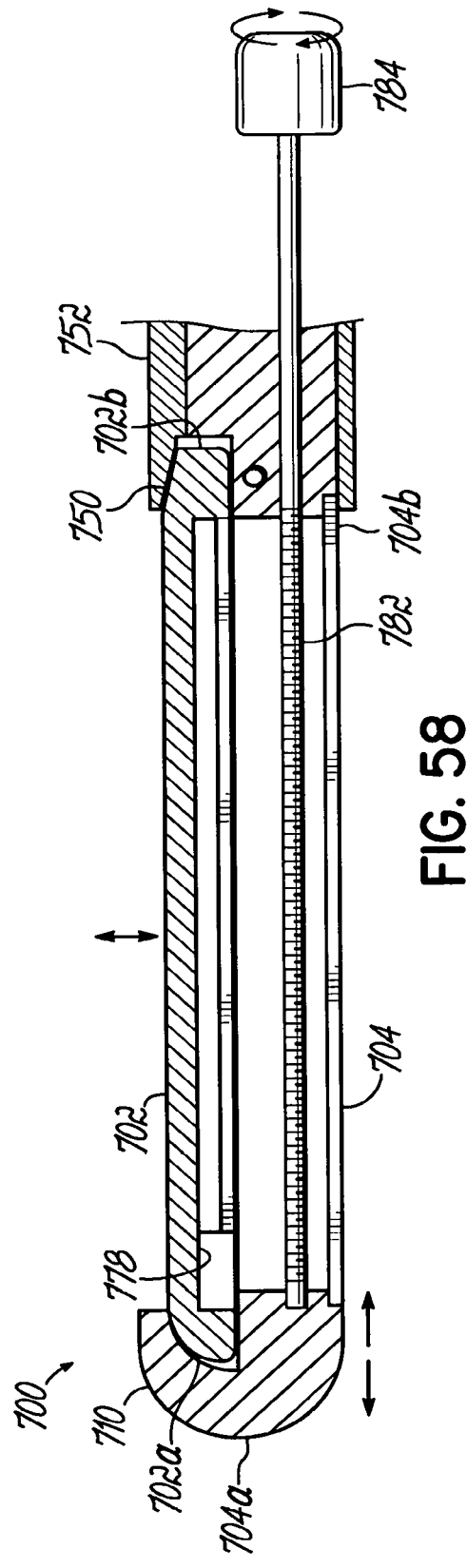

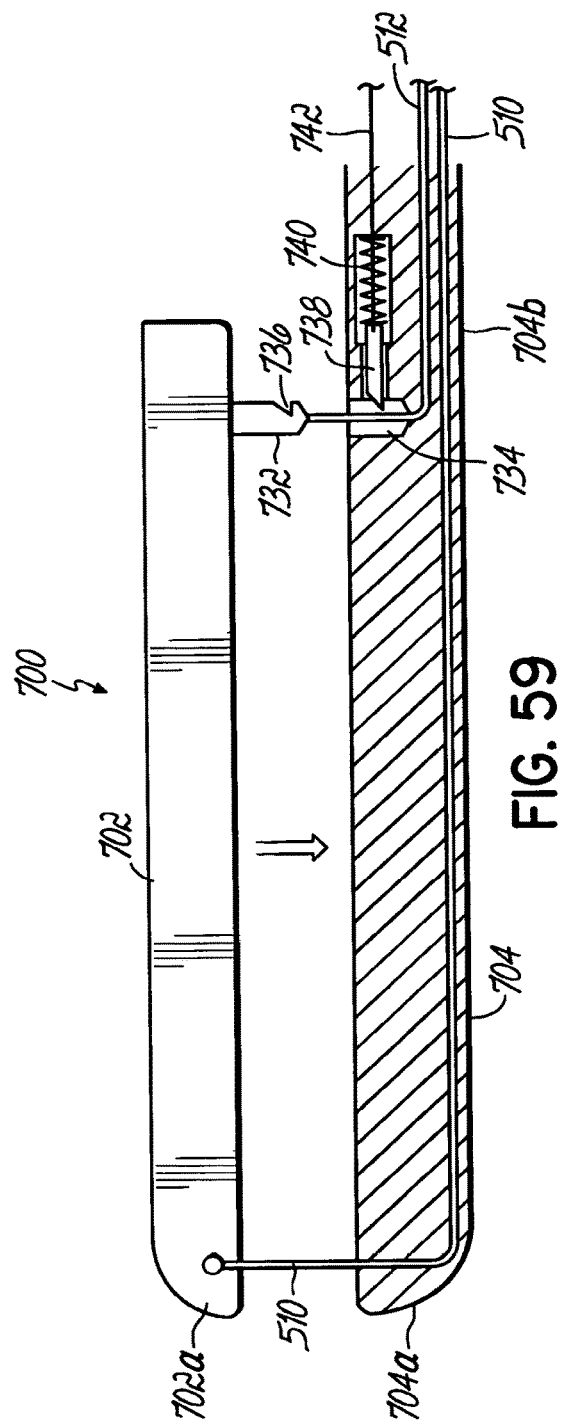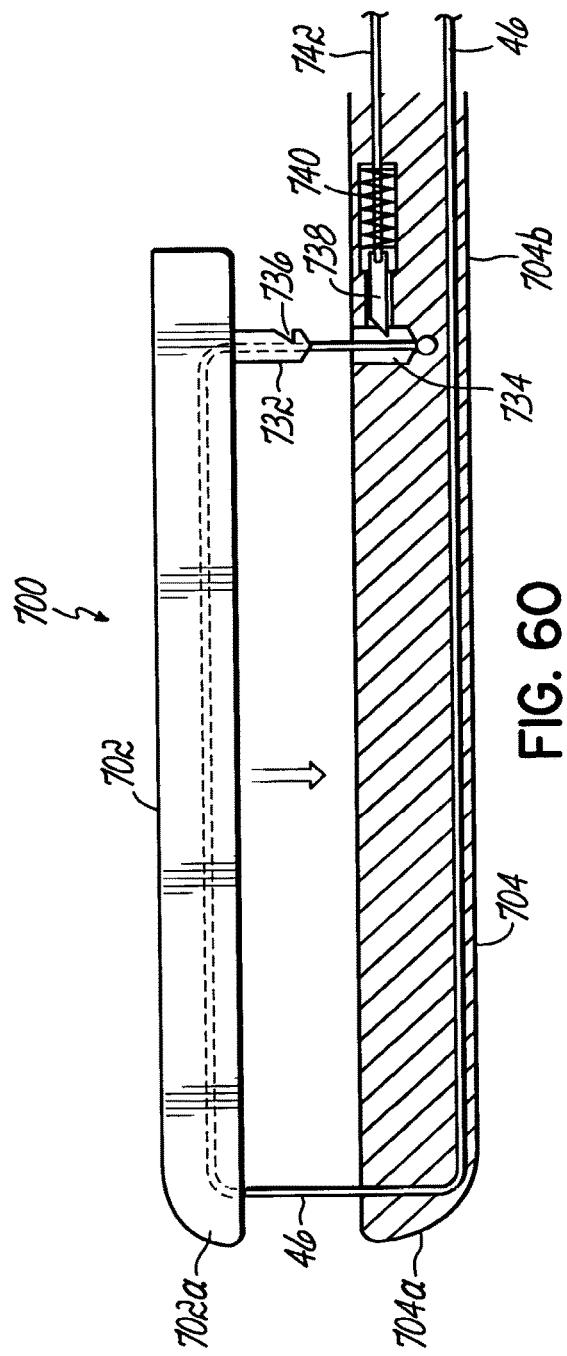

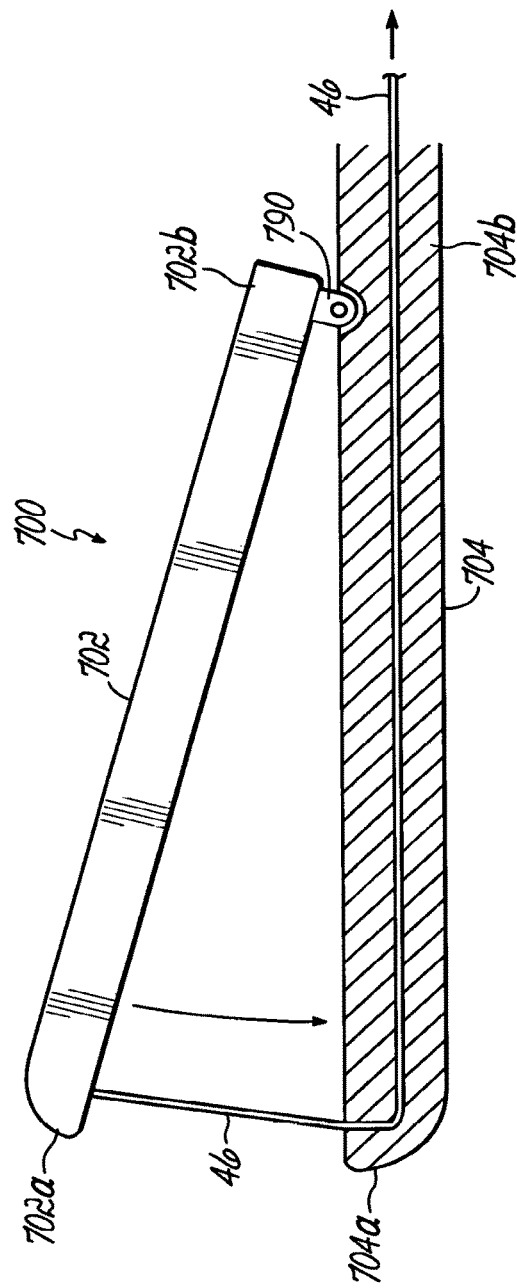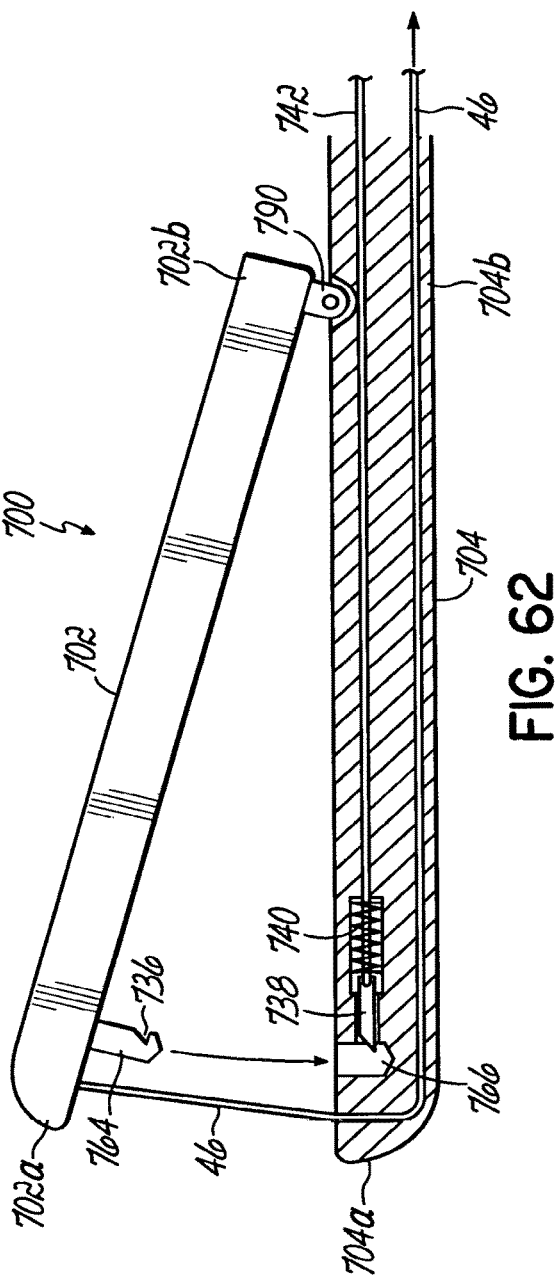

END EFFECTORS, SURGICAL STAPLING DEVICES, AND METHODS OF USING SAME

CROSS REFERENCE TO RELATED APPLICATIONS

This application is a continuation application of U.S. Non-Provisional patent application Ser. No. 15/920,196, filed Mar. 3, 2018, which claims priority to U.S. Non-Provisional application Ser. No. 15/129,385 filed Sep. 26, 2016, now U.S. Pat. No. 9,936,953, which claims priority to U.S. Provisional Patent Application Ser. No. 61/972,274 filed Mar. 29, 2014 and U.S. Provisional Patent Application Ser. No. 62/046,726 filed Sep. 5, 2014, the disclosures of which are incorporated by reference herein in their entireties.

TECHNICAL FIELD

The invention relates to surgical staplers, and more particularly to end effectors and stapling devices and methods of using those devices in medical procedures.

BACKGROUND

Surgeons have implemented surgical staplers for many years. In general, there are three main types of linear surgical staplers—open linear staplers, open gastrointestinal anastomosis (i.e., a linear cutter), and endocutters. Staplers are often used in surgical procedures involving the lung, liver, and stomach and are typically used in resection of an organ.

Surgical staplers have some common components. These include a handle, an actuator, and an end effector including a clamping mechanism. The clamping mechanism often has a cartridge and an anvil. For these staplers, the surgeon clamps two members (i.e., the anvil and the cartridge) on the organ and compresses the organ between them. Once compressed, the surgeon uses the stapler to drive or fire staples through the organ. With proper compression and alignment of the clamping mechanism, a B-shaped staple is formed. Some surgical procedures may require multiple staple firings. Each firing often requires the surgeon to reload the stapler with more staples. For example, some staple lines may require 5 to 8 reloads depending on the length and/or the staple capacity of the stapler.

The integrity of a staple line depends on the proper formation of B-shaped staples. This in turn depends on the stapler's capability of compressing tissue while, at the same time, withstanding the forces associated with proper B-shaped staple formation. A B-shaped staple is the standard of care for gastrointestinal, vascular, pulmonary, and hepatic applications of surgical tissue fastening devices. Alignment in each of the X, Y, and Z axes of the clamping mechanism with itself (e.g., alignment of the anvil with the cartridge) on each side of the organ is necessary for proper formation of B-shaped staples.

Alignment difficulties are intensified by the trend toward minimally invasive surgical procedures in which the organ is remotely accessed through small incisions. A trocar or other cannula is inserted into each incision and becomes the access point into the body cavity for surgical devices, including staplers.

Typically, the surgeon inserts at least the end effector of the stapler through the trocar to perform the surgical procedure. By way of example, minimally invasive surgical procedures include a laparoscopic vertical sleeve gastrectomy. Due to this restricted special environment, minimally invasive surgical stapling devices must be relatively small compared to open linear surgical staplers. Minimally invasive devices are generally long (e.g., 35 cm to 45 cm) and thin (e.g., 5 mm to 15 mm diameter) devices. This long and thin configuration is necessary to fit through the trocar into the body cavity. The limited size presents a mechanical issue as B-shaped staple formation typically requires a pressure of about 100 psi. Under these pressures, small, less rigid, staplers deform and so prevent proper B-shaped staple formation.

Along the same lines, current devices used in minimally invasive surgical procedures have a fixed hinge at a proximal end. The hinge allows the anvil and cartridge to separate into a V-shaped configuration. Once separated, the surgeon may place the V around the organ and then collapse the V onto the organ. As the length of the anvil and cartridge increase, typically to provide a single, longer staple line across the organ, alignment between the anvil and the cartridge becomes more difficult, and the end effector is more difficult to manipulate through the trocar. Poor alignment is problematic, because with a hinge design, the anvil and/or cartridge at the most distant ends are more likely to be displaced from an ideal alignment due to deflection associated with the forces necessary to compress the tissue. Because of this deflection, the length of current V-shaped staplers for minimally invasive procedures is limited. As a result of this limitation, the anvil and the cartridge are limited in length. Limitations on length are problematic because this may require multiple staple reloads. Each reload may require the surgeon to withdraw the stapler from the trocar and then reinsert and reposition the stapler on the organ. Ultimately, these devices require more surgical time and are more likely to fail to provide consistent B-shaped staples when activated.

One solution to deflection is to provide two points of connection between the anvil and the cartridge instead of a single, hinged connection. That is, the anvil and the cartridge are coupled together at each end. However, this connection has been limited to open surgical procedures in which the surgeon has direct access to each end of the stapler and in which relatively large staplers may be utilized. In open surgery, the surgeon can directly manipulate one or both of the connections by hand. Furthermore, two-pointed connections require that the anvil and the cartridge extend beyond the full dimension of the organ. This requires a large device that, while possibly appropriate for open surgery, is not usable in minimally invasive procedures.

While current staplers are adequate, new devices and methods are needed to address the shortcomings of existing staplers and methods in minimally invasive surgical procedures. More particularly, new minimally invasive staplers and methods are needed that offer improved maneuverability and more uniform pressure application on the tissue, while providing consistent and quality resection lines created during medical procedures, such as during a vertical sleeve gastrectomy.

SUMMARY

An end effector for use by a surgeon to staple an anatomical structure of a patient during a minimally invasive procedure addresses these and other shortcomings and, in one embodiment, includes an anvil that includes a first end, a second end, and a face that is positionable on a first side of the anatomical structure. The end effector further includes a cartridge that is configured to house a plurality of staples. The cartridge has a first end, a second end, and a face that is positionable on a second side of the anatomical structure. A flexible member movably couples the first end of the cartridge to the first end of the anvil, and the second end of the cartridge is movably coupled to the second end of the anvil. Each of the anvil and the cartridge is insertable through a trocar into the patient. The end effector is remotely operable from outside the patient with at least a portion of one of the anvil and the cartridge being movable toward the other to clamp the end effector to the anatomical structure.

In one embodiment, the flexible member movably couples the second end of the anvil to the second end of the cartridge.

In one embodiment, at least one of the anvil and the cartridge slidably receives the flexible member when the end effector is clamped onto the anatomical structure.

In one embodiment, the anvil and the cartridge slidably receive the flexible member.

In one embodiment, the flexible member is anchored to the anvil.

In one embodiment, the flexible member is anchored to the cartridge.

In one embodiment, the end effector includes a tensioning device operable by the surgeon for selectively tensioning the flexible member to provide at least a portion of the clamping force on the anatomical structure. In one embodiment, the tensioning device includes a spring operably coupled to the flexible member.

In one embodiment, the first end or the second end of the cartridge includes a cam tube.

In one embodiment, the flexible member passes into the cam tube such that tensioning the flexible member pulls the anvil into the cam tube.

In one embodiment, the cam tube includes a first arcuate surface and the anvil includes a second arcuate surface that is configured to cooperate with the first arcuate surface.

In one embodiment, the anvil includes at least one pin and the cam tube includes at least one channel to receive the at least one pin to facilitate alignment between the anvil and the cartridge when the anvil enters the cam tube.

In one embodiment, the anvil includes a lever and the cam tube includes a slot to receive the lever to facilitate alignment between the anvil and the cartridge when the anvil enters the cam tube.

In one embodiment, the cam tube is slidable along an axis that is generally parallel to the longitudinal axis of the cartridge.

In one embodiment, the cam tube includes a wedge-shaped surface and the anvil includes a tapered surface on one end thereof that engages the wedge-shaped surface when the anvil enters the cam tube.

In one embodiment, the end effector further includes a screw and the cam tube is operably coupled to the screw. Rotating the screw moves the cam tube along a longitudinal axis of the cartridge.

In one embodiment, when the cam tube moves along a longitudinal axis of the cartridge, a gap between the anvil and the cartridge changes.

In one embodiment, the flexible member extends in a non-linear path from proximate the first end to proximate the second end of one of the anvil and the cartridge.

In one embodiment, the end effector further includes a strut mechanism that slidably cooperates with the flexible member and that includes a strut member that is coupled to one of the anvil and the cartridge between the first end and the second end thereof and is pivotal with respect thereto between a disengaged position in which the strut member is substantially parallel with the anvil and the cartridge and an engaged position in which the strut member extends transversely to the anvil and the cartridge.

In one embodiment, the manipulator includes an adjustment mechanism configured to adjust a gap between the anvil and the cartridge. In one embodiment, the adjustment mechanism includes a knob and a spring in line with at least one end of the flexible member.

In one embodiment, one of the anvil and the cartridge includes at least one alignment pin extending outwardly from the face thereof and the other of the anvil and the cartridge includes a mating recess configured to receive the alignment pin as the anvil and cartridge are moved toward one another.

In one embodiment, the flexible member extends through the mating recess and is coupled to the alignment pin such that retraction of each flexible member moves the alignment pin into the recess.

In one embodiment, the end effector further includes a compression mechanism that operably couples the anvil to the cartridge, that is separate from the flexible member, and that is configured to apply compressive force to the anatomical structure.

In one embodiment, the compression mechanism includes a hook member that extends from the anvil, a pin that is engagable with the hook member, and a compression slide that carries the pin and is selectively slidable relative to the cartridge. The compression mechanism is engagable when the hook member is positioned to engage the pin and, when the compression slide is forcibly moved relative to the cartridge, the pin engages the hook member to compress the anatomical structure separate from the flexible member.

In one embodiment, the compression mechanism includes a wedge that extends from the anvil and a collar that is engagable with the wedge and is movable relative to the cartridge. The compression mechanism is engagable when the wedge is positioned to engage the collar, and when the collar is moved relative to the cartridge, the wedge engages the collar to compress the anatomical structure separate from the flexible member.

In one embodiment, the compression mechanism further includes a second wedge that extends from the anvil and a cam tube that is engagable with the second wedge and is movable relative to the cartridge. The compression mechanism is engagable when the second wedge is positioned to engage the cam tube, and when the cam tube is moved relative to the cartridge, the wedge engages the cam tube to compress the anatomical structure separate from the flexible member.

In one embodiment, at least one of the first end and the second end of the cartridge includes a cam tube.

In one embodiment, the first end of the cartridge includes a first cam tube and the second end of the cartridge includes a second cam tube.

In one embodiment, the first and second cam tubes are configured to move along a longitudinal axis of the cartridge, and when at least one of the first and second cam tubes moves, a gap between the anvil and the cartridge changes.

In one embodiment, the end effector includes an alignment mechanism configured to facilitate alignment between the anvil and the cartridge as the anvil is moved toward the cartridge. In one embodiment, the alignment mechanism includes a pin on one of the anvil and the cartridge and a recess on the other of the anvil and the cartridge.

In one embodiment, the alignment mechanism includes a knife that has a first flange, a second flange, and a web connecting the first and second flanges and including a cutting edge. A housing extends from the cartridge adjacent the first end, and the knife resides in the housing when the anvil and the cartridge are moved toward one another. A recess in the anvil is adjacent the first end of the end effector and receives the housing. A first slot in the anvil is open to the anvil face and to the recess and is configured to slidably receive the web during cutting of the anatomical structure with the cutting edge. A second slot in the cartridge is open to the cartridge face and is configured to slidably receive the web during cutting of the anatomical structure with the cutting edge.

In one embodiment, each of the first ends and the second ends of the anvil and the cartridge are movably coupled together by a hinge joint, a flexible member, a latch, or combinations thereof.

In one embodiment, the second end of the anvil is coupled to the second end of the cartridge by a hinge joint, a flexible member, a latch, or combination thereof.

In one embodiment, a hinge pivotally couples the first end of the anvil to the first end of the cartridge, and a flexible member movably couples the second end of the anvil to the second end of the cartridge.

In one embodiment, the end effector further includes a spring operably coupled to each of the anvil and the cartridge and biasing the anvil and the cartridge away from each other.

In one embodiment, one of the anvil and the cartridge further includes a stud at the second end, the flexible member configured to couple to the stud.

In one embodiment, the anvil and the cartridge are coupled by a snap fit connection at the first end.

In one embodiment, one of the anvil and the cartridge includes a hook on the first end, the other of the anvil and the cartridge includes a lever at the first end, and the hook is configured to engage the lever to couple the anvil and the cartridge at the first end.

In one embodiment, the end effector further includes a first flexible member that movably couples the first end of the anvil to the first end of the cartridge, and a second flexible member that movably couples the second end of the anvil to the second end of the cartridge.

In one embodiment, the first and second flexible members are independently operable such that a clamping force between the first ends is capable of being different from a clamping force between the second ends.

In one embodiment, the first and second flexible members are independently operable such that a gap between the first ends of the anvil and the cartridge is capable of being different from a gap between the second ends of the anvil and the cartridge.

In one embodiment, the anvil and the cartridge are coupled by a latch at one of the first and second ends and a flexible member at the other of the first and second ends.

In one embodiment, the latch is a projection from one of the anvil and the cartridge and the other of the anvil and the cartridge includes a recess configured to receive the latch.

In one embodiment, the latch includes a notch and the other of the anvil and the cartridge further includes a pin that projects into the recess and engages the notch when the latch enters the recess.

In one embodiment, the end effector further includes a spring that biases the pin into engagement with the notch.

In one embodiment, the end effector further includes a release cable coupled to the pin and operable to release the pin from the notch.

In one embodiment, the anvil and the cartridge are curved.

In one embodiment, the end effector is insertable through a trocar.

In one embodiment, an endocutter stapling device may be used by a surgeon to staple an anatomical structure of a patient during a minimally invasive surgical procedure. The endocutter stapling device may include the end effector, a manipulator, and a flexible member. The manipulator is configured to be accessible to the surgeon outside of the patient and includes a shaft coupled to the end effector and a clamping mechanism for selectively moving the anvil and the cartridge toward one another to clamp the anatomical structure. The flexible member extends through the shaft to the end effector and is operably coupled to at least one of the anvil and the cartridge and to the clamping mechanism such that operating the clamping mechanism withdraws the flexible member from the end effector and clamps the anatomical structure between the anvil and the cartridge.

In one embodiment, the clamping mechanism is capable of selectively tensioning the flexible member to clamp the anvil and the cartridge to the anatomical structure with a first stage clamping force that permits the end effector to be repositioned relative to the anatomical structure.

In one embodiment, the first stage clamping force is between about 0.1 $g/mm^2$ and about 4 $g/mm^2$.

In one embodiment, the clamping mechanism is capable of selectively tensioning the flexible member to clamp the anvil and the cartridge to the anatomical structure with a second stage clamping force that substantially prevents the end effector from moving relative to the anatomical structure during the medical procedure.

In one embodiment, the second stage clamping force is between about 4 $g/mm^2$ and about 70 $g/mm^2$.

In one embodiment, the manipulator includes a handpiece that at least partially houses the clamping mechanism. The clamping mechanism further includes a lever that is pivotable relative to the handpiece and is operable to activate the clamping mechanism. In one embodiment, the clamping mechanism includes a first push bar that is pivotably coupled to the lever, a second push bar that is pivotably coupled to the first push bar, and a pin that is coupled to the second push bar, the flexible member extending around the pin. Rotation of the lever relative to the handpiece moves the pin and withdraws the flexible member from the end effector.

In one embodiment, the clamping mechanism includes a hub that is pivotable relative to the handpiece with the lever extending from the hub, a torque arm that extends outwardly from the hub, a push bar that is pivotably coupled to the torque arm at a first end, a clamping rod that is pivotably coupled to the push bar at a second end and is slidably engaged with the handpiece, and two or more additional rods that are fixed in relation to the clamping rod with the clamping rod between at least two additional rods. The flexible member is in contact with the clamping rod and with two of the additional rods such that, when the clamping mechanism is engaged, the clamping rod slides relative to the at least two additional rods and withdraws the flexible member from the end effector.

In one embodiment, the manipulator further includes a locking mechanism for selectively locking the clamping mechanism in an engaged position in which the anvil and the cartridge clamp the anatomical structure.

In one embodiment, the locking mechanism includes a locking arm that extends from the hub, a release lever that is pivotably coupled relative to and that projects from the handpiece, and a locking finger that extends from the release lever and is biased into engagement with the locking arm.

Rotation of the lever to engage the clamping mechanism engages the locking arm with the locking finger.

In one embodiment, the manipulator includes a stapling mechanism that has an actuator coupled to an actuator plate that is slidable relative to the end effector and at least one wedge coupled to the actuator plate, wherein activating the actuator slides the actuator plate and the at least one wedge in the direction of the end effector to force the wedge into engagement with staples.

In one embodiment, the actuator is a thumb plate.

In one embodiment, the actuator is a lever and the stapling mechanism further includes a chain consisting of a plurality of links coupled to the actuator plate. The lever is operably coupled to the chain such that rotation of the lever moves the chain and the actuator plate.

In one embodiment, the manipulator includes a cutting mechanism having a knife push bar that is slidably coupled to the actuator plate and a cutting edge at one end of the knife push bar. When the stapling mechanism is engaged, the actuator plate slides relative to the knife push bar for a predetermined distance during which the knife push bar is substantially stationary and after which the actuator plate engages the knife push bar.

In one embodiment, the wedge is engaged over the predetermined distance.

In one embodiment, the manipulator includes a cutting mechanism that is configured to cut the anatomical structure and is coupled to the actuator plate and, when the actuator is engaged, the stapling mechanism begins stapling the anatomical structure prior to the cutting mechanism cutting the anatomical structure.

In one embodiment, the end effector is pivotable relative to the shaft.

In one embodiment, the device further includes an articulation mechanism that includes a clevis and a rotation collar, the rotation collar frictionally coupling the end effector to the clevis.

In one embodiment, the device further includes a compression mechanism that operably couples the anvil to the cartridge, that is separate from the flexible member, and that is configured to apply compressive force to the anatomical structure. The compression mechanism includes a hook member that extends from the anvil, a pin that is engagable with the hook member, and a compression slide that carries the pin and is selectively slidable relative to the cartridge. The compression mechanism is engagable when the hook member is positioned to engage the pin and, when the compression slide is forcibly moved relative to the cartridge, the pin engages the hook member to compress the anatomical structure separate from the flexible member.

In one embodiment, the device further includes a compression mechanism that operably couples the anvil to the cartridge, that is separate from the flexible member, and that is configured to apply compressive force to the anatomical structure. The compression mechanism includes a wedge that extends from the anvil and a collar that is engagable with the wedge and is movable relative to the cartridge. The compression mechanism is engagable when the wedge is positioned to engage the collar, and when the collar is moved relative to the cartridge, the wedge engages the collar to compress the anatomical structure separate from the flexible member.

In one embodiment, a method of stapling an anatomical structure during a minimally invasive medical procedure includes inserting the end effector through a trocar into a patient adjacent the anatomical structure, positioning the anvil and the cartridge on opposing sides of the anatomical structure, clamping the end effector to the anatomical structure at a first end and a second end of the end effector to secure the position of the end effector relative to the anatomical structure, and actuating the end effector to staple the anatomical structure.

In one embodiment, a method of stapling an anatomical structure during a minimally invasive medical procedure includes inserting the cartridge of the end effector through a trocar into a patient adjacent the anatomical structure, inserting the anvil of the end effector of claim 1 through a trocar into a patient adjacent the anatomical structure, positioning the anvil and the cartridge on opposing sides of the anatomical structure, clamping the end effector to the anatomical structure at a first end and a second end of the end effector to secure the position of the end effector relative to the anatomical structure, and actuating the end effector to staple the anatomical structure.

In one embodiment, an end effector for use by a surgeon to staple an anatomical structure of a patient during a minimally invasive procedure, the anatomical structure having a first side, a second side, a proximal end, and a distal end, includes an anvil that includes a first end, a second end, and a face that is positionable on the first side of the anatomical structure. The first end of the anvil is configured to extend beyond one of the proximal end or the distal end, and the second end of the anvil being configured to extend beyond the other of the proximal end or the distal end. The end effector further includes a cartridge that is configured to house a plurality of staples and that includes a first end, a second end, and a face that is positionable on the second side of the anatomical structure. The first end of the cartridge is configured to extend beyond one of the proximal end or the distal end, and the second end of the cartridge is configured to extend beyond the other of the proximal end or the distal end. The first end of the cartridge is movably coupled to the first end of the anvil and the second end of the cartridge is movably coupled to the second end of the anvil. Each of the anvil and the cartridge is insertable through a trocar and the end effector is remotely operable from outside the patient with at least a portion of one of the anvil and the cartridge being movable toward the other to clamp the end effector on a targeted resection line from the proximal end to the distal end of the anatomical structure.

In one embodiment, a method of stapling an anatomical structure during a minimally invasive medical procedure includes inserting the end effector through a trocar into a patient adjacent the anatomical structure, positioning the anvil and the cartridge on opposing sides of the anatomical structure on a target resection line such that the first end of each of the anvil and the cartridge extends beyond a proximal end of the anatomical structure and the second end of each of the anvil and the cartridge extends beyond a distal end of the anatomical structure, clamping the end effector to the anatomical structure to secure the position of the end effector on the resection line, and actuating the end effector only a single time to staple the anatomical structure from the proximal end to the distal end along the target resection line.

In one embodiment, an end effector is coupled to a manipulator having a shaft. The end effector is for use by a surgeon to staple an anatomical structure of a patient during a minimally invasive procedure. The anatomical structure has a first side and a second side. The end effector includes an anvil and a cartridge. The anvil includes a first end, a second end, and a face that is positionable on the first side of the anatomical structure. The cartridge is configured to house a plurality of staples and includes a first end, a second end, and a face that is positionable on the second side of the anatomical structure. The end effector further includes a housing that extends from one end of the anvil or the cartridge and that includes a flange. The flange defines a longitudinal axis. The end effector further includes a clevis and a rotation collar. The clevis is coupled to the shaft and is operable to pivot relative to the shaft. The rotation collar is rotatably coupled to the flange and is coupled to the clevis. The flange is capable of rotating within the rotation collar. Each of the anvil, the cartridge, the housing, the clevis, and the rotation collar is insertable through a trocar. The end effector is rotatable about the longitudinal axis, is pivotable relative to the shaft at the clevis, and is remotely operable from outside the patient with at least a portion of one of the anvil and the cartridge being movable toward the other to clamp the end effector to the anatomical structure.

In one embodiment, the first end of the cartridge is movably coupled to the first end of the anvil and the second end of the cartridge is movably coupled to the second end of the anvil.

In one embodiment, the first end of the anvil is configured to extend beyond one of a proximal end or a distal end, and the second end of the anvil is configured to extend beyond the other of the proximal end or the distal end. The first end of the cartridge is configured to extend beyond one of the proximal end or the distal end, and the second end of the cartridge is configured to extend beyond the other of the proximal end or the distal end.

In one embodiment, the end effector is for use by a surgeon to staple an anatomical structure of a patient during a minimally invasive procedure, the anatomical structure having a first side and a second side. The end effector includes an anvil that includes a first end, a second end, and a face that is positionable on the first side of the anatomical structure. The end effector further includes a cartridge that is configured to house a plurality of staples and that includes a first end, a second end, and a face that is positionable on the second side of the anatomical structure. The first end of the cartridge is separably coupled to the first end of the anvil, and the second end of the cartridge is separably coupled to the second end of the anvil. Each of the anvil and the cartridge is insertable through a trocar, and the end effector is remotely operable from outside the patient with at least a portion of one of the anvil and the cartridge being movable toward the other to clamp the end effector to the anatomical structure.

In one embodiment, the first end of the cartridge includes a first cam tube and the second end of the cartridge includes a second cam tube.

In one embodiment, the first and second cam tubes are configured to move along a longitudinal axis of the cartridge, and when at least one of the first and second cam tubes moves, a gap between the anvil and the cartridge changes.

In one embodiment, the first and second cam tubes are configured to move along a longitudinal axis of the cartridge, and when at least one of the first and second cam tubes moves, a gap between the anvil and the cartridge changes.

In one embodiment, the anvil and the cartridge are coupled by a snap fit connection at the first end.

In one embodiment, one of the anvil and the cartridge includes a hook on the first end, the other of the anvil and the cartridge includes a lever at the first end, and the hook is configured to engage the lever to couple the anvil and the cartridge at the first end.

In one embodiment, the end effector further includes a flexible member that couples the first end of the anvil to the first end of the cartridge.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 6 is a cross-sectional view of the endocutter stapling device taken along section line 6-6 of FIG. 4.

FIG. 7 is a cross-sectional view of the endocutter stapling device taken along section line 7-7 of FIG. 3.

FIG. 8 is an enlarged perspective view of a handpiece of the endocutter stapling device of FIG. 3.

FIG. 9 is an enlarged view of the encircled area 9 shown in FIG. 8.

FIG. 10 is a cross-sectional view of the endocutter stapling device similar to that shown in FIG. 7 during stapling and cutting according to one embodiment of the invention.

FIG. 11 is an enlarged view of the encircled area 11 of the endocutter stapling device of FIG. 10.

FIG. 12 is an enlarged view of the endocutter stapling device similar to FIG. 11 during use of the endocutter stapling device.

FIG. 40A is a perspective hidden line view of a distal portion of the end effector shown in FIG. 36 during use of the end effector.

FIG. 40B is a perspective hidden line view of the distal portion of the end effector shown in FIG. 40A after completion of a medical procedure.

FIGS. 43 and 44 are schematic elevation views of an end effector according to one embodiment of the invention.

FIGS. 45A and 45B are schematic elevation views of an end effector according to one embodiment of the invention.

FIGS. 46-48 are schematic elevation views of an end effector according to one embodiment of the invention.

FIG. 53 is a schematic elevation view of an end effector according to one embodiment of the invention.

FIGS. 54-56 are schematic elevation views of an end effector according to one embodiment of the invention.

FIGS. 57 and 58 are schematic views of an end effector according to one embodiment of the invention.

FIGS. 59-63 are schematic elevation views of end effectors according to embodiments of the invention.

DETAILED DESCRIPTION

In its broadest aspects, embodiments of the present invention are directed to an end effector and/or an endocutter stapling device (collectively referred to as "devices" herein) for forming a resection line during resection of an organ, tissue, or other anatomical structure. The devices may be used during minimally invasive surgical procedures. As it is described herein, one or both of the devices may be used, for example, in a vertical sleeve gastrectomy procedure. It will be appreciated, however, that the devices may be used in other procedures involving other anatomical structures. For example, the devices may be used in a parencymal resection, lung volume reduction surgery, or other procedures involving the lung. Further, the devices may be useful in an anatomic resection, such as, a lobectomy, a non-anatomic parencymal resection, or other procedures involving the liver and in a partial nephrectomy, total nephrectomy, or other procedures involving the kidney.

Figure 1:
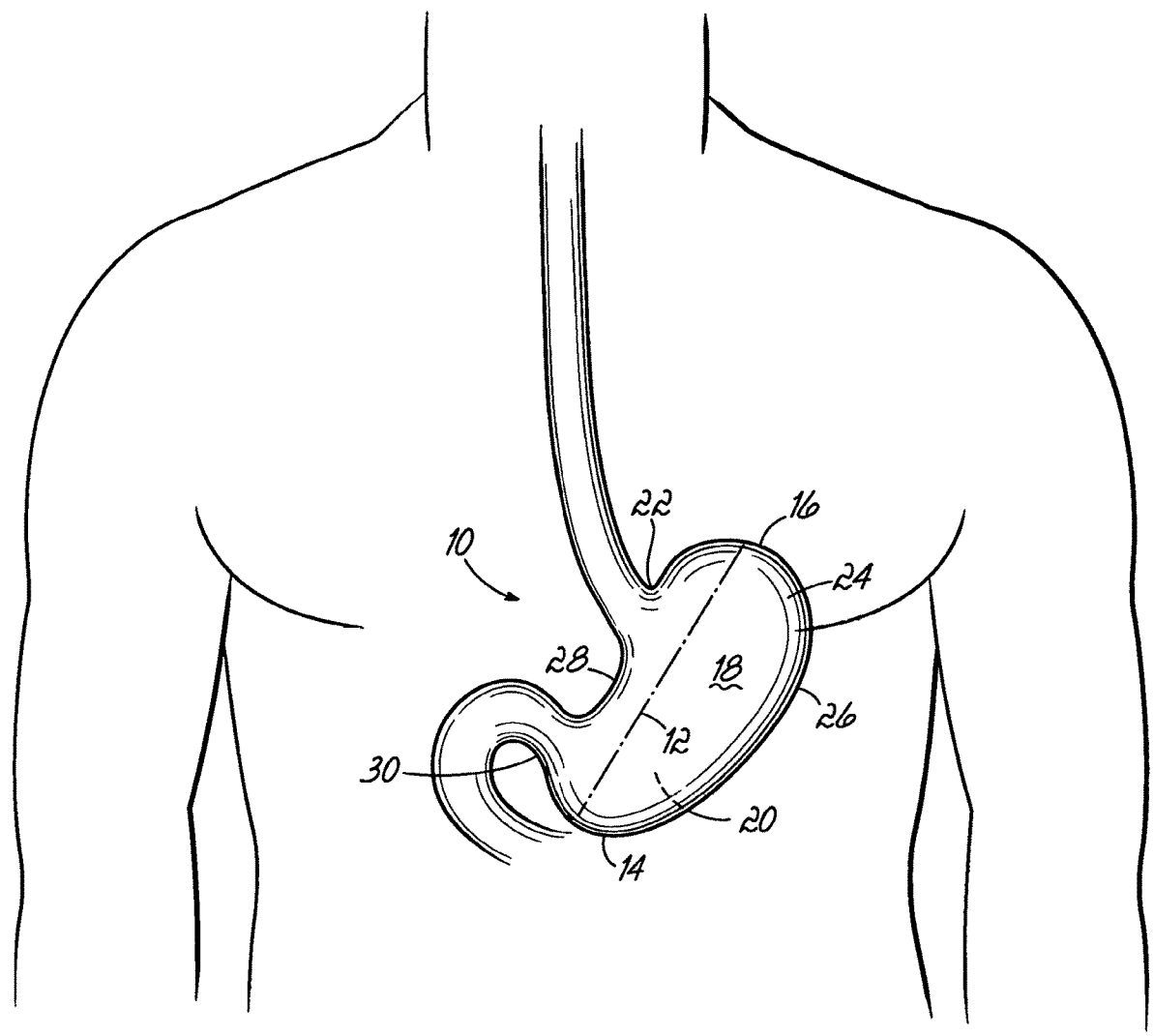
FIG. 1 depicts the anatomy of a stomach.

To these and other ends, and with reference to the figures, FIG. 1 illustrates the anatomy of the stomach 10 and a resection line 12 for a vertical sleeve gastrectomy. The stomach 10 generally includes a proximal end 14, a distal end 16, an anterior side 18, and a posterior side 20. The proximal end 14 and the distal end 16 of the stomach 10 are described from the perspective of the surgeon. A gastroesophageal junction 22 opens into the stomach 10 and is a common landmark in bariatric surgeries. A fundus 24 and the section of the stomach 10 defined by a greater curvature 26 are generally the parts of the stomach 10 removed during a vertical sleeve gastrectomy. The remaining pouch is generally defined by a lesser curvature 28 and the resection line 12 and presents a stomach with a significantly reduced volume. The desired location of the resection line 12 is about 0.5 cm to about 2 cm away from the gastroesophageal junction 22 and about 2 cm to about 10 cm away from a pylorus 30. In accordance with aspects of the invention, endocutter stapling devices may be utilized to form high quality, consistent resection lines during a vertical sleeve gastrectomy. Embodiments of the devices are advantageous because they are easily positionable laparoscopically, accommodate different thicknesses of tissue along the resection line length, are capable of providing substantially uniform compressive pressure on the tissue along the resection line, and enable a low staple firing force.

Figure 2A:
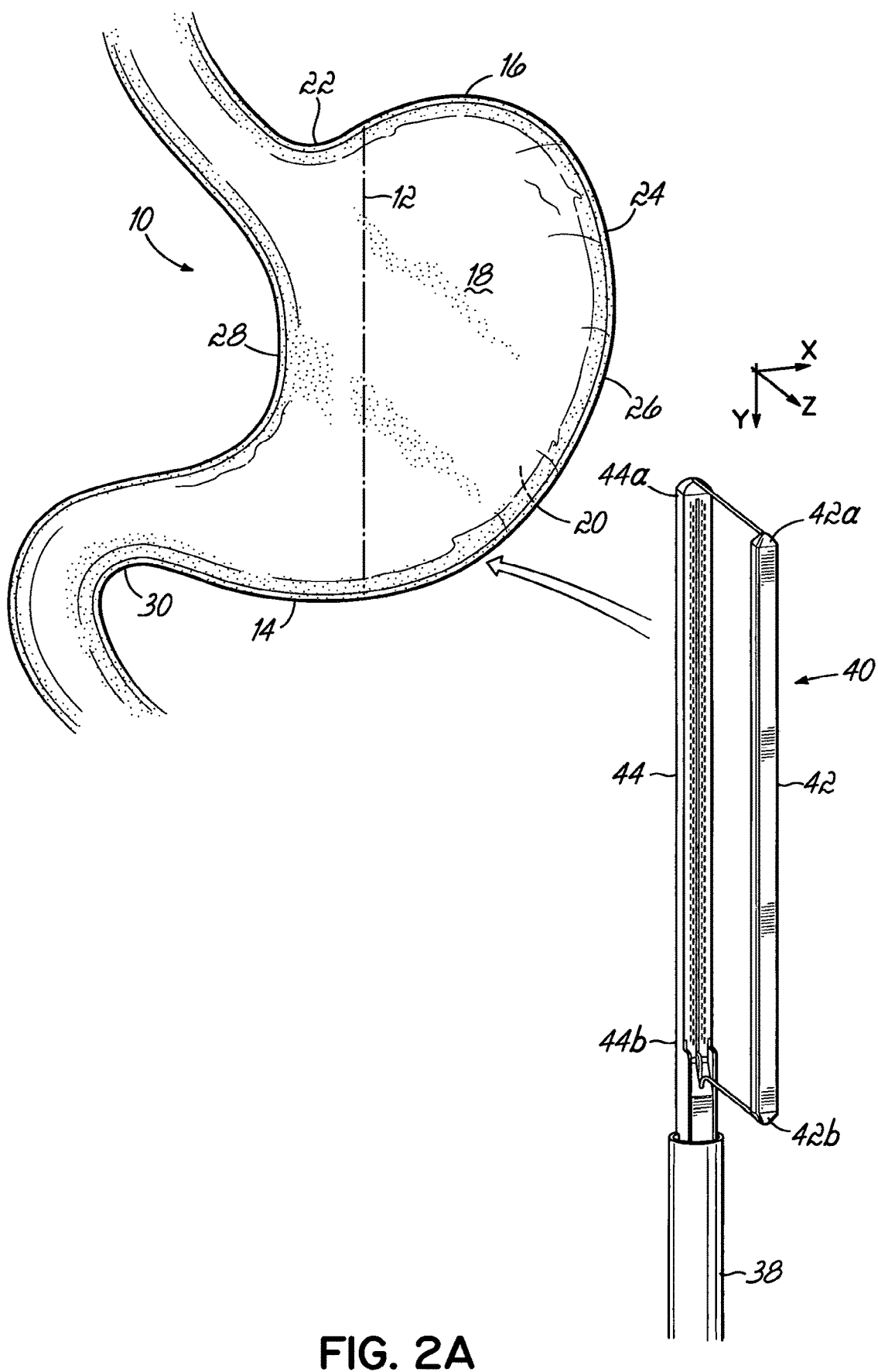
FIG. 2A is an elevation view of an end effector of an endocutter stapling device according to one embodiment of the invention.

With reference to FIG. 2A, embodiments of the present invention may include a shaft 38 to which is coupled an end effector 40. The end effector 40 has two clamping members 42, 44 coupled to one another. As is described below in reference to FIGS. 2B-2G, the surgeon may forcibly drive the members 42, 44 toward one another to clamp an anatomical structure between the members 42, 44. The surgeon may close the members 42, 44 remotely from the end effector 40. That is, no direct manual access to the end effector 40 is required. For this reason, the end effectors, as disclosed herein, may be designed specifically for use in minimally invasive surgical procedures in which the anatomical structure or organ is accessed through a trocar. Clamping onto the anatomical structure permits the surgeon to be able to accurately position the end effector 40 and ensures creation of a straight sleeve gastrectomy pouch, which is desirable. In the exemplary embodiment, and with reference to FIG. 2B, the member 42 may be an anvil generally positionable on the anterior side 18 of the stomach 10, and the member 44 may be a cartridge coupled directly to the shaft 38 and generally positionable on the posterior side 20 of the stomach 10. As shown, the anvil 42 may be sufficiently long to extend beyond each of the proximal end 14 and the distal end 16 of the stomach 10. The cartridge 44 may also be sufficiently long to extend beyond the proximal end 14 and the distal end 16 of the stomach 10. The cartridge 44 may house a plurality of surgical staples and a knife, each described below, for forming the resection line 12. The anvil 42 and the cartridge 44 are movably coupled together via a flexible member 46 and collectively operate as clamping members for purposes described below. While embodiment of the invention are not limited to movably coupling the anvil 42 to the cartridge 44, as is described herein, by movably coupling the anvil 42 to the cartridge 44, the anvil 42 has may directions in which it may move relative to the cartridge 44. For example, the flexible member 46 may only restrict movement away from the cartridge 44 when the flexible member 46 is already taut. Otherwise, the flexible member 46 may allow relative movement in all other directions. The present invention is not limited to the illustrated arrangement. For example, the arrangement of the members 42, 44 may be reversed such that the anvil 42 is coupled to the shaft 38 and is positioned adjacent the posterior side 20 of the stomach 10 and the cartridge 44 is coupled to the anvil 42 via the flexible member 46 and is positioned on the anterior side 18 of the stomach 10 (not shown). Other alternative arrangements may also be possible depending on the surgical procedure and the surgeon's preference, among other factors.

While the flexible member 46 is shown, the anvil 42 and the cartridge 44 may be coupled together at each end using a variety of engagement elements. For example, the anvil 42 and the cartridge 44 may be configured to connect using magnets, a clip-in connection, or other types of connections or connectors that are generally well known in the art. The connection method used at the proximal and distal ends of the anvil 42 and the cartridge 44 do not need to be similar. There are many ways to couple the anvil 42 and the cartridge 44 and the invention is not limited to the flexible member shown. By way of example, many of the connection methods described in PCT Application No. PCT/US2014/070869, which is incorporated by reference herein in its entirety, may be utilized to connect the anvil and the cartridge described herein.

Figure 2B:
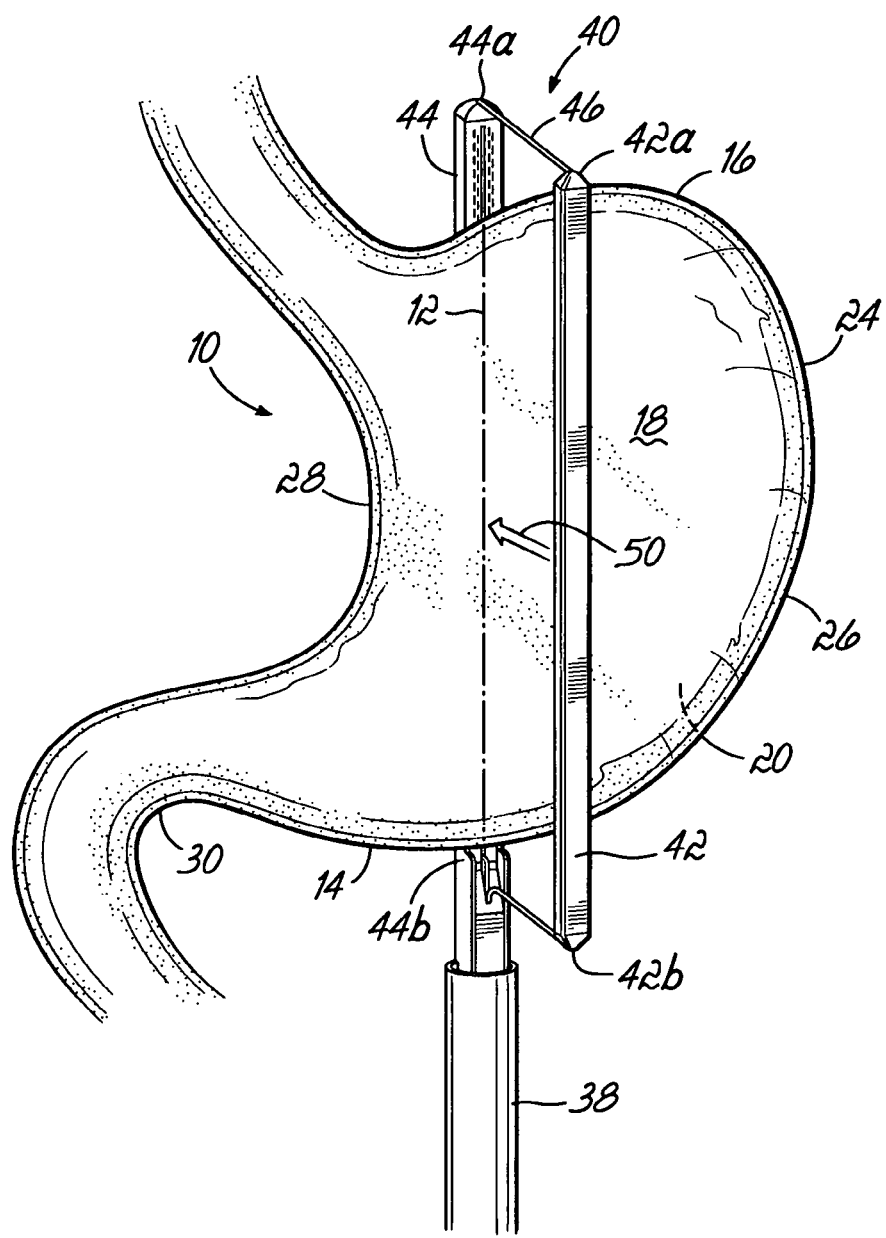
FIG. 2B is an elevation view of the end effector of FIG. 2A positioned on the stomach.

In one embodiment, the surgeon may position the end effector 40 proximate the stomach 10 as is shown in FIG. 2B. In this regard, FIG. 2B illustrates the end effector 40 placed around the stomach 10 on a target resection line 12 with the anvil 42 and the cartridge 44 coupled together at both the proximal end 14 and the distal end 16 of the stomach 10. By way of example, the anvil 42 and the cartridge 44 may be coupled to each other with the flexible member 46 at each of the proximal end 14 and the distal end 16 of the stomach 10. The length of the anvil 42 and the cartridge 44 may be sufficient for the anvil 42, the cartridge 44, and the flexible member 46 to encircle the stomach 10, as shown. The length of the anvil and/or the cartridge as described herein is not particularly limited. By way of example and not limitation, the length of each may measure from about 35 mm to about 350 mm. The end effector 40 may be put in place and used with or without having to mobilize the greater curvature 26. For example, a surgeon may prefer to leave the greater curvature 26 attached to the momentum (not shown), which could improve stability of the stomach 10 during stapling.

As is described below, the flexible member 46 may be coupled to a tensioning mechanism by which the anvil 42 and the cartridge 44 may be moved toward one another and to provide a sufficient clamping force on the stomach 10. In addition, the flexible member 46 may be coupled to a release mechanism that releases tension on the flexible member 46 and allows the anvil 42 to be separated from the cartridge 44, such that the end effector 40 may be repositioned prior to stapling or after forming the resection line 12. Further, the end effector 40 may be operably coupled to a stapling and/or cutting mechanism by which the surgeon may drive staples and a cutting element housed in the cartridge 44, each of which is described below. In one embodiment where the ends of the anvil 42 and the cartridge 44 extend beyond the proximal and distal ends 14, 16 of the stomach 10, the end effector 40 may be advantageously configured to complete the staple line 12 after actuating the stapling and/or cutting mechanisms only a single time. This is in contrast to current procedures that require repeated activation of the stapling and/or cutting mechanisms.

In one aspect of the invention, the end effector 40 may be positioned relative to the stomach 10 using a two-stage clamping process. In the first clamping stage, the anvil 42 and the cartridge 44 may be clamped onto the stomach 10 to provide a threshold amount of resistance to unintentional movement of the end effector 40 relative to the stomach 10. For example, the range of clamping pressure in the first stage may be about 0.1 g/mm$^2$ to about 4 g/mm$^2$. While preventing undesirable or unintentional movements of the end effector 40, the surgeon may move the end effector 40 to a desired position relative to the stomach 10 without significant difficulty.

In the second clamping stage, and with the end effector 40 in the desired location relative to the stomach 10, the clamping force of the end effector 40 may be increased to effectively prevent or minimize the end effector 40 from moving relative to the stomach 10. For example, the clamping pressure in the second stage may be about 4 g/mm$^2$ to about 70 g/mm$^2$. In an exemplary embodiment, the clamping pressure in the second stage may be about 8 g/mm$^2$. The upper limit to which the end effector 40 may be clamped is selected so as to avoid any damage to the underlying tissue being clamped but also allow for adequate tissue compression for staple formation. This upper limit may be, for example, about 70 g/mm$^2$. Additionally, the lower limit in the disclosed range of about 4 g/mm$^2$ represents a threshold clamping force below which constitutes the first stage clamping and above which constitutes the second stage clamping. It will be recognized that these values are merely exemplary and the particular values may depend on several factors, including the anatomical structure being clamped. Thus, embodiments of the invention are not limited to the range of values provided herein.

In an advantageous aspect of the invention, when the end effector 40 is placed on the stomach 10 (e.g., in the first clamping stage as described above), the surgeon has a clear visualization of the intended results of the vertical sleeve gastrectomy prior to actually performing the resection of the stomach 10 at the resection line 12. Hence, the surgeon has an indication of what the resultant stomach shape and volume defined by the lesser curvature 28 and the resection line 12 will likely be prior to stapling and/or cutting the stomach tissue. If the surgeon is not satisfied with the indication of the expected stomach shape and volume, the surgeon may adjust and manipulate the location and alignment of the end effector 40 prior to stapling and cutting the stomach 10. This is in contrast to current procedures, where the resection line is generally not well visualized prior to activating the stapler, thus the ultimate outcome is less certain. It will be appreciated that the end effector 40 should be positioned such that it does not provide lateral stretching or tension of the stomach 10, which may create an undesirable environment for stapling and cutting. Using the end effector 40 ensures proper alignment of the resection line 12 so that removing the fundus 24 occurs at a safe distance away from both the lesser curvature 28 and the gastroesophageal junction 22. The result is a resection line 12 that is squared off at the fundus 24 of the stomach 10 to prevent or reduce the likelihood of necrotic tissue development.

Figure 2C:
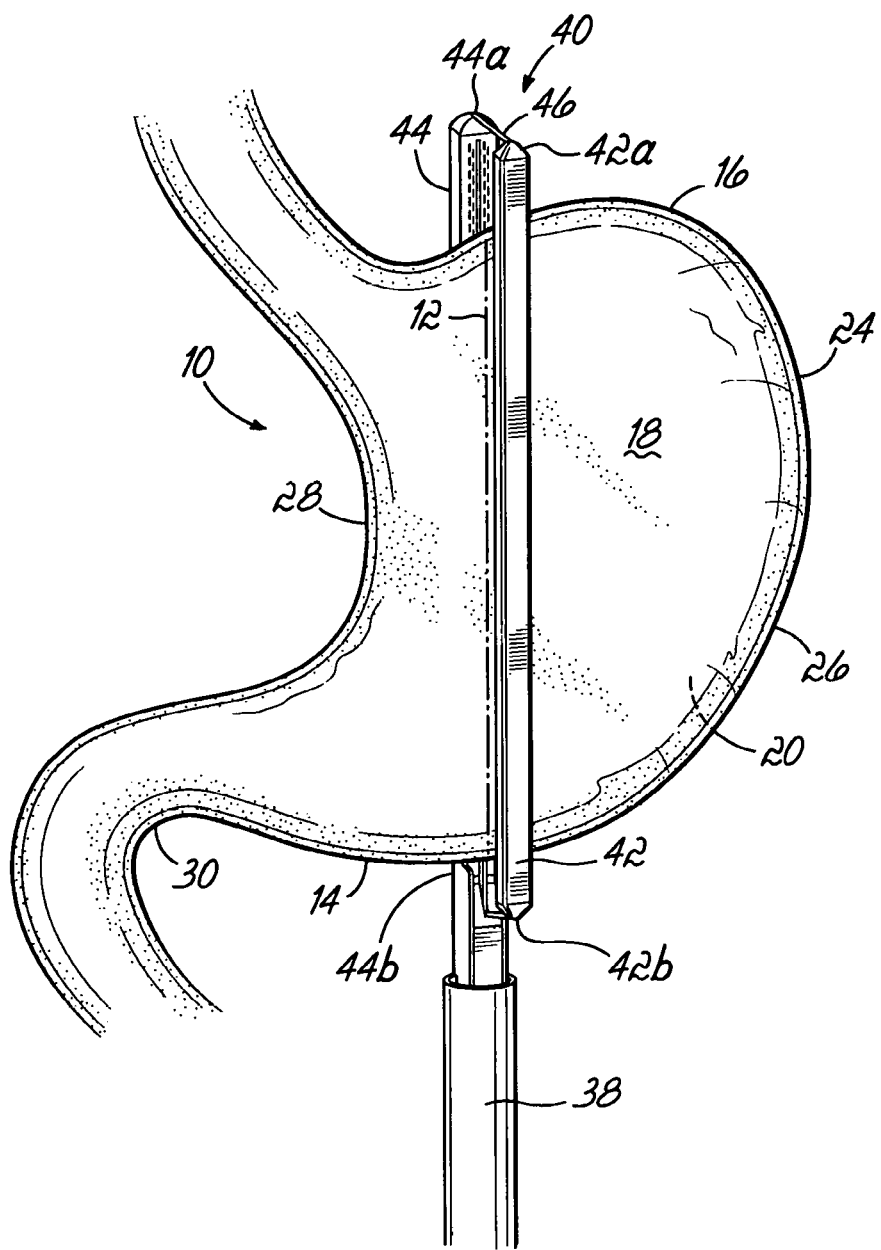
FIG. 2C is an elevation view of the end effector of FIG. 2A during resection of a portion of the stomach.
Figure 2D:
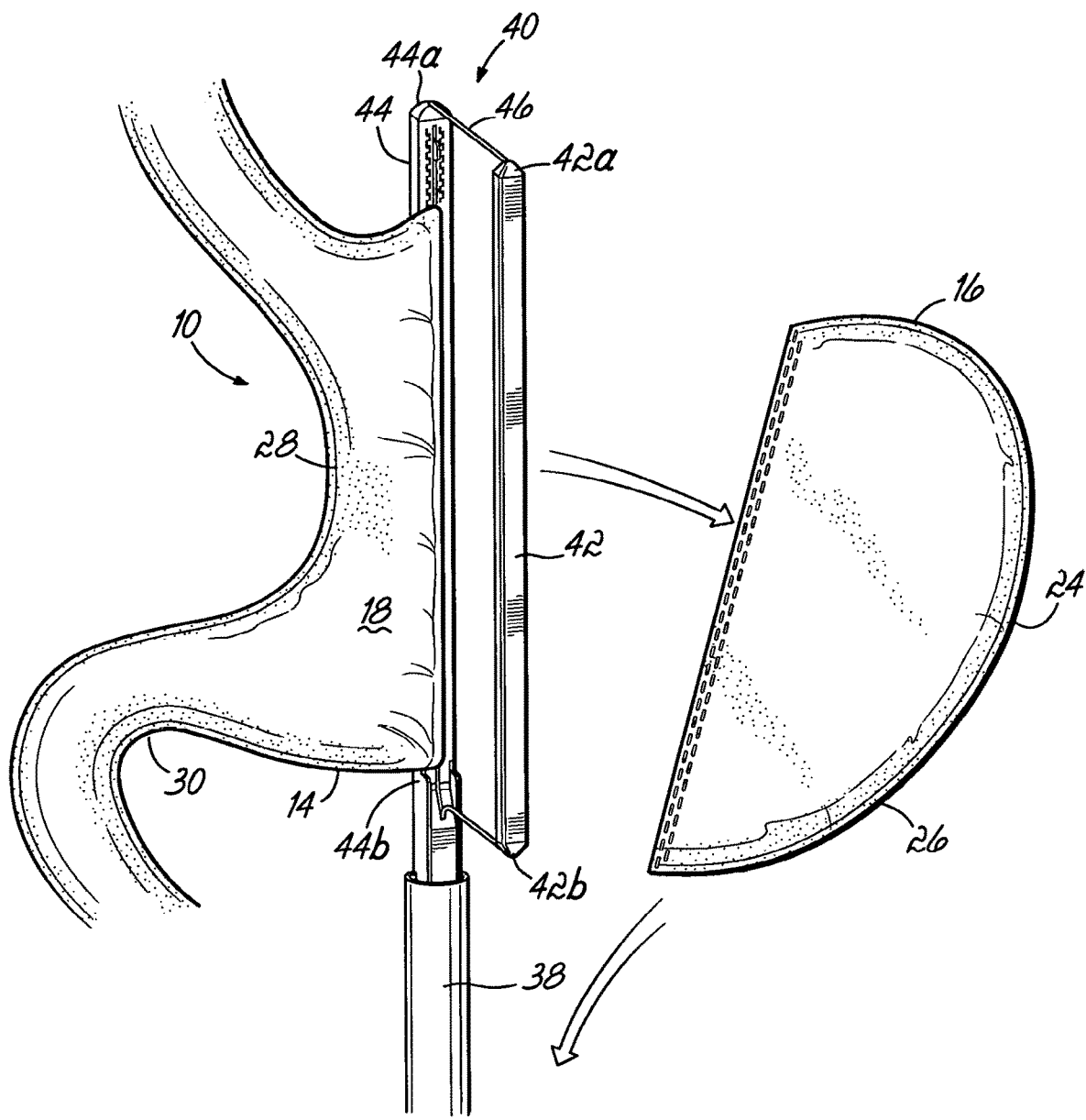
FIG. 2D is an elevation view of the end effector of FIG. 2A following resection of a portion of the stomach.
Figure 2E:
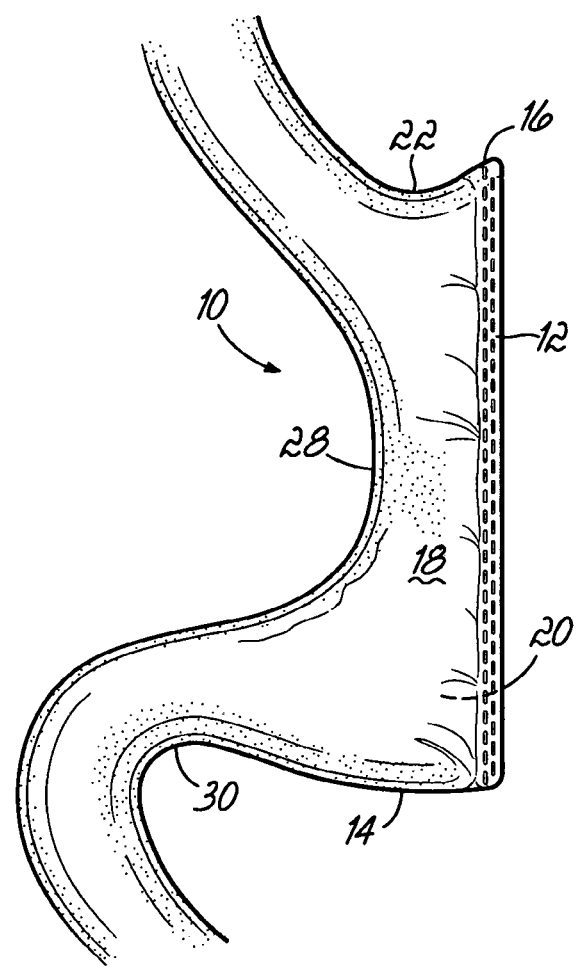
FIG. 2E depicts the stomach anatomy resulting from an exemplary vertical sleeve gastrectomy.

Once the end effector 40 is properly positioned, as is shown in FIG. 2B, the surgeon may then engage the tensioning mechanism, described below, to compress the anvil 42 and the cartridge 44 on the stomach 10, as is shown by the arrow 50 in FIG. 2B. In this regard, the end effector 40 may be coupled to a device for tensioning the flexible member 46 to draw the anvil 42 and the cartridge 44 onto the stomach 10. As the anvil 42 and the cartridge 44 are brought together, the flexible member 46 may align one with the other. In this regard, the end effectors disclosed herein may be self-aligning due, in part, to coupling of the anvil 42 to the cartridge 44 at each end. Tensioning the flexible member 46 may also compress the tissue. For instance, as the flexible member 46 is tensioned, the distance between the anvil 42 and the cartridge 44 decreases, and ultimately compresses the stomach 10. Once positioned and the anvil 42 and the cartridge 44 are compressed, the surgeon may activate a cutting and stapling mechanism, described below, to cut and staple the tissue using the end effector 40 until complete resection of the stomach 10 occurs, as is illustrated in the sequence of FIGS. 2C, 2D, and 2E.

As noted above, the end effector 40 may be secured to the stomach 10 so that it resists movement once the surgeon begins stapling. As illustrated in FIGS. 2A-2E, the use of the end effector 40 aids in creating an ideal gastric sleeve pouch size and shape (e.g., shown in FIG. 2E). In one embodiment, the surgeon may engage a release mechanism after completing the resection of the stomach 10. This allows slack to be introduced in the flexible member 46 such that the anvil 42 may be separated from the cartridge 44. Consequently, once the anvil 42 and the cartridge 44 are separated, the end effector 40 may be removed from the abdominal cavity.

In embodiments of the present invention that include a flexible member for tensioning the anvil and the cartridge, the flexible member may take several forms. By way of example and without limitation, the flexible member may include a wire, suture, thread, chain, or other elongate flexible member. The flexible member may be made of metal, plastic, or any other material that is suitable for a biological environment. The flexible member may be, for example, a braided cable. The flexible member may be capable of a radius of bend of approximately 0.030 inches and further be generally resistant to kinking, knotting, etc. Additionally, the flexible member should be able to accommodate a tensile load sufficient to generate a clamping force (pressure) above the maximum clamping force expected to be imposed during a procedure. By way of example, the flexible member should be able to accommodate a tensile load sufficient to create a clamping force of about 70 g/mm² on the anatomical structure. In an exemplary embodiment, the flexible member may be a multi-strand stainless steel cable or a polymer, such as vectran.

As illustrated in FIG. 2A, the end effector 40 may be pre-assembled and then inserted into the abdominal cavity as a unit. In this regard, and with reference to FIG. 2B, using standard laparoscopic instruments and graspers, the surgeon may manipulate the end effector 40 across the stomach 10 so that the anvil 42 is generally positioned along the anterior side 18 of the stomach 10 and the cartridge 44 is generally positioned along the posterior side 20 of the stomach 10. A distal end 42a of the anvil 42 generally extends beyond the distal end 16 of the stomach 10. A distal end 44a of the cartridge 44 may also generally extend beyond the distal end 16 of the stomach 10. A similar configuration exists at the opposite end. Proximal ends 42b, 44b of the anvil 42 and the cartridge 44, respectively, generally extend beyond the proximal end 14 of the stomach 10. The section of the flexible member 46 between the anvil 42 and the cartridge 44 may loop or extend around the distal end 16 of the stomach 10, as illustrated in FIG. 2B. The anvil 42 and the cartridge 44 may then be manipulated to provide a clamping force on the stomach 10. This clamping may be achieved by tensioning the flexible member 46, as is described below.

Figure 2F:
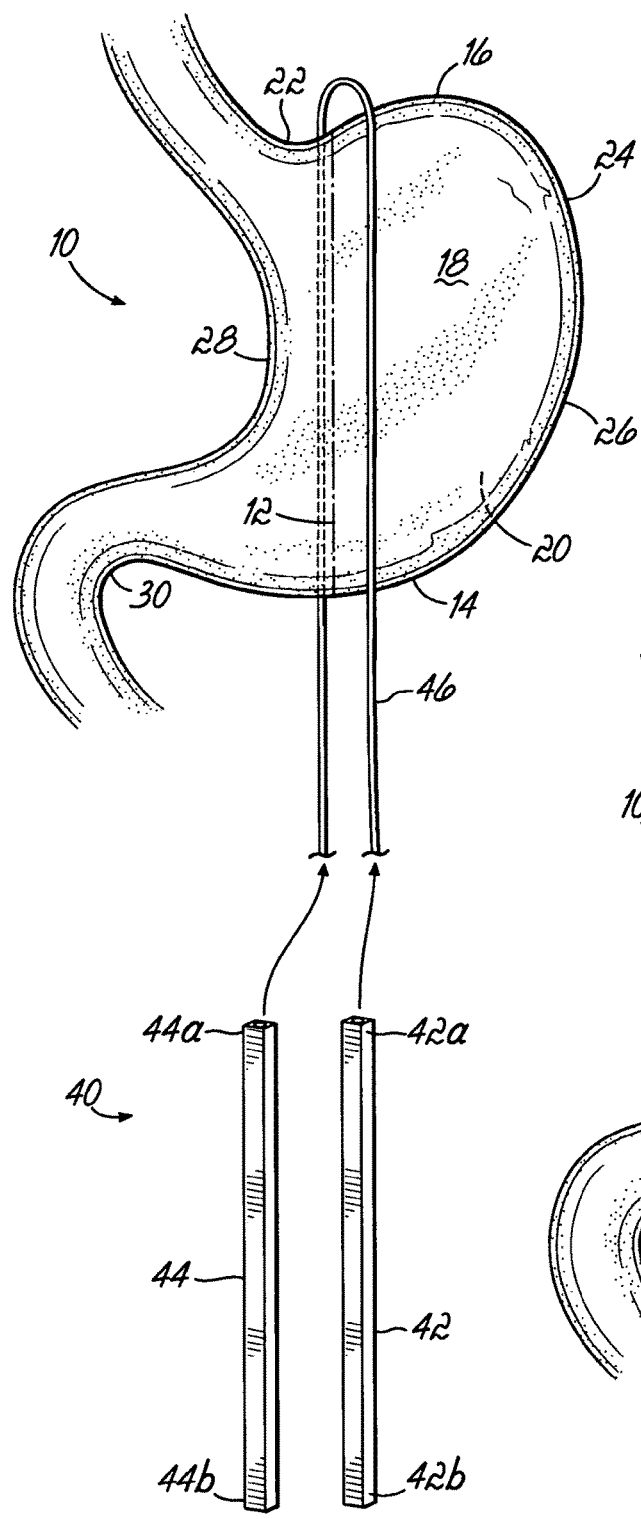
FIG. 2F is an elevation view of an anvil and a cartridge for insertion onto a flexible member according to another embodiment of the invention.
Figure 2G:
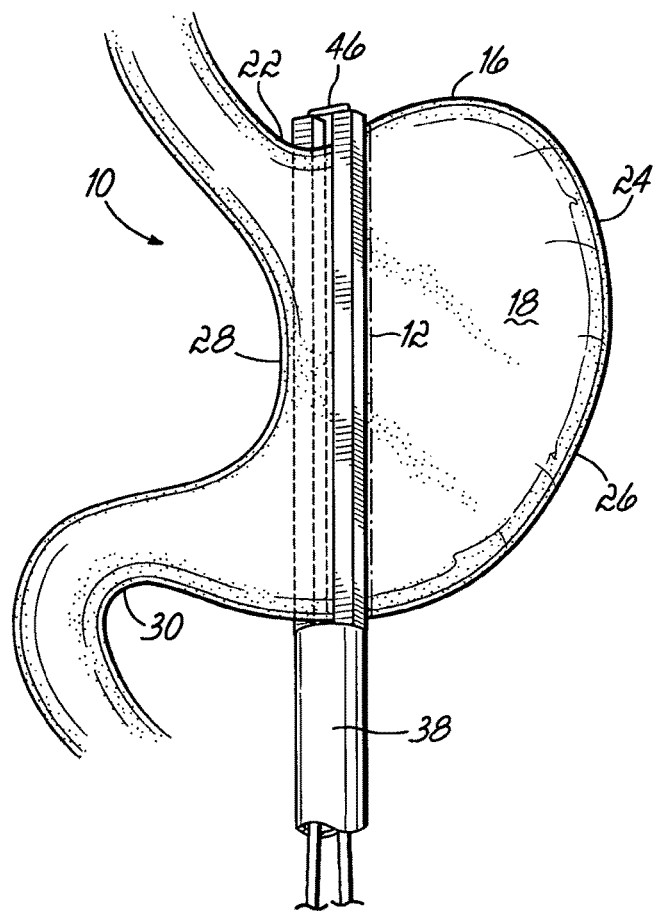
FIG. 2G is an elevation view of the anvil and the cartridge shown in FIG. 2F clamped onto a stomach according to one embodiment of the invention.

As an alternative to pre-assembling the end effector 40 externally, the end effector 40 may be assembled inside the abdominal cavity. In this regard, and with reference to FIGS. 2F and 2G and in one embodiment, the flexible member 46 may be inserted through a trocar (not shown). Using laparoscopic instruments and graspers, the surgeon may manipulate the flexible member 46 around the stomach 10, as shown in FIG. 2F. Through the same or another trocar, the surgeon may then insert the member 42 and/or the member 44. Each of the members 42, 44 may be engaged with the flexible member 46 and with the shaft 38. The surgeon may then perform the procedure.

Figure 2H:
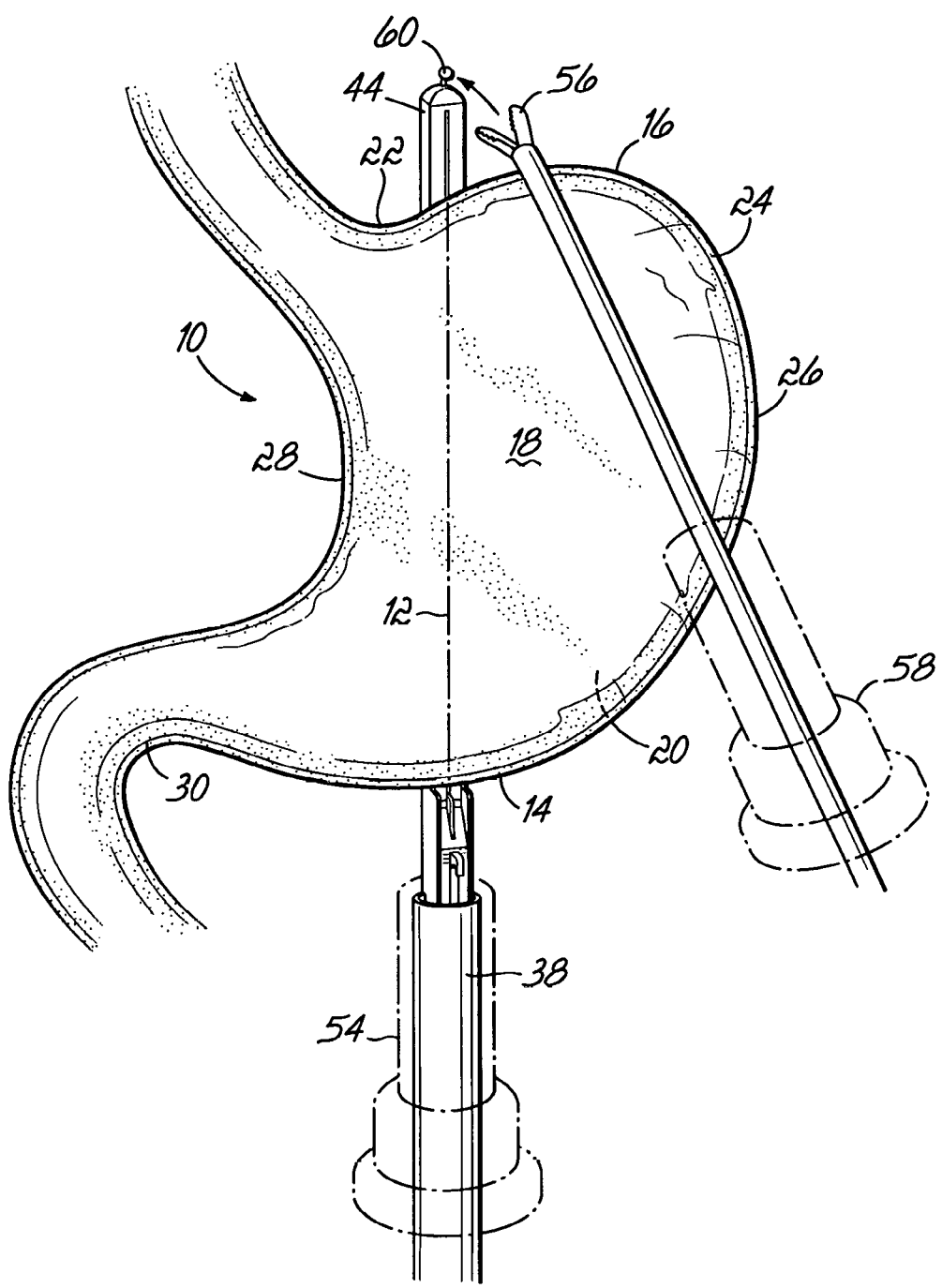
FIGS. 2H-2N are schematic views of multiple methods of assembling an end effector according to embodiments of the invention.
Figure 2I:
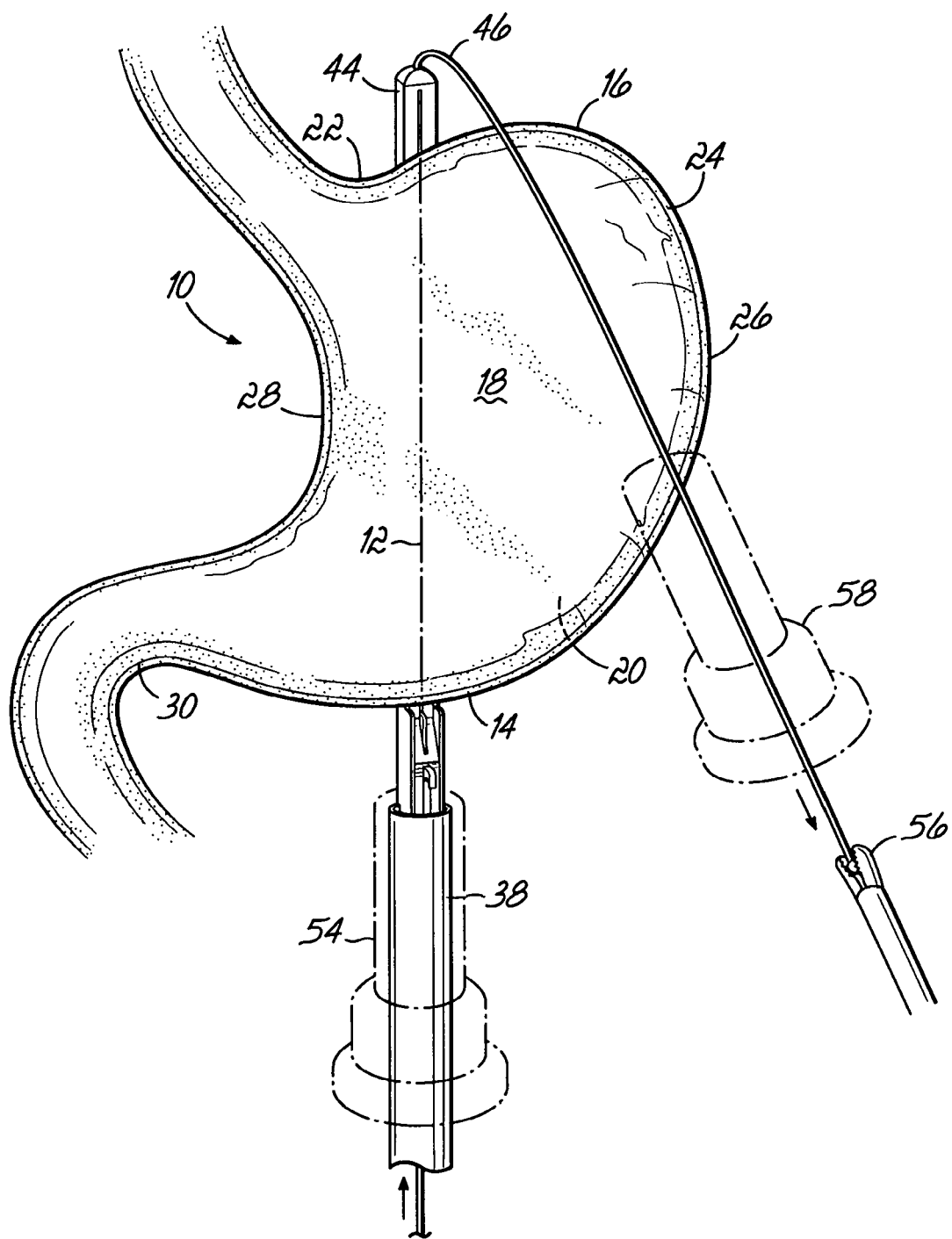
Figure 2J:
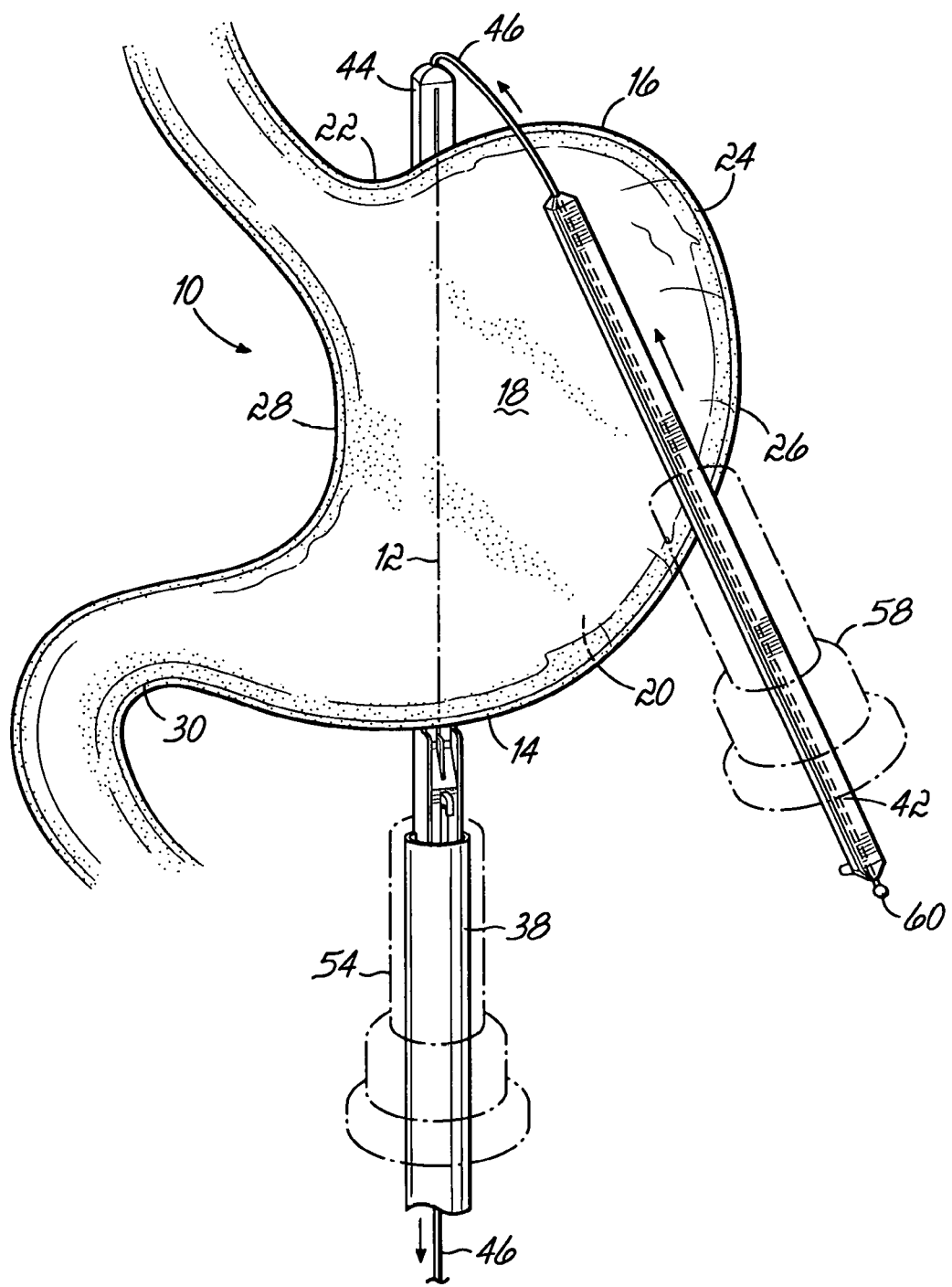
Figure 2K:
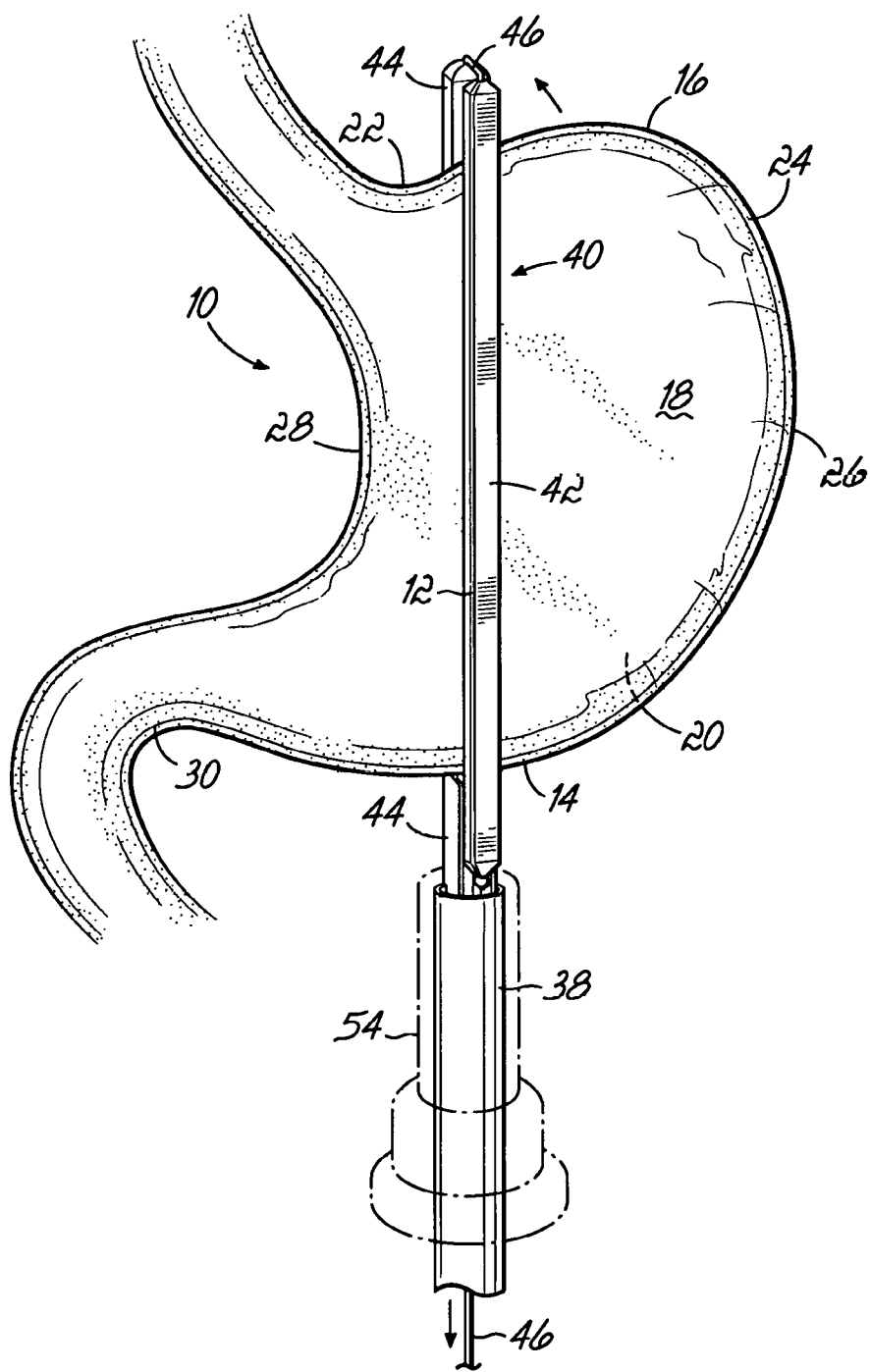

Another method for partial external assembly is shown in FIGS. 2H-2K, in which the surgeon may use two trocars to assemble and manipulate the end effector 40 to perform a procedure. With reference to FIG. 2H, the surgeon may manipulate the cartridge 44 with the shaft 38 through a first trocar 54 and insert a pair of graspers 56 through a second trocar 58. The shaft 38 may be coupled to the cartridge 44 via a ball joint to aid in the proper placement of the cartridge 44. In FIG. 2I, the surgeon may use the graspers 56 to grip a retraction tab 60 that is coupled to the flexible member 46 and pull the retraction tab 60 and, consequently, the flexible member 46 through the second trocar 58. As is shown in FIG. 2H, the retraction tab 60 extends from the cartridge 44. With reference to FIG. 2J, the surgeon may couple the anvil 42 to the flexible member 46 outside of the abdominal cavity and then slide the anvil 42 through the second trocar 58. The end effector 40 may initially be disarticulated so that the surgeon may retract the flexible member 46 to draw the anvil 42 proximate the stomach 10 and then secure the flexible member 46 to the cartridge 44. That is, the anvil 42 may be a separable member that is coupled to the other components such that the anvil 42 is movably coupled to the cartridge 44, as is described above. Once assembled, as is shown in FIG. 2K, the surgeon may perform the procedure with the end effector 40.

Figure 2L:
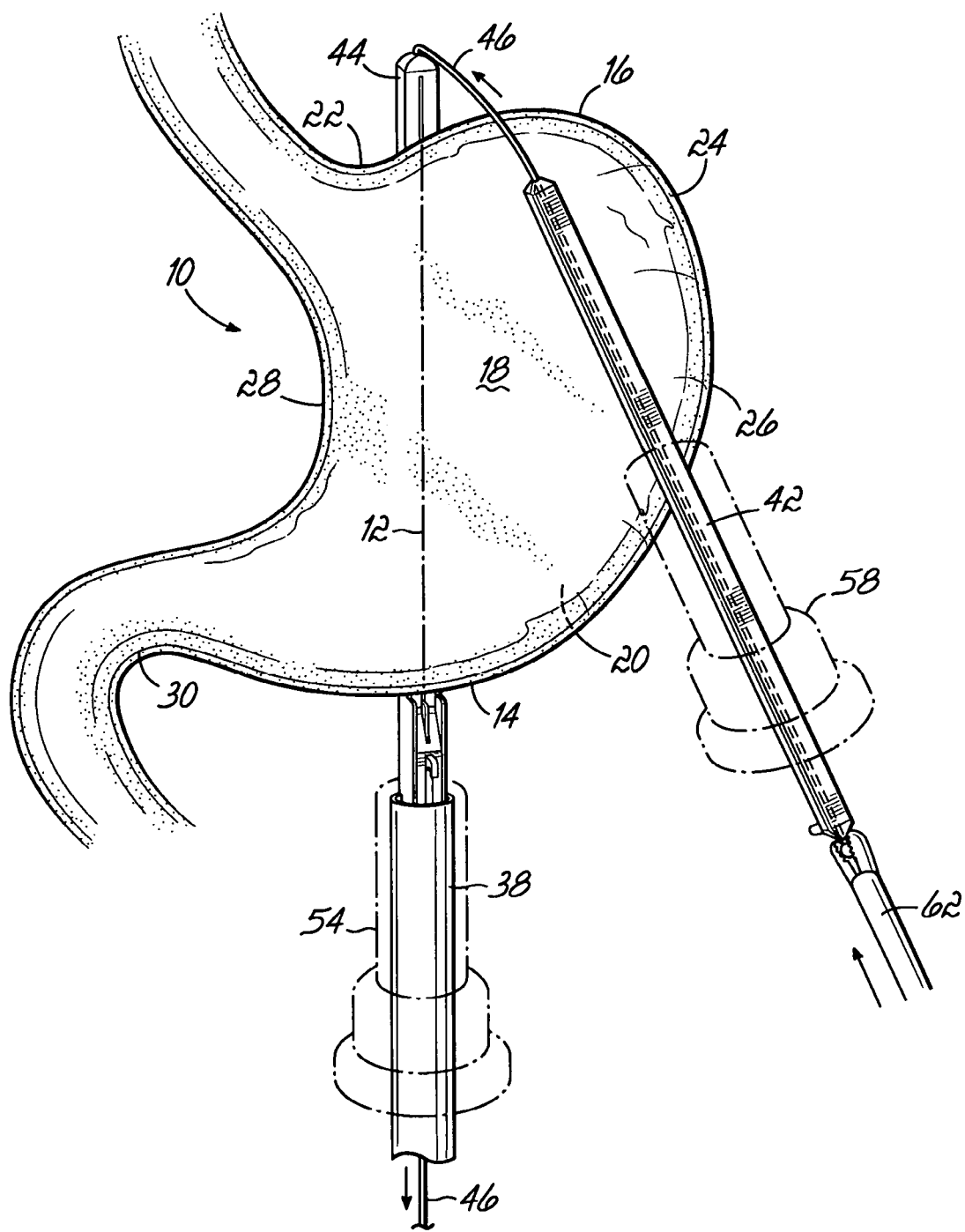
Figure 2M:
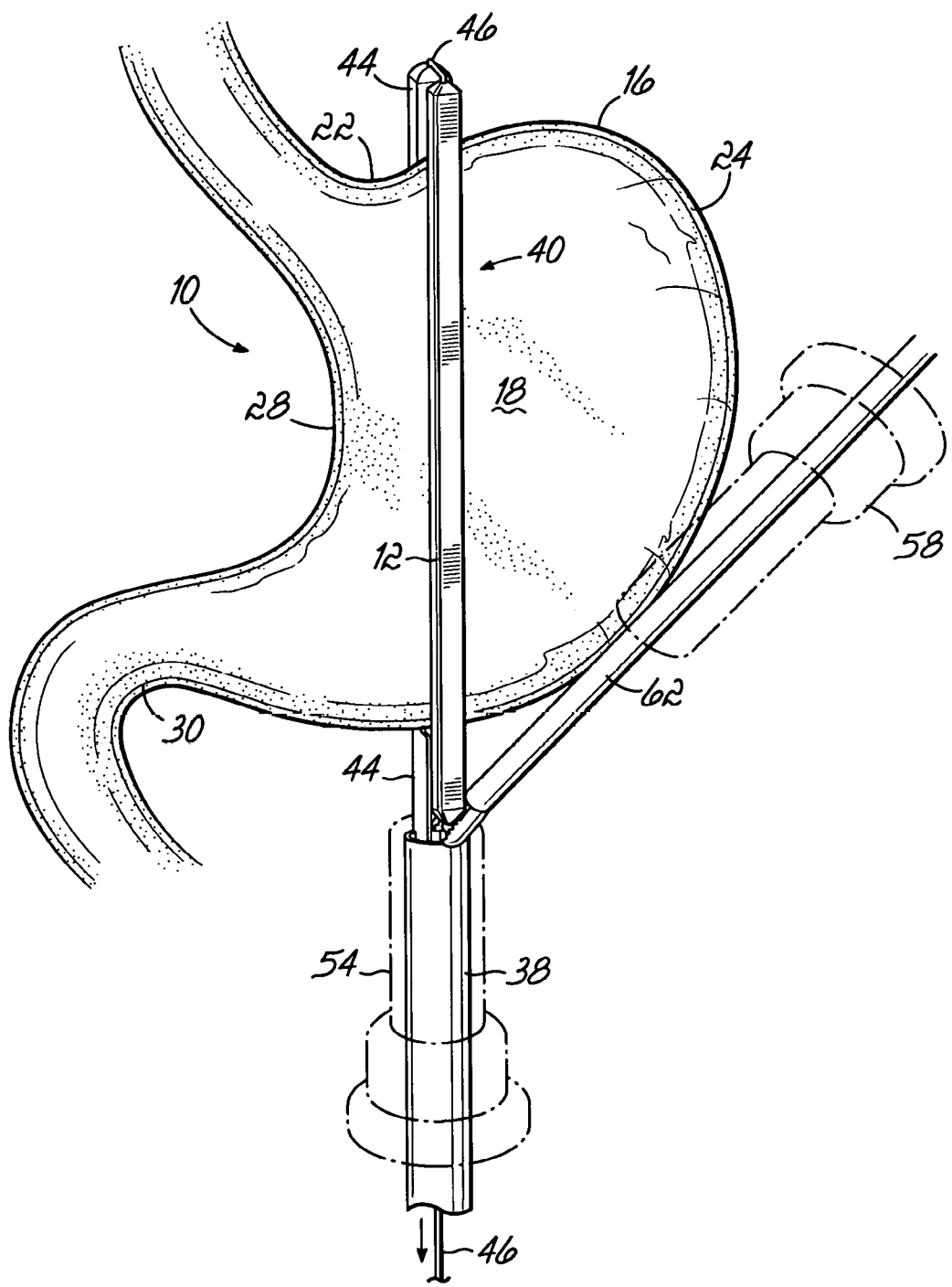
Figure 2N:
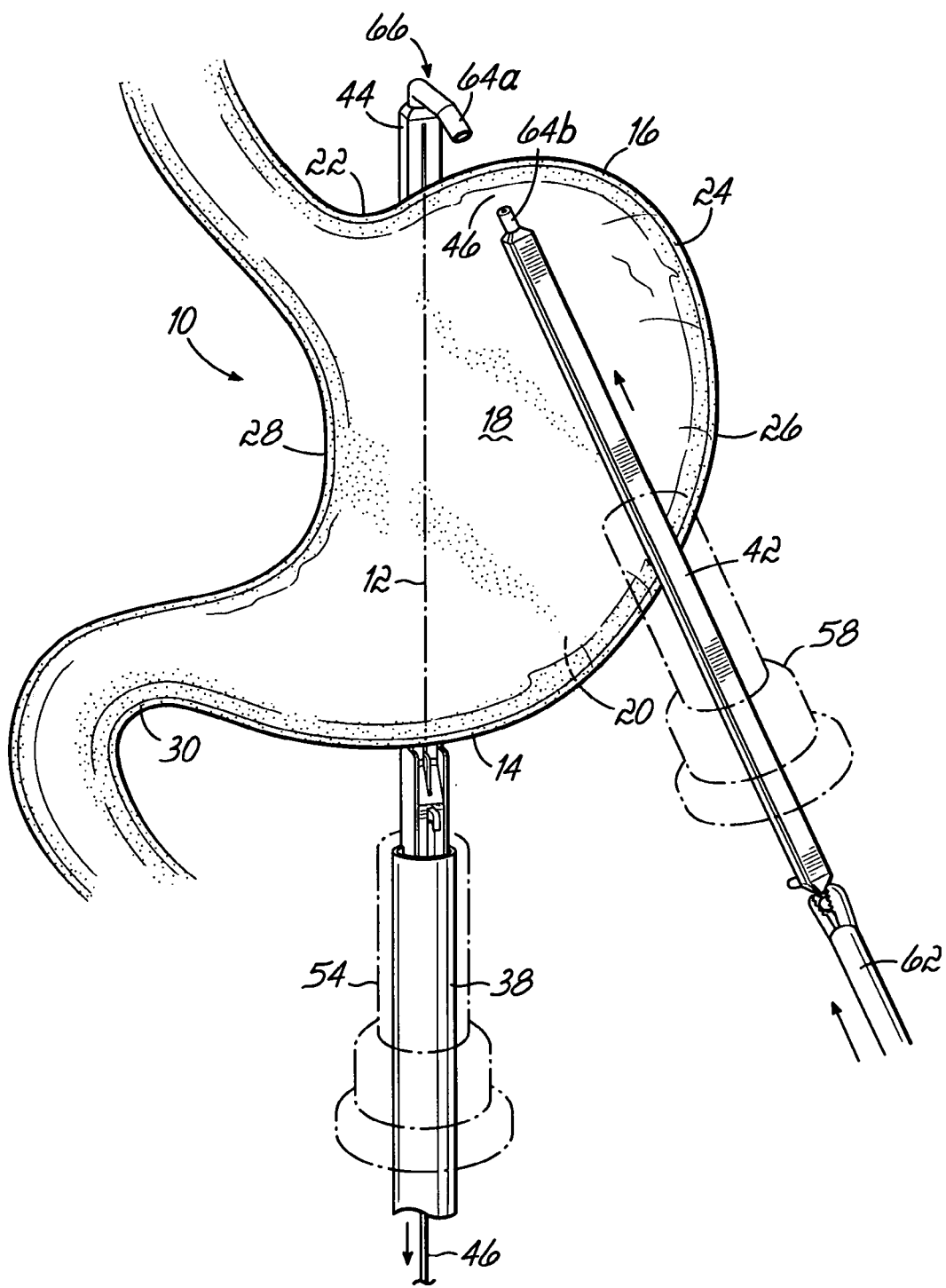

With reference to FIGS. 2L and 2M, another method for assembling an end effector is shown. In that regard, the anvil 42 may be coupled to a manipulation shaft 62, such as, by a ball joint. The manipulation shaft 62 may be maneuvered through the second trocar 58 to align and movably couple the anvil 42 to the cartridge 44. The anvil 42 may be a separable member in this embodiment that is coupled to the other components such that the anvil 42 is movably coupled to the cartridge 44. By way of example only, the anvil 42 may be coupled to the cartridge 44 with a latch at one end and the flexible member at the other end, though other connection methods may be utilized. Alternative connection methods may include latches at each end of the end effector or magnets that assist the surgeon in alignment of the members 42, 44. Another alternative connection is shown in FIG. 2N. As shown, the members 42, 44 may be coupled together at a snap fit connection 64a, 64b with a ball joint 66. The anvil 42 and cartridge 44 may be inserted through separate trocars and assembled intra-abdominally. The anvil 42 may be introduced to the abdominal cavity and coupled to the cartridge 44 by an externally controlled instrument 62. The snap fit connection may separably couple the anvil 42 to the cartridge, though in the absence of a flexible member. As yet another alternative (not shown), one of the cartridge or the anvil may include a flexible member in the form of a loop and having a pull tab positioned to be withdrawn from the abdominal cavity so that the other of the cartridge and the anvil may be coupled to the flexible member.

With reference to FIGS. 3-16, the surgeon may operate the end effector 40 above, including one or both of the anvil 42 and the cartridge 44, during a vertical sleeve gastrectomy procedure with another mechanical device that is operably coupled to the one or both of the anvil 42 and the cartridge 44. In one embodiment, an endocutter stapling device 100 includes the end effector 40 operatively coupled to a manipulator 102. As shown, the manipulator 102 includes an elongate member or shaft 104 coupled to a handpiece 106 at one end and the end effector 40 at the other end thereof. During a surgical procedure, the end effector 40 and a portion of the shaft 104 may be inserted into the patient, such as via a trocar. The surgeon may then manipulate the end effector 40 and/or articulate the end effector 40 relative to the manipulator 102 to perform a procedure. Thus, embodiments of the present invention may include mechanisms for effectuating a surgical procedure with the end effector 40 (including clamping, stapling, and cutting tissue) and for allowing the end effector 40 to articulate relative to the shaft 104, each described below.

Figure 3:
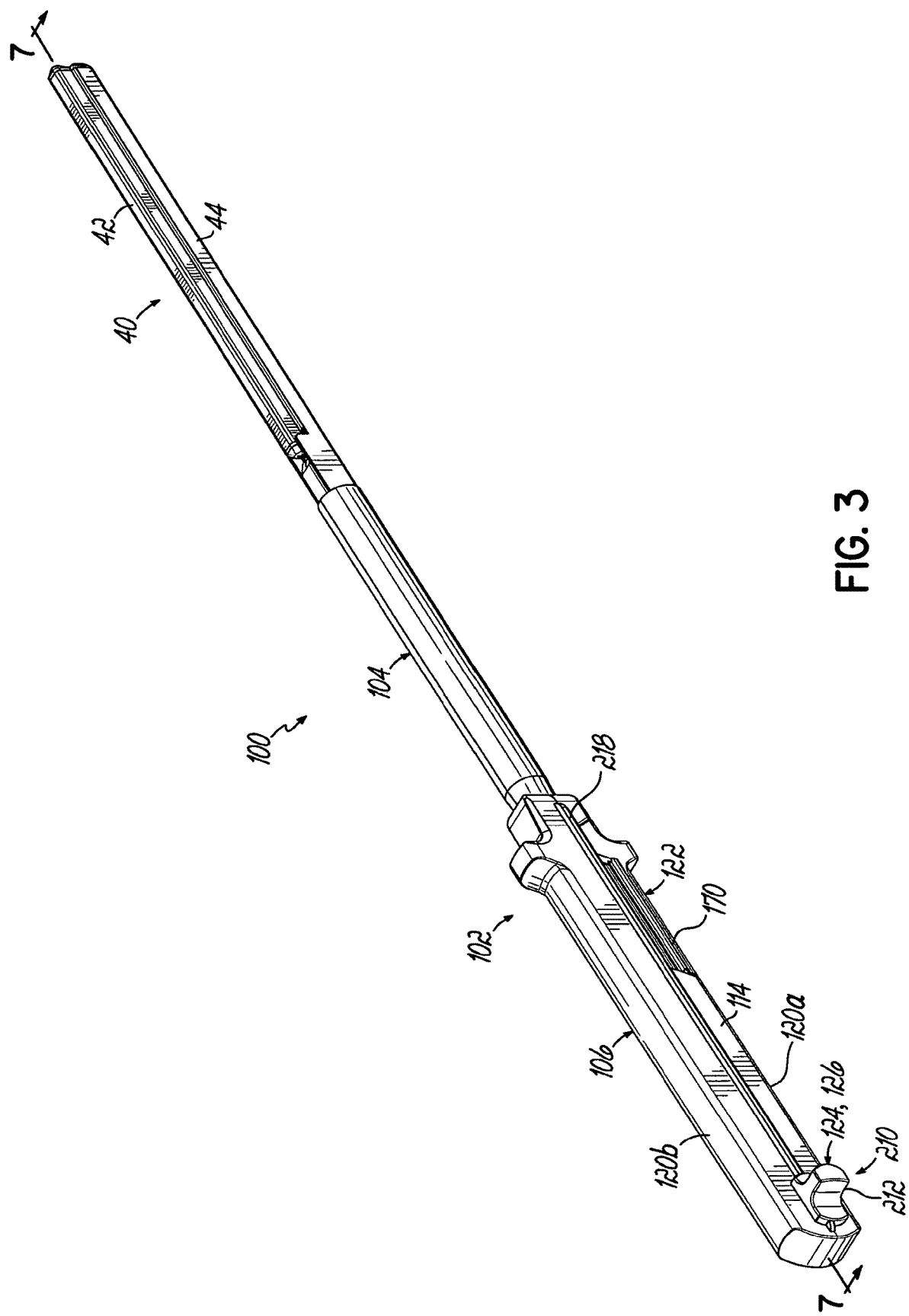
FIG. 3 is a perspective view of an endocutter stapling device according to one embodiment of the invention.
Figure 4:
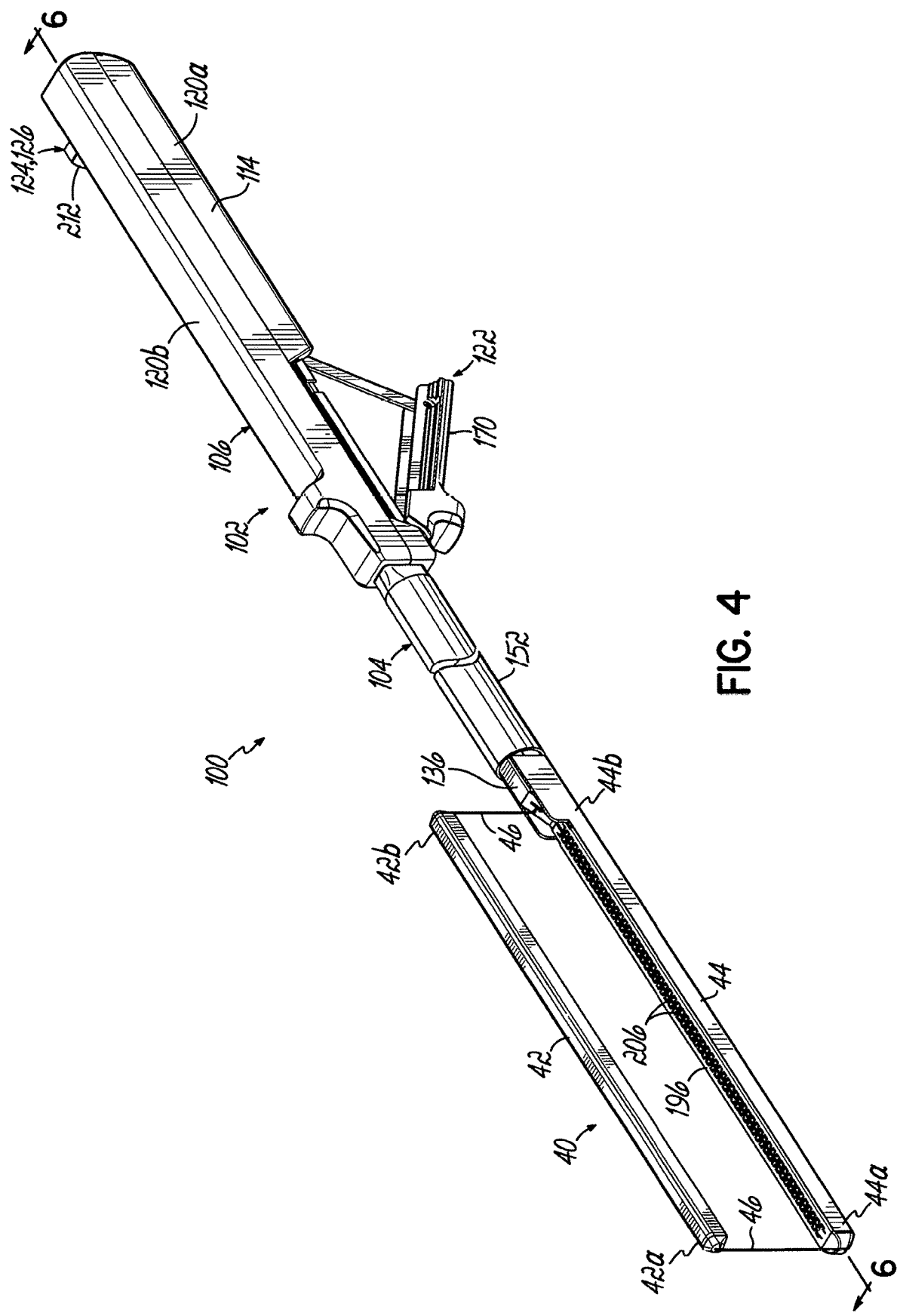
FIG. 4 is a perspective view of the endocutter stapling device of FIG. 3 with an end effector shown in an opened position.
Figure 4A:
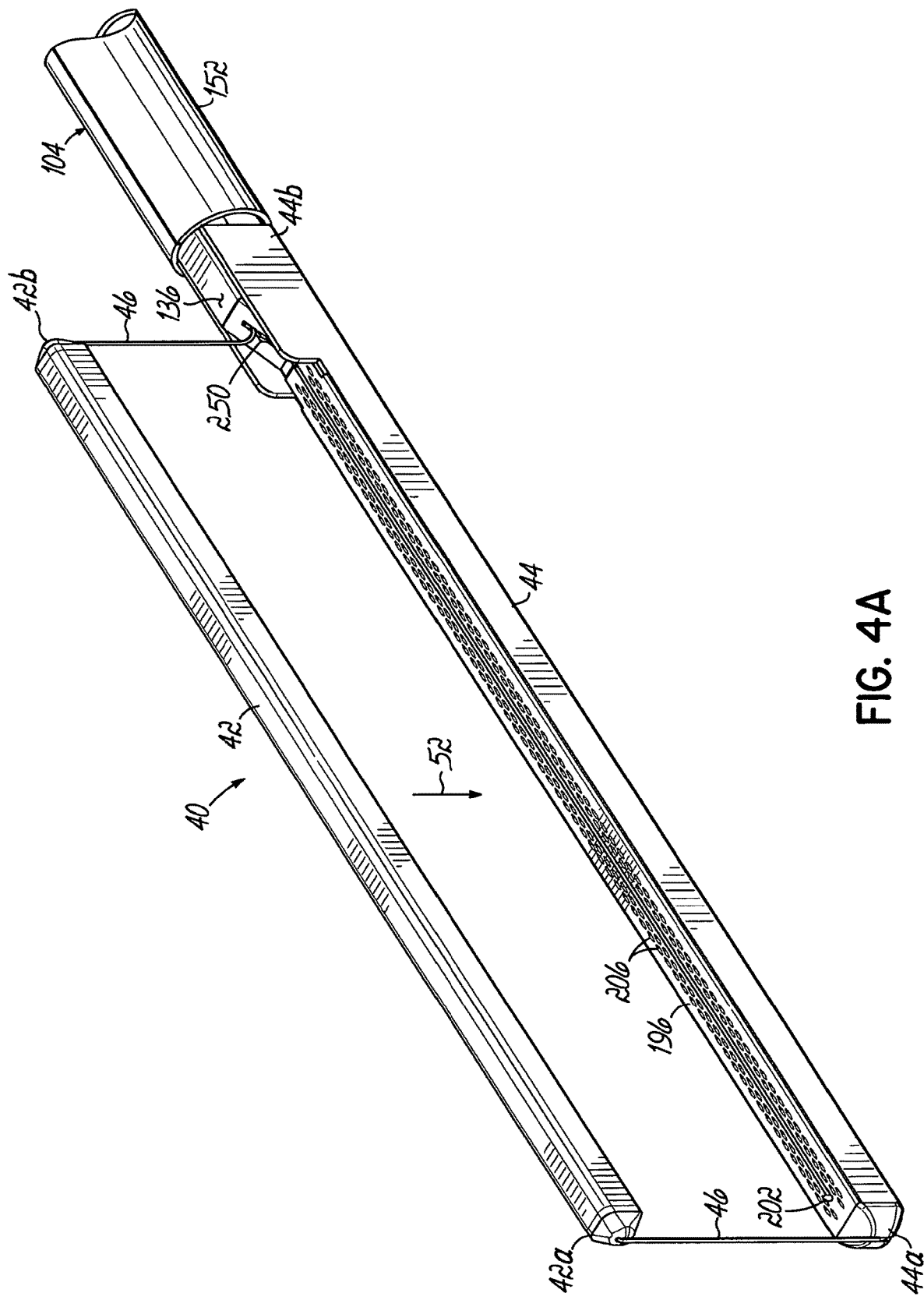
FIG. 4A is an enlarged perspective view of the end effector shown in FIG. 4.

With reference to FIGS. 3, 4, and 4A, the anvil 42 and the cartridge 44 are movably coupled together via the flexible member 46 as is described above. The flexible member 46 passes through hollow portions of the anvil 42 and the cartridge 44 and is movable relative to one or both of the anvil 42 and the cartridge 44. The flexible member 46 may be anchored to one of the anvil 42 or the cartridge 44, as is described below. In the exemplary embodiment shown, the anvil 42 may be separated from or brought closer to the cartridge 44 by extending or retracting the flexible member 46. Retraction of the flexible member 46 moves the anvil 42 toward the cartridge 44 as is shown generally by arrow 52 in FIG. 4A.

Figure 5:
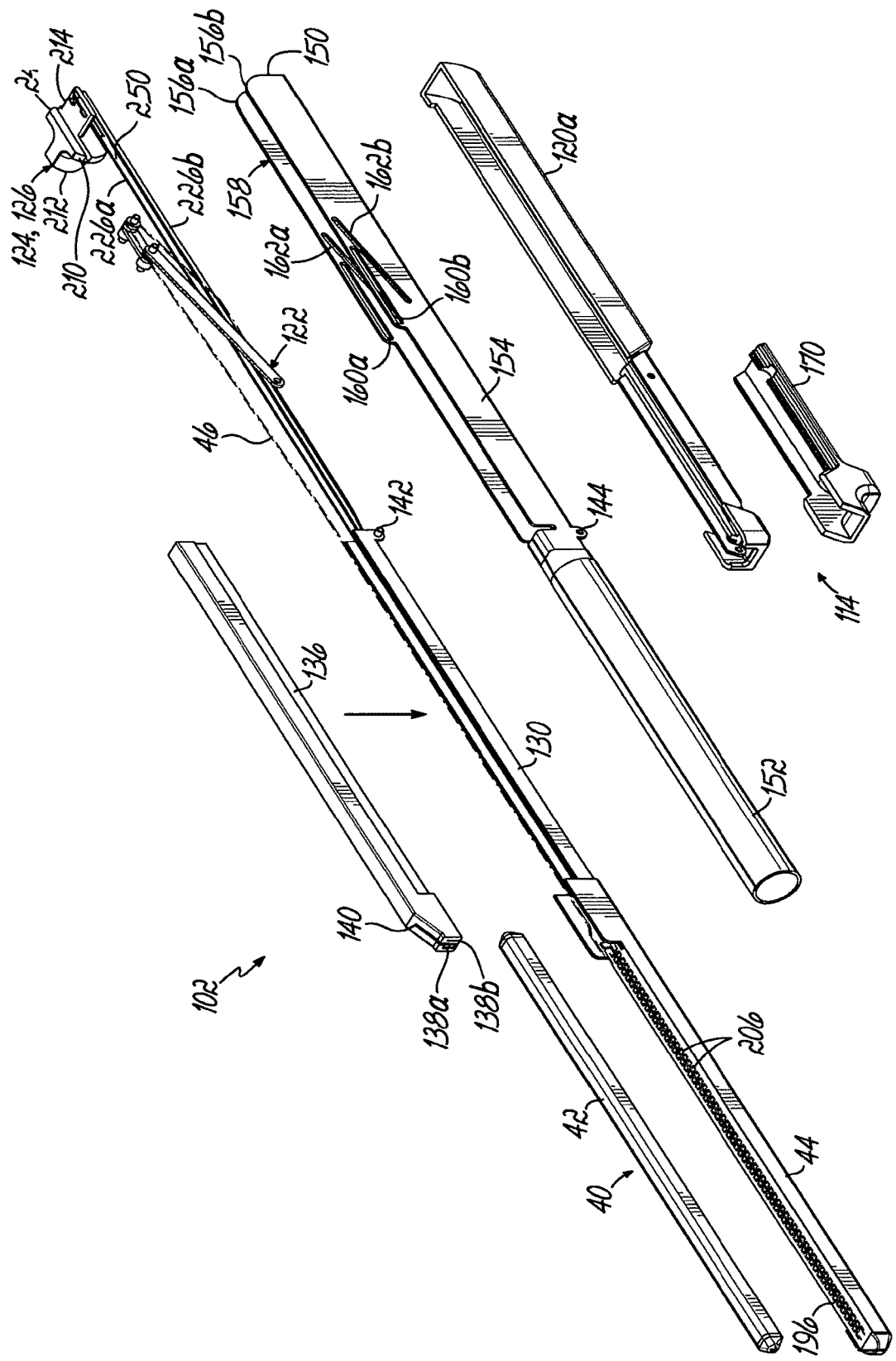
FIG. 5 is a disassembled perspective view of the endocutter stapling device of FIG. 3.

In this regard, in the exemplary embodiment shown in FIGS. 4-6, the flexible member 46 extends from the shaft 104 into the cartridge 44 at a proximal end 44b and ultimately couples the anvil 42 to the cartridge 44. While numerous pathways for the flexible member 46 are described below with reference to at least FIGS. 21-35, in the exemplary embodiment, the flexible member 46 passes from the cartridge 44 and is coupled to the anvil 42 adjacent each of a distal end 42a and a proximal end 42b thereof and may be anchored within the anvil 42 by anchors 110 and 112 (shown in FIG. 6).

Retraction of the flexible member 46 from the end effector 40 (and into the manipulator 102 described below) therefore moves at least one of the anvil 42 and/or the cartridge 44 as is shown generally by the arrow 52 in FIG. 6. It will be appreciated that because the flexible member 46 is anchored to the anvil 42 (e.g., proximate each of the distal end 42a and the proximal end 42b), retraction of the flexible member 46 produces a substantially symmetrical closing force on tissue situated between the anvil 42 and the cartridge 44. This configuration, with connectivity between the anvil 42 and the cartridge 44 at each end of the end effector 40, is advantageous.

In this regard, in embodiments in which the anvil 42 and/or the cartridge 44 are sufficiently rigid at pressures encountered during a surgical procedure, the clamping force may be more symmetrical and uniformly distributed along the length of the anvil 42 and the cartridge 44. Thus, the tissue situated between the anvil 42 and the cartridge 44 may be more uniformly compressed. It will be appreciated that even though there may be more uniform compression on the tissue, the anvil 42 and the cartridge 44 may not be parallel to one another in the clamped position because the tissue may not be uniformly thick. Nevertheless, there may be uniformity in applied pressure. This may be unlike prior art devices in which clamping members are attached together at a single, hinge-like location and have a jaw-like motion, rather than a vice-like motion. With a single connection, the end of the clamp member most distant from the connection may deflect. As a result of the deflection, the clamp member may not apply uniform, symmetrical compression to the tissue along its length. According to embodiments of the invention, producing a substantially uniformly applied clamping pressure on the organ may enhance the formation of the resection line following stapling and cutting.

With reference to FIGS. 3, 4, 5, and 6, in one embodiment, the handpiece 106 includes a main body 114 with housing halves 120a, 120b. When assembled, the housing halves 120a, 120b enclose control features by which the surgeon may operate clamping of the anvil 42 and the cartridge 44 on tissue and stapling and cutting of the stomach 10. In that regard, the manipulator 102 includes a clamping mechanism 122 for applying tension to the flexible member 46, a stapling mechanism 124 for stapling the tissue captured between the anvil 42 and the cartridge 44, and a cutting mechanism 126 for cutting the tissue. Each of these mechanisms is described below. Thus, in one aspect, the surgeon may operate the clamping mechanism 122 to control the extension and retraction of the flexible member 46 from the end effector 40. In another aspect, the surgeon may actuate the stapling mechanism 124 to fire staples and actuate the cutting mechanism 126 to cut tissue.

To these and other ends, with continued reference to FIG. 5, the manipulator 102 includes a support 130 having a U-shaped cross-section coupled to the end effector 40 at a proximal end. A guide beam 136 of about the same length as the support 130 reinforces the support 130 and may include three channels 138a, 138b, and 140 that may receive portions of each of the stapling mechanism 124, the cutting mechanism 126, and the clamping mechanism 122. While each of these mechanisms is described herein with respect to one or more embodiments, embodiments of the present invention may omit the cutting mechanism 126, in which case, the device may be referred to as a stapling device.

In the embodiment shown, the manipulator 102 further includes a frame 150 having a shaft portion 152 and a handpiece portion 154. The shaft portion 152 may have a tubular configuration, for example, a right circular tubular configuration and may enclose the support 130 and the guide beam 136 when the manipulator 102 is assembled. The support 130 may be configured to receive a pin 142 that cooperates with a corresponding bore 144 in the shaft portion 152 to secure the support to the frame 150.

The handpiece portion 154 of the frame 150 includes opposing flanges 156a, 156b defining a channel 158. Each of the flanges 156a, 156b includes one or more slots that guide a portion of the clamping mechanism 122, described below. In the embodiment shown, each flange 156a, 156b includes two pairs of slots 160a, 160b, 162a, 162b. The pair of slots 160a, 162a on the flange 156a is a mirror image of the pair of slots 160b, 162b on the flange 156b. As shown, each of the slots 160a, 160b is elongated in a direction generally parallel with the longitudinal axis of the manipulator 102. The slots 162a, 162b are also elongated but are angled with respect to the longitudinal axis of manipulator 102 and angled relative to the slots 160a, 160b.

The clamping mechanism 122 includes a lever 170 pivotably coupled between the housing halves 120a, 120b for manipulating the flexible member 46. With reference to FIGS. 6 and 7, the surgeon may squeeze the lever 170 by which motion the flexible member 46 is withdrawn from the end effector 40. As is described above, withdrawing or pulling the flexible member 46 from the end effector 40 draws the anvil 42 toward the cartridge 44 and may tension the flexible member 46 when the anvil 42 and the cartridge 44 meet resistance to movement. By applying a force to the flexible member 46, the anvil 42 and the cartridge 44 may be moved toward one another (as is indicated by arrow 52) and may also apply a clamping force to tissue situated between the anvil 42 and the cartridge 44. It will be appreciated that the surgeon may operate the lever 170 with one or more fingers during operation of the endocutter stapling device 100 between a disengaged position (e.g., FIGS. 3 and 6) in which the clamping mechanism 122 does not restrict movement of the flexible member 46 and an engaged position (e.g., FIGS. 4 and 7) in which the clamping mechanism 122 contacts the flexible member 46.

To that end, the clamping mechanism 122 further includes a push bar 164 pivotably coupled to the lever 170 by a pin 166 at one end thereof. The push bar 164 extends from outside the housing half 120a, where it is pivotally attached to the lever 170 by the pin 166, into the channel 158 through a slot (unlabeled) in the handpiece portion 154 of the frame 150. The push bar 164 is pivotally coupled to a push bar 174 by a pin 172. The pin 172 extends through the push bar 164 at one end thereof across the channel 158 and is slidably received in each of the slots 160a, 160b (FIG. 5). The push bar 174 is coupled to a second pin 176 at the opposing end of the bar 174 from the pin 172. The pin 176 is slidably received in each of the slots 162a, 162b (FIG. 5). The pins 172 and 176 interact with the flexible member 46 when the surgeon squeezes the lever 170. By way of example only, and not limitation, one or both of the pins 172 and 176 may be coupled to a sheave (not shown), which slidably receives the flexible member 46, to guide the flexible member 46 during motion of the clamping mechanism 122.

With continued reference to FIG. 6, the flexible member 46 extends between the flanges 156a, 156b and is looped over the pin 172 and the pin 176 (e.g., in sheaves on each pin 172, 176). In the exemplary embodiment, an additional pin 178 may extend across the channel 158 in fixed relation to the frame 150. The pin 178 may be positioned at a location that maintains the flexible member 46 in alignment with the shaft 104. In other words, the pin 178 may be configured to align the flexible member 46 with the shaft 104 independent of the position of the pins 172, 176 as the pins 172, 176 slide in relation to the slots 160a, 160b, 162a, 162b. Thus, while the flexible member 46 may move in response to actuation of the clamping mechanism 122 along each of the pins 172, 176, the additional pin 178 may maintain alignment of the flexible member 46 with the longitudinal axis of the manipulator 102.

Figure 6A:
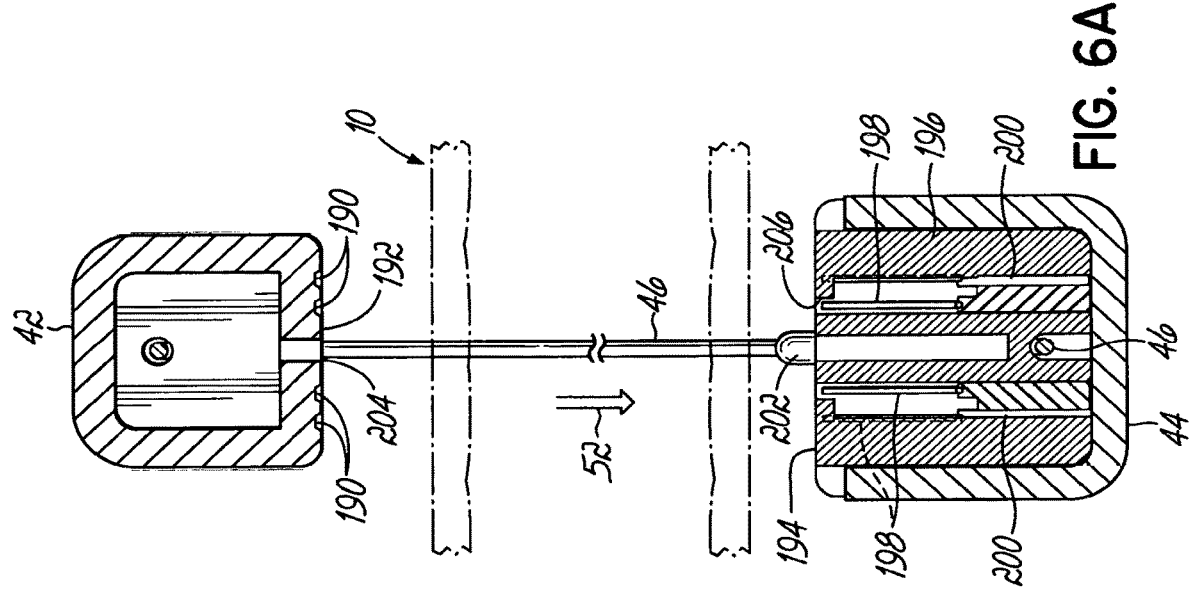
FIG. 6A is a cross-sectional view of the end effector shown in FIG. 6 taken along section line 6A-6A.

With reference to FIGS. 6 and 6A, depression of the clamping lever 170 toward the housing half 120a in the direction of the arrow 180 in FIG. 6 may cause movement of each of the push bars 164, 174 generally away from the end effector 40 in the direction of the longitudinal axis of the handpiece 106. Specifically, as is shown in FIG. 6, the push bars 164, 174 initially have a generally L-shaped arrangement when the lever 170 is extended from the handpiece 106. In this disengaged position of the lever 170, the anvil 42 is spaced apart from the cartridge 44, as is shown in FIGS. 6 and 6A. As the lever 170 is compressed towards the handpiece 106 (according to the arrow 180), the push bar 164 pushes the pin 172 along the slots 160a, 160b (according to the arrow 184). This movement also simultaneously forces the push bar 174 along the longitudinal axis of the manipulator 102 as guided by the pin 172 in the slots 162a, 162b (according to the arrow 186). The pins 172, 176 carry the flexible member 46 in the same direction away from the end effector 40. Overall, the flexible member 46 is withdrawn from the end effector 40 resulting in movement of the anvil 42 toward the cartridge 44.

Figure 7A:
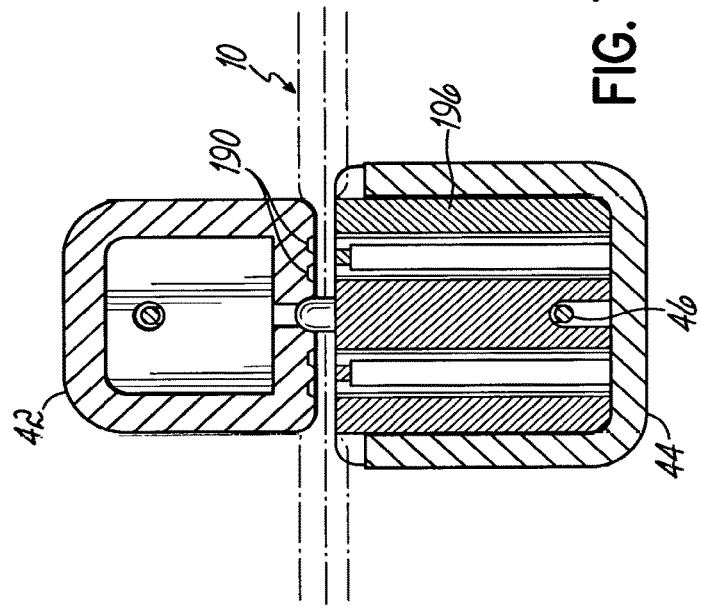
FIG. 7A is a cross-sectional view of the endocutter stapling device taken along section line 7A-7A in FIG. 7.

Compression of the lever 170 into the engaged position results in the configuration of the endocutter stapling device 100 shown in FIGS. 7 and 7A, in which the push bars 164, 174 are generally aligned with respect to one another and the anvil 42 and cartridge 44 are compressed onto the stomach 10. In the generally aligned configuration between the push bars 164, 174, the path around which the flexible member 46 extends is lengthened relative to the L-shaped arrangement shown in FIG. 6. By lengthening the path, the flexible member 46 is carried rearwardly within the handpiece 106 during actuation of lever 170. This results in a corresponding withdrawal of the flexible member 46 from the end effector 40. Accordingly, the compression of the lever 170 toward the housing half 120a pulls the anvil 42 towards the cartridge 44 as is indicated by arrow 52 in FIG. 7. This motion may result in compression of the stomach 10 between the anvil 42 and the cartridge 44, as is shown in FIG. 7A. In one embodiment, the surgeon may use a variable gripping force on the lever 170 to effectuate the first stage of compression. In this regard, the surgeon may approximate a first stage gripping force on the clamping mechanism 122 where the tissue is still slidable between the anvil 42 and the cartridge 44. This is useful in positioning the end effector around an anatomical structure, such as the stomach, where both anterior and posterior halves of the anatomical structure must be managed. This is especially useful in a procedure such as a sleeve gastrectomy where the surgeon desires to create the resultant stomach pouch using equal amounts of anterior and posterior stomach. By way of example and not limitation, the clamping mechanism 122 may be capable of tensioning the flexible member 46 to about 200 lb at each end of the anvil 42. This may provide a clamping pressure of over 100 psi. Specifically, in an exemplary embodiment, the anvil 42 and the cartridge 44 may have a length of about 250 mm and a width of about 10 mm providing a surface area of about 25 cm$^2$. With 400 lb of total tension on the flexible member 46 (i.e., 200 lb on each side), the total compression pressure may be about 103 psi. At these pressures, the clamping mechanism 122 squeezes tissue fluid out of the stomach and thereby approves staple line integrity.

With reference now to FIG. 6A, in one embodiment, the anvil 42 includes a plurality of staple pockets 190 along a face 192 of the anvil 42. The cartridge 44 includes a face 194 that opposes the face 192 of the anvil 42. Each of the faces 192, 194 is configured to sandwich the stomach 10 therebetween. A cartridge body 196 may at least partially enclose the cartridge 44. The staple pockets 190 in the face 192 generally align and correspond to a plurality of staples 198 and a plurality of staple drivers 200 that are housed in a plurality of staple channels 206 in the cartridge 44. The staples 198 are configured to be forced through the stomach 10 and be deformed by the staple pockets 190. It will be appreciated that deforming the staples 198 into a B-shaped configuration secures opposing sides of the stomach 10 together.

In one embodiment, to facilitate alignment between the anvil 42 and the cartridge 44, and in particular, alignment between the staples 198 and the staple pockets 190, an alignment pin 202 may extend beyond the face 192 at the distal end 42a of the anvil 42 or the face 194 at the distal end 44a of the cartridge 44. The other face 192, 194 of the anvil 42 or the cartridge 44 includes a mating recess 204. Once the lever 170 is compressed, the flexible member 46 is pulled into the handpiece 106 by the clamping mechanism 122 as described above. This motion pulls the anvil 42 toward the cartridge 44 and the alignment pin 202 in conjunction with the recess 204 to facilitate proper alignment between the anvil 42 and the cartridge 44 to align the staples 198 with a corresponding pocket 190. With reference to FIG. 7A, the anvil 42 and the cartridge 44 are shown to compress the stomach 10 between the face 192 of the anvil 42 and the face 194 of the cartridge 44 with the alignment pin 202 being received in the mating recess 204. In another aspect of the present invention, once the lever 170 is compressed, as is shown in FIG. 7, with the anvil 42 and the cartridge 44 compressing the stomach 10 therebetween, the surgeon may staple and cut the stomach 10 along the resection line 12 (FIG. 1). To staple the stomach 10, the surgeon activates the stapling mechanism 124.

In that regard and with reference to FIGS. 3, 8, and 9, the stapling mechanism 124 includes a staple actuator 210 having a thumb tab 212. The staple actuator 210 further includes an actuator plate 214 that is coupled to the thumb tab 212. The actuator plate 214 is slidably received in a slot 218 (FIG. 3) formed between the housing halves 120a, 120b and is movable relative to the handpiece 106 as is indicated by the arrow 232 in FIGS. 8 and 9. The actuator plate 214 includes slots 222a, 222b spaced apart from an elongated slot 224. In the embodiment shown, the slots 222a, 222b each receive a wedge push bar 226a, 226b, respectively. As is shown in FIGS. 5 and 10, the wedge push bars 226a, 226b are elongated members that extend generally along the length of the handpiece 106 and through the shaft 104 and terminate proximate the end effector 40. The wedge push bars 226a, 226b are slidably received in corresponding channels 138a, 138b of the guide beam 136 and are positioned to slide into engagement with the staples 198 and the staple drivers 200 in the cartridge 44.

Figure 11A:
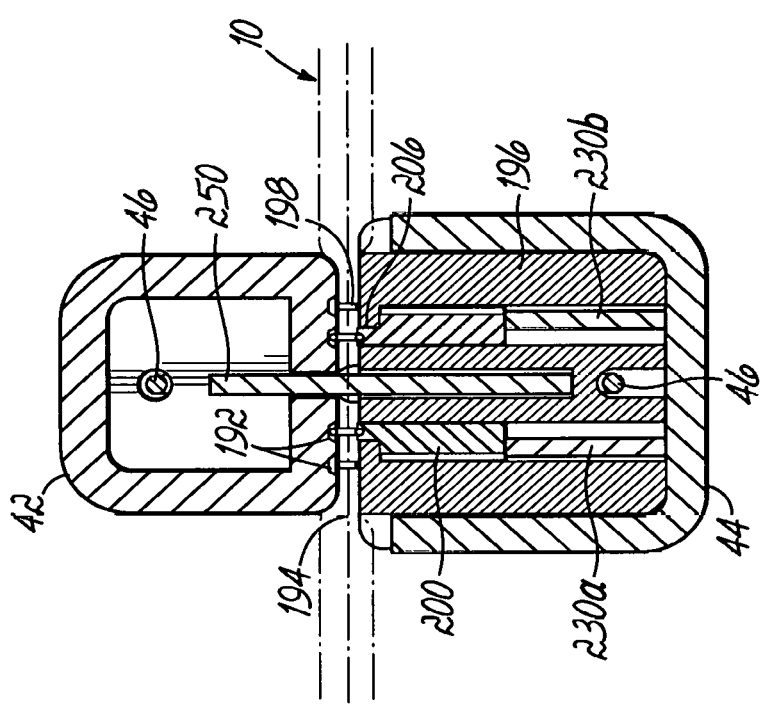
FIG. 11A is a cross-sectional view of the endocutter stapling device taken along section line 11A-11A in FIG. 11.
Figure 13:
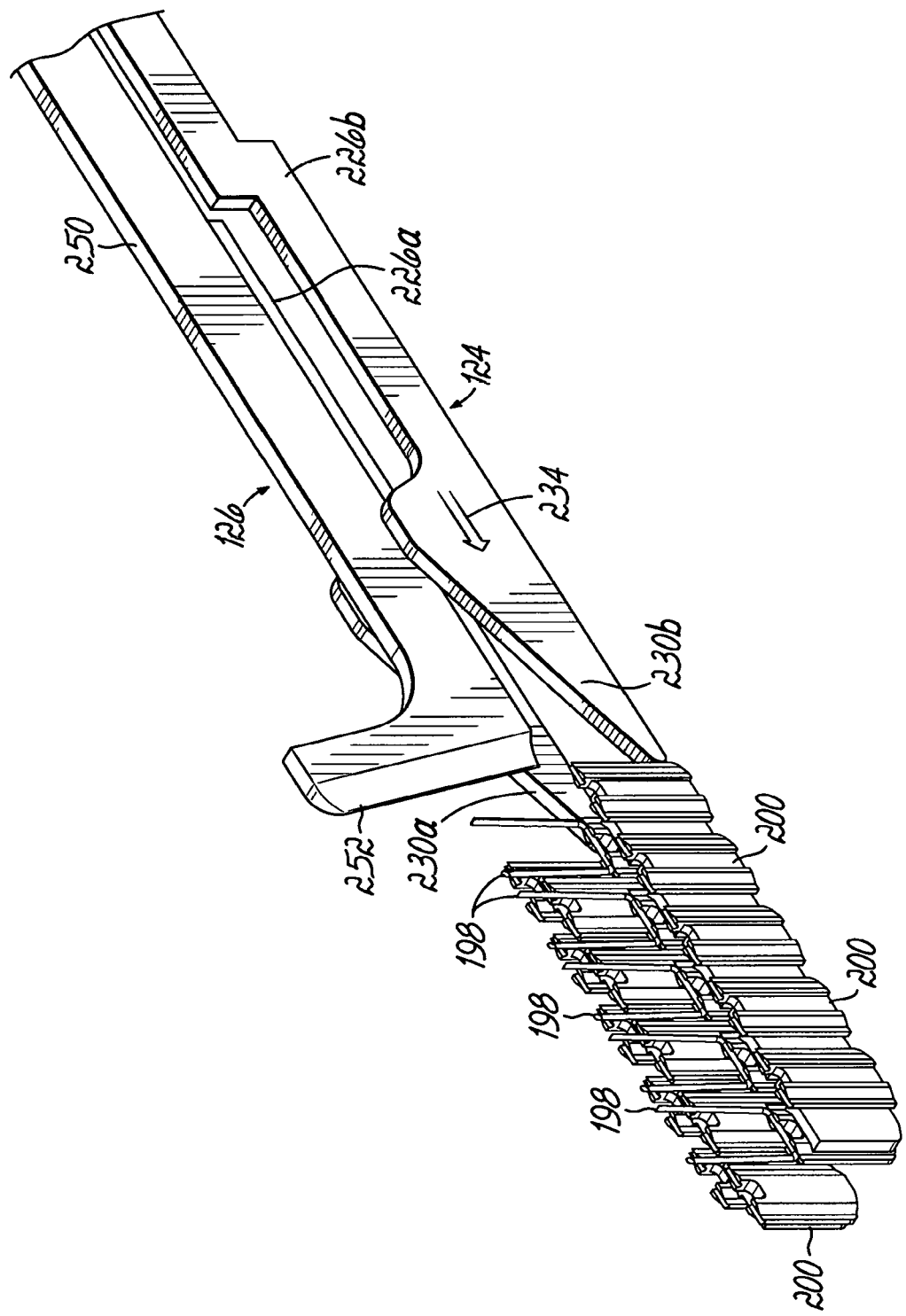
FIG. 13 is a perspective view of a knife and a pair of wedges of the endocutter stapling device of FIG. 3.
Figure 14:
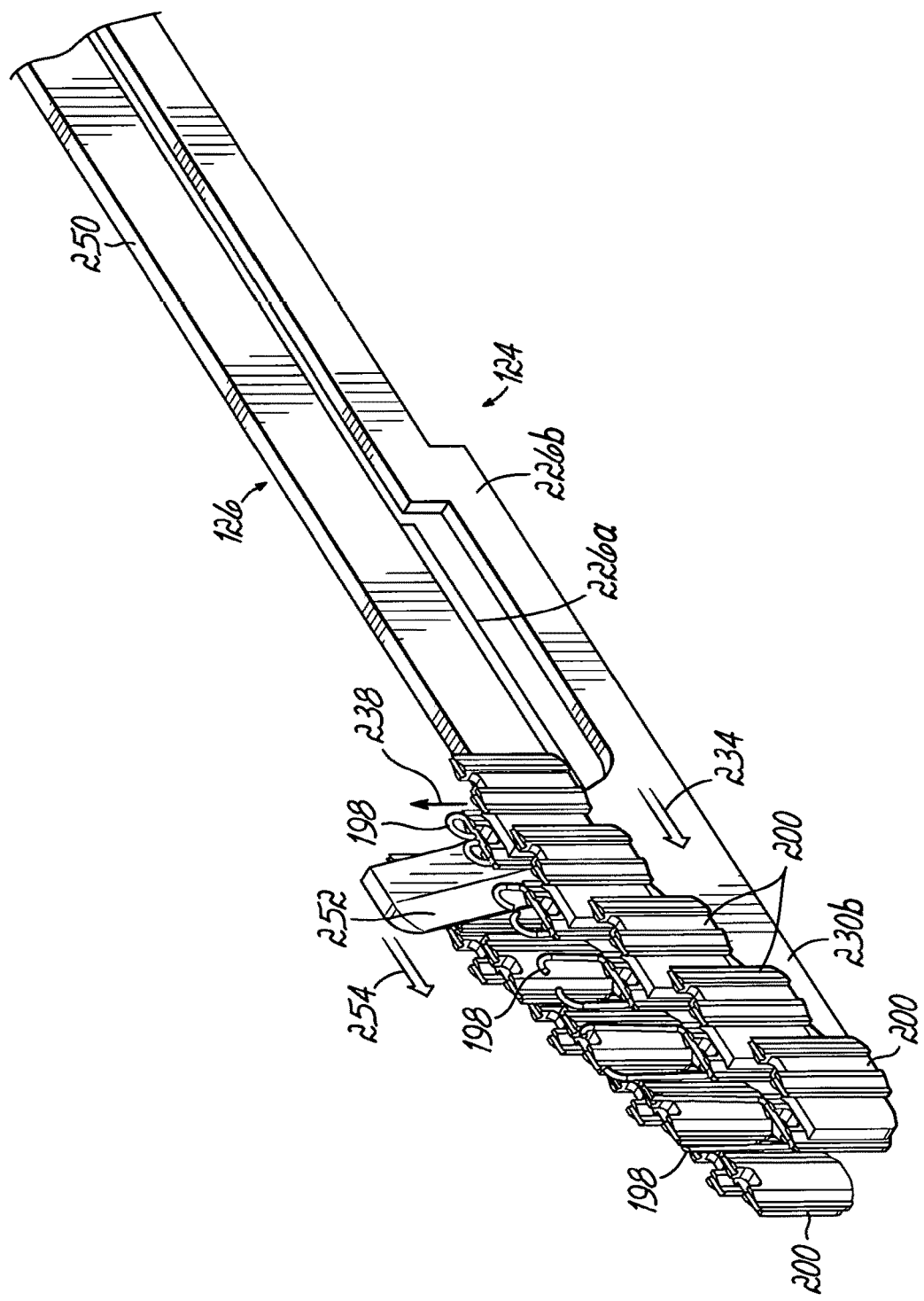
FIG. 14 is a perspective view of the knife and the pair of wedges shown in FIG. 13 during use of the endocutter stapling device.

In one embodiment, shown in FIGS. 10 and 11, each wedge push bar 226a, 226b terminates in a wedge tip 230a, 230b which, prior to activation of the stapling mechanism 124, is positioned to engage respective rows of the staple drivers 200 in the cartridge 44. The wedge tips 230a, 230b have a wedge-shaped configuration and, during a sliding motion through the end effector 40, are configured to force the staple drivers 200 toward the anvil 42 and drive the corresponding staples 198 through the compressed stomach 10 and into contact with the corresponding staple pockets 190 of the anvil 42. As shown best in FIGS. 11 and 12, the shape of the wedge tips 230a, 230b forces the staples 198 into contact with the staple pockets 190 of the anvil 42 with sufficient force to deform the staples 198 and produce a B-shaped staple.

In one embodiment, the surgeon activates the stapling mechanism 124 by pushing the thumb tab 212 in the direction of the end effector 40 as is indicated by the arrow 232 in FIGS. 8 and 9. Pushing the thumb tab 212 slides each of the wedge push bars 226a, 226b and the corresponding wedge tips 230a, 230b in the direction of the end effector 40. Specifically, and with reference now to FIGS. 10-14, pushing the thumb tab 212 (FIG. 8) moves the wedge push bars 226a, 226b in the direction of the arrow 234. The wedge tip 230a engages the staple drivers 200 in sequence and thereby forces the staples 198 into the corresponding staple pockets 190 on the anvil face 192 as is indicated by the arrows 238.

In another aspect of the present invention, the surgeon may cut the stomach 10 along the resection line 12 following stapling, described above. In one embodiment and with reference to FIG. 5, to cut the stomach 10, the surgeon activates the cutting mechanism 126. The cutting mechanism 126 includes a knife actuator 248 including the thumb tab 212 coupled to the actuator plate 214. As described above and with reference to FIGS. 8 and 9, the actuator plate 214 is slidably received in the slot 218 formed between the housing halves 120a, 120b and is movable relative to the handpiece 106 in a direction that is indicated by the arrow 232 in FIGS. 8 and 9.

With reference to FIGS. 8-14, in one embodiment, the cutting mechanism 126 includes the elongated slot 224 in the actuator plate 214. A knife push bar 250 is slidably engaged in the elongated slot 224 and may be an elongated member extending from the actuator plate 214 through the handpiece 106 and the shaft 104 to a location adjacent the end effector 40. In that regard, the knife push bar 250 is slidably received in the channel 140 of the guide beam 136 and terminates in a cutting edge 252 proximate the end effector 40 (shown best in FIGS. 11 and 12). As can be appreciated by FIGS. 5, 13, and 14, the knife push bar 250 lies in between the wedge push bars 226a, 226b.

In one embodiment, the surgeon activates the cutting mechanism 126 by pushing the thumb tab 212 in the direction of the end effector 40 as is indicated by the arrow 232 in FIGS. 8 and 10. Pushing the thumb tab 212 slides the knife push bar 250 via the actuator plate 214 and pushes the corresponding cutting edge 252 in the direction of the end effector 40. Specifically, and with reference now to FIGS. 10-12, pushing the thumb tab 212 moves the cutting edge 252 in the direction of the arrow 254 (FIG. 11) along the longitudinal axis of the endocutter stapling device 100. Although not shown, the cutting edge 252 cuts the stomach that may be sandwiched between the anvil 42 and the cartridge 44.

In one embodiment, and with reference to FIGS. 8 and 9, the thumb tab 212 may activate each of the stapling mechanism 124 and the cutting mechanism 126. As is described above, the actuator plate 214 captures each of the wedge push bars 226a, 226b and the knife push bar 250 in slots 222a, 222b and elongated slot 224, respectively. In one embodiment, even though the actuator plate 214 is operably coupled to each of the wedge push bars 226a, 226b and the knife push bar 250, engagement of the stapling mechanism 124 occurs prior to actuation of the cutting mechanism 126. In other words, the stapling mechanism 124 engages prior to engagement of the cutting mechanism 126. The elongated slot 224 in the actuator plate 214 is oversized relative to the portion of the knife push bar 250 that is engaged with it. This configuration results in sliding space between the slot 224 and the knife push bar 250. The knife push bar 250 therefore slides relative to the actuator plate 214 during initial movement of the plate 214. The length of the movement of the actuator plate 214 without movement of the knife push bar 250 is predetermined.

The elongated slot 224 is also longer than each of the slots 222a, 222b. Because the knife push bar 250 is slidably received in the elongated slot 224, the initial movement of the actuator plate 214 in the direction of arrow 232 in FIG. 8 causes each of the wedge push bars 226a, 226b to move in direct relation to the movement of the actuator plate 214. The movement of the knife push bar 250 is however delayed relative to the movement of the wedge push bars 226a, 226b. This means that there is a delay between activation of the stapling mechanism 124 and the cutting mechanism 126. This delay is proportional to the free sliding space between the elongated slot 224 and the knife push bar 250. When the surgeon pushes the thumb tab 212 in the direction of the arrow 232 in FIG. 8, the actuator plate 214 moves in the same direction and carries the wedge push bars 226a and 226b with it. The knife push bar 250 does not initially move. Instead, the actuator plate 214 must move a predetermined distance corresponding to the free sliding space in the direction of the end effector 40 before the actuator plate 214 engages the knife push bar 250. This is shown by way of comparison between FIGS. 8 and 9. In FIG. 8, the actuator plate 214 has not engaged the knife push bar 250. In FIG. 9, the actuator plate 214 has moved a distance at least equivalent to the free sliding space and so the actuator plate 214 engages the knife push bar 250. This delay in movement between the wedge push bars 226a, 226b and the knife push bar 250 results in a difference in activation time between the stapling mechanism 124 and the cutting mechanism 126. In this manner, in one embodiment, activation of the stapling mechanism 124 precedes activation of the cutting mechanism 126.

Once the surgeon activates each of the stapling mechanism 124 and the cutting mechanism 126 by pushing on the thumb tab 212, stapling and cutting may occur substantially simultaneously. By way of example only, the stapling of the stomach 10 may precede the cutting of the stomach 10. That is, after an initial delay between stapling and cutting, during which the stapling mechanism 124 is activated, both of the stapling mechanism 124 and the cutting mechanism 126 are active. The surgeon may continue stapling and cutting the stomach 10 by continuing to push on the thumb tab 212 until the thumb tab 212 reaches the end of its stroke. It will be appreciated that the stroke of the thumb tab 212 may be greater than the overall length of the stomach 10. Further, the stroke of the thumb tab 212 may be approximately equal to the length of the end effector 40. At this point, the wedge tip 230a, 230b may be proximate the distal end 42a, 44a of the end effector 40. The end effector 40 and the shaft 104 may then be removed from the abdominal cavity with the stomach 10 having the configuration shown in, for example, FIG. 2E.

While embodiments of the present invention are shown and described as cutting the stomach 10, embodiments of the present invention are not limited to those that both cut and staple the stomach. It may be preferable to staple without cutting in some instances. Accordingly, the staple line may be applied to the whole stomach or only a portion thereof without cutting the stomach. Resection may be performed with a separate device, such as, with a tissue welding device (e.g., a bipolar vessel sealing and cutting device). In this situation, the end effector 40 may remain clamped to the stomach 10 while the surgeon uses the separate device. The end effector 40 may be used to guide the separate device during resection.

In one embodiment and with reference now to FIGS. 15-19 in which like reference numerals refer to like elements in FIGS. 3-14, the surgeon may operate the end effector 40 above, including one or both of the anvil 42 and the cartridge 44, during a vertical sleeve gastrectomy procedure with an endocutter stapling device 300 that includes the end effector 40 operatively coupled to a manipulator 302. As shown, the manipulator 302 includes an elongate member or shaft 304 coupled to a handpiece 306 at one end and the end effector 40 at the other end thereof. During a surgical procedure, the end effector 40 and a portion of the shaft 304 may be inserted into an abdominal cavity of the patient, such as, via a trocar. The surgeon may then manipulate the end effector 40 and/or articulate the end effector 40 relative to the manipulator 302 to perform a procedure. As described above, the procedure may include clamping, stapling, and cutting a stomach or other tissue. Thus, embodiments of the present invention may include mechanisms to effectuate a surgical procedure with the end effector 40 and may allow the end effector 40 to articulate relative to the shaft 304.

Figure 15:
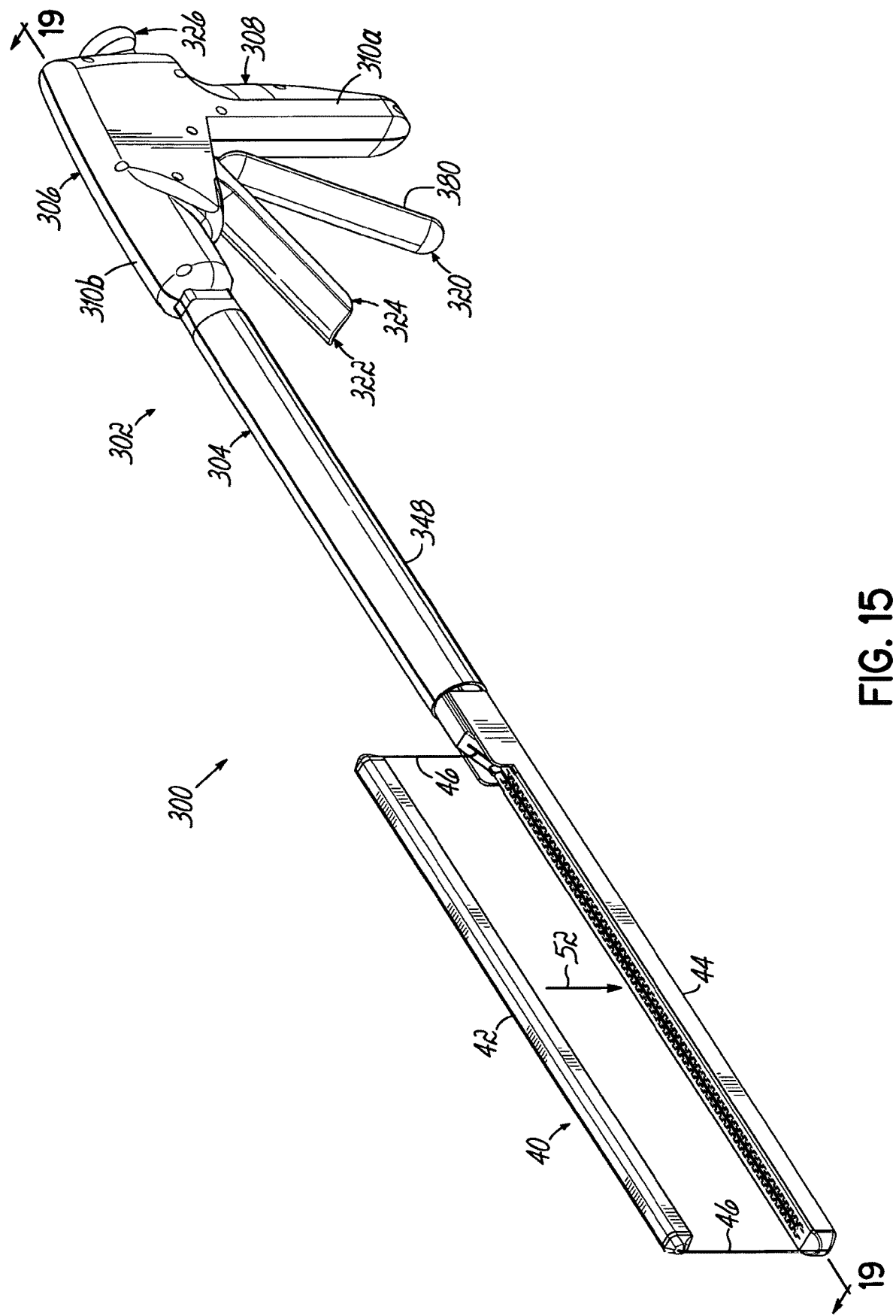
FIG. 15 is a perspective view of an endocutter stapling device according to one embodiment of the invention.
Figure 16:
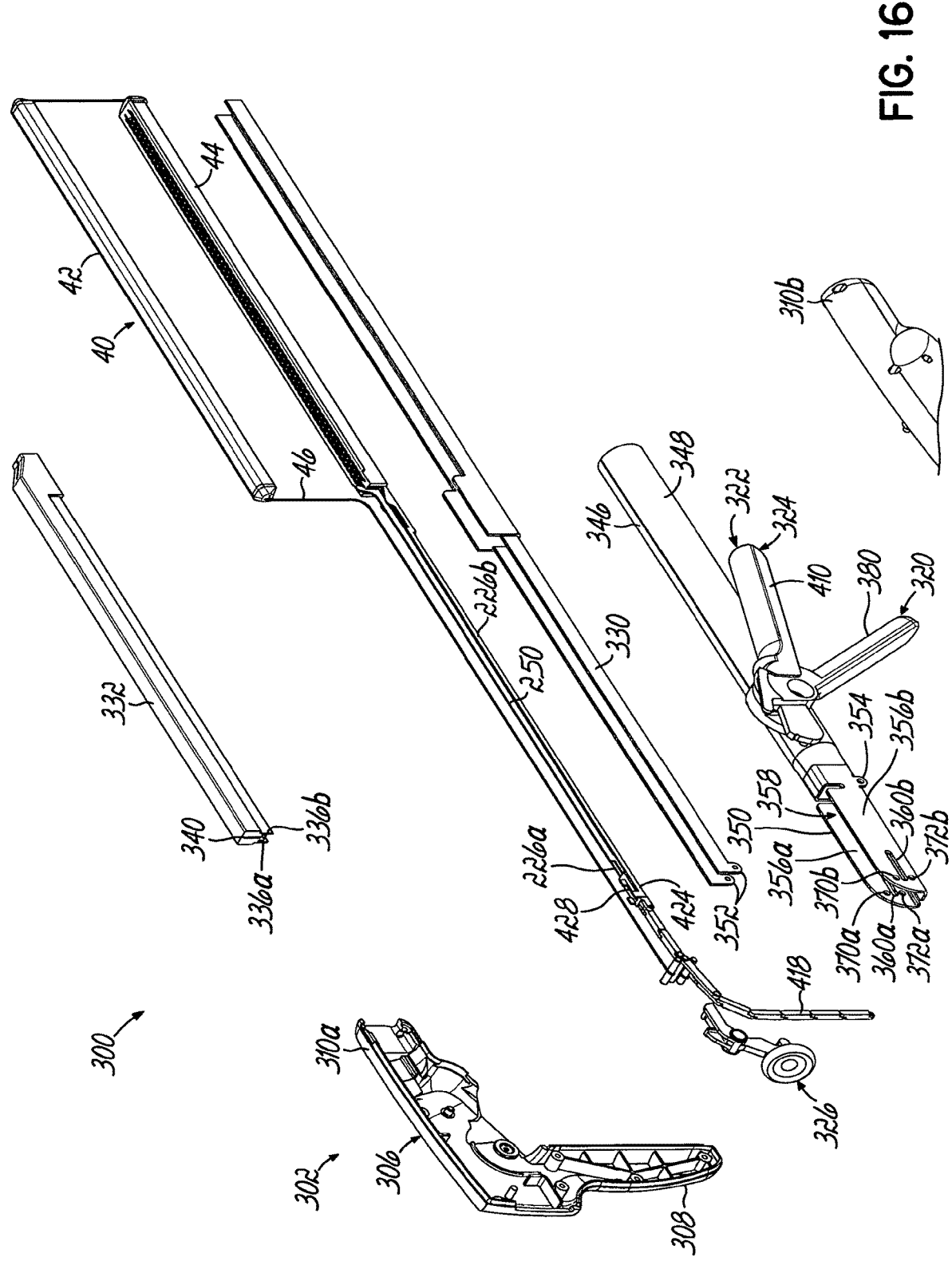
FIG. 16 is a disassembled perspective view of the endocutter stapling device shown in FIG. 15.

With reference to FIGS. 15 and 16, the anvil 42 and the cartridge 44 of the end effector 40 are movably coupled together via the flexible member 46 similar to that described above and further below. In one embodiment, the manipulator 302 includes a main body 308 having housing halves 310a and 310b which produce a pistol-grip like handle. When assembled, the housing halves 310a, 310b enclose control features by which the surgeon may operate the end effector 40 to perform the medical procedure. For example, the surgeon may open and close the anvil 42 and the cartridge 44 and staple and/or cut the stomach 10.

In that regard, the manipulator 302 includes a clamping mechanism 320 for applying tension to the flexible member 46, a stapling mechanism 322 for stapling the tissue captured between the anvil 42 and the cartridge 44, and a cutting mechanism 324 for cutting the tissue captured between the anvil 42 and the cartridge 44. Further, the main body 308 may include a locking mechanism 326 for locking the clamping mechanism 320 in an engaged position. Each of these mechanisms is described below. Thus, according to one aspect, the surgeon may operate the clamping mechanism 320 to control the retraction of the flexible member 46 from the end effector 40 and lock the end effector 40 in an engaged position, and according to another aspect, the surgeon may actuate the stapling mechanism 322 to fire staples and actuate the cutting mechanism 324 to cut tissue, as is described below.

To those and other ends, in one embodiment and with reference to FIG. 16, the manipulator 302 includes a support 330 having a U-shaped cross-sectional channel that is coupled to the end effector 40 at a proximal end. The support 330 may include a pair of bores 352 through a pair of tabs at a proximal end thereof. A guide beam 332 of about the same length as the support 330 reinforces the support 330 and may include three longitudinally extending channels 336a, 336b, and 340 that may receive portions of each of the stapling mechanism 322, the cutting mechanism 324, and the clamping mechanism 320.

The manipulator 302 further includes a frame 346 having a shaft portion 348 and a handpiece portion 350. The shaft portion 348 may have a tubular configuration, for example, a right circular tubular configuration, and may enclose the support 330 and the guide beam 332 when the manipulator 302 is assembled. The shaft portion 348 may enclose the support 330 when the manipulator 302 is assembled. The bores 352 of the support 330 may align with a corresponding pair of bores 354 in the handpiece portion 350. A pin (not shown) may secure the support 330 to the frame 346 in each of the bores 352 and 354. In the exemplary embodiment shown, the shaft portion 348 may form the exterior surface of the shaft 304.

In one embodiment, the handpiece portion 350 of the frame 346 includes opposing flanges 356a, 356b defining a channel 358. The handpiece portion 350 may therefore have a U-shape cross-sectional configuration and is enclosed in the housing halves 310a, 310b. Each of the flanges 356a, 356b includes one or more slots that guide a portion of the clamping mechanism 320, described below. In the exemplary embodiment shown, each flange 356a, 356b includes a slot 360a, 360b, respectively. As shown, each of the slots 360a, 360b is elongated in a direction generally parallel with the longitudinal axis of the frame 346. In addition, each flange 356a, 356b may include a pair of through bores 370a, 370b and 372a, 372b. As shown in FIG. 16, the bores 370a, 370b and 372a, 372b are spaced apart with the corresponding slot 360a, 360b in between the pairs of bores 370a, 372a and 370b, 372b.

Figure 17:
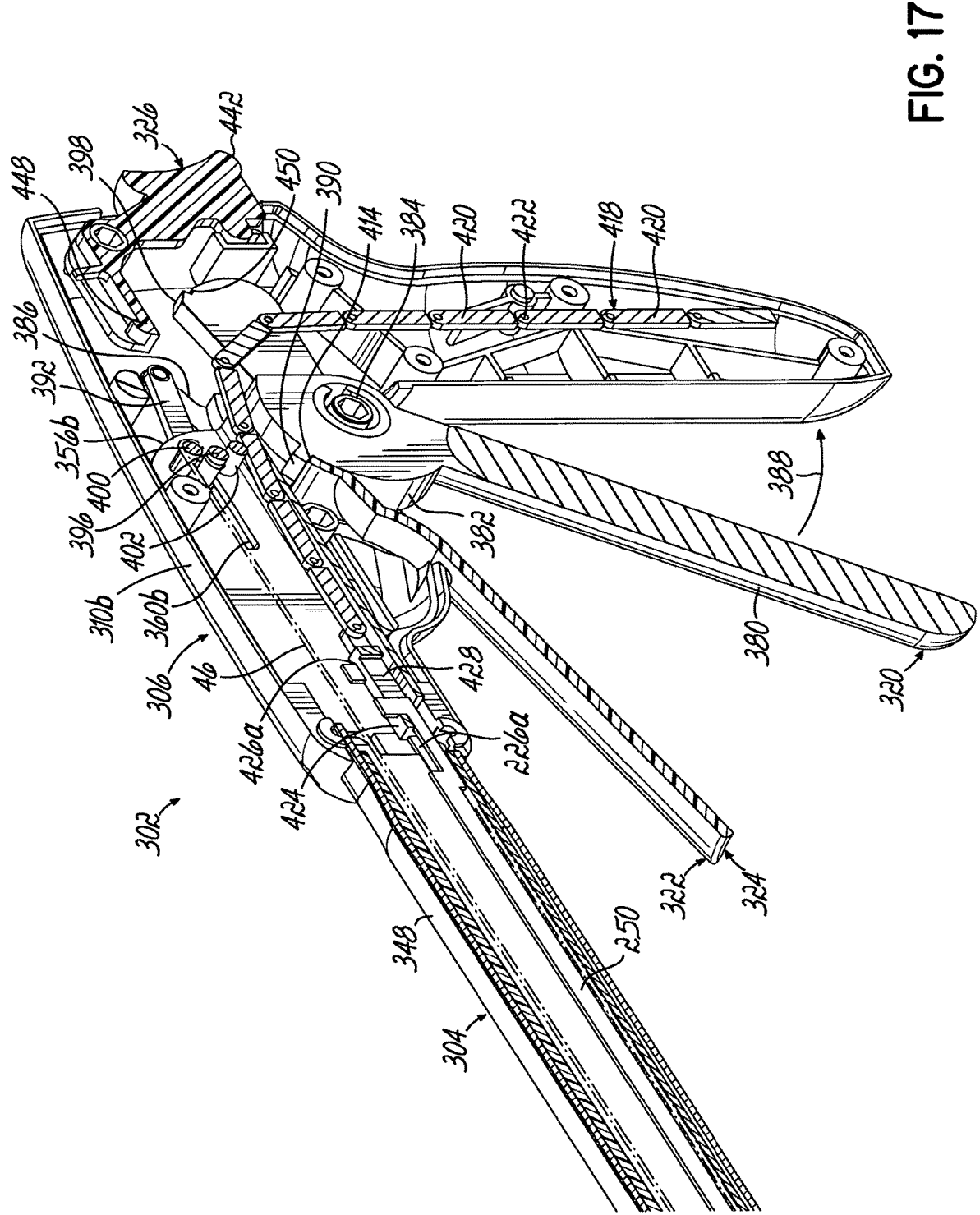
FIG. 17 is a cross-sectional perspective view of a manipulator of the endocutter stapling device shown in FIG. 15.
Figure 18:
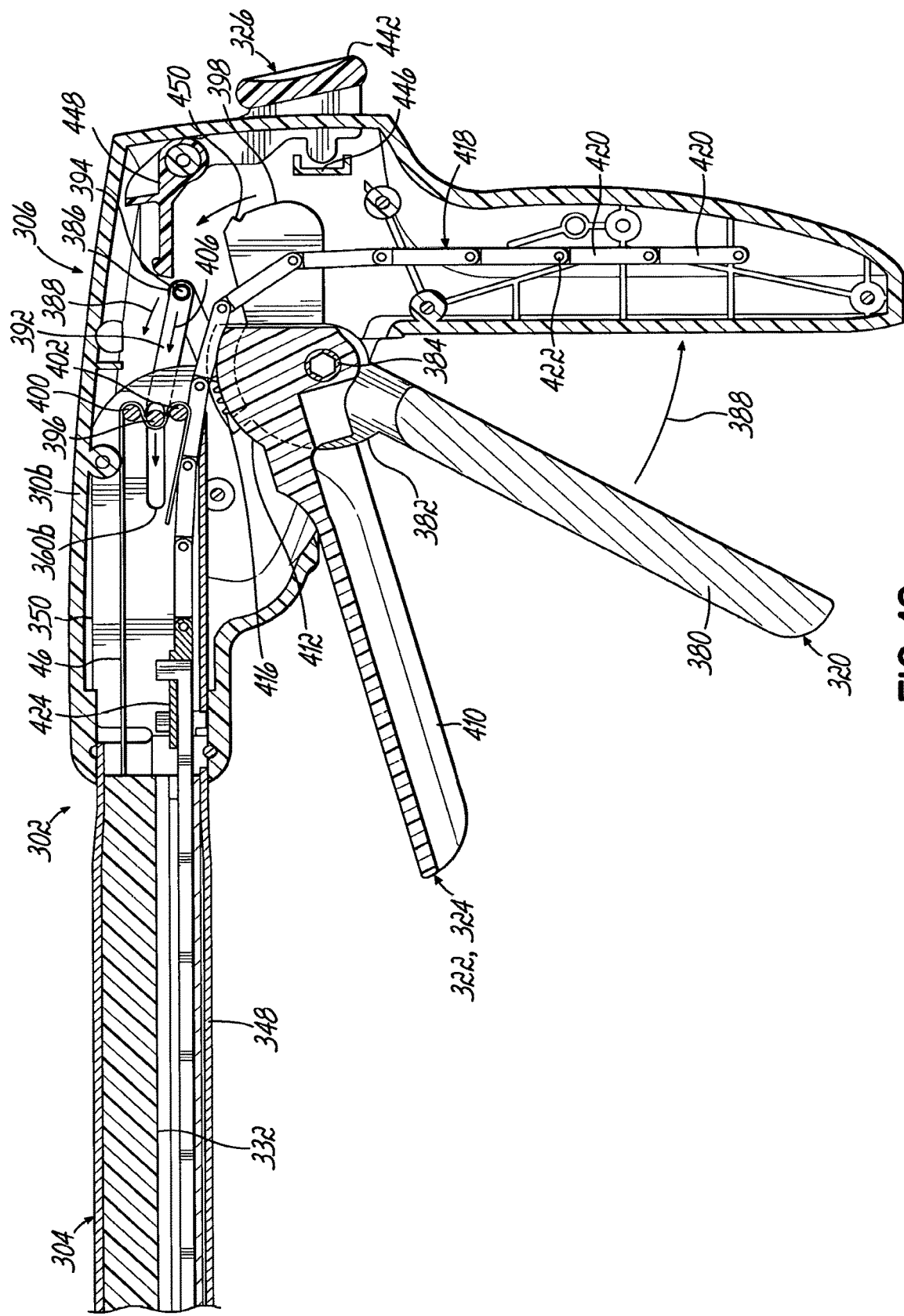
FIG. 18 is a cross-sectional view of the manipulator shown in FIG. 17 prior to compression of one lever.

With reference to FIGS. 16, 17, and 18, during an operation, the surgeon may engage the clamping mechanism 320, which withdraws the flexible member 46 from the end effector 40. As is described above, withdrawing or pulling the flexible member 46 from the end effector 40 draws the anvil 42 toward the cartridge 44 and tensions the flexible member 46 when the anvil 42 and the cartridge 44 meet resistance to movement. By applying a force to the flexible member 46, the anvil 42 and the cartridge 44 may be moved toward one another (as is indicated by arrow 52 in FIG. 15) and may also apply a clamping force to tissue situated between the anvil 42 and the cartridge 44.

To that end, and with reference to FIG. 16-19, the clamping mechanism 320 includes a lever 380 pivotally coupled between housing halves 310a, 310b and movable between a disengage position (FIGS. 17 and 18) in which the anvil 42 is spaced apart from the cartridge 44 and an engaged position (FIG. 19) in which the anvil 42 is moved toward the cartridge 44 and may clamp the tissue situated between the anvil 42 and the cartridge 44. The lever 380 may be pivotally coupled within the handpiece 306 via a hub 382, which is rotatable about a fastener 384. A torque arm 386 extends outwardly from the hub 382 and is rotatable in the same direction as the lever 380. For example, as is shown in FIGS. 17 and 18, the lever 380 is rotatable in the counterclockwise direction (as is indicated by arrow 388), and the torque arm 386 also rotates in the counterclockwise direction. A tab 390 extends from the hub 382 and cooperates with the stapling mechanism 322 and/or the cutting mechanism 324, described below. A locking arm 398 also extends from the hub 382 and is described in conjunction with the locking mechanism 326 below.

With reference to FIGS. 17 and 18, the torque arm 386 is pivotably coupled to a push bar 392 by pin 394 at one end thereof. The push bar 392 is coupled to a clamping rod 396 at the other end thereof. As shown, the clamping rod 396 is oriented generally perpendicularly to the longitudinal axis of the shaft 304 and is slidably engaged with each of the slots 360a and 360b of the frame 346. Additional rods 400 and 402 having a similar orientation as the clamping rod 396 and are positioned in the through bores 370a, 370b and 372a, 372b. As is shown best in FIG. 18, the flexible member 46 alternately weaves partway around each of the rod 400, the clamping rod 396, and the rod 402. With this configuration, the clamping rod 396 interacts with the flexible member 46 when the surgeon squeezes the lever 380.

In that regard, as the surgeon squeezes the lever 380, it rotates counterclockwise toward the main body 306, the torque arm 386 rotates counterclockwise forcing the push bar 392 generally in the direction of the end effector 40 as is indicated by arrow 406. In turn, the clamping rod 396 is pushed longitudinally along the slot 360a, 360b which carries the flexible member 46 in the same direction. Because each of the rods 400 and 402 are stationary and the flexible member 46 is woven around the rods 400, 402 in the opposing direction as compared to the clamping rod 396, the path length of the flexible member 46 through the rods 396, 400, and 402 is increased as the clamping rod 396 moves toward the end effector 40. That is, squeezing the lever 380 increases the path length of the flexible member 46 in the manipulator 302. This increase in the path length of the flexible member 46 withdrawals the flexible member 46 from the end effector 40 and so retracts the anvil 42 toward the cartridge 44.

Figure 19:
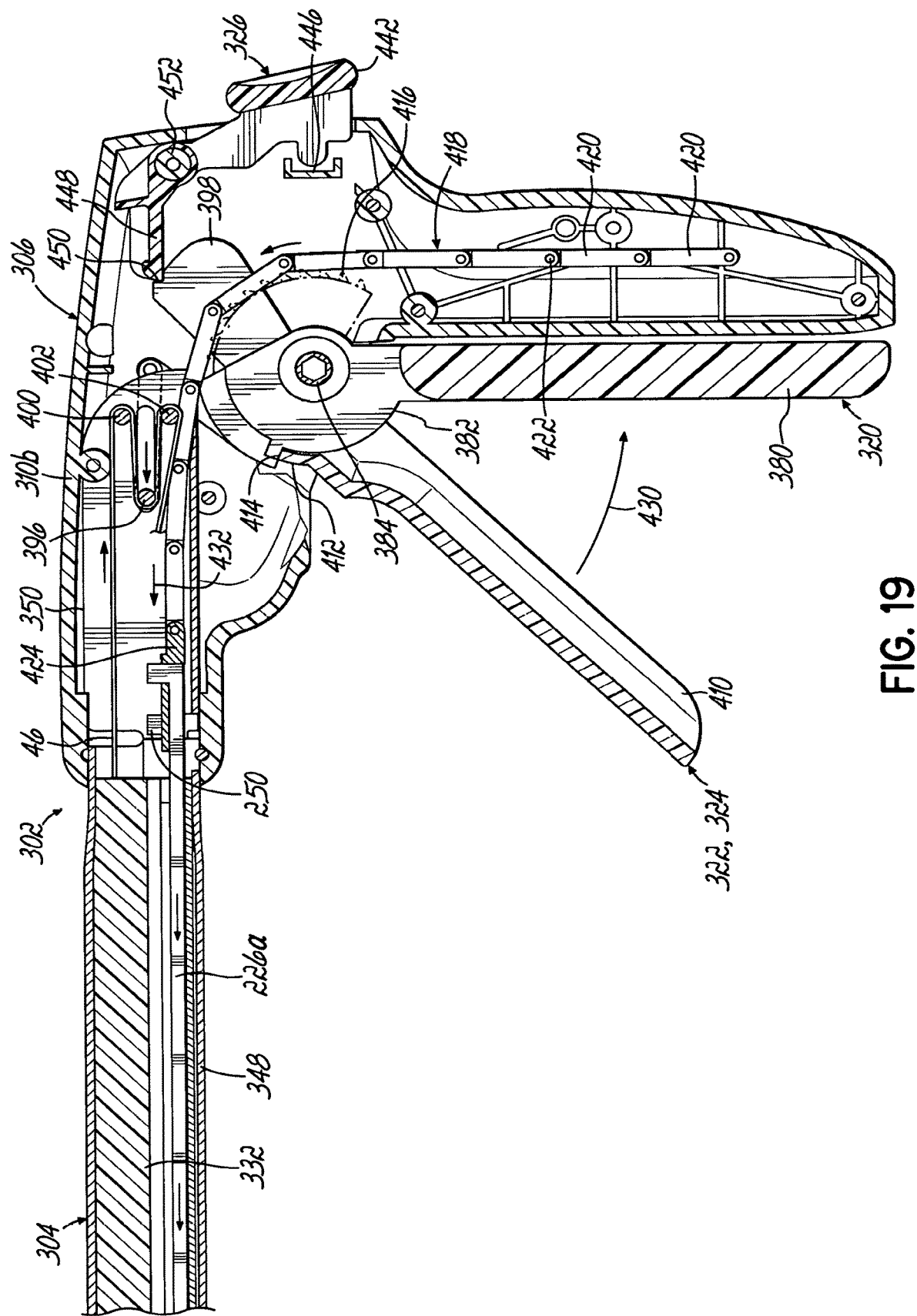
FIG. 19 is a cross-sectional view of the manipulator shown in FIG. 18 following compression of one lever.

In FIG. 19, the clamping mechanism 320 is fully engaged where the lever 380 is proximate the main body 306. When the lever 380 is fully depressed, the rod 396 may be pushed to the other end of the slots 360a and 360b. In other words, prior to engaging the clamping mechanism 320, the clamping rod 396 may be positioned at the end of the slots 360a and 360b furthest from the end effector 40, and, following engagement of the clamping mechanism 320, the clamping rod 396 may be positioned at the end of the slots 360a and 360b closest the end effector 40. The length of the slots 360a, 360b and the stroke of the torque arm 386 may determine how much of the flexible member 46 is withdrawn from the end effector 40. It will be appreciated that the anvil 42 and the cartridge 44 may sufficiently compress the stomach 10 before the clamping rod 396 reaches the furthest extent of the slots 360a and 360b. That is, less than full depression of the lever 380 may achieve clamping of the stomach 10.

Once the surgeon engages the clamping mechanism 320, the surgeon may then engage each of the stapling mechanism 322 and the cutting mechanism 324. With reference to FIGS. 18 and 19, the stapling mechanism 322 may include a stapling lever 410, which is operably coupled to a stapling hub 412. The hub 412 is pivotably coupled between the housing halves 310a, 310b via the fastener 384. The hub 412 may be adjacent the hub 382 on the fastener 384. The stapling lever 410 has a U-shaped cross section and so surrounds the clamping lever 380 when the stapling lever 410 is fully depressed. The U-shaped cross-section of the stapling lever 410 includes a stop surface 414, which is configured to engage the tab 390 on the hub 382. In this regard, squeezing the lever 380 rotates the tab 390 into contact with the stop surface 414. As a consequence, squeezing the clamping lever 380 may also slightly engage the stapling mechanism 322 and/or the cutting mechanism 324 as is generally shown by comparison of FIGS. 18 and 19.

With reference to FIGS. 17-19, one or more engagement elements 416 may project from the hub 412 to frictionally engage a chain 418 consisting of a plurality of links 420 coupled at joints 422. Each of the links 420 may be between a minimum length and a maximum length sufficient to allow the chain 418 to bend around the hub 412 in contact with the elements 416 while being capable of being forcibly pushed by the engagement elements 416 toward the end effector 40 without kinking, the reason for which is described below. By way of example and not limitation, each link 420 may be from about 20 mm to about 40 mm long.

Figure 16A:
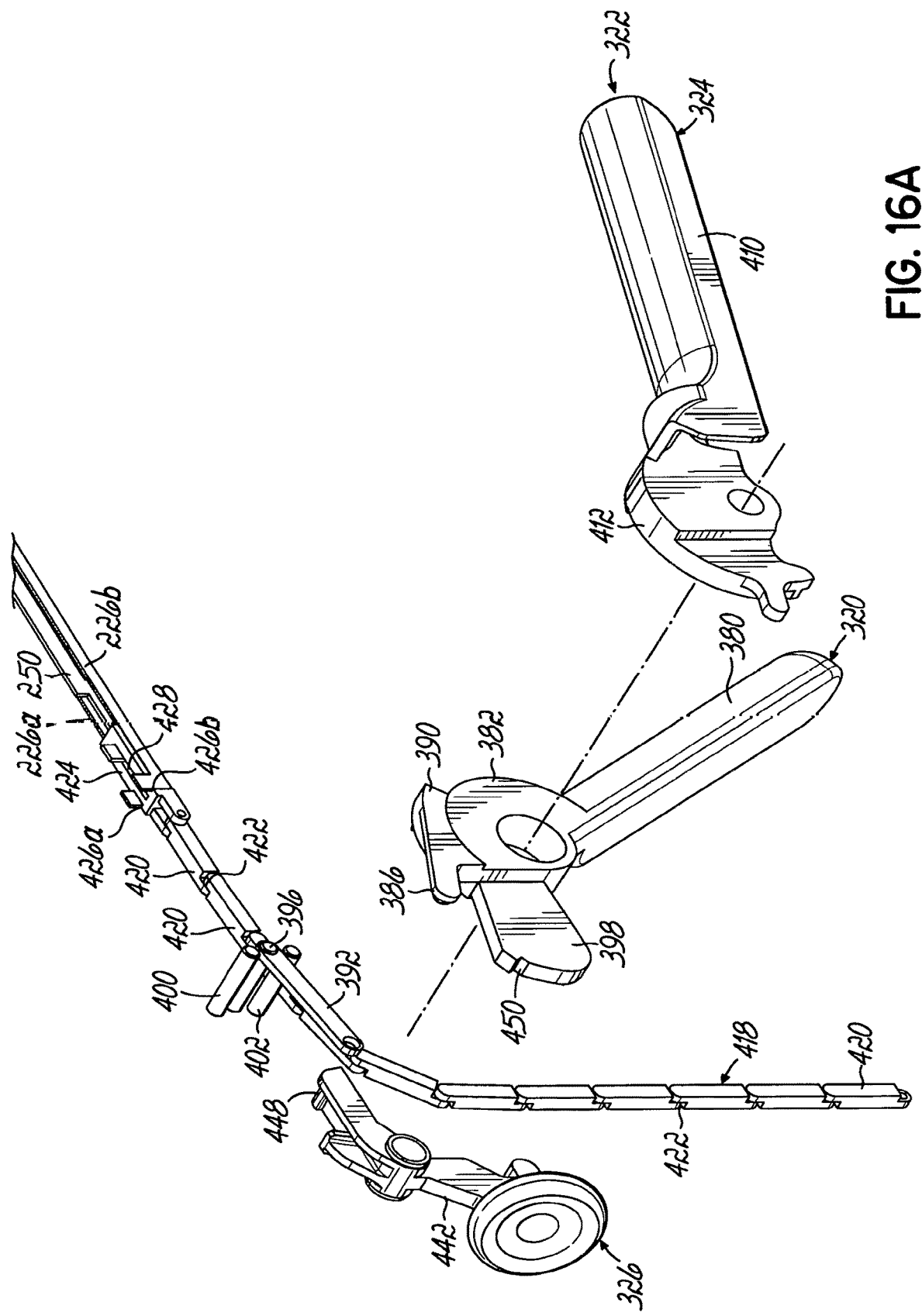
FIG. 16A is a disassembled perspective view of selected components of the endocutter stapling device shown in FIG. 16.

As shown, one portion of the chain 418 may be loose or freely hanging within a portion of the housing halves 310a, 310b. Another portion of the chain 418 may be coupled to an actuator plate 424 proximate the shaft portion 348 of the frame 346. The actuator plate 424 may be similar to the actuator plate 214 described with reference to FIGS. 8 and 9, above. In that regard, the actuator plate 424 may include slots 426a and 426b (shown best in FIG. 16A). Each slot 426a, 426b cooperates with the corresponding wedge push bar 226a, 226b. The actuator plate 424 also includes an elongated slot 428 which slidably receives the knife push bar 250. Each of the push bars 226a, 226b and 250 are described above with reference to the embodiment shown in FIGS. 3-14.

Figure 20:
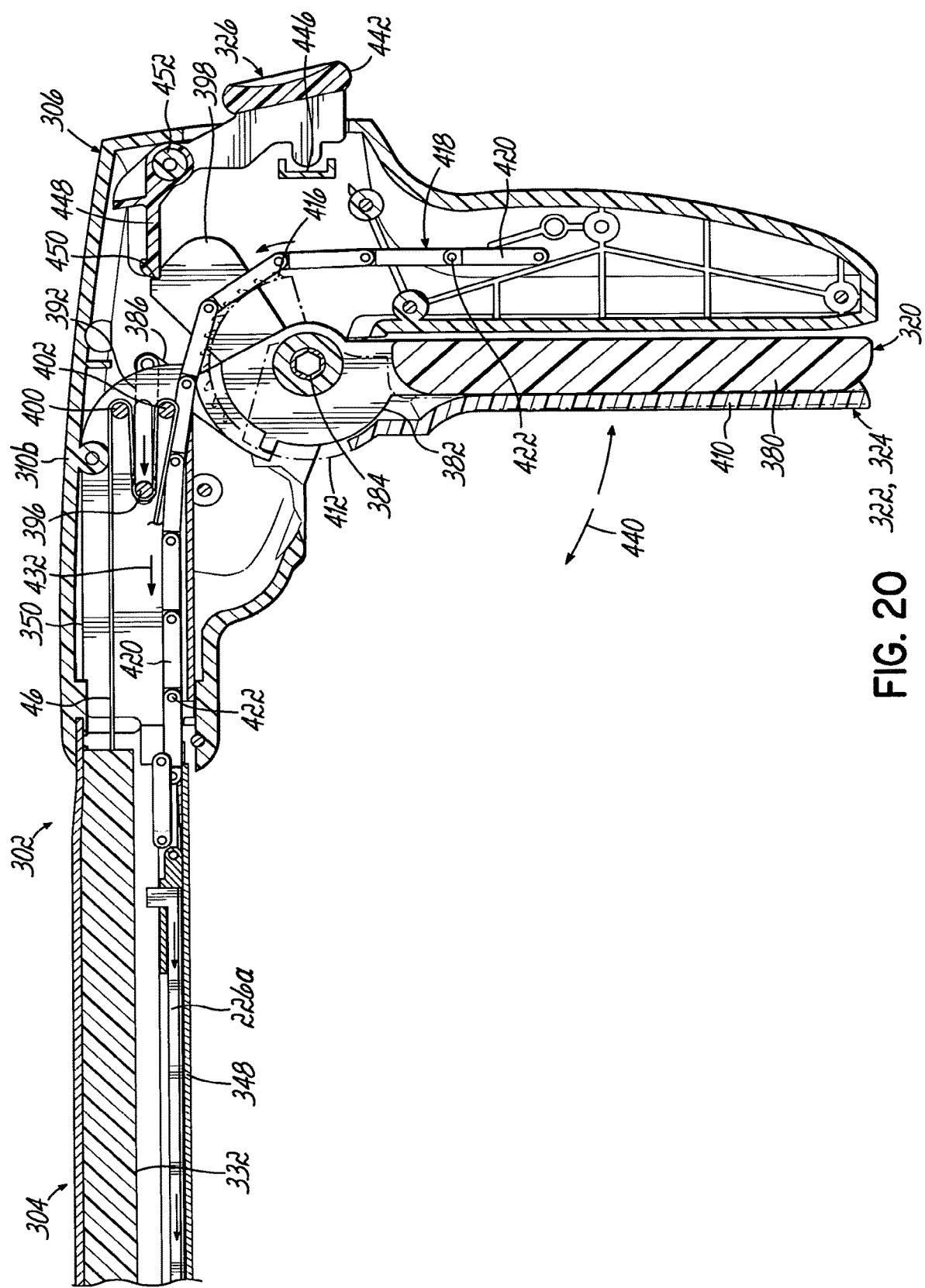
FIG. 20 is a cross-sectional view of the manipulator shown in FIG. 19 following compression of a second lever.

With reference to FIGS. 19 and 20, once the clamping mechanism 320 is engaged, the surgeon may engage the stapling mechanism 322 by squeezing the lever 410. Rotating the lever 410 in the counterclockwise direction according to arrow 430 also rotates the engagement elements 416 counterclockwise. The engagement elements 416 therefore forcibly push the chain 418 and consequently the actuator plate 424 toward the end effector 40, as is indicated by the arrow 432. In this manner, the wedge push bars 226a, 226b are extended into the end effector 40 with the wedges 230a, 230b forcing staples through the stomach 10 as is described above with reference to FIGS. 10-12.

With reference to FIG. 20, the stapling lever 410 may then be cycled in a clockwise direction as is indicated by arrow 440 while the clamping lever 380 remains compressed. Cycling the lever 410 may be required to further push the chain 418 toward the end effector 40 to drive the wedges 230a, 230b across the full length of the stomach. This may require a ratcheting type motion in which the surgeon repeatedly cycles the lever 410 to gradually push the chain 418 toward the end effector 40. In this regard, it will be appreciated that the length of the chain 418 may be about equal to the length of the end effector 40 so that cycling the lever 410 continuously drives the wedges 230a, 230b and the cutting edge 252 the length of the end effector 40.

In one embodiment, once the surgeon engages the stapling mechanism 322, the surgeon may then engage the cutting mechanism 324. In the exemplary embodiment shown, the cutting mechanism 324 shares the same structure as the stapling mechanism 322. In particular, with reference to FIGS. 18-20, the cutting mechanism 324 may include the lever 410 that drives the engagement elements 416, and thus the chain 418, toward the end effector 40. The chain 418 drives the actuator plate 424, which may also drive the knife push bar 250. Thus, squeezing the lever 410 drives the cutting edge 252 across the length of the cartridge 44, as is described above in conjunction with FIGS. 8 and 9. Similar to the stapling mechanism 322, the surgeon may repeatedly cycle the lever 410 in a clockwise and counterclockwise manner to drive the cutting edge 252 across the length of the cartridge 44. In the embodiment shown, cycling the lever 410 engages both the stapling mechanism 322 and the cutting mechanism 324.

In one embodiment, even though the actuator plate 424 is operably coupled to each of the wedge push bars 226a, 226b and the knife push bar 250, engagement of the stapling mechanism 322 occurs prior to actuation of the cutting mechanism 324. In other words, the stapling mechanism 322 engages prior to engagement of the cutting mechanism 324. The elongated slot 428 in the actuator plate 424 is oversized relative to the portion of the knife push bar 250 that is engaged with it. These configuration results in sliding space between the slot 428 and the knife push bar 250. The knife push bar 250 therefore slides relative to the actuator plate 424 during initial movement of the plate 424. The length of the movement of the actuator plate 424 without movement of the knife push bar 250 is predetermined.

The elongated slot 428 is also longer than each of the slots 426a, 426b. Because the knife push bar 250 is slidably received in the elongated slot 428, the initial movement of the actuator plate 424 in the direction of arrow 432 in FIG. 19 causes each of the wedge push bars 226a, 226b to move in direct relation to the movement of the actuator plate 424. The movement of the knife push bar 250 is however delayed relative to the movement of the wedge push bars 226a, 226b. This means that there is a delay between activation of the stapling mechanism 322 and the cutting mechanism 324. This delay is proportional to the free sliding space between the elongated slot 428 and the knife push bar 250. When the surgeon cycles the lever 410, the actuator plate 424 moves in the same direction and carries the wedge push bars 226a and 226b with it. The knife push bar 250 does not initially move. Instead, the actuator plate 424 must move a predetermined distance corresponding to the free sliding space in the direction of the end effector 40 before the actuator plate 424 engages the knife push bar 250. This delay in movement between the wedge push bars 226a, 226b and the knife push bar 250 results in a difference in activation time between the stapling mechanism 322 and the cutting mechanism 324. In this manner, in one embodiment, activation of the stapling mechanism 322 precedes activation of the cutting mechanism 324.

Once the surgeon activates each of the stapling mechanism 322 and the cutting mechanism 324 by squeezing the lever 410, stapling and cutting may occur substantially simultaneously. By way of example only, the stapling of the stomach 10 may precede the cutting of the stomach 10. That is, after an initial delay between stapling and cutting, during which the stapling mechanism 322 is activated, both of the stapling mechanism 322 and the cutting mechanism 324 are active. The surgeon may continue stapling and cutting the stomach 10 by cycling the lever 410 until there are no more links 420 in the chain 18 available or until the wedges 230a, 230b reaches the end of the cartridge 44. It will be appreciated that the stroke of the stapling mechanism 322 and the cutting mechanism 324 may be greater than the overall length of the stomach 10 or may be approximately equal to the length of the end effector 40. At this point, the wedge tips 230a, 230b may be proximate the distal end 42a, 44a of the end effector 40. The end effector 40 and the shaft 304 may then be removed from the abdominal cavity with the stomach 10 having the configuration shown in, for example, FIG. 2E.

With reference to FIGS. 16-19, in which like reference numerals refer to like features throughout the figures, in one embodiment, the locking mechanism 326 locks the clamping mechanism 320 in the engaged position. That is, when the surgeon engages the clamping mechanism 320 to a predetermined clamping force, the locking mechanism 326 engages. The surgeon may therefore then release the lever 380 and the clamping force produced by the clamping mechanism 320 is at least partially maintained. For example, the locking mechanism 326 may maintain a pressure equivalent to the second stage clamping pressure described above from about 4 g/mm² to about 70 g/mm². At these pressures, the clamping mechanism 320 squeezes tissue fluid out of the stomach and thereby approves staple line integrity.

To that end, in one embodiment, the housing halves 310a, 310b enclose a portion of the locking mechanism 326. The locking mechanism 326 includes a release lever 442 (shown in the form of a button) that projects from the housing halves 310a, 310b, for example, from a backside of the pistol-grip device 306. The surgeon may therefore operate the lever 442 with a thumb or a forefinger. The release lever 442 may be pivotally mounted within the housing halves 310a, 310b about a fastener 452 and operably coupled to a spring (not shown) mounted on a support 446 which may bias the lever 442 in an outwardly direction from the pistol-grip device 306. The lever 442 may include a locking finger 448 that is positioned proximate the locking arm 398. The locking finger 448 may be biased into engagement with the locking arm 398 during manipulation of the clamping lever 380 and so automatically engage after a predetermined rotation of the lever 380.

With reference to FIGS. 19 and 20, during use of the endocutter stapling device 300, the surgeon may compress the clamping lever 380, as described above. At a predetermined amount of rotation of the hub 382, the locking arm 398 slidably contacts the locking finger 448. The locking mechanism 326 may include structural features that permit only one-way rotational movement of the lever 380. By way of example only, the locking arm 398 may include a notch 450 that slidably receives the locking finger 448. The notch 450 is configured to receive the locking finger 448 when the locking arm 398 rotates in the counterclockwise direction but inhibits relative movement between the locking finger 448 and the locking arm 398 in the clockwise direction. Once the surgeon releases the clamping lever 380 with the locking finger 448 engaged in the notch 450, the clamping lever 380 is not free to rotate in the clockwise direction. That is, the locking mechanism 326 prevents release of the clamping mechanism 320.

When the surgeon lets go of the clamping lever 380, the locking mechanism 326 maintains the clamping mechanism 320 at a predetermined engagement level. It will be appreciated that while the locking mechanism 326 is shown to engage the clamping mechanism 320 when the lever 380 is fully compressed, embodiments of the present invention are not limited to full compression of the clamping lever 380 for engagement of the locking mechanism 326. Rather, the position of the locking arm 398 and the notch 450 relative to the locking finger 448 may be adjusted to a location at which the clamping lever 380 is only partially depressed before the locking finger 448 engages the notch 450. In this regard, the surgeon may continue to compress the lever 380 such that the notch 450 rotates past the locking finger 448. The surgeon may then release the clamping lever 380 such that the locking arm 398 rotates clockwise for a predetermined distance before the locking finger 448 engages the notch 450.

Once the locking mechanism 326 is engaged by rotating the locking arm 398 to a position at which the notch 450 engages or rotates past the locking finger 448, the surgeon may release the locking mechanism 326 by pressing the lever 442. When the lever 442 is pressed, the locking finger 448 rotates out of interference with the notch 450 and the locking arm 398 is free to rotate clockwise to a disengaged position.

Figure 21:
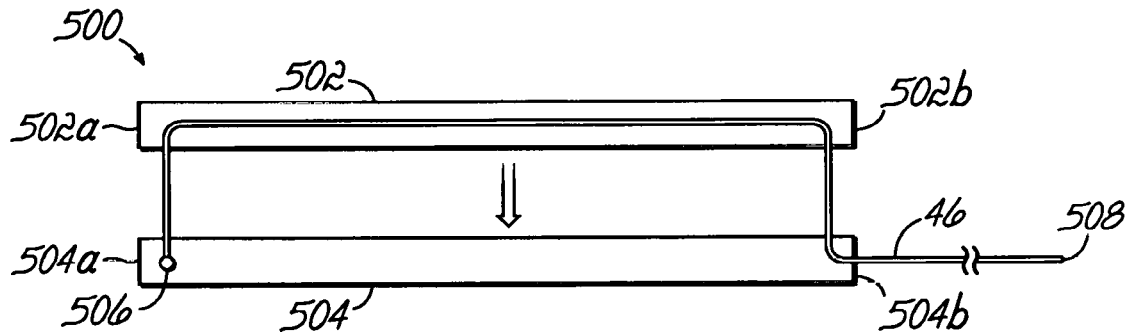
FIGS. 21-35 are schematic views of end effectors including one or more flexible members according to one or more embodiments of the invention.
Figure 22:
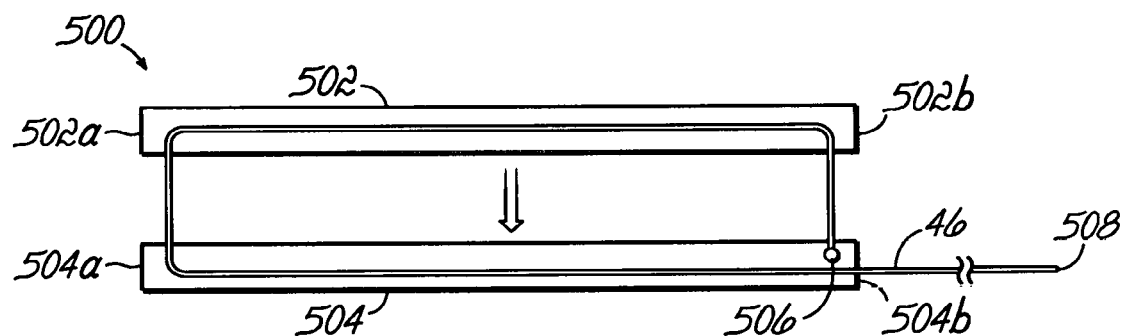
Figure 23:
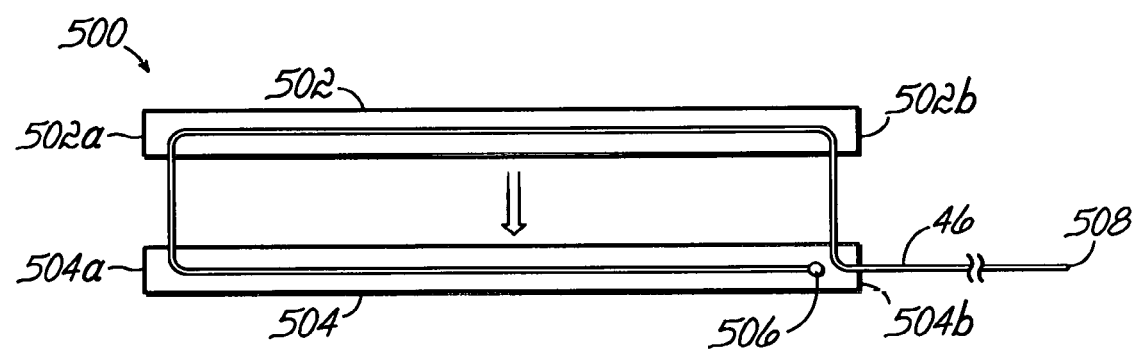

With reference now to FIGS. 21-68, in addition to the end effector 40 described above, there may be several alternative arrangements of the flexible member 46 relative to the anvil 42 and the cartridge 44 in the exemplary endocutter stapling devices 100, 300. In this regard, FIGS. 21-23 are schematic illustrations of exemplary end effectors that may be alternatives to the end effector 40 described above. In the exemplary alternative configurations, the pathway of the flexible member differs from the end effector 40 described above. However, in each embodiment, the flexible member(s) movably couple the anvil and the cartridge and is configured to be tensioned to provide a clamping force and that clamping force is distributed between the anvil and cartridge by two points of connection at each end of the end effector. Each anvil may be separable from each cartridge so that they may be individually inserted through a trocar and then movably coupled together. Further, while a specific arrangement of anvil and cartridge may be inferred from any single one of the figures, it is contemplated that the arrangement may be reversed. Thus, embodiments of the invention are not limited to the arrangement inferred from the figures unless otherwise stated. It will be appreciated that each of the end effectors described herein may be operably coupled to a manipulator, such as, the manipulator 102 or 302 described above with reference to FIGS. 3 and 15, or another manipulator unless stated otherwise. The surgeon may therefore tension the flexible member via a manipulator.

In FIGS. 21-23, an end effector 500 includes an anvil 502 and a cartridge 504. The flexible member 46 has a first end 506 that is fixed to the cartridge 504 at one location. The paths by which the flexible member 46 exits the end effector 500 differ between each of the FIGS. 21-23. A second end 508 of the flexible member 46 may be positioned outside the patient and be pulled or otherwise manipulated by the surgeon so as to increase the tension in the flexible member 46, and thereby generate a clamping force between the anvil 502 and the cartridge 504.

By way of example, in FIG. 21, the end 506 of the flexible member 46 is fixed to the cartridge 504 adjacent a distal end 504a thereof, passes into the anvil 502 at a distal end 502a, passes along the anvil 502, out of a proximal end 502b thereof, and into then out of a proximal end 504b of the cartridge 504. The end 508 of the flexible member 46 then extends to one of the manipulators 102, 302 and may be manipulated as described above. In FIG. 22, the end 506 of the flexible member 46 is fixed to the cartridge 504 near the proximal end 504b and passes into the anvil 502 near the proximal end 502b, extends along the anvil 502, out of the distal end 502a of the anvil 502, into the cartridge 504 near the distal end 504a, along the cartridge 504, and out of the cartridge 504 at the proximal end 504b. The second end 508 of the flexible member 46 may be positioned outside the patient and be pulled or otherwise manipulated by the surgeon so as to increase the tension in the flexible member 46, and thereby generate a clamping force between the anvil 502 and the cartridge 504.

In FIG. 23, the end 506 of the flexible member 46 is fixed to the cartridge 504 adjacent the proximal end 504b thereof and extends along the length of the cartridge 504 toward the distal end 504a. The flexible member 46 passes out of the cartridge 504 adjacent the distal end 504a thereof and passes into the anvil 502 adjacent the distal end 502a thereof. The flexible member 46 extends along the length of the anvil 502 and out of the anvil 502 adjacent the proximal end 502b thereof. The flexible member 46 then passes back into the cartridge 504 adjacent the proximal end 504b thereof and out the proximal end 504b of cartridge 504. The second end 508 may be positioned outside the patient and pulled or otherwise manipulated by the surgeon to increase the tension in the flexible member 46, and thereby generate a clamping force between the anvil 502 and the cartridge 504.

Figure 24:
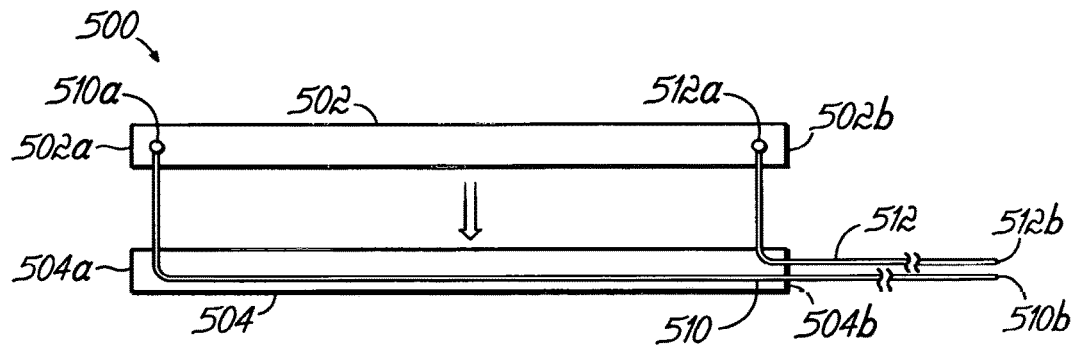
Figure 25:
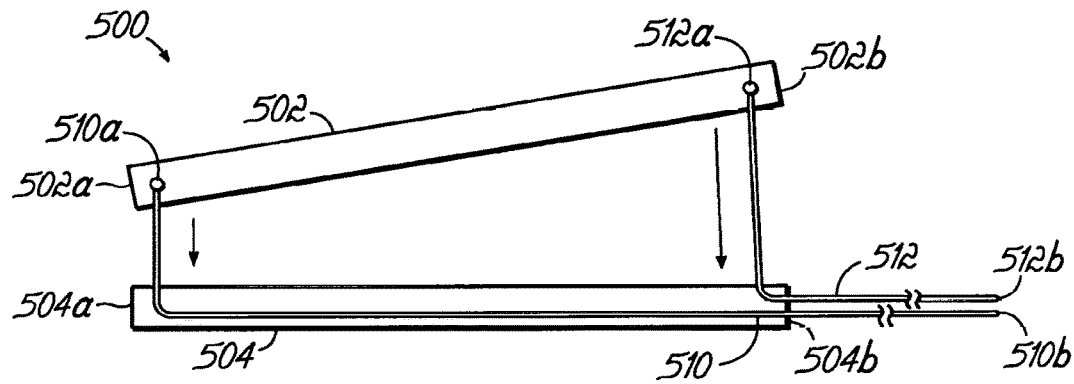
Figure 26:
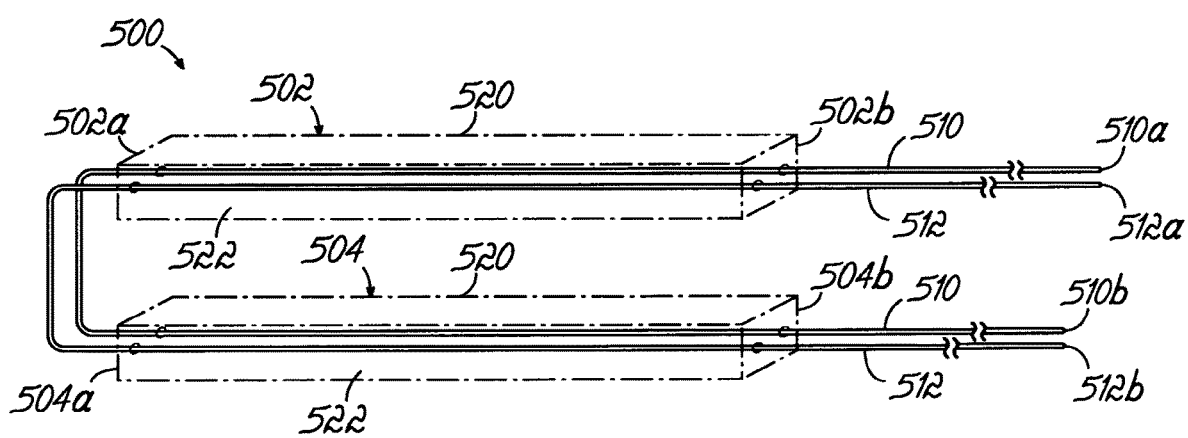

In alternative embodiments, there may be more than one flexible member used to tension the anvil and cartridge to generate a clamping force on the tissue. In this regard, FIGS. 24-26 are schematic illustrations of exemplary configurations of the anvil 502 and the cartridge 504 coupled together via two flexible members configured to be tensioned to provide a clamping force between the anvil 502 and the cartridge 504. In FIG. 24, a first flexible member 510 has a first end 510a fixed to the anvil 502 adjacent the distal end 502a thereof and passes out of the anvil 502 adjacent the distal end 502a. The first flexible member 510 then passes into the cartridge 504 adjacent a distal end 504a thereof and extends along the cartridge 504 and out of the proximal end 504b of the cartridge 504. The second end 510b of the first flexible member 510 may be positioned outside the patient. The arrangement further includes a second flexible member 512 having a first end 512a fixed to the anvil 502 adjacent the proximal end 502b thereof and passes out of the anvil 502 adjacent the proximal end 502b thereof. The second flexible member 512 then passes into the cartridge 504 adjacent the proximal end 504b and passes out of the cartridge 504 at the proximal end 504b. The second end 512b of the second flexible member 512 may be positioned outside the patient.

With this arrangement, the second ends 510b, 512b may be kept separate or joined and may be pulled or otherwise manipulated by the surgeon with a manipulator, as described herein, to increase the tension in the flexible members 510, 512 and thereby generate a clamping force between the anvil 502 and the cartridge 504. In one aspect, this arrangement advantageously provides for independent control of the clamping forces at the distal ends 502a, 504a and the proximal ends 502b, 504b of the end effector 500. In this regard, increasing the tension in the first flexible member 510 will draw the distal ends 502a, 504a of the anvil 502 and the cartridge 504 towards each other, as shown. As the distance between the distal ends 502a and 504a decreases, the clamping force at the distal end of the end effector 500 may increase. In a similar manner, increasing the tension in the second flexible member 512 will draw the proximal ends 502b, 504b of clamp members 502, 504 towards each other. As the distance between the proximal ends 502b, 504b decreases, the clamping force at the proximal end of the end effector 500 may increase. The increase in tension may depend on whether the anvil 502 and the cartridge 504 encounter resistance to movement, such as when the anvil 502 and the cartridge 504 begin compressing tissue. In another aspect of the exemplary embodiment shown in FIG. 24, the independent control of the flexible members 510, 512 allows for independent control of the gap between the anvil 502 and the cartridge 504 at the distal ends 502a, 504a and the proximal ends 502b, 504b of the end effector 500.

FIG. 25 illustrates the end effector 500 according to the embodiment in FIG. 24 where the distance between the distal end 502a of the anvil 502 and the distal end 504a of the cartridge 504 is less than the distance between the proximal ends 502b, 504b creating an overall shape of the end effector 500 that is generally trapezoidal. In other words, the anvil 502 and the cartridge 504 may be in non-parallel relation, as was described above. The gap between the anvil 502 and the cartridge 504 varies from one end to the other. This non-fixed, or adjustable, gap configuration permits adjustment of the distance between the anvil 502 and the cartridge 504 to accommodate variations in thickness of the anatomical structure, such as the stomach, as it is compressed. This feature may be beneficial because it allows for different tissue thicknesses to be clamped at nearly the same clamping force both proximally and distally and may prevent overcompression of the tissue and, as a consequence, may prevent tissue damage. By way of example, and with reference to FIG. 1, the proximal end 14 of the stomach 10 generally has a thickness less than that of the distal end 16 of the stomach 10. Accordingly, the ranges of clamping force used in the two-stage clamping process, as described above, may vary at the distal and proximal ends 14, 16 of the stomach 10. The end effector according to embodiments of the invention may permit the surgeon to vary the clamping force along the length of the stomach 10 and may aid in creating an improved resection line. Further, the end effector according to embodiments of the invention may permit the surgeon to vary the gap between the anvil and the cartridge along the length of the stomach 10 from parallel-gap configurations to non-parallel gap configurations.

With reference to FIG. 26, the end effector 500 includes two flexible members in a side-by-side U-shaped arrangement. A first flexible member 510 passes through each of the anvil 502 and the cartridge 504, and a second flexible member 512 passes through each of the anvil 502 and the cartridge 504. Notably, the first flexible member 510 extends along each of the anvil 502 and the cartridge 504 adjacent a first edge 520 of the anvil 502 and the second flexible member 512 extends through each of the anvil 502 and the cartridge 504 adjacent a second edge 522 of the anvil 502. This arrangement advantageously provides for independent control of the opposing sides, as well as the ends, of the end effector 500. In this regard, increasing the tension in the first flexible member 510 will increase the clamping force between the edges 520. In a similar manner, increasing the tension in the second flexible member 512 will increase the clamping force between the edges 522. This ability to control the clamping force along the opposing edges 520, 522 of the end effector 500 may be advantageous in certain applications and may additionally facilitate axial alignment between the anvil 502 and the cartridge 504.

Figure 27:
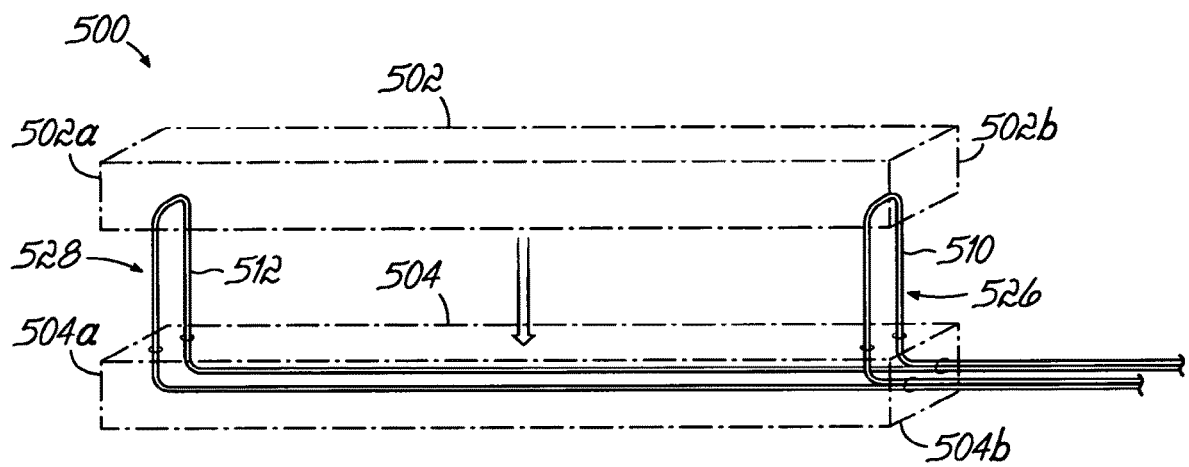

With reference to FIG. 27, the end effector 500 includes two flexible members in a double loop configuration. A proximal loop 526 is formed with the first flexible member 510, which passes into the proximal end 504b of the cartridge 504 at two spaced apart locations, out of the cartridge 504 adjacent the proximal end 504b at two spaced apart locations, and into the anvil 502 at the proximal end 502b at two spaced apart locations to complete the loop 526. A distal loop 528 is formed with the second flexible member 512, which passes into the proximal end 504b of the cartridge 504 at two spaced apart locations, along the cartridge 504 at spaced apart travel paths, out of the cartridge 504 at two spaced apart locations adjacent the distal end 504a, and into the anvil 502 at the distal end 502a at two spaced apart locations to complete the loop 528. This configuration may provide increased clamping force, improve alignment, and improved stability between the anvil 502 and the cartridge 504. In addition, the surgeon may selectively control one of the proximal loop 526 and/or the distal loop 528.

Figure 28:
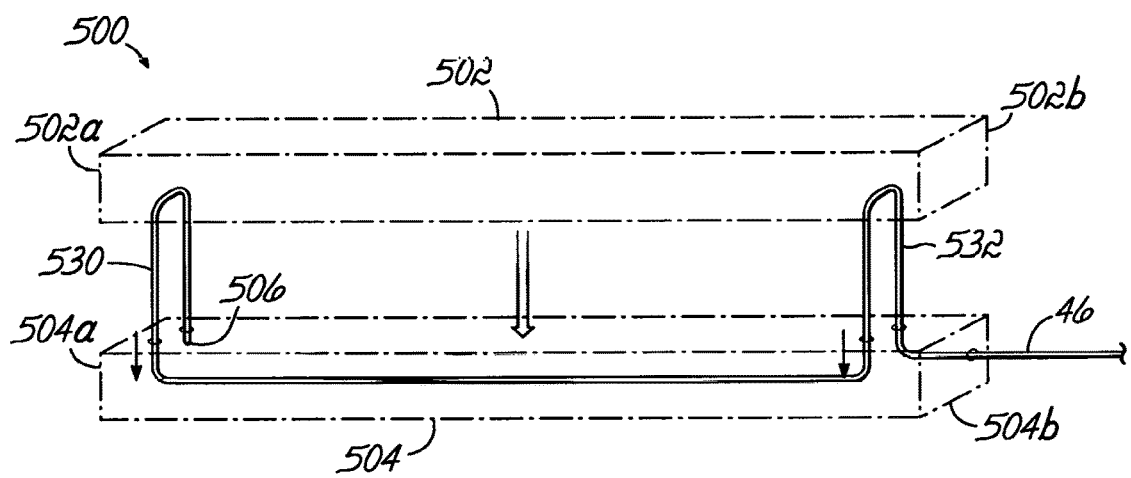

With reference to FIG. 28, the end effector 500 includes a single flexible member that is double looped. The end 506 of the flexible member 46 is anchored to the cartridge 504 and forms a loop 530 through the anvil 502, passes through the cartridge 504, forms a second loop 532 through the anvil 502, and passes out of the proximal end 504b of the cartridge 504.

Figure 29:
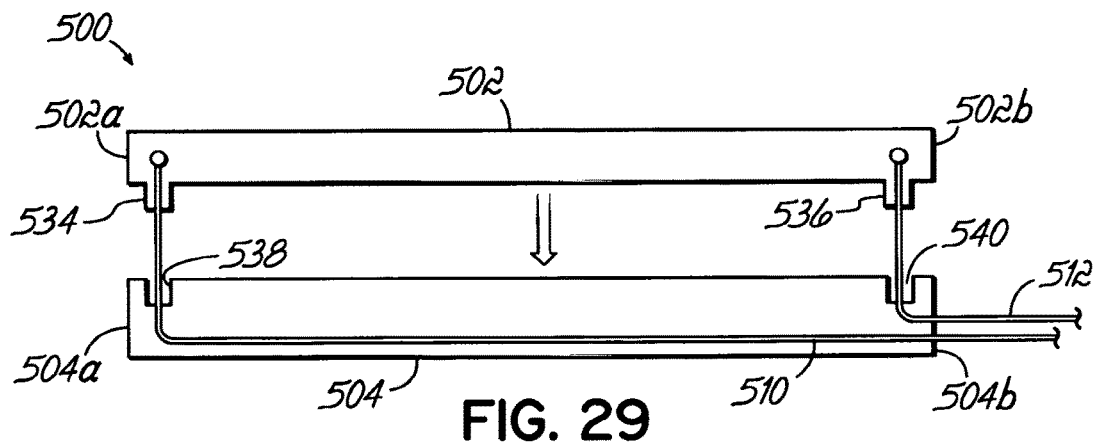

In FIG. 29, the flexible members 510, 512 has an arrangement similar to the end effector 500 shown in FIG. 24 with the addition of structural features that facilitate alignment of the anvil 502 with the cartridge 504. In that regard, the anvil 502 includes an alignment pin 534 adjacent the distal end 502a and an alignment pin 536 adjacent the proximal end 502b. The cartridge 504 includes a mating recess 538 and 540 for each of the pins 534 and 536 at each end 504a and 504b of the cartridge 504. The flexible member 510 may pass through the alignment pin 534 and the recess 538 and is anchored to the anvil 502. The flexible member 512 passes through the alignment pin 536 and the recess 540 and is also anchored to the anvil 502. During use, the recesses 538 and 540 receive alignment pins 534, 536 and facilitate alignment between the anvil 502 and the cartridge 504.

Figure 30A:
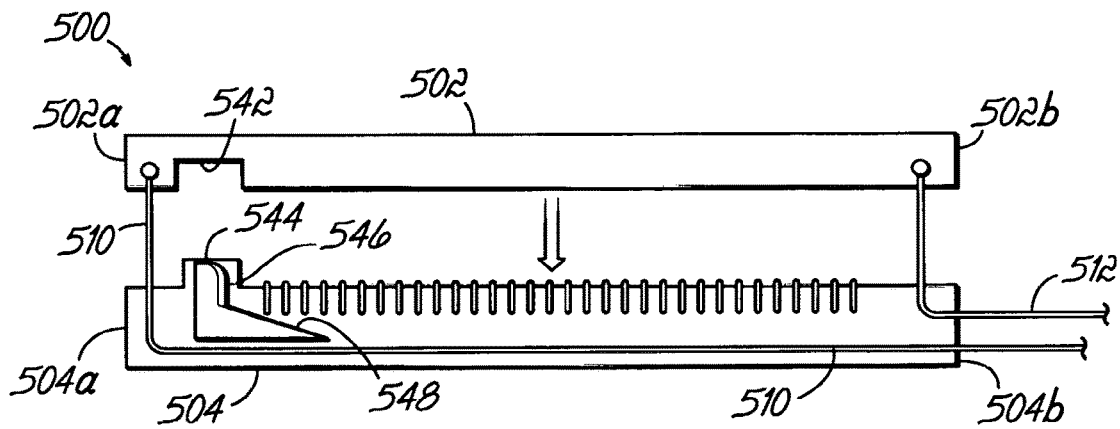
Figure 30B:
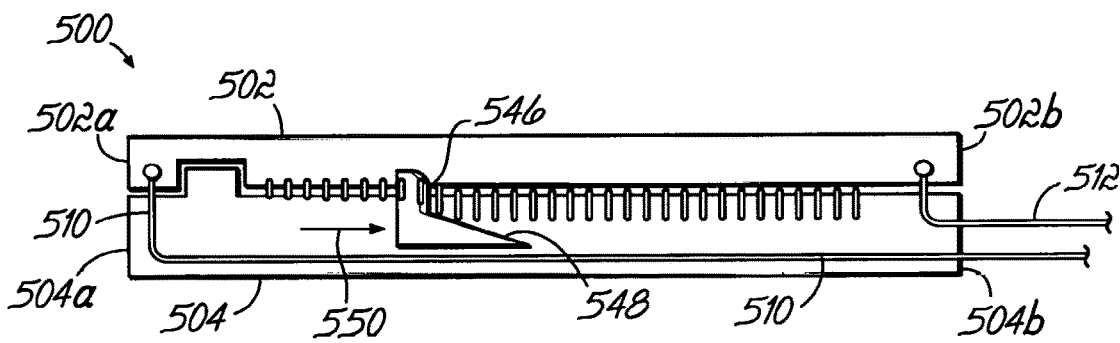
Figure 31:
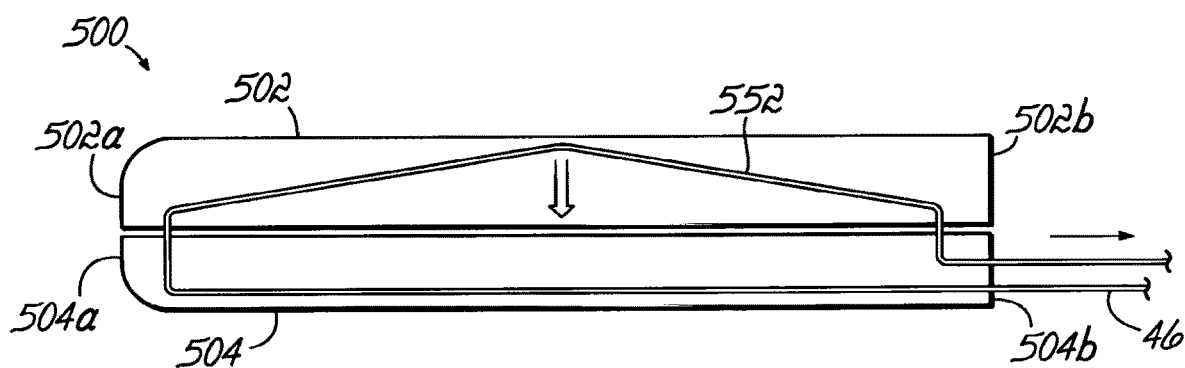

In the embodiment shown in FIGS. 30A and 30B, the flexible members 510, 512 have a similar arrangement as the flexible members 510, 512 shown in FIG. 24. In addition, the anvil 502 includes a recess 542 adjacent the distal end 502a. The recess 542 receives a hood 544 that covers a knife edge 546. The hood 544 may align with the recess 542 during use of the end effector 500 when the anvil 502 is retracted toward the cartridge 504 (shown in FIG. 30B). The end effector 500 also includes a wedge sled 548, which is pulled according to arrow 550 from the distal end toward the proximal end of the end effector 500 to staple and cut tissue.

While the flexible members are shown to follow straight paths through the anvil 502 and the cartridge 504, such as through a straight hollow passage, embodiments of the present invention are not limited to straight paths. For example, in the embodiment shown in FIG. 31, the flexible member 46 follows a non-linear path 552 through the anvil 502. In the exemplary embodiment shown, the non-linear path 552 may be triangular or arcuate shaped, however, other configurations are possible. This configuration may facilitate additional compression in the middle portion of the anvil 502 and so counteract any tendency of the anvil 502 to bow and bulge outwardly in the middle during compression of the tissue.

Figure 32A:
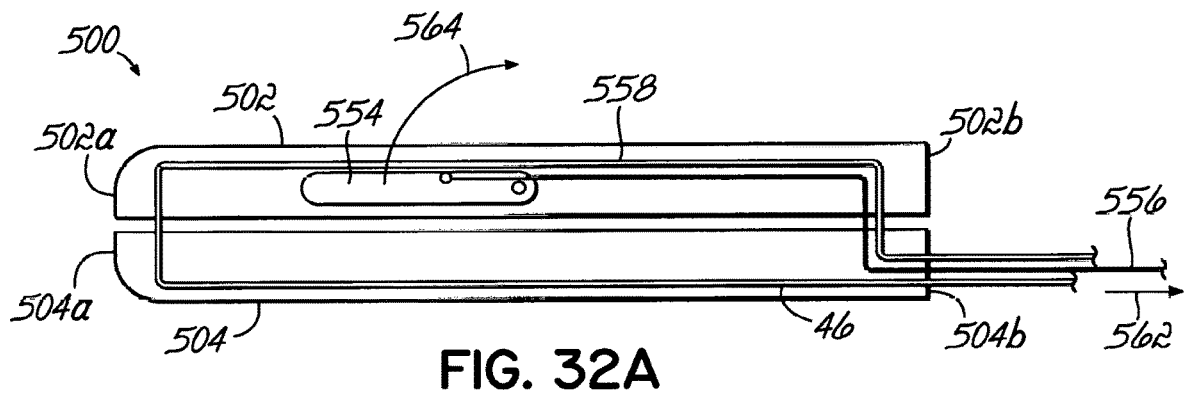
Figure 32B:
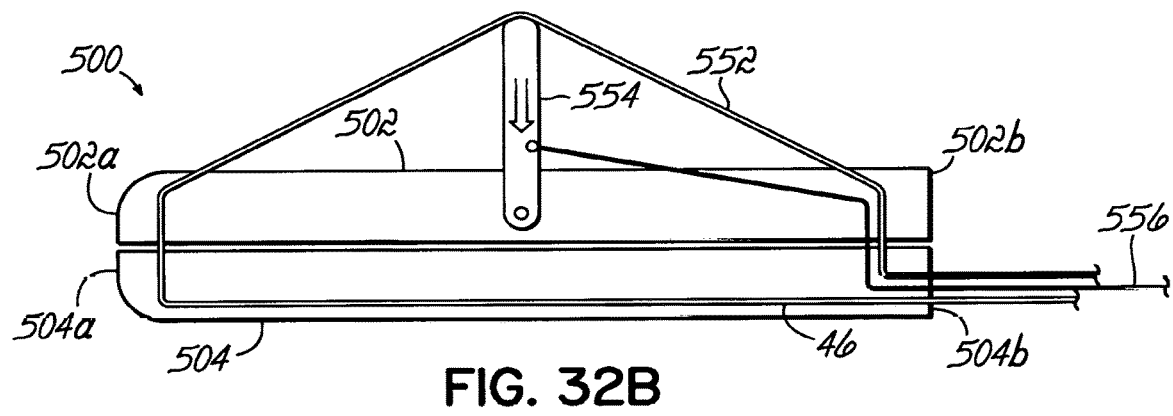

In an exemplary embodiment that counteracts bowing of the anvil and with reference to FIGS. 32A and 32B, a non-linear path 552 may be achieved with a strut mechanism 554, which is coupled to a guide line 556. It will be appreciated that the guide line 556 may extend outside the patient and be accessible to the surgeon. The strut mechanism 554 is pivotably coupled to the anvil 502 and is rotatable about a pivot point 558. In FIG. 32B, the strut mechanism 554 is activated by pulling the guide line 556 in the direction of arrow 562 (in FIG. 32A). The strut mechanism 554 pivots into position according to arrow 564 in FIG. 32A under the tension from the guide line 556. Once the strut mechanism 554 is active, tension on the flexible member 46 substantially prevents the anvil 502 from bowing in the central portion during compression of the stomach between the anvil 502 and the cartridge 504.

Figure 33:
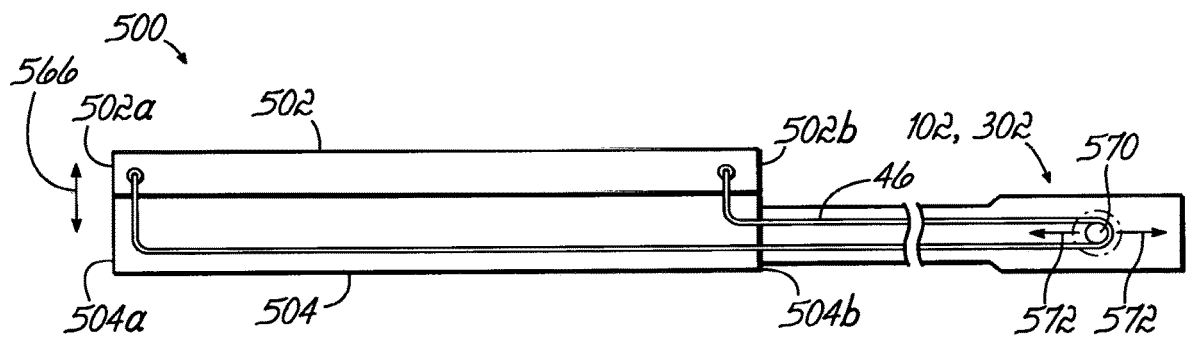

In one embodiment and with reference to FIG. 33, a gap 566 between the anvil 502 and the cartridge 504 is adjustable. By way of example only, and not limitation, the gap 566, or the finishing position of the anvil 502 when clamped, is adjustable by an adjustment mechanism 570, such as, by a knob (which may be located on the manipulator 102 or the manipulator 302). The surgeon may adjust the knob 570 to essentially reposition the flexible member 46 relative to the cartridge 504 and thus change the gap 566. In one aspect, this arrangement advantageously provides for control of the clamping force provided by the end effector 500. In this regard, as the gap 566 decreases, the clamping force on the anatomical structure may increase. Adjustment of the gap 566 may include relocation of the knob 570 along an axial direction 572 toward and away from the end effector 500. This may be advantageous in that the finish position of the anvil 502 may determine the configuration of the staple (not shown) once deformed. It will be appreciated that as the finish position of the anvil 502 is moved toward the cartridge 504, the final, deformed configuration of the staples may change from a less than optimal open B-shaped to a more optimal B-shape. In this way, the surgeon may correct the gap 566 to optimize the deformed staple configuration. In this embodiment, the gap 566 may remain in a parallel configuration before and after adjustment.

Figure 34:
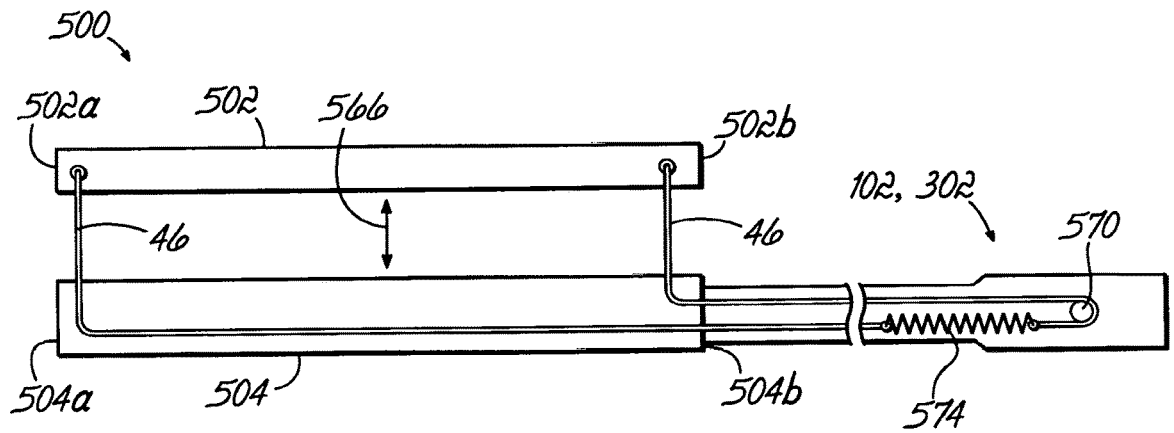
Figure 35:
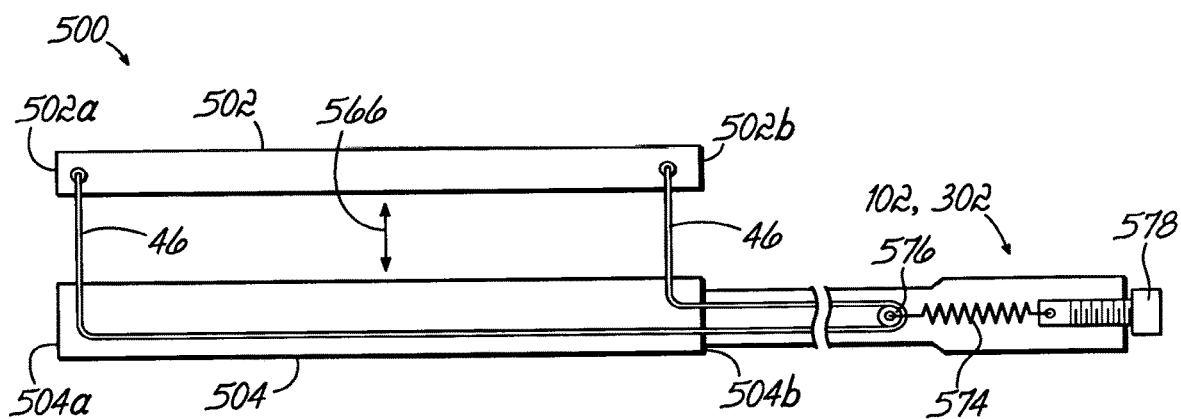

In one embodiment and with reference to FIG. 34, there is a similar gap adjustment device to that shown in FIG. 33 and described above. In addition to the knob 570 for adjustment of the gap 566, the manipulator 102, 302 may include a spring 574 in line with a least one end of the flexible member 46. While FIG. 34 depicts the spring 574 joining ends of the flexible member 46, it will be appreciated that the spring 574 may be positioned in series with one end of the flexible member 46, and not be connected to each end thereof. The spring 574 provides a spring force to the flexible member 46 and thus may enable more consistent application of clamping pressure to the stomach. For example, the spring 574 may facilitate application of from about 8 $g/mm^2$ to about 70 $g/mm^2$ of compression on the stomach. By way of example, the spring 574 may have a spring force of about 44 lb. By way of further example, the spring 574 may have a spring force of about 385 lb. In one exemplary embodiment, shown in FIG. 35, the spring 574 is secured to the flexible member 46 in a loop configuration by a pulley 576. (By comparison, the spring 574 in FIG. 34 is in line with the flexible member 46.) In particular, in FIG. 35, the spring 574 is secured to a threaded nut 578 at one end and the pulley 576 at the other end. The surgeon may adjust the nut 578 to provide the optimal gap for a target closing pressure between the anvil 502 and the cartridge 504. The nut 578 may be locked in position during stapling to lock in the gap during staple formation.

In one embodiment and with reference to FIGS. 36-40B, in which like reference numerals refer to like elements in FIGS. 3-20, an end effector 600 has connections at the distal end and the proximal end with each being of a different type. In the exemplary embodiment shown, the end effector 600 has a hinge 602 between an anvil 604 and a cartridge 606 at a distal end 600a of the end effector 600. The flexible member 46 connects the anvil 604 and the cartridge 606 at the proximal end 600b of the end effector 600, similar to embodiments disclose above. With the hinge 602, the anvil 604 rotates substantially in a plane between a disengaged position (shown in FIGS. 36 and 37) prior to and following the procedure and an engaged position when the anvil 604 is positioned to compress the stomach against the cartridge 606 (shown in FIGS. 38 and 39). To rotate the anvil 604 from the disengaged position to the engaged position, the surgeon pulls the flexible member 46 (according to arrow 608) from the end effector 600. Pulling the flexible member 46 rotates the anvil 604 (according to arrow 610) toward the engaged, closed position shown in FIG. 38. Tension on the flexible member 46 clamps tissue between the anvil 604 and the cartridge 606 and may be responsible for the clamping force.

Figure 37:
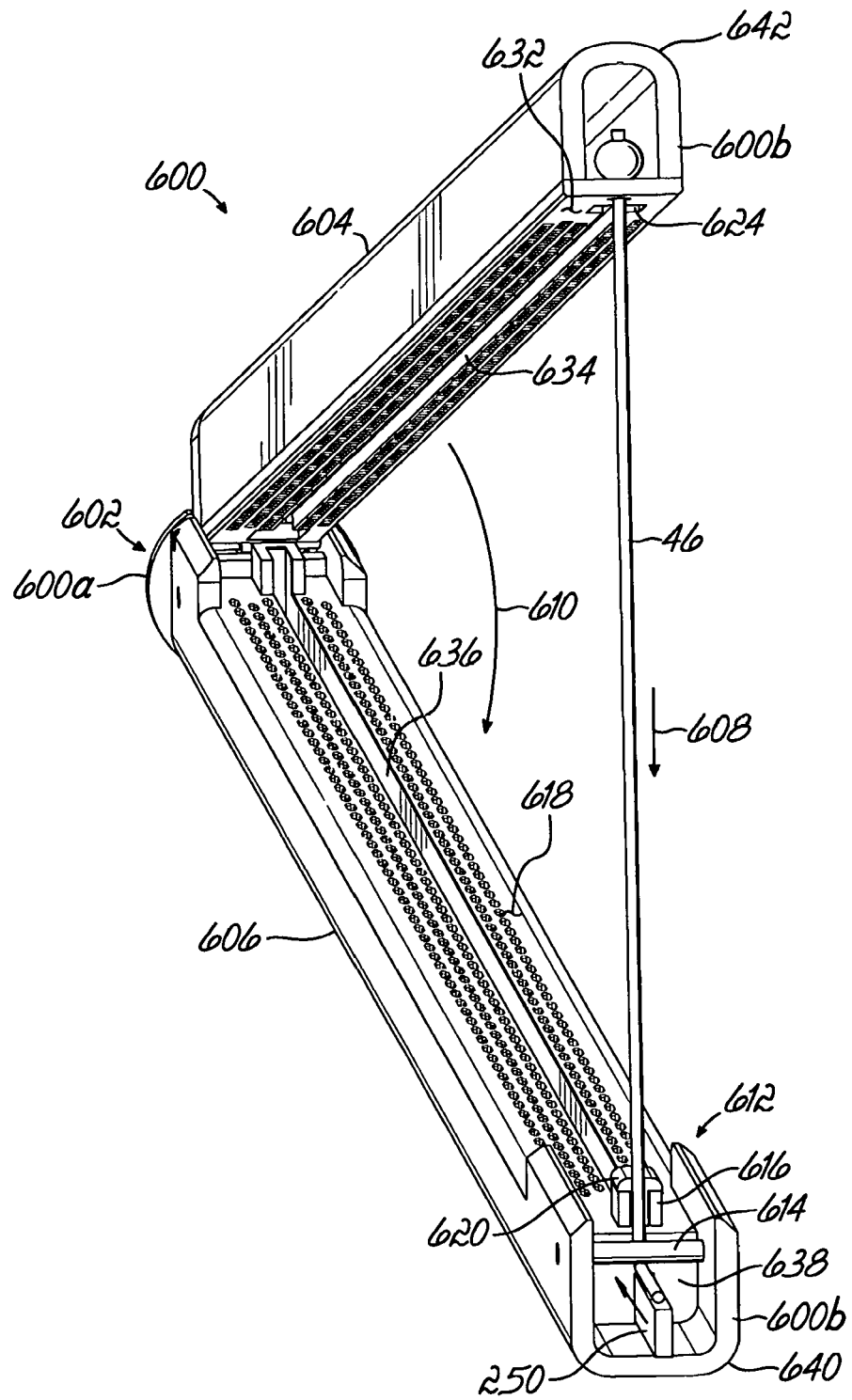
FIG. 37 is a different perspective view of the end effector shown in FIG. 36.
Figure 38:
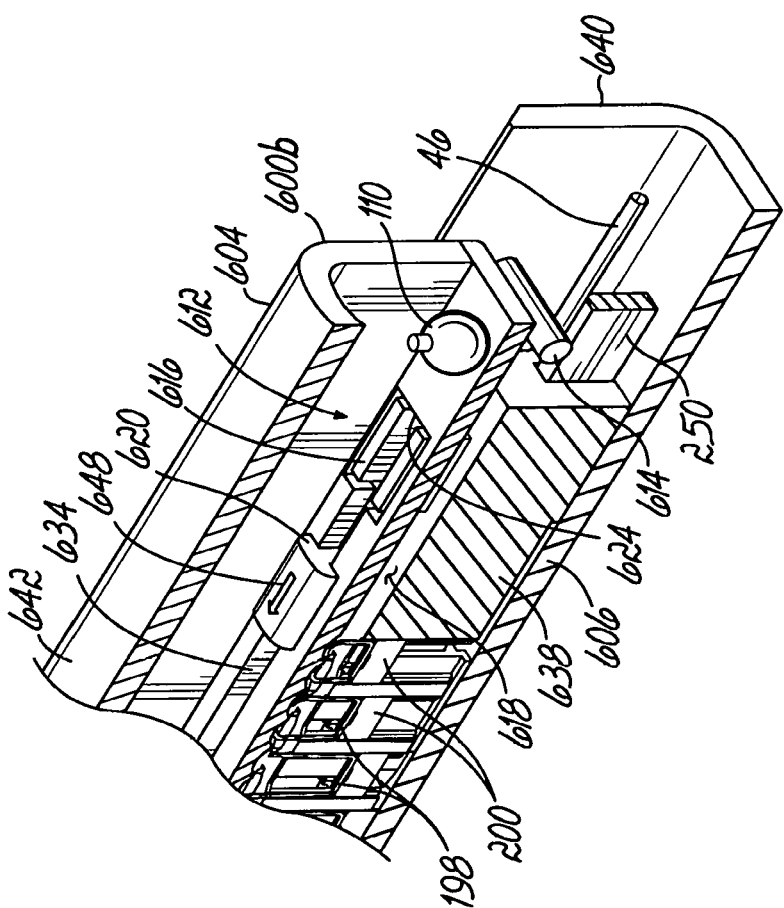
FIG. 38 is an enlarged cross-sectional perspective view of a proximal portion of the end effector shown in FIG. 36 shown in the closed position.

In one embodiment, and with reference to FIGS. 37 and 38, the end effector 600 includes an alignment mechanism 612 to more accurately align the anvil 604 with the cartridge 606 in the closed position. To that end, a pin 614 guides the flexible member 46 as the surgeon pulls it from the end effector 600. As the anvil 604 approaches the engaged, closed position, the alignment mechanism 612 ensures that the anvil 604 is accurately positioned relative to the cartridge 606. By way of example, and not limitation, alignment between the anvils and cartridges, as described herein, may mean an accuracy of plus or minus 0.002 inches. Alignment between the two improves the quality of the staple placement and deformation. The alignment mechanism 612 is positioned at at least the proximal end 600b of the end effector 600 and may guide the anvil 604 into the closed position. To do so, the alignment mechanism 612 may engage the anvil 604 just prior to the anvil 604 reaching the closed position. The last portion of the movement of the anvil 604 toward the cartridge 606 may be guided by the alignment mechanism 612.

Figure 36:
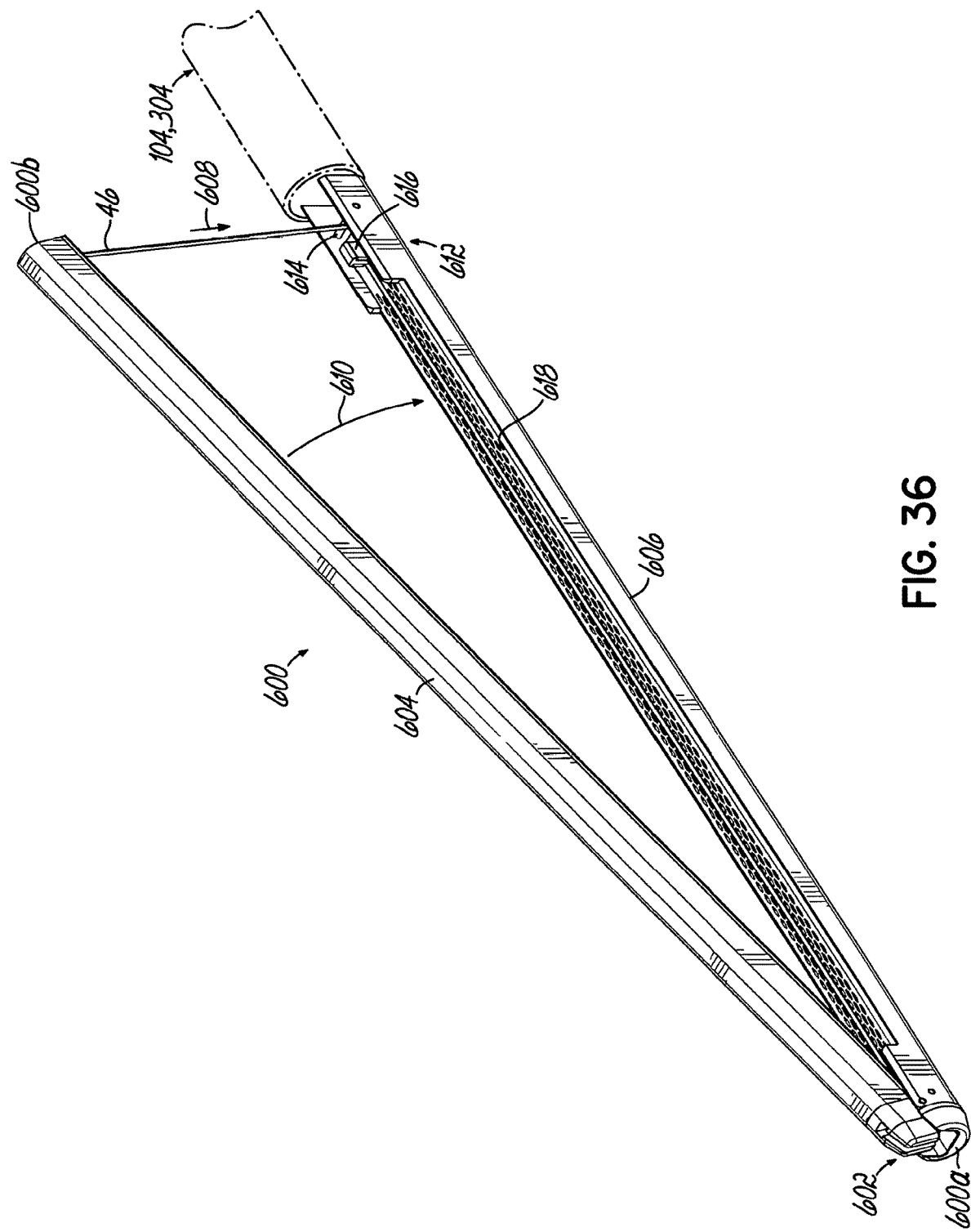
FIG. 36 is a perspective view of an end effector shown in the opened position according to one embodiment of the invention.

To that end, in the exemplary embodiment shown in FIGS. 36, 37, and 38, the cartridge 606 includes a frame 640 at least partially enclosing a cartridge body 638 defining a face 618. The cartridge body 638 houses the staples 198 and staple drivers 200. A slot 636 opens to the face 618 and extends through the cartridge body 638 and the frame 640 to open to an outer surface of the cartridge frame 640 (shown best in FIG. 38). The anvil 604 includes a tubular body 642 having an anvil plate 644 that defines an anvil face 632 and an interior surface 646. A slot 634 opens to each of the face 632 and the interior surface 646.

Figure 39:
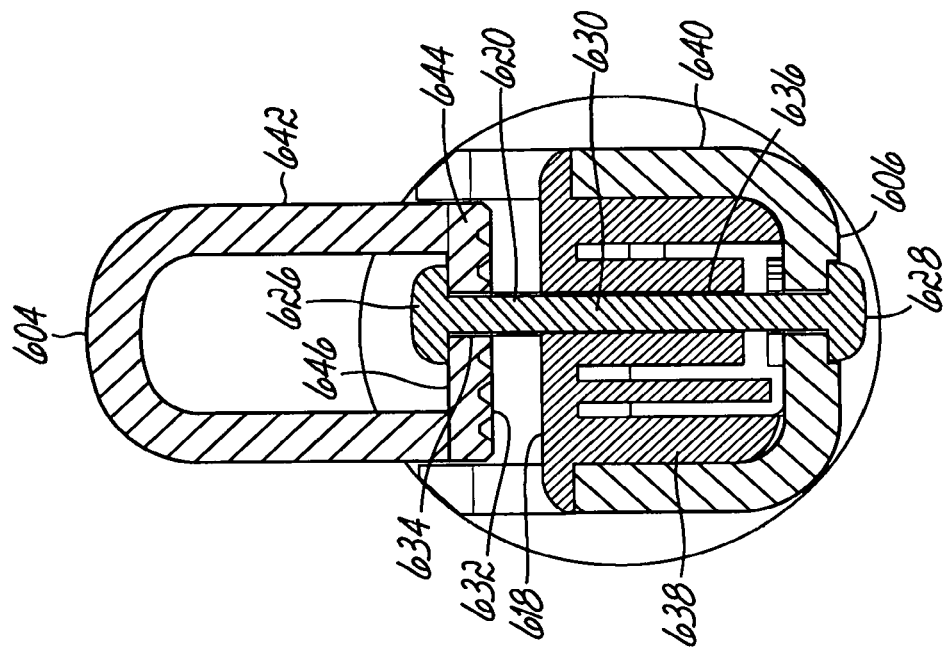
FIG. 39 is a cross-sectional view of a distal portion of the end effector shown in FIG. 36 with the end effector shown in the closed position.

The alignment mechanism 612 includes a housing 616 that extends outwardly beyond the face 618 of the cartridge 606 (shown best in FIG. 36). The housing 616 may support a knife 620, described below, having a cutting edge (not shown), which performs substantially the same function as the cutting edge 252 described above and shown, for example, in FIG. 6. The alignment mechanism 612 may also include a recess 624 in the plate 644 of the anvil 604. The recess 624 is connected to the slot 634 and is sized to receive the housing 616 and/or the knife 620. With reference to FIG. 39, the knife 620 has an I-shaped configuration, much like an I-beam, and has a top flange 626, a bottom flange 628, and a web 630 connecting the top flange 626 to the bottom flange 628. A portion of the web 630 that faces the distal end 600a of the end effector 600 includes the cutting edge. As shown in FIG. 38, the top flange 626 may have a slightly rounded configuration. When the knife 620 resides in the housing 616, they collectively form a protrusion.

With reference to FIGS. 37 and 38, during the closing motion of the anvil 604, as the anvil 604 approaches the cartridge 606, the housing 616 and the flange 626 are received in the recess 624. Thus, if the anvil 604 is not aligned with the cartridge 606 as it approaches the engaged position, the housing 616 and the top flange 626 may contact the face 632 of the anvil 604, the rounded surface of the top flange 626 may urge realignment of the anvil 604 with the cartridge 606 so that the recess 624 may be brought into full engagement with the top flange 626 in the housing 616. In this manner, the alignment mechanism 612 facilitates alignment between the anvil 604 and the cartridge 606.

Once the anvil 604 is aligned with the cartridge 606, the surgeon may engage a stapling mechanism and a cutting mechanism, each similar to the stapling mechanism 124, 322 and the cutting mechanism 126, 324 described above with reference to FIGS. 3-20. In that regard and with reference to FIGS. 38 and 39, the slot 634 slidably receives the web 630 of the knife 620. Similarly, the slot 636 also slidably receives the web 630 of the knife 620 as the knife 620 is forced toward the distal end 600a of the end effector 600 according to arrow 648. The flanges 626 and 628 also engage the anvil 604 and the cartridge 606, respectively. Specifically, the flange 626 engages the interior surface 646 of the face plate 644 and the flange 628 engages the exterior surface of the frame 640. This configuration improves the rigidity of the end effector 600 during cutting/stapling by capturing each component and preventing separation of the anvil 604 from the cartridge 606 in multiple directions. The I-beam configuration may substantially prevent any torque produced by the stapling/cutting action from twisting the anvil 604 relative to the cartridge 606 as can be appreciated by the cross-section shown in FIG. 39 in which the knife 620 is shown to positively lock the anvil 604 relative to the cartridge 606 and thereby prevent their separation as well as prevent any significant relative side-to-side motion during cutting/stapling.

With reference to FIGS. 40A and 40B, in one embodiment, the face plate 644 includes a distal recess 652 and a distal housing 654 extends from the cartridge body 638. As the knife 620 is forced along the slots 634, 636, it enters the housing 654 (shown in FIG. 40B) to complete stapling and/or cutting. The anvil 604 may then be rotated about the hinge 602 to a disengaged position. The recess 652 allows the knife 620 and housing 654 to pass through the plate 644 as the anvil 604 is pivoted about the hinge 602.

Embodiments of the present invention are not limited to a distal hinge, as other structures may be utilized to secure and align the proximal and distal ends of the anvil relative to the cartridge. With reference to FIGS. 41-63, in which like reference numerals refer to like features through the figures, in one embodiment of the invention, an end effector 700 includes an anvil 702 and a cartridge 704, for performing for compressing, stapling, and/or cutting a stomach. As with the end effectors described above, the end effector 700 may be coupled to a manipulator, such as, the manipulator 102 and 302 (shown in FIGS. 3-20 and described above), or another manipulator, by which the surgeon may remotely operate the end effector 700. The anvil 702 has a face 706 and the cartridge 704 has a face 708. During use of the end effector 700, and as is schematically shown in FIG. 42, the face 706 of the anvil 702 is pulled into a position opposite the face 708 of the cartridge 704. Instead of a hinge, the cartridge 704 includes a cam tube 710 that slidably receives the anvil 702 during a surgical procedure. The cam tube 710 may be a hollowed out area within the cartridge 704 that projects above the face 708 of the cartridge 704. As shown, the cam tube 710 includes a curved or arcuate surface 712. The anvil 702 includes an arcuate surface 714 that is configured to cooperate with the arcuate surface 712 of the cam tube 710, as is shown in FIG. 42.

Similar to the configuration shown in FIG. 24, described above, the surgeon may manipulate two flexible members 510, 512 that are connected to the anvil 702 to compress a stomach or other tissue between the anvil 702 and the cartridge 704. In particular, and by way of example only, the flexible member 510 is anchored to a distal end 702a of the anvil 702, passes into a distal end 704a of the cartridge 704 through the cam tube 710. From the distal end 704a of the cartridge 704, the flexible member 510 passes along the length of the cartridge 704 and out of a proximal end 704b of the cartridge 704 for manipulation by the surgeon. The flexible member 512 is anchored to a proximal end 702b of the anvil 702, passes into the cartridge 704 adjacent the proximal end 704b of the cartridge 704, and passes out of the proximal end 704b for manipulation by the surgeon.

As the surgeon tensions the flexible member 510, the anvil 702 is pulled into the cam tube 710 (shown in FIG. 42). It will be appreciated that the surfaces 712, 714 may cooperate to provide a compressive force generally toward the face 708 of the cartridge 704 when the surgeon tensions the flexible member 510 to pull the distal end 702a of the anvil 702 into the cam tube 710. Tensioning the flexible member 512 pulls the proximal end 702b of the anvil 702 toward the cartridge 704 to compress tissue situated between the face 706 and the face 708. Once the anvil 702 is in position relative to the cartridge 704 or a target compression of the tissue is achieved as determined by the tension on one or both of the flexible members 510, 512, the surgeon may staple and cut the compressed tissue, as described above with reference to FIGS. 3-20. It will be appreciated that the configuration of the cartridge 704 shown in FIG. 41 may require the surgeon to tension the flexible member 510 first to guide the distal end 702a into the cam tube 710. The surgeon may then tension the flexible member 512 to bring the anvil 702 into the position shown in FIG. 42.

Figure 41:
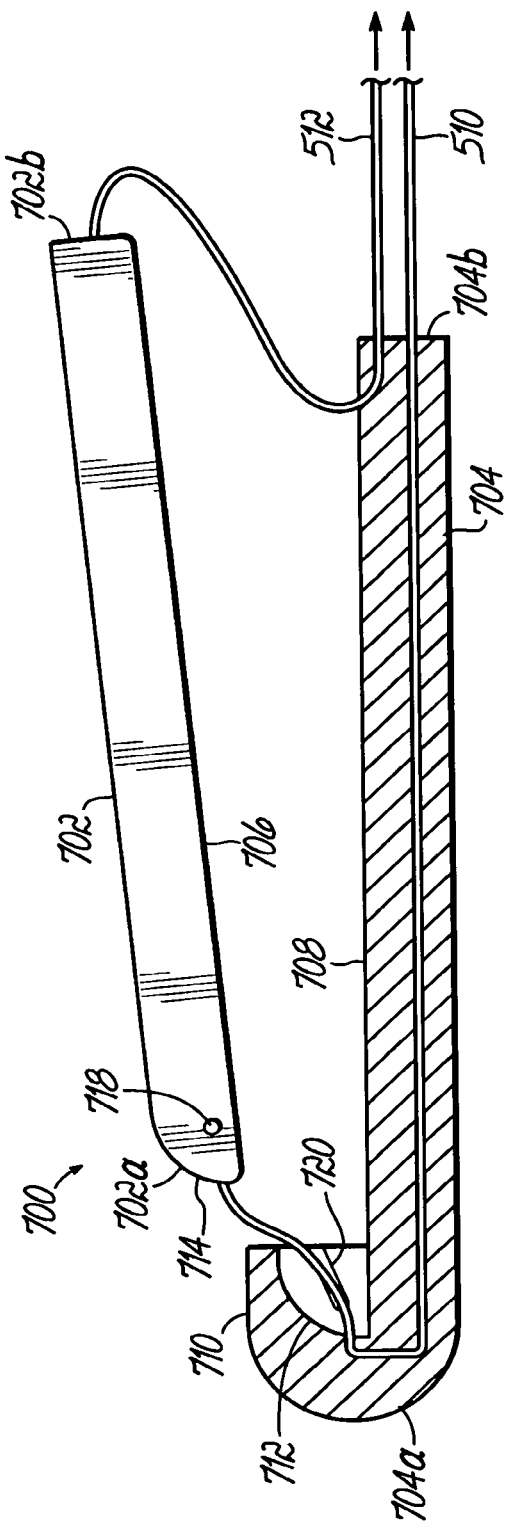
FIGS. 41 and 42 are schematic elevation views of an end effector according to one embodiment of the invention.
Figure 42:
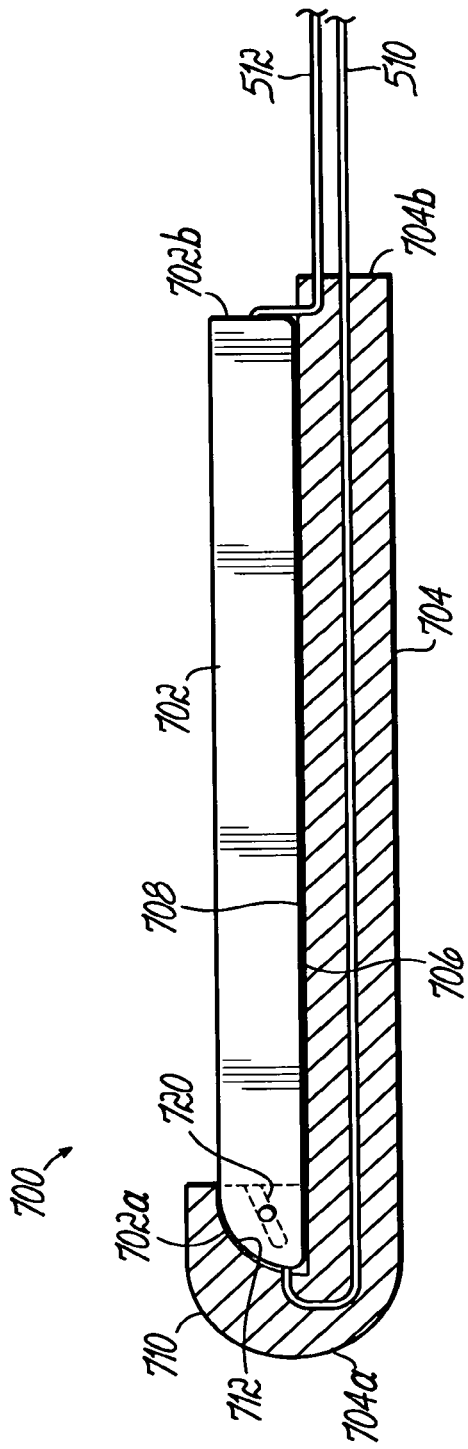

With continued reference to FIGS. 41 and 42, in one embodiment, the anvil 702 includes anvil pins 718, and the cartridge 704 includes channels 720 that are configured to receive the anvil pins 718. As shown, the anvil pin 718 is disposed proximate the distal end 702a of the anvil 702 and projects outwardly from the outer surface of the anvil 702. The channels 720 are disposed proximate the distal end 704a of the cartridge 704 within the cam tube 710. As shown, the channel 720 is open toward the proximal end 704b of the cartridge 704 and is angled in a direction toward the face 708 of the cartridge 704. The channel 720 terminates proximate the distal end 704a of the cartridge 704 nearer to the face 708 than the opening of the channel 720. While not shown in FIGS. 41 and 42, it will be appreciated that an anvil pin may be disposed on each of the right and left sides of the anvil 702. Similarly, the cartridge 704 may include channels disposed inside the cam tube 710 on either side to receive the anvil pins.

During use of the end effector 700 shown in FIGS. 41 and 42, tensioning the flexible member 510 pulls the anvil 702 within the cartridge 704 to engage the surfaces 712, 714. This motion is also engages the anvil pin 718 within the channel 720. Further tensioning the flexible member 510 produces a compressive force generally in the direction of the face 708 of the cartridge 704 due to the engagement between one or both of the surfaces 712, 714 and the anvil pin 718 with the channel 720. Advantageously, in addition to the above, the anvil pin 718 and channel 720 facilitates alignment between the anvil 702 and the cartridge 704.

With reference now to FIGS. 43 and 44, in which like reference numerals refer to like features of FIGS. 41 and 42, in one embodiment of the invention, the anvil 702 includes an anvil lever 724 positioned on the surface 714 proximate the distal end 702a. The cartridge 704 includes a slot 726 configured to receive the anvil lever 724 as the cartridge 704 is drawn into the cam tube 710. Advantageously, the combination of the anvil lever 724 and the slot 726 aligns the anvil 702 with the cartridge 704. This alignment ensures that the staple channels (described below) are adjacent to the corresponding staple pockets (described above) on the anvil 702. In addition, as shown in FIGS. 43 and 44, a single flexible member 46 may be anchored to the cartridge 704 proximate the proximal end 704b similar to the configuration shown in FIG. 22 and described above.

In one embodiment of the invention and with reference to FIGS. 45A and 45B, in which like reference numerals refer to like features of FIGS. 21-42, the end effector 700 includes a distal hinge 730 coupling the distal end 702a of the anvil 702 with the distal end 704a of the cartridge 704. The hinge 730 may provide alignment between the anvil 702 and the cartridge 704 in at least two directions with respect to the face 708 of the cartridge 704. The anvil 702 may further include a latch 732 projecting from the face 706 proximate the proximal end 702b of the anvil 702. The cartridge 704 may include a recess 734 and is configured to receive the latch 732 when the anvil 702 is brought to be engaged position. As shown, the latch 732 may include a notch 736. The cartridge 704 may house a pin 738 that projects into the recess 734 and that may be biased in one direction by a spring 740.

The anvil 702 may be rotated about the hinge 730 to an engaged position with tissue situated between the face 706 of the anvil 702 and the face 708 of the cartridge 704. Guided by the hinge 730 the surgeon may rotate the anvil 702 by pulling on the flexible member 46 through the cartridge 704. In the exemplary embodiment, the flexible member 46 is anchored to the latch 732 and passes through the recess 734. With reference to FIG. 45B, the latch 732 may enter the recess 734 to engage the pin 738, which enters the notch 736 under the bias of the spring 740. Thus, in this embodiment, each of the proximal end and the distal end of the end effector 700 is positively locked with respect to at least outward movement of the anvil 702 relative to the cartridge 704. In view of the above, the latch 732 may align the anvil 702 with the cartridge 704 and maintain that alignment against forces that tend to push the anvil 702 an outward direction relative to the face 708.

Following stapling and/or cutting, the surgeon may withdraw the pin 738 from the notch 736 by pulling a release cable 742. The anvil 702 may then be rotated to an opened or disengaged position. In one embodiment, the end effector 700 further includes a release spring 744 (shown in FIG. 45B) that is coupled to each of the anvil 702 and the cartridge 704. In the exemplary embodiment shown, the cartridge 704 houses the release spring 744. When the anvil 702 is in the engaged position with the latch 732 and recess 734, the release spring 744 is biased in a direction to push the anvil 702 away from the cartridge 704. That is, the release spring 744 is biased to disengage the anvil 702 from the cartridge 704 when the anvil 702 is in the engaged position. Thus, in this embodiment, when the surgeon pulls on the release cable 742, the release spring 744 acts to push apart or separate the anvil 702 from the cartridge 704. In this way, the release spring 744 assists the surgeon in opening the end effector 700.

In one embodiment, and with reference to FIGS. 46-48, in which like reference numerals refer to like features of FIGS. 21-45B, the anvil 702 is coupled to the cartridge 704 by the distal hinge 730. The flexible member 46 passes through the cartridge 704 at the proximal end 704b and is anchored to the anvil 702 at the proximal end 702b. As with the embodiment shown in FIGS. 45A-45B, the surgeon may rotate the anvil 702 to the engaged position by tensioning the flexible member 46. In this way, the anvil 702 rotates about the hinge 730 toward the cartridge 704 as is indicated by arrow 748 in FIG. 46. With reference to FIG. 46, the anvil 702 includes a tapered surface 750 at the proximal end 702b that forms a wedge-like configuration at the proximal end 702b of the anvil 702.

The end effector 700 further includes a proximal cam tube 752 that is movable relative to the cartridge 704 according to the arrow 754 in FIG. 47. The cam tube 752 includes a cavity 756 that faces the proximal end 702b of the anvil 702 when the anvil 702 is in an engaged position. The cavity 756 includes a wedge surface 760 that is positioned to engage the tapered surface 750 of the anvil 702. After the surgeon pulls the flexible member 46 to engage the anvil 702 with the tissue between the anvil 702 and the cartridge 704, the surgeon may force the cam tube 752 toward the proximal end 702b as is indicated by arrow 754. As the surgeon does so, the wedge surface 760 engages the tapered surface 750. The forcible contact between the two surfaces 750 and 760 forces the anvil 702 toward the cartridge 704. Thus, in this embodiment, each end 702a, 702b of the anvil 702 is captured to substantially prevent separation of the anvil 702 from the tissue. Pressure on the tissue may be increased by the forced engagement of the tapered surface 750 and the wedge surface 760.

Figure 49:
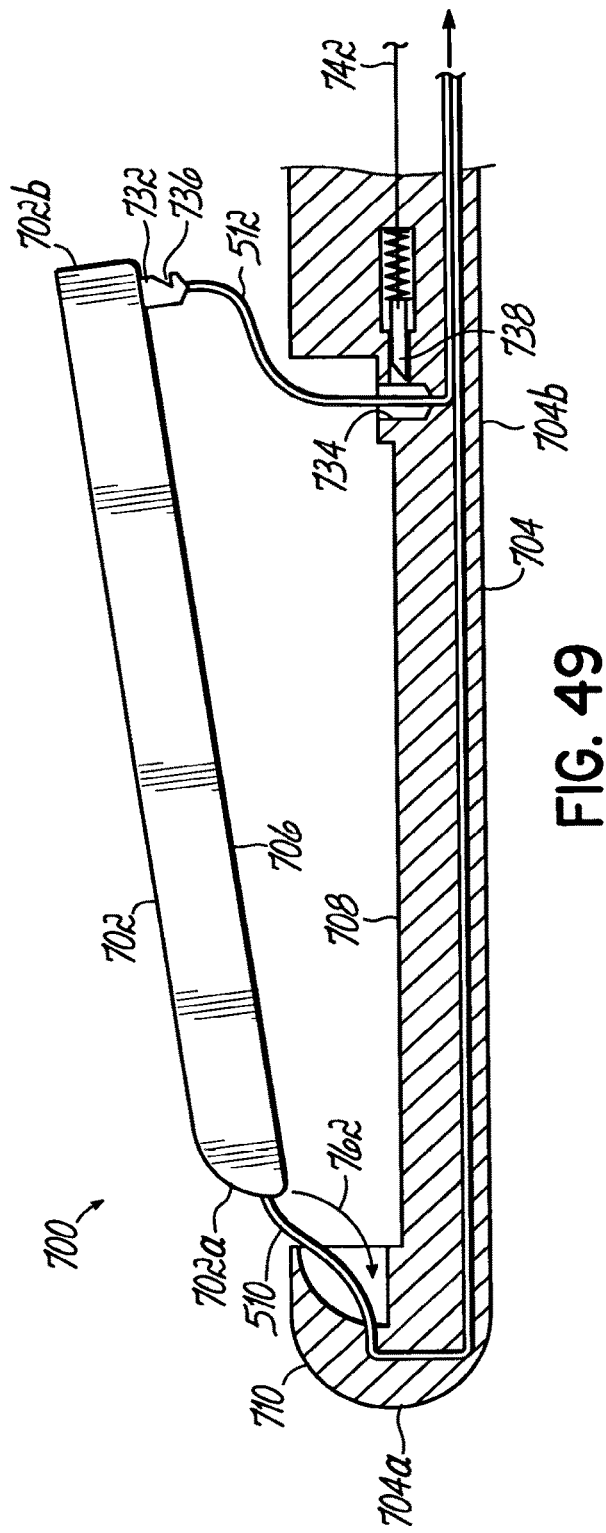
FIGS. 49 and 50 are schematic elevation views of an end effector according to one embodiment of the invention.
Figure 50:
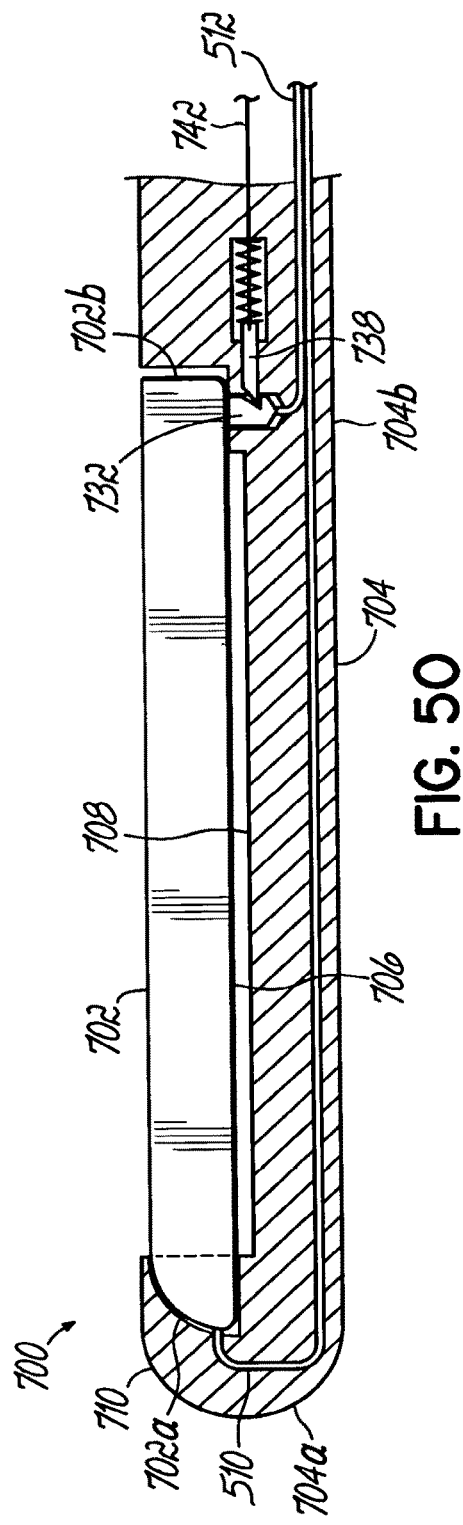

In one embodiment, and with reference to FIGS. 49 and 50, in which like reference numerals refer to like features of FIGS. 41-48, the end effector 700 combines various features of end effectors shown and described above. In that regard, the end effector 700 combines the distal cam tube 710 and the proximal latch 732. The surgeon may therefore withdraw the flexible member 510 to pull the anvil 702 into the distal cam tube 710 as is indicated by the arrow 762. Once inserted therein, the surgeon may withdraw the flexible member 512 to pull the latch 732 into the recess 734 with the pin 738 engaging the notch 736, as is shown in FIG. 50.

Figure 51:
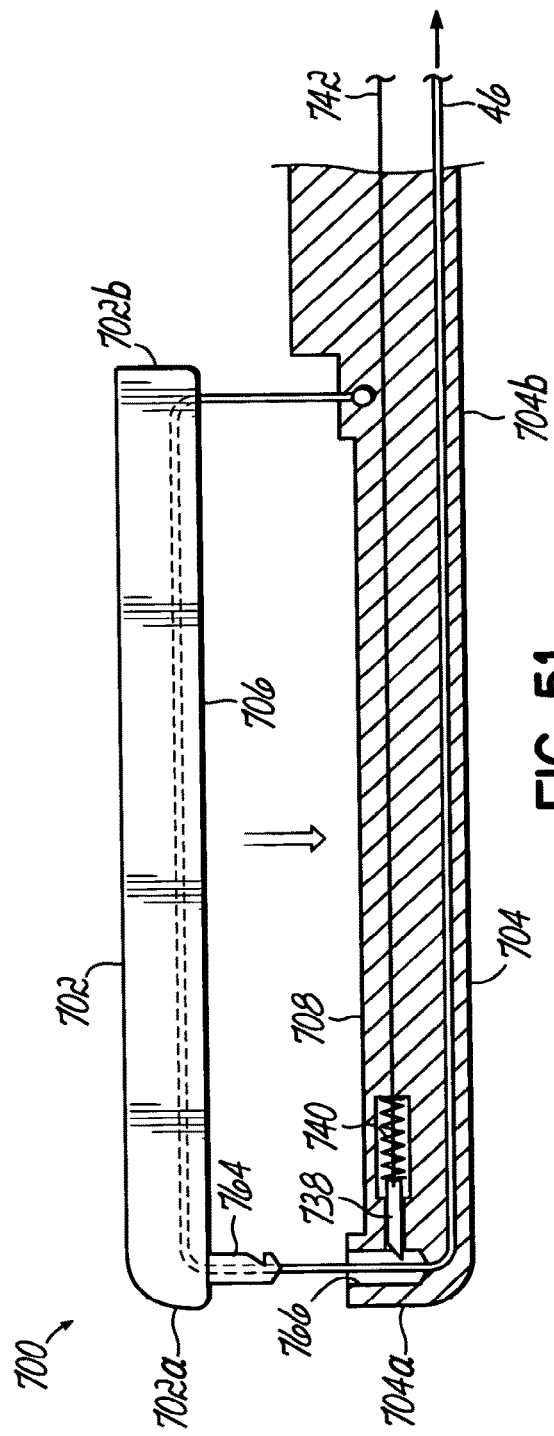
FIG. 51 is a schematic elevation view of an end effector according to one embodiment of the invention.

In one embodiment, and with reference to FIG. 51, in which like numerals refer to like features in FIGS. 41-50, the end effector 700 includes a distal latch 764 similar to the proximal latch 732 described above. The distal latch 764 on the anvil 702 fits within a recess 766 on the cartridge 704. While the latch 764 is shown to be part of the anvil 702, it will be appreciated that the latch 764 may be a part of the cartridge 704. That is, the orientation may be reversed from that shown in FIG. 51 or in any of the figures described above. As shown, the flexible member 46 passes through the cartridge 704, out of the distal end 704a, into the distal end 702a of the anvil 702, out of the proximal end 702b of the anvil 702, and into the proximal end 704b of the cartridge 704 where it is anchored to the cartridge 704. The surgeon may withdrawal the flexible member 46 to move the anvil 702 toward the cartridge 704. Withdrawing the flexible member 46 pulls the distal latch 764 into the recess 766. Each of the distal end 702a and the proximal end 702b of the anvil 702 is secured to the cartridge 704. The latch 764 may be released by pulling the release cable 742.

Figure 52:
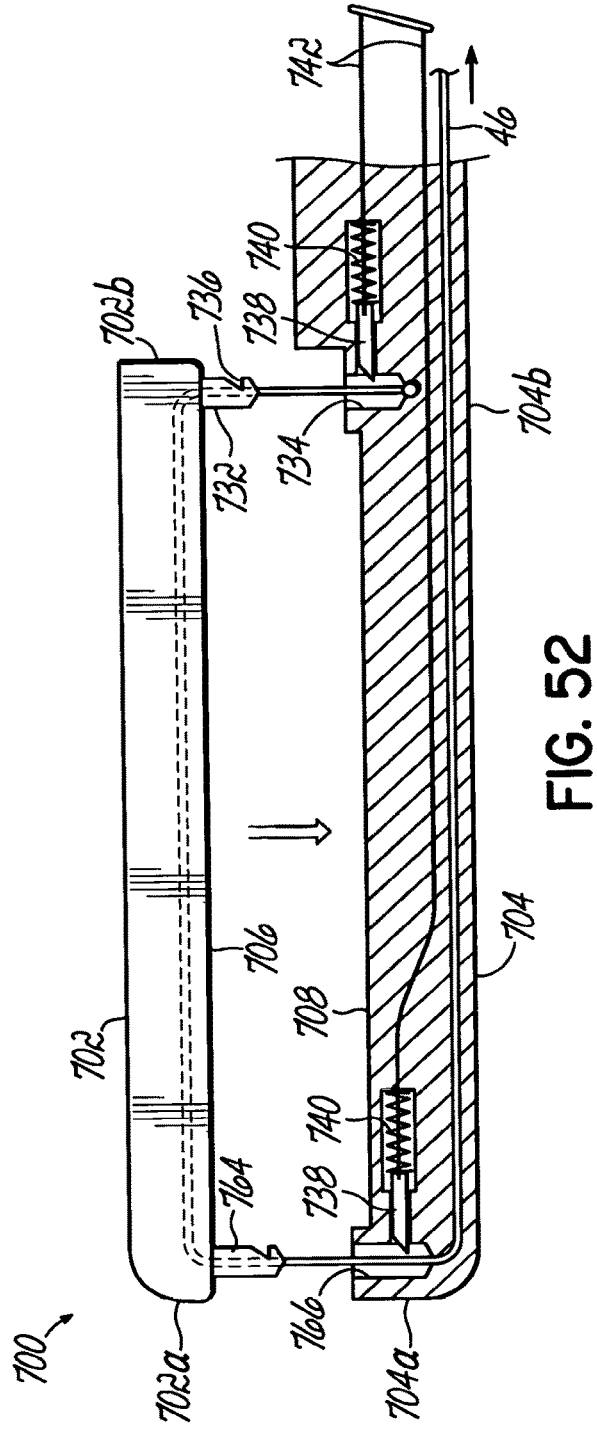
FIG. 52 is a schematic elevation view of an end effector according to one embodiment of the invention.

In one embodiment and with reference to FIG. 52, in which like reference numerals refer to like features in FIGS. 41-51, the end effector 700 includes latches at each of the ends 702a, 702b of the anvil 702. In that regard, the end effector 700 includes the proximal latch 732 and the distal latch 767. The surgeon may withdrawal the flexible member 46 to pull the anvil 702 toward the cartridge 704. Pulling the flexible member 46 pulls each of the latches 732, 767 into the corresponding recess 734, 766 to secure each of the ends 702a, 702b of the anvil 702 to the cartridge 704. The surgeon may pull the release cables 742 to release the anvil 702 from the cartridge 704. The release cables 742 may be separate or may be linked within the end effector 700 or another portion of the device.

In one embodiment and with reference to FIG. 53, in which like reference numerals refer to like features in FIGS. 51-52, the end effector 700 includes a distal latch 764 and a proximal cam tube 752. When the surgeon pulls the flexible member 46, the distal latch 764 enters the recess 766 and the pin 738 engages the notch 736 to secure the distal end 702a of the anvil 702 to the cartridge 704. Once the anvil 702 is proximate the cartridge 704, the surgeon may push the proximal cam tube 752 into engagement with the proximal end 702b of the anvil 702. The wedge surface 760 may engage a corresponding tapered surface 750 on the anvil 702. As described above, forcing the wedge surface 760 into contact with the anvil 702 produces a force in the direction of the cartridge 704 and secures the proximal end 702b to the anvil 702 to the cartridge 704. The surgeon may release the anvil 702 by pulling the release cable 742 to disengage the latch 764 at the distal end 702a of the anvil 702 and pulling the proximal cam tube 752 to disengage the proximal end 702b of the anvil 702.

In one embodiment and with reference to FIGS. 54-56, in which like reference numerals refer to like features throughout FIGS. 41-53, the end effector 700 may include a knife 770 having a cutting edge 772 and a wedge sled 774. The knife 770 may have an I-beam cross-sectional configuration similar to that shown in FIG. 39 and described above. The knife 770 is received in a channel 776 in the cartridge 704 and in a channel 778 in the anvil 702 when the anvil 702 compresses tissue between the anvil 702 and the cartridge 704. The flexible member 46 may pass through the cartridge 704 in the channel 776, through the knife 770 in the channel 778 to the proximal end 702b of the anvil 702, out of the proximal end 702b, and into the proximal end 704b of the cartridge 704 where it is anchored. The surgeon may pull on the flexible member 46 to draw the anvil 702 toward the cartridge 704.

With reference to FIG. 55, doing so pulls the knife 770 into the channel 778 and aligns the anvil 702 with the cartridge 704 at the distal ends 702a, 704a. At the proximal ends 702b, 704b, the surgeon may push the proximal cam tube 752 into engagement with the proximal end 702b of the anvil 702, as is described above, to secure and align the proximal ends 702b, 704b. Once secured and aligned, as is shown in FIG. 56, the surgeon may continue to pull the flexible member 46. Pulling the flexible member 46 draws the knife 770 along each channel 776, 778 to staple and cut tissue which is described above with reference to FIGS. 30A and 30B.

In one embodiment and with reference to FIGS. 57 and 58, in which like reference numerals refer to like elements in FIGS. 41-56, the end effector 700 includes the distal cam tube 710 and the proximal cam tube 752. Each of the anvil 702 and the cartridge 704 are separably coupled together by the cam tubes 710 and 752. In this regard, the surgeon may move the anvil 702 and the cartridge 704 independently of each other. Once positioned proximate the other, at least one of the cam tubes 710 and 752 is movable relative to the other along a screw 782 operable by the surgeon, for example, with a knob 784 to movably couple the anvil 702 to the cartridge 704. In the embodiment shown, the cam tube 752 is movable relative to cam tube 710. Rotating the knob 784 in one direction draws the cam tube 752 toward the other cam tube 710, and rotating the knob 784 in the opposite direction pushes the cam tube 752 away from the cam tube 710. In addition to capturing and aligning the anvil 702 relative to the cartridge 704, the surgeon may control the gap between the cam tubes 710, 752 by rotating the knob 784 to predetermined positions at which the gap between the anvil 702 and the cartridge 704 is known. In this regard, the gap may be varied by the amount of engagement between one or both of the cam tubes 710, 752 and the anvil 702. By moving both cam tubes 710, 752, the surgeon may control the gap between the anvil 702 and the cartridge 704 in a parallel configuration. By moving one of the cam tubes 710, 752, the surgeon may control the gap between the anvil 702 and the cartridge 704 in a non-parallel configuration. Further, this arrangement advantageously provides for control of the clamping force provided by the end effector 700. In this regard, as the gap between the anvil 702 and the cartridge 704 decreases, the clamping force on the anatomical structure may increase.

In one embodiment and with reference to FIG. 59, in which like reference numerals refer to like elements of FIGS. 41-58, the end effector 700 includes the proximal latch 732 with two flexible members 510 and 512. The flexible member 510 passes through the cartridge 704, out of the distal end 704a, and into the anvil 702 proximate the distal end 702a where it is anchored to the anvil 702. The flexible member 512 passes through the cartridge 704, out of the proximal end 704b through the recess 734, and may be anchored to the latch 732. Pulling each of the flexible members 510, 512 draws the anvil 702 toward the cartridge 704 with the latch 732 entering the recess 734. The pin 738 engages the notch 736 under the influence of the bias produced by the spring 740 to align and secure the anvil 702 against movement away from the cartridge 704. Once the surgical procedure is complete, to release the anvil 702, the surgeon may pull the release cable 742 allowing the pin 738 to disengage from the latch 732. Releasing each of the flexible members 510, 512 permits the anvil 702 to be moved apart from the cartridge 704.

In one embodiment, and with reference now to FIG. 60, in which like reference numerals refer to like features of FIGS. 41-59, the end effector 700 includes a single flexible member 46 having a pathway similar to that shown in FIG. 51, for example. The flexible member 46 is anchored proximate the proximate end 704b of the cartridge 704. The function of the end effector 700 shown in FIG. 60 may be somewhat like that shown in FIG. 59 with movement of the anvil 702 being achieved by pulling the flexible member 46. The anvil 702 may be released by pulling the release cable 742.

In one embodiment, and with reference to FIG. 61, in which like reference numerals refer to like features of FIGS. 41-60, the end effector 700 includes a proximal hinge 790 to pivotally secure the anvil 702 to the cartridge 704. The flexible member 46 passes along the length of the cartridge 704, exits the distal end 704a of the cartridge 704, and may be anchored to the distal end 702a of the anvil 702. The surgeon may withdraw the flexible member 46 from the end effector 700 to rotate the distal end 702a toward the distal end 704a of the cartridge 704. The proximal hinge 790 ensures alignment between the anvil 702 and the cartridge 704 at the proximal ends 702b, 704b thereof and also secures the anvil 702 to the cartridge 704. In one embodiment, and with reference to FIG. 62, in which like reference numerals refer to like features of FIGS. 41-61, the end effector 700 is similar to the end effector 700 shown in FIG. 61, but with the distal latch 764 described above with reference to FIG. 51. In this embodiment, the surgeon may pull the flexible member 46 to pivot the anvil 702 about the hinge 790. The latch 764 may enter the recess 766 with the pin 738 engaging the notch 736 to align and secure the anvil 702 to the cartridge 704 at the distal end 702a, 704a. The hinge 790 secures the anvil 702 to the cartridge 704 at the proximal end 702b, 704b. The surgeon may release the distal end 702a from the cartridge 704 by pulling on the release cable 742.

Figure 63:
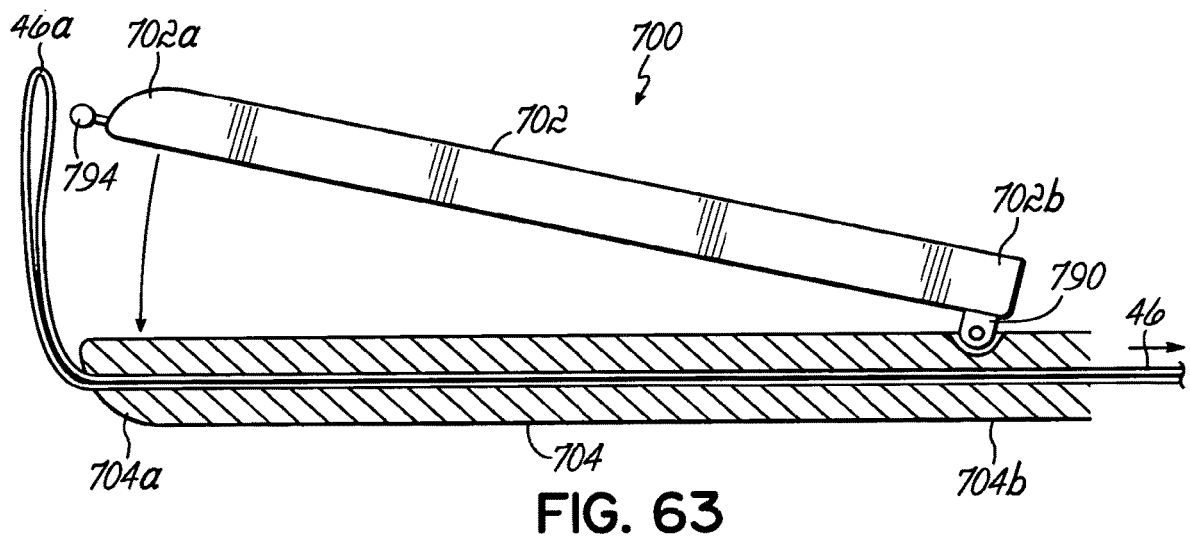

In one embodiment, and with reference to FIG. 63, in which like reference numerals refer to like features of FIGS. 41-62, the end effector 700 includes the proximal hinge 790 but is secured at the distal end 702a, 704a by the flexible member 46. In particular, the flexible member 46 passes through the cartridge 704 and exits the distal end 704a and is configured with a loop 46a. The anvil 702 includes a stud 794 that projects from the distal end 702a. Although not shown, the loop 46a may be coupled to the stud 794. The surgeon may withdraw the flexible member 46 from the end effector 700 to rotate the anvil 702 toward the cartridge 704. The hinge 790 secures the anvil 702 to the cartridge 704 at the proximal end 702b, 704b and the loop 46a secures the anvil 702 to the cartridge 704 at the distal end 702a, 704a.

Figure 64:
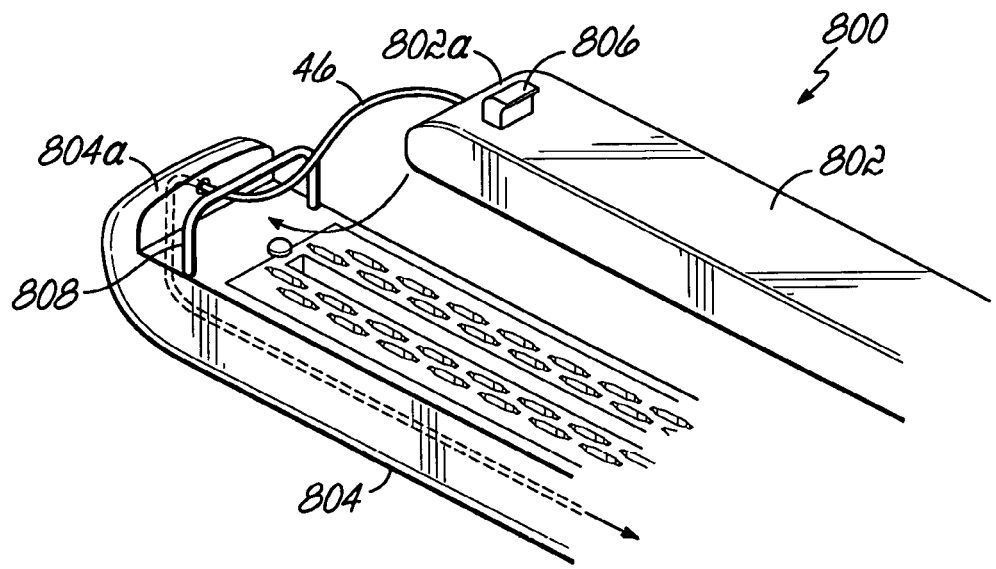
FIGS. 64 and 65 are perspective views of an end effector in a disengaged position and an engaged position, respectively, according to one embodiment of the invention.
Figure 65:
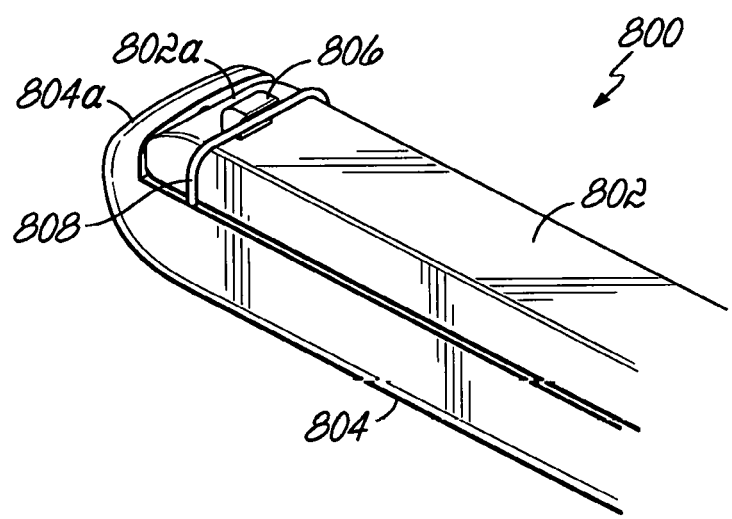

In one embodiment, and with reference to FIGS. 64 and 65, in which like reference numerals refer to like features throughout the drawings, the end effector 800 includes an anvil 802 and a cartridge 804. As with the end effectors described above, the end effector 800 may be coupled to a manipulator, such as, the manipulator 102 and 302 (shown in FIGS. 3-20 and described above), or another manipulator, by which the surgeon may remotely operate the end effector 800. In FIG. 64, a distal end 802a of the anvil 802 is shown as having a hook 806. A distal end 804a of the cartridge 804 has a lever 808. As the surgeon pulls the flexible member 46, the distal end 802a is pulled beneath the lever 808 as is shown FIG. 65. In particular, the hook 806 engages the lever 808 to align and secure the anvil 802 to the cartridge 804.

Figure 66:
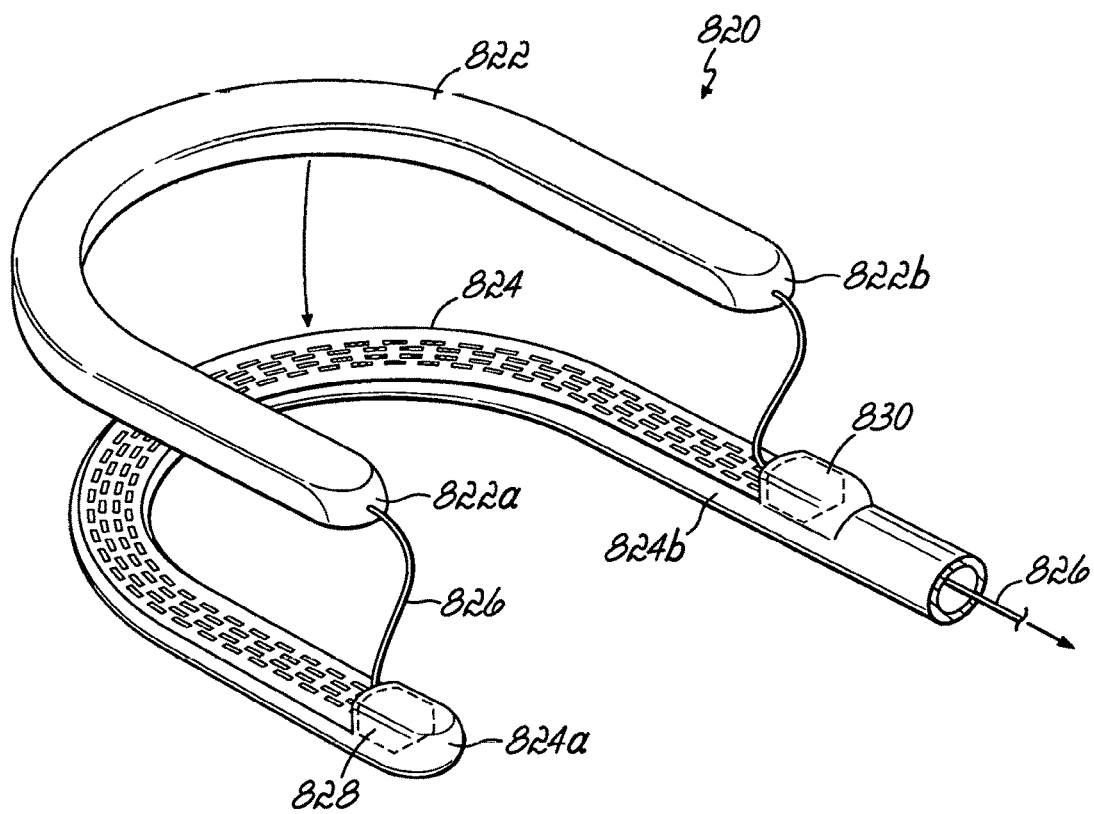
FIG. 66 is a perspective view on an end effector according to one embodiment of the invention.

With reference to FIG. 66, in which like reference numerals refer to like features throughout the drawings, an end effector 820 includes a curved anvil 822 having a first end 822a and a second end 822b and a curved cartridge 824 having a first end 824a and a second end 824b. The anvil 822 and the cartridge 824 are shaped to fit together with the first ends 822a, 824a and second ends 822b, 824b in alignment when the anvil 822 aligns with the cartridge 824. The cartridge 824 includes a first cam tube 828 and a second cam tube 830. A flexible member 826 movably couples the anvil 822 with the cartridge 824. The surgeon withdraws the flexible member 826 from the end effector 820. Doing so draws the anvil 822 and cartridge 824 together with the first end 822a of the anvil 822 entering the distal cam tube 828. This configuration is similar to the distal cam tube 710 disclosed above with reference to FIG. 41, for example. To secure the second ends 822b, 824b, the surgeon pushes the proximal cam tube 830 to engage the anvil 822. Proximal cam tubes are shown in at least FIGS. 46-48 described above.

Figure 67:
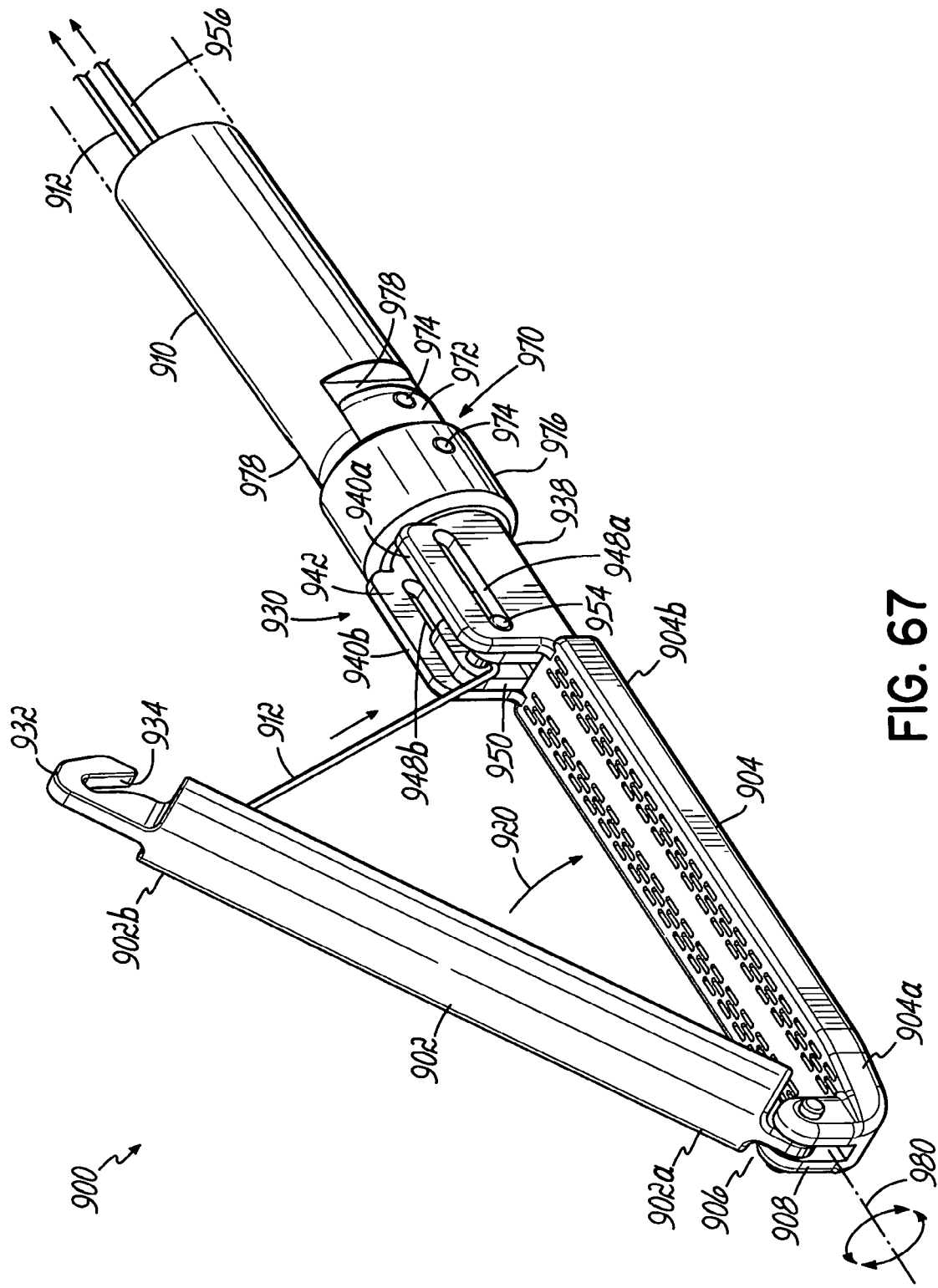
FIG. 67 is a perspective view of one embodiment of an end effector.
Figure 68A:
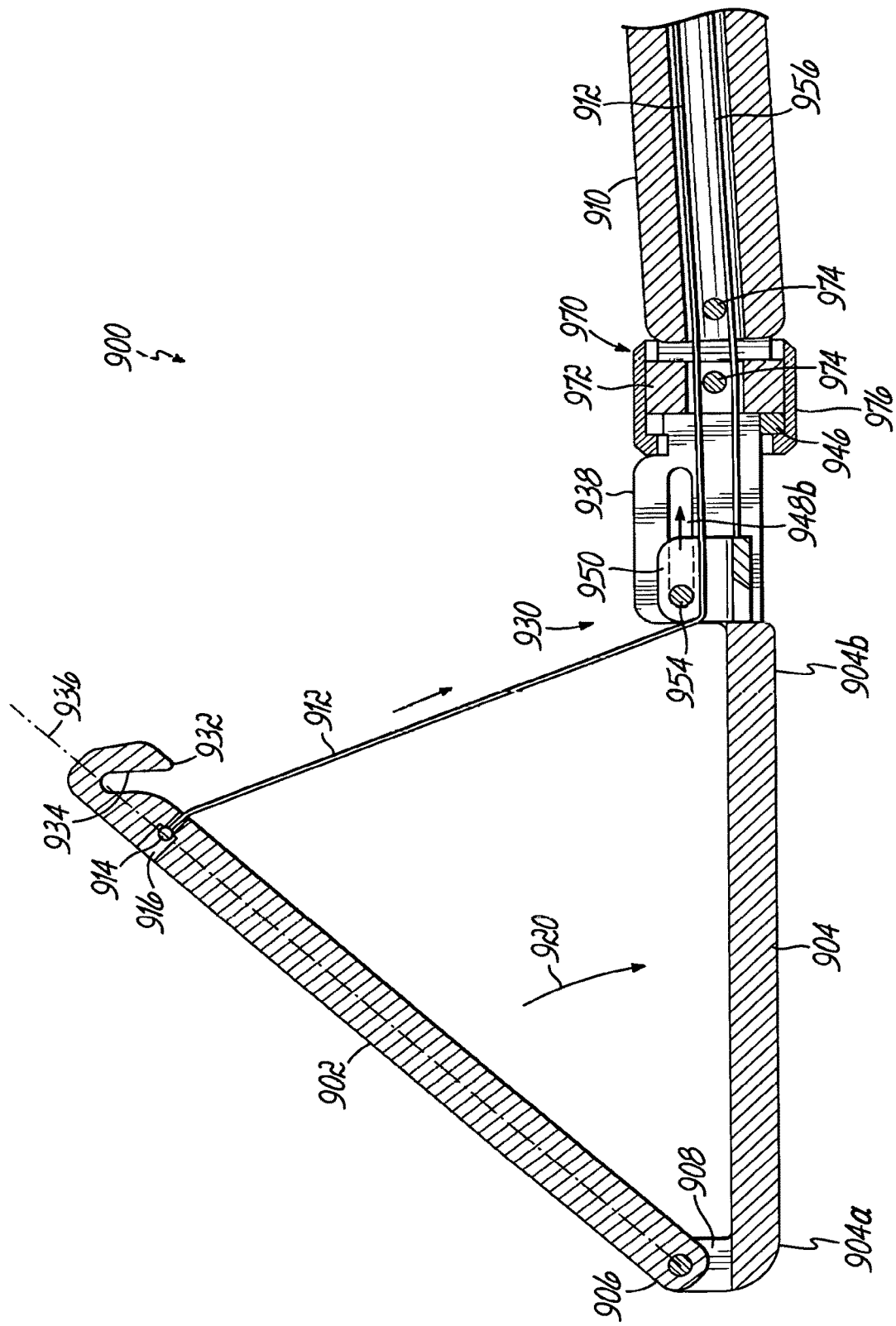
FIGS. 68A and 68B are cross-sectional views of the end effector shown in FIG. 67 in a disengaged position and an engaged position, respectively.
Figure 68B:
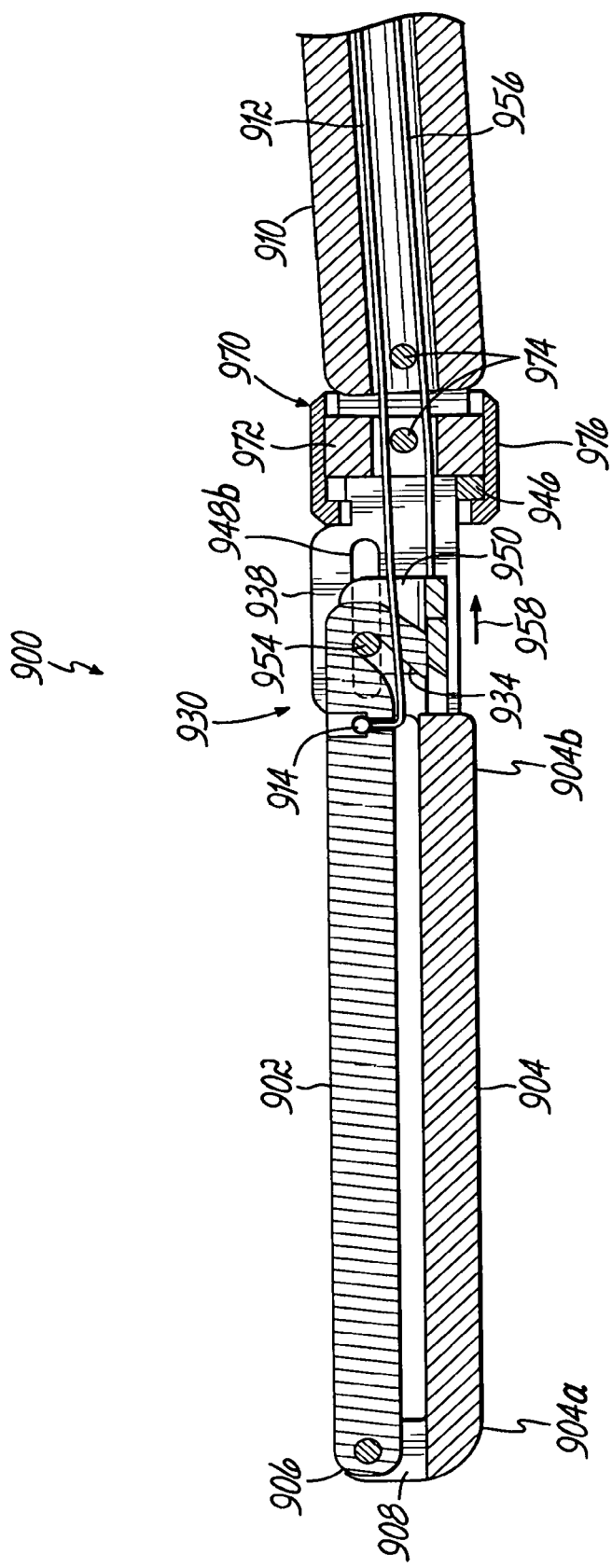
Figure 68C:
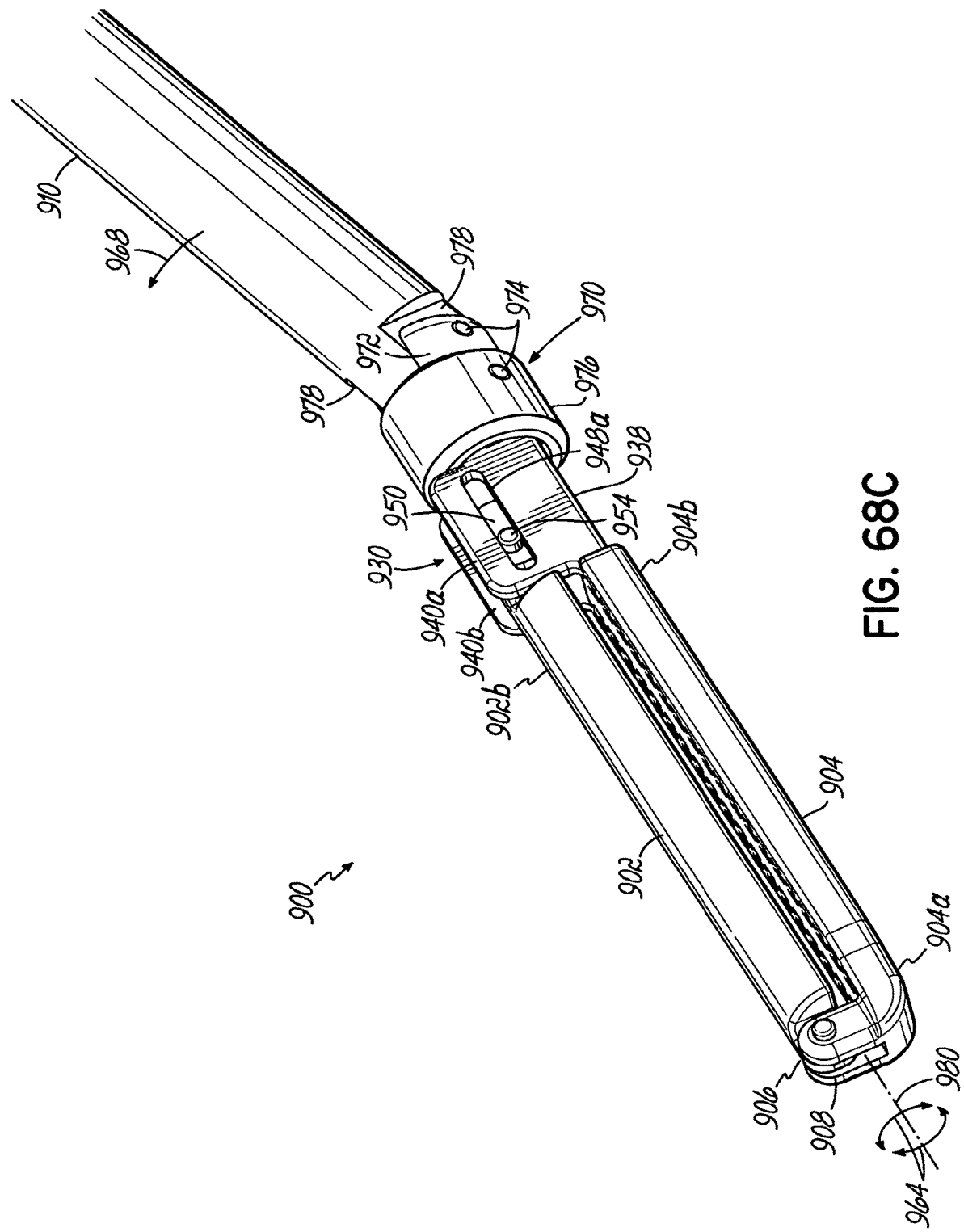
FIG. 68C is a perspective view of the end effector shown in FIG. 67 in an engaged position.

In one embodiment, and with reference to FIGS. 67-68C, in which like reference numerals refer to like features throughout the drawings, an end effector 900 is capable of clamping tissue. The end effector 900 is coupled to a shaft 910, which may be any of shafts 104, 304, described above, or another shaft that is operatively coupled to a manipulator. The end effector 900 is capable of articulating relative to the shaft 910 in one or more directions. The end effector 900 includes an anvil 902 and a cartridge 904 coupled together at a distal end 906 thereof by a hinge 908. In particular, the hinge 908 couples distal ends 902a, 904a of the anvil 902 and cartridge 904, respectively, together. A flexible member 912 is operatively coupled to a proximal end 902b of the anvil 902 and couples the proximal end 902b to the cartridge 904. By way of example only, and not limitation, as is shown in FIG. 68A, an anchor 914 secured to an end of the flexible member 912 resides within an undersized bore 916 and couples the flexible member 912 to the anvil 902. The flexible member 912 passes through the shaft 910 and may be accessible to the surgeon. Similar to previous embodiments, the surgeon may withdraw the flexible member 912 from the end effector 900 to rotate the anvil 902 about the hinge 908 toward the cartridge 904 as is indicated by arrow 920 in FIGS. 67 and 68A.

In addition, the end effector 900 may further include a compression mechanism 930 by which additional compressive force may be applied to the tissue situated between the anvil 902 and the cartridge 904. In the embodiment shown in FIGS. 67-68B, the compression mechanism 930 includes a hook member 932 that extends from the proximal end 902b of the anvil 902. The hook member 932 defines a slot 934. As shown in FIG. 68A, the slot 934 opens toward the cartridge 904 and is angled relative to a longitudinal axis 936 of the anvil 902. By way of example only, the slot 934 is angled from about 25° to less than about 90° from the longitudinal axis 936.

The compression mechanism 930 may also include a compression housing 938 that extends from a proximal end 904b of the cartridge 904 and couples the end effector 900 to the remainder of the medical device (not shown) via the shaft 910. The compression housing 938 includes two spaced-apart flanges 940a, 940b defining a channel 942 between them. As shown, the flexible member 912 passes through the compression housing 938. In the exemplary embodiment shown, the flexible member 912 passes through the channel 942. Each of the flanges 940a, 940b defines a slot 948a, 948b, respectively, that generally extends parallel to the longitudinal axis of the cartridge 904. A rotation flange 946 (FIG. 68A) defines one end of the housing 938 and extends generally radially outwardly relative to the spaced-apart flanges 940a, 940b and is described below. A compression slide 950 is slidable relative to the compression housing 938 in a direction defined by the channel 942. The compression slide 950 carries a compression pin 954 that is slidably received in the slots 948a, 948b of the compression housing 938. As is shown best in FIG. 68A, a compression cable 956 is coupled to the compression slide 950 and extends through the shaft 910 and may be accessible to the surgeon.

During a surgical procedure, the surgeon may withdraw the flexible member 912 from the end effector 900. Doing so rotates the anvil 902 toward the cartridge 904 and clamps tissue between the anvil 902 and the cartridge 904. The anvil 902 approaches the cartridge 904 with the hook 932 entering the channel 944 of the compression housing 938. It will be appreciated that additional tension on the flexible member 912 may be insufficient to further compress the tissue between the anvil 902 and the cartridge 904. If so, the surgeon may engage the compression mechanism 930 to apply additional pressure to the tissue. In that regard, the surgeon may retract the compression cable 956 from the end effector 900.

With reference to FIG. 68B, as the surgeon retracts the compression cable 956, the compression slide 950 is forced toward the shaft 910 according to arrow 958. Sliding movement of the compression slide 950 in the channel 944 forces the pin 954 into the slot 934. Because the slot 934 is angled relative to the longitudinal axis 936 (FIG. 68A), forcing the compression slide 950 and the pin 954 in the direction indicated by arrow 958 produces a clamping force in the direction of the cartridge 904. This force pulls the anvil 902 toward the cartridge 904 and so provides additional compression of the tissue.

In one embodiment, and with reference now to FIG. 68C, according to one aspect of the invention, the end effector 900 may be articulated relative to the shaft 910. An articulation mechanism 970 may provide this motion (indicated by arrows 964 in FIG. 68C). With reference to FIGS. 67 and 68C, in one embodiment, the articulation mechanism 970 includes a clevis 972 that is secured to the end effector 900 at one end and the shaft 910 at the other end by pins 974. A portion of the clevis 972 is coupled to the shaft 910 at a pair of cutouts 978 at one end of the shaft 910. The pin 974 provides a pivot point about which the shaft may rotate relative to the end effector 900. In addition, the clevis 972 is coupled to a rotation collar 976 by another pin 974. The rotation collar 976 surrounds at least a portion of each of the clevis 972 and the rotation flange 946 of the compression housing 938. The rotation collar 976 thus frictionally couples the end effector 900 to the clevis 972 and may define a longitudinal axis 980 about which the end effector 900 may be rotatable. Embodiments of the present invention may therefore be configured to rotate about an axis nearest the end effector and pivot about an axis nearest the shaft. That is, according to embodiments of the invention, there may be an ordered arrangement between the rotation and the pivoting motion, as shown. While it may be possible for the end effector 900 to rotate relative to the clevis 972 within the rotation collar 976, rotation of the shaft 910 may also rotate the end effector 900 via frictional engagement between the clevis 972 and the rotation collar 976.

During a surgical procedure, the surgeon may desire to rotate the shaft 910 relative to the end effector 900. Relative movement between the shaft 910 and the compression housing 938 is permitted by a combination of the clevis 972 and the rotation collar 976. The clevis 972 allows bending between the end effector 900 and the shaft 910 (as indicated by arrow 968 in FIG. 68C), and the collar 976 allows rotation around the longitudinal axis of the end effector 900 (as is indicated by arrows 964 in FIG. 68C) by allowing relative movement between the clevis 972 and the compression housing 938. It will be appreciated that when the surgeon pulls the compression cable 956, the compression housing 938 may be forced against the clevis 972. This additional applied pressure may substantially prevent relative rotation between the housing 938 and the clevis 972 and so essentially locks the orientation of the end effector 900 relative to the shaft 910.

Figure 69:
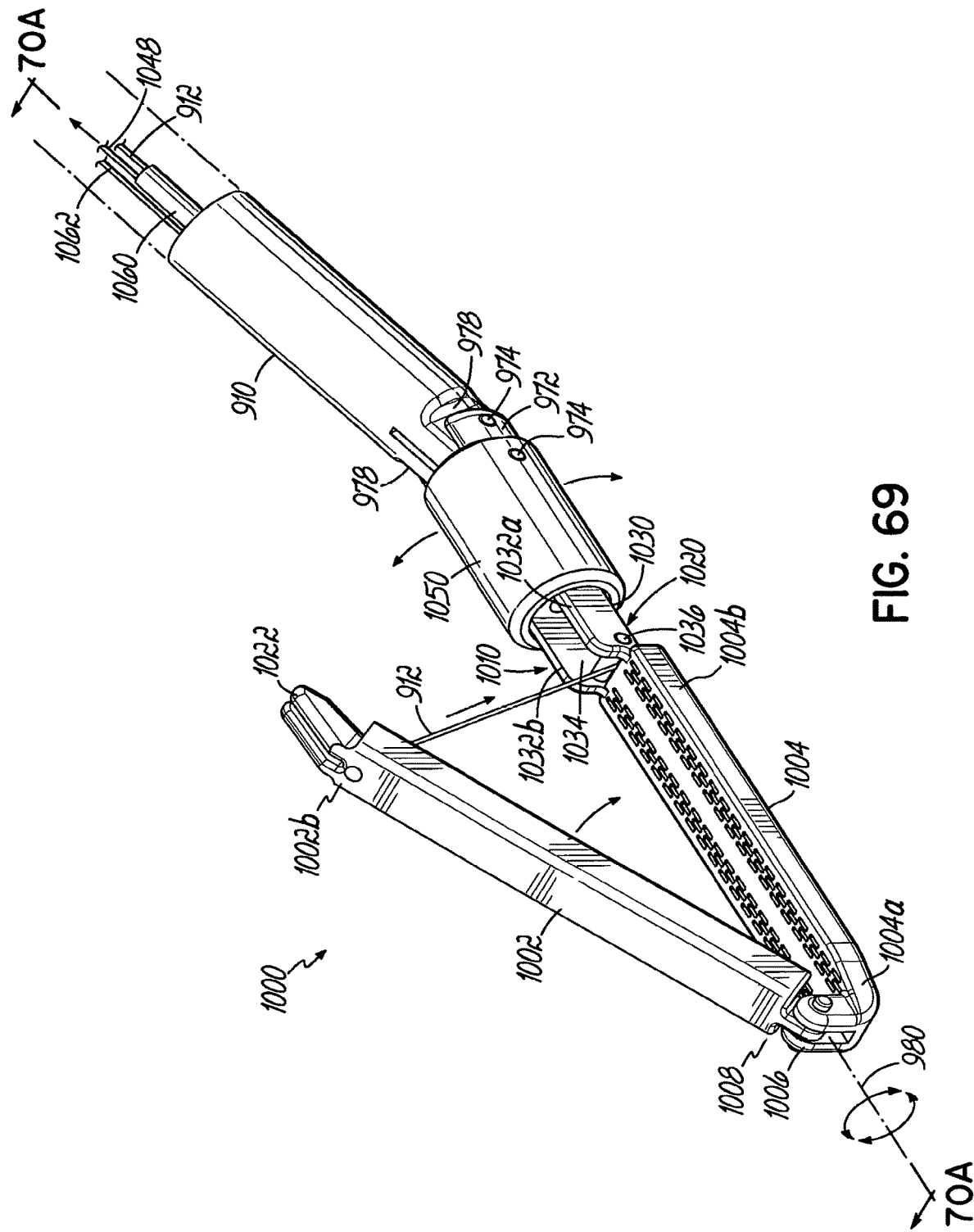
FIG. 69 is a perspective view of one embodiment of an end effector in a disengaged position.
Figure 70A:
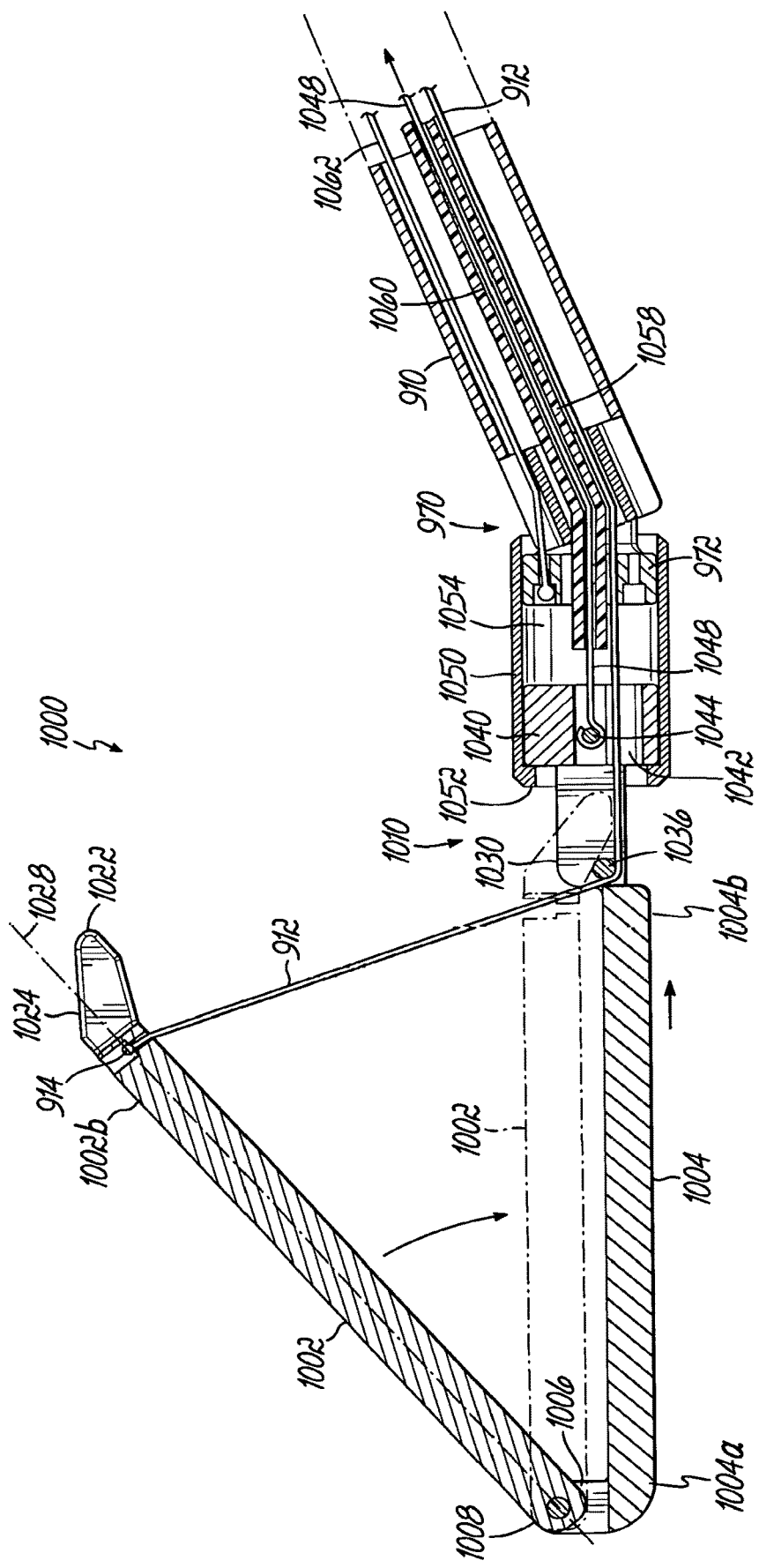
FIG. 70A is a cross-sectional view of the end effector shown in FIG. 69 taken along section line 70A-70A.
Figure 70B:
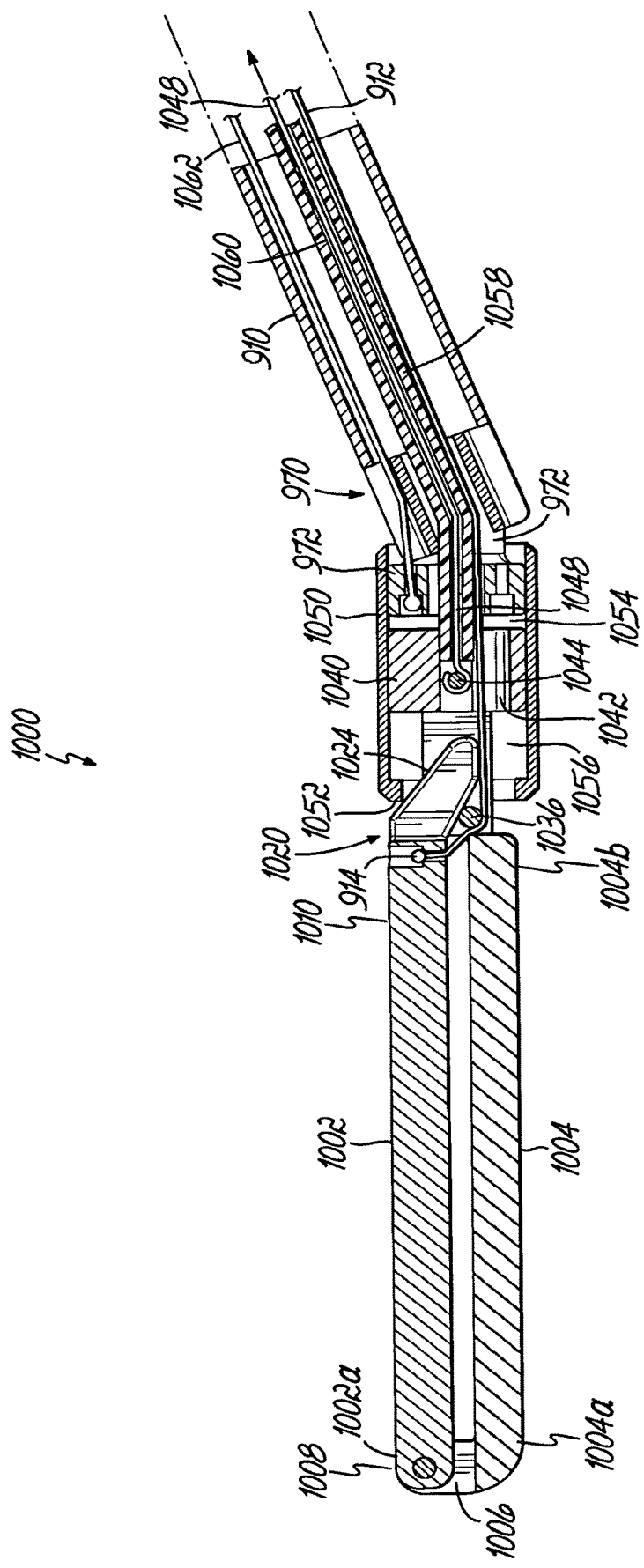
FIG. 70B is a cross-sectional view of the end effector shown in FIG. 69 in an engaged position.

In one embodiment, and with reference to FIGS. 69-70B, in which like reference numerals refer to like features of FIGS. 67-68B, an end effector 1000 is capable of clamping tissue. The end effector 1000 is coupled to the shaft 910 by the clevis 972 and is capable of articulating relative to the shaft 910. To those ends, the end effector 1000 includes an anvil 1002 pivotally coupled to a cartridge 1004 at a hinge 1006 at a distal end 1008 thereof. The flexible member 912 couples the anvil 1002 to the cartridge 1004 at a proximal end 1010 thereof and is assessable to the surgeon. As with the embodiment shown in FIGS. 67-68B and described above, the surgeon may withdraw the flexible member 912 from the end effector 1000 to clamp tissue between the anvil 1002 and the cartridge 1004. However, the clamping pressure achievable with the flexible member 912 may be insufficient. To provide additional clamping, the end effector 1000 may include a compression mechanism 1020 capable of applying additional pressure to the tissue situated between the anvil 1002 and the cartridge 1004.

In that regard, the compression mechanism 1020 may include a compression wedge 1022 extending from the proximal end 1002b of the anvil 1002. The compression wedge 1022 may have a dogleg-like configuration and so project from the proximal end 1002b of the anvil 1002 at an angle. With reference to FIG. 70A, the compression wedge 1022 includes a wedge surface 1024 that is oriented at a transverse angle relative to a longitudinal axis 1028 of the anvil 1002. The wedge surface 1024 is angled relative to the longitudinal axis 1028 of the anvil 1002. By way of example only, the surface 1024 is angled from about 10° to about 60° from the longitudinal axis 1028, and by way of further example, the surface 1024 may be angled from about 10° to about 45° or from about 20° to about 30° from the longitudinal axis 1028. It will be appreciated that the steeper the angle, the shorter the clamping stroke and the higher the clamping forces that have to be supplied. The reverse may also be true. That is, the shallower the angle, the longer the clamping stroke and the lower the clamping forces that have to be supplied.

The compression mechanism 1020 may also include a compression housing 1030 extending from the proximal end 1004b of the cartridge 1004. As shown best in FIG. 69, the compression housing 1030 includes opposing flanges 1032a, 1032b that define a channel 1034, which is configured to receive at least a portion of the compression wedge 1022 as the anvil 1002 clamps tissue between the anvil 1002 and the cartridge 1004. As is shown in FIGS. 69 and 70B, a routing pin 1036 is coupled to each of the flanges 1032a, 1032b and spans the channel 1034. The flexible member 912 is slidably coupled to the pin 1036 and so the pin 1036 guides the flexible member 912 through the channel 1034 and into the shaft 910.

With reference to FIGS. 70A and 70B, the compression housing 1030 further includes a radially extending flange 1040 that defines the proximal end of the compression housing 1030. The radially extending flange 1040 defines a through bore 1042 through which passes the flexible member 912. An attachment pin 1044 is coupled to the flange 1040 and spans the through bore 1042. A compression cable 1048 is coupled to the attachment pin 1044 and extends through the shaft and may be accessible by the surgeon. A rotation collar 1050 slidably couples the compression housing 1030 to the shaft 910 (e.g., by the clevis 972). The rotation collar 1050 has a partially closed end 1052, which provides an interference fit with the flange 1040 and functions as a stop to distal movement of the compression housing 1030 within the flange 1040. The rotation collar 1050 may define the longitudinal axis 980 about which the surgeon may rotate the end effector 1000.

As is shown best in FIG. 70A, the rotation collar 1050 is an elongated tubular body with an overall length that exceeds the corresponding length dimension of the flange 1040 of the compression housing 1030. Accordingly, when the anvil 1002 is in the disengaged position, as is shown in FIG. 70A, the flange 1040 is positioned adjacent the partially closed end 1052 within the rotation collar 1050. In view of the relative difference in lengths of the flange 1040 and the collar 1050, a gap 1054 exists between the flange 1040 and the clevis 972 into which the flange 1040 may slide as the surgeon engages the compression mechanism 1020 as is described below.

With reference to FIGS. 70A and 70B, the surgeon may engage the compression mechanism 1020 by pulling on the compression cable 1048. After the anvil 1002 is clamped onto tissue between the anvil 1002 and the cartridge 1004, at least a portion of the compression wedge 1022 may reside between the flanges 1032a, 1032b in the channel 1034. To apply additional compression to the tissue, the surgeon may pull the compression cable 1048 from the end effector 1000. The applied force causes relative movement between the rotation collar 1050 and the flange 1040. Specifically, pulling on the compression cable 1048 pulls the flange 1040 in the proximal direction into the gap 1054. This drives the partially closed end 1052 of the rotation collar 1050 into contact with the wedge surface 1024 (shown in FIG. 70B). Because of the angled orientation of the wedge surface 1024, the partially closed end 1052 of the rotation collar 1050 forces the anvil 1002 toward the cartridge 1004 and accordingly applies additional pressure to the tissue situated therebetween. By this motion, a gap 1056 may be formed between the flange 1040 adjacent the partially closed end 1052 of the flange 1040 when the anvil 1002 is in an engaged position and the compression mechanism 1020 is engaged. As the gap 1056 increases, the gap 1054 is reduced.

In another aspect of the exemplary embodiment shown in FIGS. 69-70B, the surgeon may articulate the end effector 1000 relative to the shaft 910. As with the embodiment shown in FIG. 67, the shaft 910 may be coupled to the end effector 1000 by the clevis 972. The rotation collar 1050 captures a portion of the clevis 972 adjacent the flange 1040. The clevis 972 is configured to provide pivotal motion between the end effector 1000 and the shaft 910 at a pivot point defined by one of the pins 974.

In addition, and with reference to FIGS. 70A and 70B, the articulation mechanism 970 further includes a rotation tube 1058. As shown, the rotation tube 1058 passes through the clevis 972 and the shaft 910 and may be operable by the surgeon. The rotation tube 1058 defines an elongated through bore 1060 that extends axially through the length of the rotation tube 1058. The rotation tube 1058 may be a hollow flexible shaft. The compression cable 1048 may run axially from the end effector 1000 through the shaft 910 within the through bore 1060. By way of example only and not limitation, the rotation tube 1058 may be fabricated from a series of tightly wound wires of multiple layers with each layer being wound opposite directions from at least one adjacent layer. It will be appreciated that the rotation tube 1058 allows power transmission around a bend, such as, through the clevis 972 when it is bent. In one embodiment, the rotation tube 1058 is secured to the flange 1040 such that rotation of the rotation tube 1058 rotates the end effector 1000 about the longitudinal axis 980.

With continued reference to FIGS. 70A and 70B, in one embodiment, the articulation mechanism 970 includes an articulation cable 1062 that is coupled to the clevis 972. The articulation cable 1062 extends from the clevis 972 through the shaft 910 to a location accessible by the surgeon. The surgeon may pull the articulation cable 1062 to cause the end effector 1000 to articulate about the pin 974 that couples the clevis 972 to the shaft 910. Advantageously, the surgeon may control the degree to which the shaft 910 is angled with respect to the end effector 1000.

Figure 71:
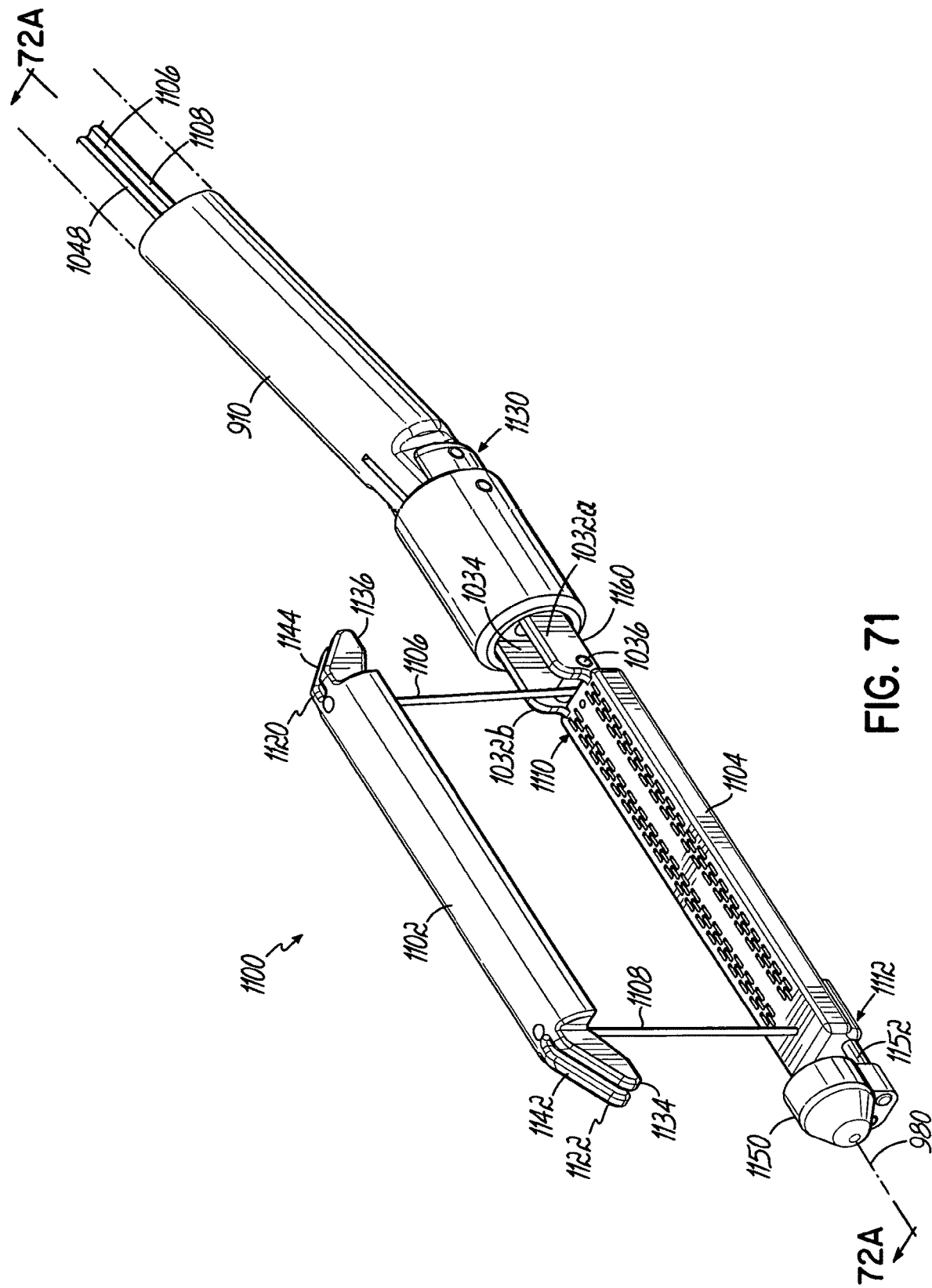
FIG. 71 is a perspective view of one embodiment of an end effector in a disengaged position.
Figure 72A:
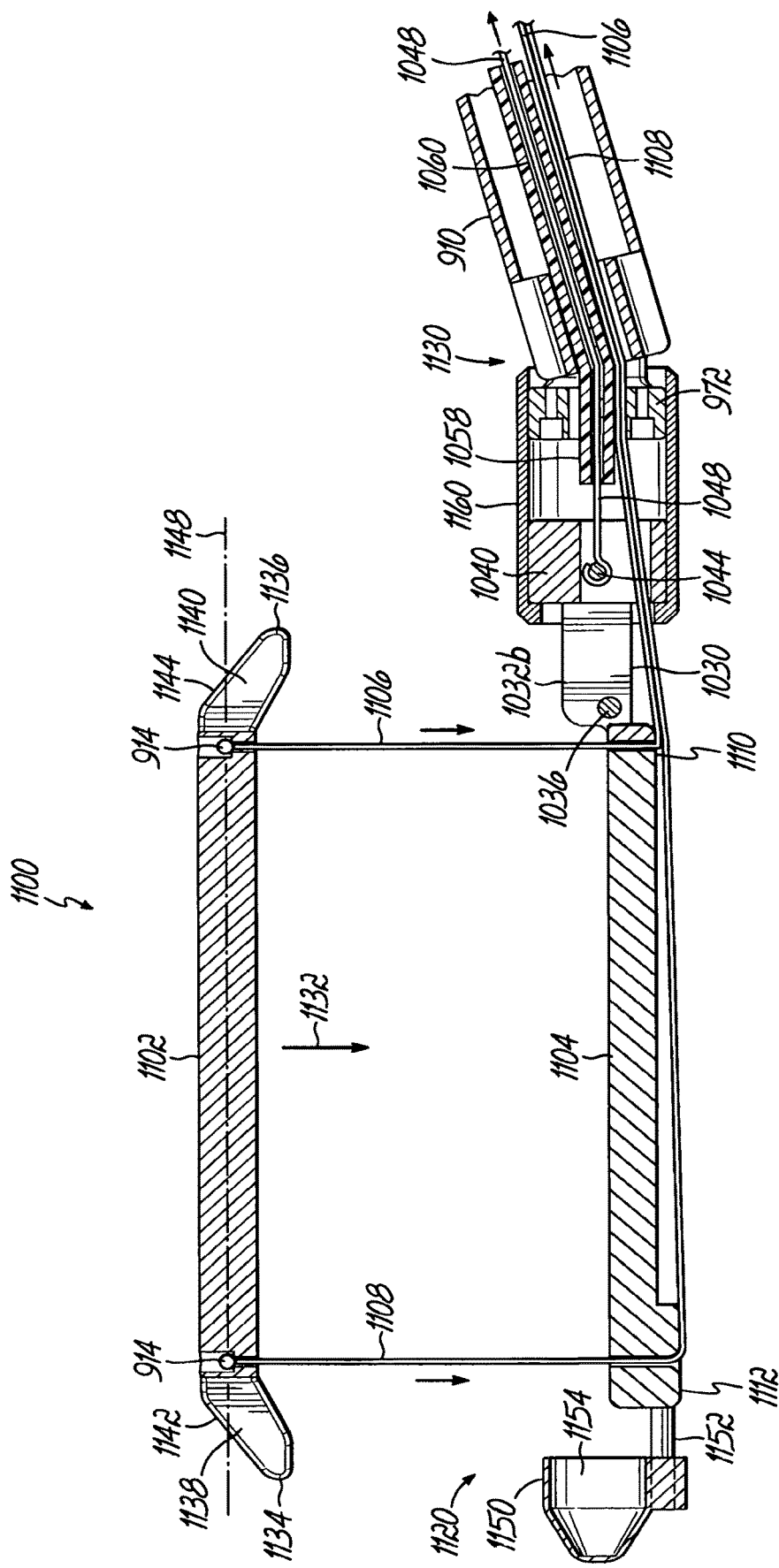
FIG. 72A is a cross-sectional view of the end effector shown in FIG. 71 taken along section line 72A-72A.
Figure 72B:
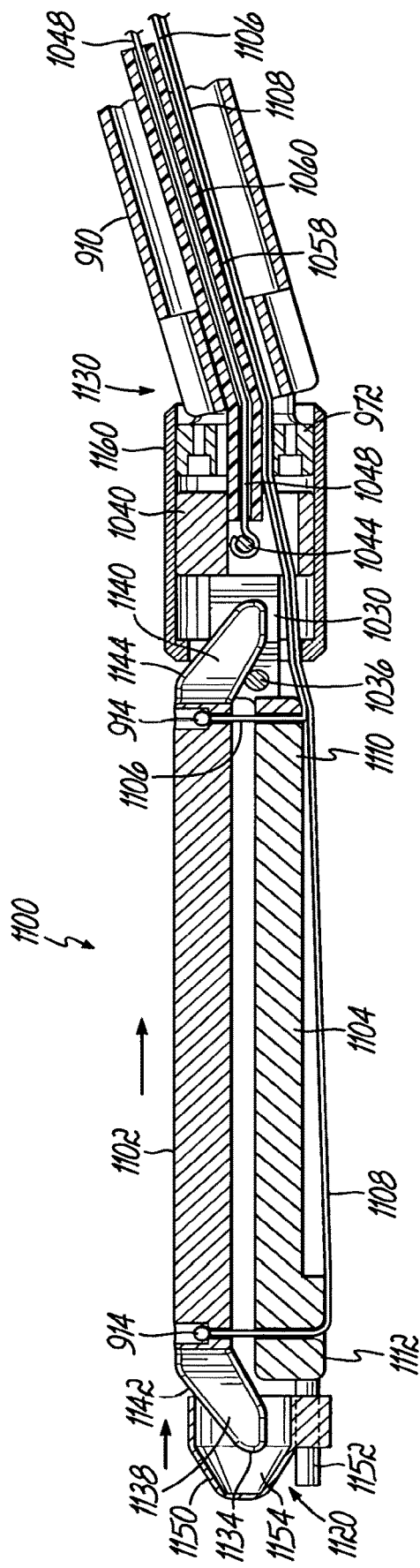
FIG. 72B is a cross-sectional view of the end effector shown in FIG. 71 in an engaged position.

In one embodiment and with reference now to FIGS. 71-72B, in which like reference numerals refer to like features of FIG. 67-70B, the end effector 1100 includes an anvil 1102 coupled to a cartridge 1104 by flexible members 1106 and 1108 at proximal and distal ends 1110, 1112 of the end effector 1100, respectively. As with previous embodiments, the end effector 1100 is configured to clamp tissue between the anvil 1102 and the cartridge 1104 and is configured to articulate relative to the shaft 910. In that regard, the end effector 1100 includes a compression mechanism 1120 and an articulation mechanism 1130 pivotally couples the end effector 1100 to the shaft 910.

With reference to FIG. 72A, in one embodiment, the flexible members 1106 and 1108 are anchored to the anvil 1102 by anchors 914, described above with reference to FIG. 68A. The flexible members 1106, 1108 pass into and through the cartridge 1104 at corresponding ends thereof and through the shaft 910 and may be accessible to the surgeon. In this regard, the surgeon may withdraw each of the flexible members 1106, 1108 from the end effector 1100 to pull the anvil 1102 toward the cartridge 1104, as is indicated by arrow 1132 in FIG. 72A. It will be appreciated that the surgeon may be unable to compress tissue between the anvil 1102 and the cartridge 1104 sufficiently by tensioning the flexible members 1106, 1108. The surgeon may then engage the compression mechanism 1120 to provide additional compression of the tissue.

Referring to FIG. 71, in one embodiment, the compression mechanism 1120 includes a distal clamping mechanism 1134 at the distal end 1112 of the end effector 1100 and a proximal clamping mechanism 1136 at the proximal end 1110 of the end effector 1100. The compression mechanism 1120 differs from the compression mechanism 1020 in that additional compressive forces may be applied to each and of the anvil 1102. The surgeon may therefore engage each of the clamping mechanisms 1134, 1136 to further compress the tissue between the anvil 1102 and the cartridge 1104. Advantageously, the clamping mechanisms 1134, 1136 may provide more uniform compression at each end 1110, 1112 of the end effector 1100.

With continued reference to FIG. 71, each of the clamping mechanisms 1134, 1136 includes a compression wedge 1138, 1140, similar to the compression wedge 1022 described above with reference to FIG. 69, and which have a dog-leg like configuration including a wedge surface 1142 and 1144, respectively. As is shown best in FIG. 72A, each of the surfaces 1142, 1144 is oriented at an angle relative to a longitudinal axis 1148 of the anvil 1102. The angles may be within the same range identified above with reference to FIG. 70A and the wedge surface 1024.

The clamping mechanism 1134 includes a distal cam tube 1150 that is movable relative to the cartridge 1104 on a slide 1152. The cam tube 1150 has a cavity 1154 that is sized to receive the compression wedge 1138. The clamping mechanism 1136 further includes the compression housing 1030 (described above with respect to FIG. 69) at the proximal end 1110 that is configured to receive the compression wedge 1140 between the flanges 1032a, 1032b in the channel 1034. A rotation collar 1160 (similar to the rotation collar 1050 described above with reference to FIG. 69) captures the flange 1040 on the compression housing 1030. As described above, the compression cable 1048 is coupled to the compression housing 1030 by attachment pin 1044.

During a surgical procedure, the surgeon may withdraw each of the flexible members 1106, 1108 from the end effector 1100. Doing so pulls the anvil 1102 toward the cartridge 1104 to compress the tissue therebetween. As set forth above, the surgeon may be unable to apply sufficient compressive pressure to sufficiently collapse the tissue between the anvil 1102 and the cartridge 1104 with the flexible members 1106, 1108 alone. The surgeon may apply additional compressive pressure by engaging the compression mechanism 1120, including each of the distal clamping mechanism 1134 and the proximal clamping mechanism 1136.

To do so, and with reference to FIGS. 72A and 72B, when the anvil 1102 is proximate the cartridge 1104 in a position in which the compression wedges 1138, 1140 are positioned to be engaged by the distal cam tube 1150 and the rotation collar 1160, respectively, the surgeon may tension the compression cable 1048 to forcibly engage the wedge surface 1144 of the compression wedge 1140 with the rotation collar 1160. At the proximal end 1110, tensioning the compression cable 1048 pulls the compression housing 1030 within the rotation collar 1160 and engages the rotation collar 1160 with the wedge surface 1144. Forcible engagement between the wedge surface 1144 and the rotation collar 1160 forces the anvil 1102 toward the cartridge 1104. At the distal end 1112, tensioning the compression cable 1048 pulls the cam tube 1150 toward the compression wedge 1138 to forcibly engage the cam tube 1150 with the wedge surface 1142. Forcible engagement between the wedge surface 1142 and the cam tube 1150 forces the anvil 1102 toward the cartridge 1104. In this way, additional compressive pressures may be applied at each end of the end effector 1100. In the exemplary embodiment shown, the articulation mechanism 1130 may be substantially similar to the articulation mechanism 970 described above with reference to FIG. 69-70B.

While the present invention has been illustrated by a description of various preferred embodiments and while these embodiments have been described in some detail, it is not the intention of the inventor to restrict or in any way limit the scope of the appended claims to such detail. Though the embodiments described herein were primarily directed to a resection line guide, it is clear that many of the aspects of the present invention may be utilized with additional devices. By way of example, the embodiments described herein may operate as a surgical clamp or a stabilizing device independent of the aspects of the present invention that allow the embodiments to act as an endocutter stapling device or a component thereof. Additional advantages and modifications will readily appear to those skilled in the art. The various features of the invention may be used alone or in any combination depending on the needs and preferences of the user.

What is claimed is:

1. An end effector for use by a surgeon to staple an anatomical structure of a patient during a minimally invasive procedure, the anatomical structure having a first side and a second side, the end effector comprising:
    an anvil that includes a proximal end, a distal end, and a face that is positionable on the first side of the anatomical structure;
    a cartridge that is configured to house a plurality of staples and that includes a proximal end, a distal end, and a face that is positionable on the second side of the anatomical structure; and
    a knife, having a first flange, a second flange, and a cutting edge, wherein the knife is operably configured to move from a first position at about a distal end of the end effector to a second position at about a proximal end of the end effector;
    wherein the distal end of the anvil is movably coupled to the distal end of the cartridge, each of the anvil and the cartridge is insertable through a trocar, and the end effector is remotely operable from outside the patient with at least a portion of one of the anvil and the cartridge being movable toward the other to clamp the end effector.

2. The end effector of claim 1, wherein the distal end of the anvil is pivotally coupled with the distal end of the cartridge.

3. The end effector of claim 1, wherein the distal end of the anvil is pivotally coupled to the distal end of the cartridge with a hinge.

4. The end effector of claim 1, wherein the anvil further comprises a first track and the cartridge further comprises a second track with which the knife is selectively engageable.

5. The end effector of claim 1, further comprising an alignment mechanism operably figured to facilitate alignment between the anvil and the cartridge when the end effector transitions from an open position to a closed position.

6. The end effector of claim 1, wherein the proximal end of the anvil is movably coupled with the proximal end of the cartridge.

7. The end effector of claim 6, wherein the proximal end of the anvil is movably coupled with the proximal end of the cartridge with an engagement element.

8. An end effector for use by a surgeon to staple an anatomical structure of a patient during a minimally invasive procedure, the anatomical structure having a first side and a second side, the end effector comprising:
   an anvil that includes a proximal end, a distal end, and a face that is positionable on the first side of the anatomical structure;
   a cartridge that is configured to house a plurality of staples and that includes a proximal end, a distal end, and a face that is positionable on the second side of the anatomical structure;
   a knife, having a first flange, a second flange, a web, and a cutting edge,
   a first slot, the first slot being defined at least partially by the face of the anvil, wherein the first slot is configured to slidably receive the web of the knife during movement of the knife; and
   a second slot, the second slot being defined at least partially by the face of the cartridge, wherein the second slot is configured to slidably receive the web of the knife during movement of the knife; and
   wherein the distal end of the anvil is movably coupled to the distal end of the cartridge, each of the anvil and the cartridge is insertable through a trocar, and the end effector is remotely operable from outside the patient with at least a portion of one of the anvil and the cartridge being movable toward the other to clamp the end effector and to transect the anatomical structure, and
   wherein the knife is operably configured to move from a first position at about a distal end of the end effector to a second position at about a proximal end of the end effector.

9. The end effector of claim 8, wherein the anvil further comprises a first track with which the knife is selectively engageable and the cartridge further comprises a second track with which the knife is selectively engageable.

10. The end effector of claim 8, wherein the knife has a substantially I-shaped configuration.

11. The end effector of claim 8, wherein the first flange and the second flange of the knife cooperate to retain the end effector in a closed position.

12. The end effector of claim 8, further comprising an alignment mechanism operably configured to facilitate alignment between the anvil and the cartridge when the end effector transitions from an open position to a closed position.

13. The end effector of claim 8, wherein the distal end of the anvil is pivotally coupled to the second end of the cartridge with a hinge.

14. An end effector for use by a surgeon to staple an anatomical structure of a patient during a minimally invasive procedure, the anatomical structure having a first side and a second side, the end effector comprising:
   an anvil, the anvil comprising:
     a. a proximal end,
     b. a distal end,
     c. an anvil face,
     d. a first track defined at least partially by the anvil, and
     e. a first slot defined at least partially by the anvil face;
   a cartridge that is configured to house a plurality of staples, the cartridge comprising;
     a. a proximal end,
     b. a distal end,
     c. a cartridge face, the cartridge face being positioned substantially opposite the anvil face,
     d. a second track defined at least partially by the cartridge, and
     e. a second slot defined at least partially by the cartridge face;
   a knife, wherein the knife is operably configured to move longitudinally from a first position at the distal end of the end effector to a second position at about the proximal end of the end effector;
   wherein the first slot of the anvil and the second slot of the cartridge are configured to slidably receive the knife during movement of the knife; and
   a hinge, the hinge being positioned at the distal end of the anvil and the distal end of the cartridge, wherein the hinge pivotally couples the anvil and the cartridge; and
   wherein the distal end of the anvil is movably coupled to the distal end of the cartridge, each of the anvil and the cartridge is insertable through a trocar, and the end effector is remotely operable from outside the patient with at least a portion of one of the anvil and the cartridge being movable toward the other to clamp the end effector and to transect the anatomical structure.

15. The end effector of claim 14, wherein the knife comprises a first flange, a second flange, and a cutting portion.

16. The end effector of claim 14, further comprising an alignment mechanism operably configured to facilitate alignment between the anvil and the cartridge when the end effector transitions from an open position to a closed position.

* * * * *